US006843997B2

(12) United States Patent
Grose et al.

(10) Patent No.: US 6,843,997 B2
(45) Date of Patent: Jan. 18, 2005

(54) VARIANT VARICELLA-ZOSTER VIRUSES AND METHODS OF USE

(75) Inventors: Charles F. Grose, Iowa City, IA (US); Richard Santos, Saint Louis, MO (US)

(73) Assignee: University of Iowa Research Foundation, Iowa City, IA (US)

( * ) Notice: Subject to any disclaimer, the term of this patent is extended or adjusted under 35 U.S.C. 154(b) by 37 days.

(21) Appl. No.: 10/288,823

(22) Filed: Nov. 6, 2002

(65) Prior Publication Data

US 2003/0166168 A1 Sep. 4, 2003

Related U.S. Application Data

(62) Division of application No. 09/661,596, filed on Sep. 14, 2000, now Pat. No. 6,528,066.
(60) Provisional application No. 60/153,779, filed on Sep. 14, 1999.

(51) Int. Cl.$^7$ .............................................. A51K 39/245
(52) U.S. Cl. ............................... 424/230.1; 424/204.1; 424/130.1; 435/6; 435/975; 435/345
(58) Field of Search .......................... 424/230.1, 204.1, 424/130.1; 435/6, 975, 345

(56) References Cited

U.S. PATENT DOCUMENTS

| | | | |
|---|---|---|---|
| 3,985,615 A | 10/1976 | Kubo | |
| 5,462,734 A | 10/1995 | Letchworth, III et al. | |
| 5,595,890 A | 1/1997 | Newton et al. | |
| 5,710,248 A | 1/1998 | Grose et al. | |
| 5,849,476 A | 12/1998 | Shiraki et al. | |
| 5,952,174 A | 9/1999 | Nikiforov et al. | |
| 6,087,170 A | 7/2000 | Kemble | |

FOREIGN PATENT DOCUMENTS

WO      WO 92/06989     *  4/1992

OTHER PUBLICATIONS

Valcarcel et al, Vaccine, 1997, Vol. 15, No. 6/7, pp. 709–719.*
Wu et al., Archives of Virology, 1997, Vol 142, pp. 349–362.*
Fowler et al, Virology, 1995, Vol. 214, pp. 531–540.*
A. M. Arvin et al., "Live Attenuated Varicella Vaccine," *Annu. Rev. Microbiol., 50*, 59–100 (1996).
A. M. Arvin et al., "Immunity to Varicella–Zoster Viral Glycoproteins, gp I (gp 90/58) and gp III (gp 118), and to a Nonglycosylated Protein, p. 170," *J. Immunol. 137*, 1346–1351 (1986).
ATCC CCL–171, "*Homo sapiens* (human)," [online]. Retreived on May 16, 2001. Retrieved from the Internet; <URL:http://phage.atcc.org/cgi–bin/searchengine/longview.cgi!view=ce, 317407, CCL–171&ctext=CCL.–1,3 pages.
ATCC VR–586, "Variella–Zoster," [online]. Retrieved on Jun. 5, 2001. Retrived from the Internet <URL:http//phage.atcc.org/cgi–bin/seachengine/longview.cgi!view=av, 343894, VR–586&text=VR–586>, 2 pages.
ATCC VR–795, "Varicella–Zoster deposited as Varicella," [online]. Retrieved on May 16, 2001. Retrieved from the Internet:<URL:http://phage.atcc.org/cgi–bin/searchengine/longview.cgi!view=av,476976, VR–795&text=VR–7.9>, 2 pages.
ATCC VR–916, "Varicella–Zoster deposited as Varicella," [online]. Retrieved on Sep. 6, 2000. Retrieved from the Internet:<URL:http//phage.atcc.org/cgi–bin/searchengine/longview.cgi!view=av,554286&text=varicella>, 1 page.
ATCC VR–1367, "Varicella–Zoster," [online]. Retrieved on Jun. 5, 2001. Retrieved from the Internet:<URL:http://phage.atcc.org/cgi–bin/searchengine/longview.cgi!view=av, 871705, VR–1367&text=VR–1367>, 2 pages.
M. F. Bachman et al., "The influence of Antigen Organization on B Cell Responsiveness," *Science, 262,* 1448–1451 (1993).
R. E. Bergen et al., "Human T Cells Recognize Multiple Epitopes of an Immediate Early/Tegument Protein (IE62) and Glycoprotein I of Varicella Zoster Virus," *Viral Immunol., 4,* 151–166 (1991).
J. I. Cohen et al., "Generations of varicella–zoster virus (VZV) and viral mutants from cosmid DNAs: VZV thymidylate synthetase is not essential for replication in vitro," *Proc. Natl. Acad. Sci. USA, 90,* 7376–7380 (1993).
N. L. Cole et al., "Colchicine treatment in the preparation of varicella–zoster virus inocula," *J. Virol. Methods, 36,* 111–118 (1992).
A. J. Davison et al., "The Complete DNA Sequence of Varicella–Zoster Virus," *J. Gen. Virol., 67,* 1759–1816 (1986).
K. S. Dingwell et al., "Herpes simplex virus glycoproteins E and I facilitate cell–to–cell spread in vivo across junctions of cultured cells," *J. Virol., 68* 834–845 (1994).
K. M. Duus et al., "Cell Surface Expression and Fusion by the Varicella–Zoster Virus gH:gL Glycoprotein Complex: Analysis by Laser Scanning Confocal Microscopy," *Virology, 210,* 429–440 (1995).

(List continued on next page.)

*Primary Examiner*—Ali R. Salimi
(74) *Attorney, Agent, or Firm*—Mueting, Raasch & Gebhart, P.A.

(57) ABSTRACT

The present invention provides methods directed to detecting antibodies that specifically bind to a varicella zoster polypeptide, detecting the presence of a varicella zoster virus in an animal, diagnosing a disease caused by varicella zoster virus, and detecting a varicella zoster virus having a single nucleotide polymorphism in ORF68. The present invention also provides a vaccine composition, a method for producing a modified attenuated varicella zoster virus, isolated polynucleotides, and isolated polypeptides, and viruses.

8 Claims, 10 Drawing Sheets

OTHER PUBLICATIONS

K. M. Duus et al., "Multiple Regulatory Effects of Varicella–Zoster Virus (VZV) gL on Trafficking Patterns and Fusogenic Properties of VZV gH," *J. Virol.*, 70, 8961–8971 (1996).

J. R. Ecker et al., "Varicella zoster virus DNA exists as two isomers," *Proc. Natl. Acad. Sci. USA*, 79, 156–160 (1982).

T. Gojobori et al., "Rates of evolution of the retroviral oncogene of Maloney murine sarcoma virus and of its cellular homologues," *Proc. Natl. Acad. Sci. USA*, 82, 4198–4201 (1985).

F. L. Graham et al., "Characteristics of a Human Cell Line Transformed by DNA from Human Adenovirus Type 5," *J. Gen. Virol.*, 36, 59–74 (1977).

C. Grose et al., "Computer modeling of prototypic and aberrant nucleocapsids of varicella–zoster virus," *Virology*, 214, 321–329 (1995).

C. Grose, "Glycoproteins Encoded by Varicella–Zoster Virus: Biosynthesis, Phosphorylation, and Intracellular Trafficking," *Annu. Rev. Microbiol.*, 44, 59–80 (1990).

C. Grose, "Pathogenesis of Infection with Varicella Vaccine," *Infect. Dis. Clinics NA*, 10, 489–505 (1996).

C. Grose, et al., "*Varicella–Zoster Virus: Isolation and Propagation in Human Melanoma Cells at 36 and 32° C.*," *Infect. Immun.* 19, 199–203 (1978).

C. Grose, et al., "Monoclonal Antibodies Against Three Major Glycoproteins of Varicella–Zoster Virus," *Infect. Immun.*, 40, 381–388 (1983).

C. Grose, "The Synthesis of Glycoproteins in Human Melanoma Cells Infected with Varicella–Zoster Virus," *Virology*, 101:1–9 (1980).

B. H. Hahn et al., "Genetic variation in HTLV–III/LAV over time in patients with AIDS or at risk for AIDS," *Science*, 232, 1548–1553 (1986).

R. Harson et al., "Egress of Varicella–Zoster Virus from the Melanoma Cell: a Tropism for the Melanocyte," *J. Virol.*, 69, 4994–5010 (1995).

C. Hatfield et al., "Epitope Mapping and Tagging by Recombination PCR Mutagenesis," *Bio Techniques*, 22, 332–337 (1997).

J. Holland et al., "Rapid evolution of RNA genomes," *Science*, 215, 1577–1585 (1982).

M. Ito et al., "Human Leukocytes Kill Varicella–Zoster Virus–Infected Fibroblasts in the Presence of Murine Monoclonal Antibodies to Virus–Specific Glycoproteins," *J. Virol.*, 54, 98–103 (1985).

D. H. Jones et al., "A Rapid Method for Site–Specific Mutagenesis and Directional Subcloning by Using the Polymerase Chain Reaction to Generate Recombinant Circles," *Bio Techniques*, 8, 178–183 (1990).

F. Jones et al., "Role of cytoplasmic vacuoles in varicella–zoster virus glycoprotein trafficking and virion envelopment," *J. Virol.*, 62, 2701–2711 (1988).

P. R. Kinchington et al., "Regulated Nuclear Localization of the Varicella–Zoster Virus Major Regulatory Protein, IE62," *J. Infect. Dis.*, 178(Suppl. 1), S16–21 (1998).

P. R. Kinchington et al., "Molecular basis for a geographic variation of varicella–zoster virus recognized by a peptide antibody," *Neurology*, 45 (Suppl 8), S13–14 (1995).

P. LaRussa et al., "Restriction fragment length polymorphism of polymerase chain reaction products from vaccine and wild–type varicella–zoster virus isolates," *J. Virol.* 66, 1016–1020 (1922).

V. Litwin et al., "Receptor Properties of Two Varicella–Zoster Virus Glycoproteins, gpI and gpIV, Homologous to Herpes Simplex Virus gE and gI," *J. Virol.*, 66, 3643–3651 (1992).

V. Litwin et al., "Cell Surface Expression of the Varicella–Zoster Virus Glycoproteins and Fc Receptor," *Virology*, 178, 263–272 (1990).

S. Mallory et al., "Mutational Analysis of the Role of Glycoprotein I in Varicella–Zoster Virus Replication and Its Effect on Glycoprotein E Conformation and Trafficking," *J. Virol.*, 71, 8279–8288 (1997).

D. J. McGeoch et al., "Molecular phylogeny of the alphaherpesvirinae subfamily and a proposed evolutionary timescale," *J. Mol. Biol.*, 238, 9–22 (1994).

D. J. McGeoch et al., "Molecular phylogeny and evolutionary timescale for the family of mammalian herpesviruses," *J. Mol. Biol.*, 247, 443–458 (1995).

J. F. Moffat et al., "Tropism of Varicella–Zoster Virus for Human $CD4^+$ and $CD8^+$ T Lymphocytes and Epidermal Cells in SCID–hu Mice," *J. Virol.*, 69, 5236–5242 (1995).

J. F. Moffat et al., "Attenuation of the Vaccine Oka Strain of Varicella–Zoster Virus and Role of Glycoprotein C in Alphaherpesvirus Virulence Demonstrated in the SCID–hu Mouse," *J. Virol.*, 72, 965–974 (1998).

E. A. Montalvo et al., "Assembly and Processing of the Disulfide–Linked Varicella–Zoster Virus Glycoprotein gpII(140)," *J. Virol.*, 61, 2877–2884 (1987).

National Center for Biotechnology Information, National Library of Medicine, National Institutes of Health, Genbank X04370. Accession Number X04370 M14891 M16612, "The complete DNA sequence of varicella–zoster virus," [online]. J. Gen. Virol., 67 (Pt 9) 1759–1816 (1986), [retrieved on May 29, 2001]. Retrieved from the Internet:<URL: http://www.ncbi.nlm.nih.gov/entrez/query.fcgi!cmd=Retrieve&db=Nucleotide&list uids=599.8=GenBank>, 39 pages.

T. I. Ng et al., "Phosphorylation of Varicella–Zoster Virus Open Reading Frame (ORF) 62 Regulatory Product by Viral ORF 47–Associated Protein Kinase," *J. Virol.*, 68, 1350–1359 (1994).

N. Nishimura et al., "A Di–Acidic Signal Required for Selective Export from the Endoplasmic Reticulum", *Science*, 277, 556–560 (1997).

J. K. Olson et al., "Complex formation facilitates endocytosis of varicella–zoster virus gE:gI Fc receptor," *J. Virol.*, 72, 1542–1551 (1998).

J. K. Olson et al., "Varicella–Zoster Virus Fc Receptor gE Glycoprotein: Serine/Threonine and Tyrosine Phosphorylation of Monomeric and Dimeric Forms," *J. Virol.*, 71, 110–119 (1997).

J. K. Olson et al., "Endocytosis and Recycling of Varicella–Zoster Virus Fc Receptor Glycoprotein gE: Internalization Mediated by a YXXL Motif in the Cytoplasmic Tail," *J. Virol.*, 71, 4042–4054 (1992).

J. A. Padilla et al, "High–resolution immuno–scanning electron microscopy using a non–coating method: study of herpes simplex virus glycoproteins on the surface of virus particles and infected cells," *J. Elect. Microscopy*, 46, 171–180 (1997).

Public Law 94–279; Apr. 22, 1976, United States Statutes at Large, vol. 90.

B. Rentier, "Introduction", *Neurol, 45(Suppl. 8)*, S8 (1995).

J. E. Rodriguez et al., "Entry and egress of varicella virus blocked by same anti–gH monoclonal antibody," *Virology, 196,* 840–844 (1993).

J. Sambrook et al, *Molecular Cloning: A Laboratory Manual., Second Edition,* Cold Spring Harbor Laboratory Press (1989), (Cover Page, publication page and table of contents).

R. A. Santos et al., "Varicella–Zoster Virus gE Escape Mutant VZV–MSP Exhibits an Accelerated Cell–to–Cell Spread Phenotype in both Infected Cell Cultures and SCID–hu Mice," Virology, 275, 306–317 (September 2000).

R. A. Santos et al., "Antigenic Variation of Varicella Zoster Virus Fc Receptor gE: Loss of a Major B Cell Epitope in the Ectodomain," *Virology, 249,* 21–31 (1998).

T. Shioda et al., "Small amino acid changes in V3 hypervariable region of gp120 can affect the T–cell–line and macrophage tropsim of human immunodeficiency virus type 1," *Proc. Natl. Acad. Sci. USA, 89,* 9434–9438 (1992).

F. I. Smith et al., "Variation in influenza virus genes epidemiological, pathogenic, and evolutionary consequences", *The Influenza Virues,* (R.M. Krug, Ed.), 319–359. Plenum Press, New York (1989).

P. G. Spear, "Glycoproteins Specified by Herpes Simplex Viruses," *The Herpesviruses, 3,* (B. Roizman, Ed.), 315–356. Plenum Press, New York (1985).

E. Szomolanyi–Tsuda et al., "T cell–independent antibody–mediated clearance of polyomo virus in T cell–deficient mice," *J. Exp. Med., 183,* 403–411 (1996).

M. Takahashi et al., "Development of a Live Attenuated Varicella Vaccine," *Biken, J., 18,* 25–33 (1975).

T. A. Tatusova, et al., "BLAST 2 SEQUENCES, a new tool for comparing protein and nucleotide sequences," *FEMS Microbiol Lett, 174,* 247–250 (1999), and available at http://www.ncbi.nlm.nih.gov/gorf/bl2.html.

U.S. National Institutes of Health, "About NIH Image," [online]. Retreived on May 29, 2001. Retrieved from the Internet:<URL:http//rsb.info.nih.gov/nih–image/about.html, 2 pages.

K. A. Weigle et al., "Common expression of varicella–zoster viral glycoprotein antigens in vitro and in chickenpox and zoster vesicles," *J. Infect. Dis., 148,* 630–638 (1983).

T. H. Weller, "Serial propagation in vitro of agents producing inclusion bodies derived from varicella and herpes zoster," *Proc. Soc. Exp. Biol. Med., 83,* 340–346 (1953).

S. A. Whaton et al., "Structure function, and antigenicity of the hemagglutinin of influenza viruses," *The Influenza Viruses,* (R. M. Krug, Ed.), 153–171. Plenum Press, New York, (1989).

M. Yang et al., "Retrograde Transneuronal Spread of Pseudorabies Virus in Defined Neuronal Circuitry of the Rat Brain is Facilitated by gE Mutations that Reduce Virulence," *J. Virol., 73,* 4350–4359 (May, 1999).

Z. Yao et al., "Varicella–Zoster Virus Glycoprotein gpI/gpIV Receptor: Expression, Complex Formation, and Antigenicity within the Vaccinia Virus–T7 RNA polymerase Transfection System," *J. Virol., 67,* 305–314 (1993).

Z. Zhu et al, "Targeting of glycoprotein I (gE) of varicella–zoster virus to the trans–Golgi network by an AYRV sequence and an acidic amino acid–rich patch in the cytosolic domain of the molecule," *J. Virol., 70,* 6563–6575 (1996).

\* cited by examiner

Fig. 1A (SEQ ID NO:72)

```
  1  MGTVNKPVVG VLMGFGIITG TLRITNPVRA SVLRYDDFHT DEDKLDTNSV
 51  YEPYYHSDHA ESSWVNRGES SRKAYDHNSP YIWPRNDYDG FLENAHEHHG
101  VYNQGRGIDS GERLMQPTQM SAQEDLGDDT GIHVIPTLNG DDRHKIVNVD
151  QRQYGDVFKG DLNPKPQGQR LIEVSVEENH PFTLRAPIQR IYGVRYTETW
201  SFLPSLTCTG DAAPAIQHIC LKHTTCFQDV VVDVDCAENT KEDQLAEISY
251  RFQGKKEADQ PWIVVNTSTL FDELELDPPE IEPGVLKVLR TEKQYLGVYI
301  WNMRGSDGTS TYATFLVTWK GDEKTRNPTP AVTPQPRGAE FHMWNYHSHV
```

Fig. 1B

|  | 3B3.2 | | 3B3.13 | | | | 3B3.11 | | | |  |
|---|---|---|---|---|---|---|---|---|---|---|---|
| VZVgE (149-161) | V GTG | D GAC | Q CAA | R CGT | Q CAA | Y TAC | G GGT | D GAC | V GTG | F TTT | K AAA | G GGA | D GAT | (SEQ ID NO:73)<br>(SEQ ID NO:74)

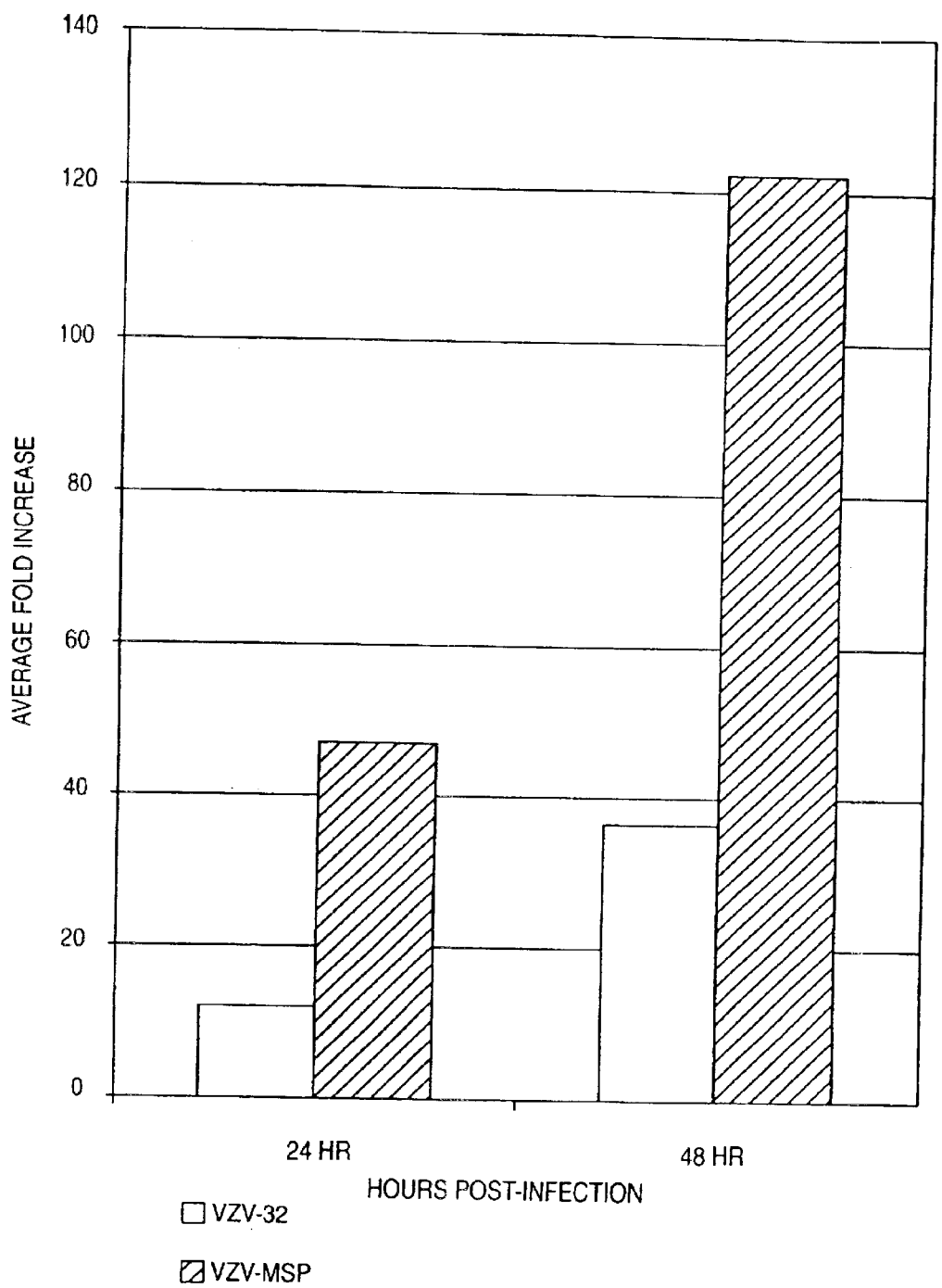

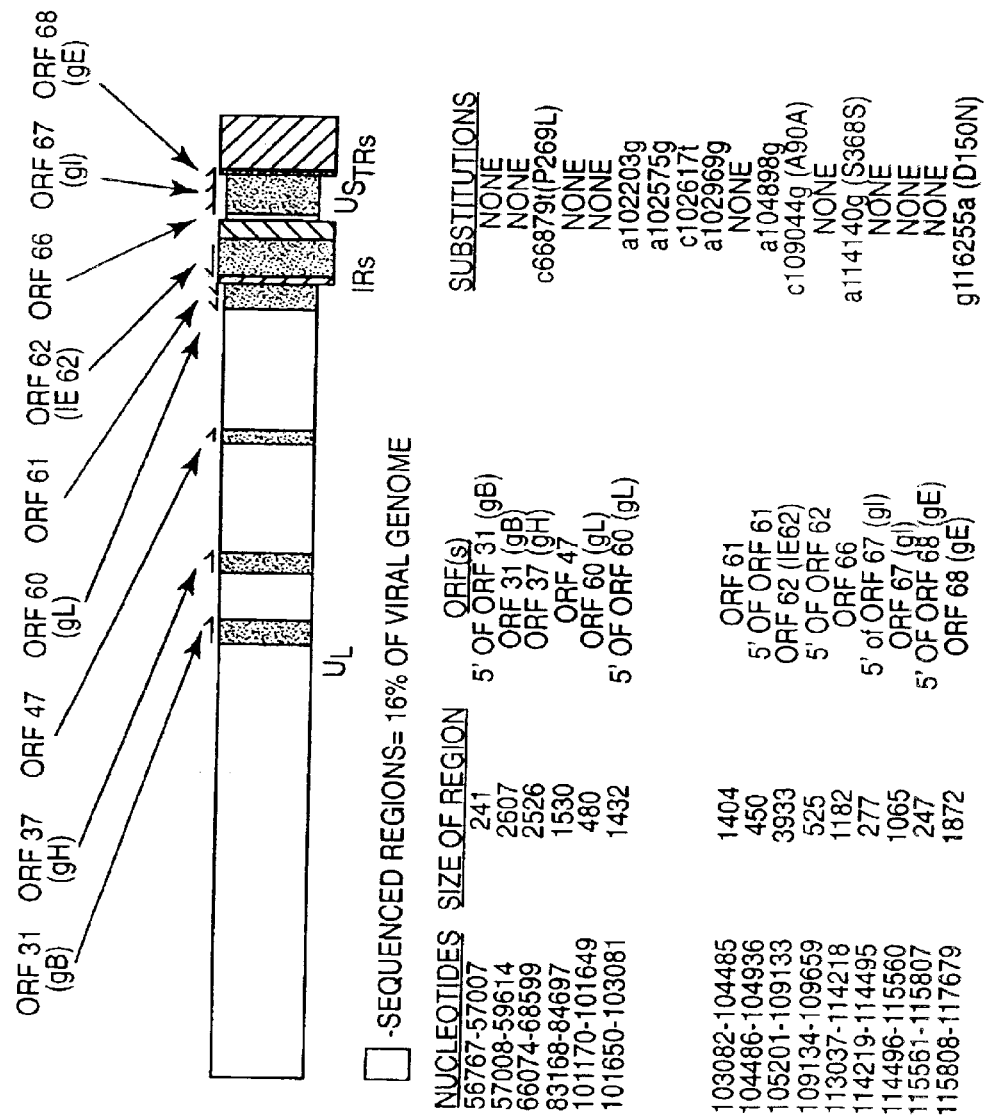

Fig. 6

Polymorphisms in gE

| bp | 119 | 448 | 660 | 1606 | 1808 |
|---|---|---|---|---|---|
| aa | T>I | D>N | silent | L>I | G>D |
|  | * | * | * | * | * |
| Dumas | —CACACCGAT-/-GTGGACCAA-/-ATATGTTTA-/-CTTCTACGA-/-TTTGGTAAC— |
| MSP | —CACATCGAT-/-GTGAACCAA-/-ATATGTTTA-/-CTTCTACGA-/-TTTGGTAAC— |
| Ellen | —CACATCGAT-/-GTGGACCAA-/-ATATGCTTA-/-CTTATACGA-/-TTTGGTAAC— |
| Iceland | —CACATCGAT-/-GTGGACCAA-/-ATATGCTTA-/-CTTATACGA-/-TTTGGTAAC— |
| 80-2 | —CACATCGAT-/-GTGGACCAA-/-ATATGCTTA-/-CTTATACGA-/-TTTGGTAAC— |
| Oka | —CACATCGAT-/-GTGGACCAA-/-ATATGCTTA-/-CTTATACGA-/-TTTGGTAAC— |
| VSD | —CACACCGAT-/-GTGGACCAA-/-ATATGTTTA-/-CTTCTACGA-/-TTTGATAAC— |
| 32 | —CACACCGAT-/-GTGGACCAA-/-ATATGTTTA-/-CTTCTACGA-/-TTTGGTAAC— |
| VIA | —CACACCGAT-/-GTGGACCAA-/-ATATGTTTA-/-CTTCTACGA-/-TTTGGTAAC— |

Fig. 7

Polymorphisms in gl

| | bp | 15 | 546 | |
|---|---|---|---|---|
| | aa | 5 Q>H | silent | |
| Dumas | —ATCCAATGT | -/- | TCTCCGTCT— |
| MSP | —ATCCAATGT | -/- | TCTCCGTCT— |
| Ellen | —ATCCAATGT | -/- | TCTCCGTCT— |
| Iceland | —ATCCAATGT | -/- | TCTCCGTCT— |
| 80-2 | —ATCCAATGT | -/- | TCTCCGTCT— |
| Oka | —ATCCAATGT | -/- | TCTCC<u>A</u>TCT— |
| VSD | —ATCCAATGT | -/- | TCTCCGTCT— |
| 32 | —ATCCA<u>C</u>TGT | -/- | TCTCCGTCT— |
| VIA | —ATCCA<u>C</u>TGT | -/- | TCTCCGTCT— |

Fig. 8

Polymorphisms in gH

```
bp        39        215       573       806       1254
aa      silent    76 R>K    silent   269 P>L    silent
Dumas   ----CCTCTTTGG-//-GATAGAAAA-//-ATTCTGGAA-//-GGACCACCG-//-AACACTATA----
MSP     ----CCTCTTTGG-//-GATAGAAAA-//-ATTCTGGAA-//-GGACTACCG-//-AACACTATA----
Ellen   ----CCTCTGTGG-//-GATAAAAAA-//-ATTCTGGAA-//-GGACTACCG-//-AACACGATA----
Iceland ----CCTCTGTGG-//-GATAAAAAA-//-ATTCTGGAA-//-GGACTACCG-//-AACACTATA----
80-2    ----CCTCTGTGG-//-GATAAAAAA-//-ATTCTGGAA-//-GGACTACCG-//-AACACTATA----
Oka     ----CCTCTTTGG-//-GATAGAAAA-//-ATTCTTGAA-//-GGACTACCG-//-AACACTATA----
VSD     ----CCTCTTTGG-//-GATAGAAAA-//-ATTCTGGAA-//-GGACCACCG-//-AACACTATA----
32      ----CCTCTTTGG-//-GATAGAAAA-//-ATTCTGGAA-//-GGACTACCG-//-AACACTATA----
VIA     ----CCTCTTTGG-//-GATAGAAAA-//-ATTCTGGAA-//-GGACTACCG-//-AACACTATA---- bp       2028      2099      2181      2445
aa      silent   700 R>K   silent    silent
Dumas   ----AAACCTCAA-//-AGCAGGGAT-//-TATTGCGGA-//-CTGGCGGTA----
MSP     ----AAACCTCAA-//-AGCAGGGAT-//-TATTGCGGA-//-CTGGCGGTA----
Ellen   ----AAACCCCAA-//-AGCAGAGAT-//-TATTGTGGA-//-CTGGCGGTA----
Iceland ----AAACCCCAA-//-AGCAGAGAT-//-TATTGTGGA-//-CTGGCGGTA----
80-2    ----AAACCCCAA-//-AGCAGAGAT-//-TATTGTGGA-//-CTGGCGGTA----
Oka     ----AAACCTCAA-//-AGCAGGGAT-//-TATTGCGGA-//-CTGGCGGTA----
VSD     ----AAACCTCAA-//-AGCAGGGAT-//-TATTGCGGA-//-CTGGCGGTA----
32      ----AAACCTCAA-//-AGCAGGGAT-//-TATTGCGGA-//-CTGGCAGTA----
VIA     ----AAACCTCAA-//-AGCAGGGAT-//-TATTGCGGA-//-CTGGCAGTA----
```

Fig. 9

Polymorphisms in gL

Dumas
aa  8   9   10  11                          106 107 108
— CTG CAG ATA GTT ————————————————————— GTT GGT GAA —
   L   Q   I   V                            V   G   E (SEQ ID NO:77)
(SEQ ID NO:78)

Oka
aa  8   9   10                              106 107 108
— CTG CAG ATG ATA ————————————————————— GTT GAT GAA —
   L   Q   M   I                            V   D   E (SEQ ID NO:79)
(SEQ ID NO:80)

Fig. 10

Polymorphisms in IE62

| AA | 30 * | 42 S>A | 61 * | 129 * | 131 * | 172 * | 190 * | 195 N>D | 341 * | 473 | 516 | 602 A>V | 609 * | 628 S>G | 657 A>T | 688 | 703 V>A | 743 * | 879 * | 958 R>G |
|---|---|---|---|---|---|---|---|---|---|---|---|---|---|---|---|---|---|---|---|---|
| Dumas | GCG | TCG | CAC | CTT | ACA | GTT | CAA | AAT | CCA | GCA | GTG | GCG | CGA | AGC | GCT | CCA | GTC | CTT | GGA | AGG |
| MSP | GCC | --- | CAT | CTC | --- | --- | --- | --- | --- | --- | --- | --- | --- | --- | --- | --- | --- | --- | --- | --- |
| Ellen | GCC | --- | CAT | CTC | ACG | GTC | CAG | GAT | CCG | --- | --- | --- | --- | --- | --- | --- | GCC | --- | --- | GGG |
| Iceland | GCC | GCG | CAT | CTC | --- | --- | --- | --- | --- | --- | --- | --- | --- | --- | --- | --- | GCC | --- | --- | --- |
| 80-2 | GCC | --- | CAT | CTC | --- | --- | --- | --- | --- | --- | --- | --- | --- | --- | ACT | --- | GCC | --- | --- | --- |
| OKA | GCC | --- | --- | --- | --- | --- | --- | --- | CCG | GCG | --- | GTG | CGG | GGC | ACT | CCG | --- | --- | --- | GGG |
| VSD | GCC | --- | --- | --- | --- | --- | --- | --- | --- | --- | GTA | --- | --- | --- | --- | --- | --- | --- | --- | --- |
| 32 | GCC | --- | --- | --- | --- | --- | --- | --- | --- | --- | GTA | GTG | --- | --- | --- | --- | --- | CTC | GGG | GGG |
| VIA | GCC | --- | --- | --- | --- | --- | --- | --- | --- | --- | --- | --- | --- | --- | --- | --- | --- | --- | --- | --- |

| AA | 963 | 1035 | 1057 | 1071 Q>R | 1072 | 1080 | 1093 * | 1143 * | 1145 | 1201 H>R | 1208 S>A | 1208 * | 1215 Q>R | 1228 L>P | 1241 S>G | 1243 E>G | 1255 S>A | 1260 I>V |
|---|---|---|---|---|---|---|---|---|---|---|---|---|---|---|---|---|---|---|
| Dumas | TTG | GCA | CGA | CAG | GCA | GCA | GCA | GCA | CCA | CAC | TCA | TCA | CAG | CTG | AGC | GAG | TCC | ATC |
| MSP | --- | --- | --- | --- | --- | --- | --- | --- | --- | --- | --- | --- | --- | --- | --- | --- | --- | --- |
| Ellen | CTG | --- | --- | --- | --- | --- | GCG | --- | --- | --- | --- | --- | --- | --- | --- | GGG | --- | --- |
| Iceland | --- | --- | AGA | --- | --- | --- | --- | --- | --- | --- | --- | --- | --- | --- | --- | GGG | GCC | --- |
| 80-2 | --- | --- | AGA | --- | --- | --- | --- | --- | --- | --- | --- | --- | --- | --- | --- | --- | --- | --- |
| OKA | --- | --- | AGA | --- | --- | --- | GCG | --- | --- | --- | GCA | --- | --- | CCG | --- | --- | --- | --- |
| VSD | --- | --- | --- | --- | --- | --- | --- | --- | --- | --- | --- | --- | --- | --- | --- | --- | --- | --- |
| 32 | GCG | CGG | --- | CGG | --- | GCG | --- | --- | CCG | CGC | --- | TCG | CGG | --- | GGC | --- | --- | --- |
| VIA | --- | CGG | --- | CGG | --- | GCG | --- | --- | --- | --- | --- | --- | --- | --- | GGC | --- | --- | GTC |

VARIANT VARICELLA-ZOSTER VIRUSES AND METHODS OF USE

CONTINUING APPLICATION DATA

This application is a Divisional Application of U.S. patent application Ser. No. 09/661,596, filed Sep. 14, 2000, now U.S. Pat. No. 6,528,066, which claims the benefit of U.S. Provisional Application Ser. No. 60/153,779, filed Sep. 14, 1999, all of which are incorporated by reference herein.

GOVERNMENT FUNDING

The present invention was made with government support under Grant No. AI 22795, awarded by the National Institutes of Health. The Government has certain rights in this invention.

BACKGROUND

Varicella-zoster virus (VZV) is an ancient virus. Estimations of its origins have established that the modern herpesviruses arose some 60–80 million years ago. VZV is a member of the alphaherpesvirus subfamily of herpesviridae. It is the etiologic agent of chickenpox in childhood, after which the virus enters a latent state in the dorsal root ganglia; decades later, the same virus reactivates and causes the disease shingles (herpes zoster). The entire sequence of the 125 kbp VZV genome has been published (see Davison et al., *J. Gen. Virol.*, 67:1759–1816 (1986)). With the subsequent publication of sequence data from other herpesviruses, the alphaherpesviruses have now been subdivided into two genera called Simplexvirus and Varicellovirus. VZV is considered to have one of the most stable genomes of all herpesviruses. The Oka strain of varicella vaccine derived from a Japanese child with chickenpox has a few minor genomic differences from North American strains, but to date no antigenic variation has been discovered amongst the major surface immunogens of the virion (Arvin et al., *Annu. Rev. Microbiol.*, 50:59–100 (1996)).

Based on their extensive analyses of herpesviral molecular evolutionary history, it has been estimated that herpesvirus DNA sequences mutate 10–100 times faster than the equivalent classes of sequences on the host genome. For glycoprotein gB, a highly conserved open reading frame (ORF) among all herpesviruses, it has been calculated that nonsynonymous substitutions have occurred at a rate of $2.7 \times 10^{-8}$ substitutions per site per year and synonymous substitutions at $10^{-7}$ substitutions per site per year. Convincing arguments have been made in favor of the concept of cospeciation; in other words, herpesvirus lineages arise by way of co-evolution with their specific host. In the case of VZV, the progenitor virus most likely arose 60–70 million years before the present.

Of all the human herpesviruses, VZV may undergo the fewest replication cycles during the lifetime of the infected host. Based on a probable schema of pathogenesis, the virus actively replicates for a period of 10–14 days after infection of the human host. During a bout of chickenpox, therefore, VZV has at most 20 replication cycles. Based on the current understanding of VZV latency and reactivation, no further replication occurs unless the individual develops herpes zoster in late adulthood. Because of the above scenario, the genetic stability of the VZV genome has been presumed.

VZV contains the smallest genome of the human herpesviruses, containing about 70 ORFs within the complete VZV-Dumas sequence. Of these ORFs, at least seven code for glycoproteins, of which glycoprotein B (gB), glycoprotein E (gE), glycoprotein H (gH), and glycoprotein I (gI) are present on the exterior of the virion. VZV gE, in complex with glycoprotein I (gI), acts as a human Fc receptor on the surface of infected cells (Litwin et al., *J. Virol.*, 66:3643–51 (1992), Litwin et al., *Virology*, 178:263–72 (1990)). The cytoplasmic tails of both gE and gI contain endocytosis motifs, allowing internalization and recycling of the complex to and from the cell (Olson et al., *J. Virol.*, 71:110–119 (1997), Olson et al., *J. Virol.*, 71:4042–4054 (1992)). The gE and gI cytoplasmic tails also are modified by both serine/threonine and tyrosine phosphorylation motifs. The fact that gE cannot be deleted suggests that it is essential (Cohen et al., *Proc. Natl. Acad. Sci. USA*, 90:7376–7380 (1993), Mallory et al., *J. Virol.*, 71:8279–88 (1997)).

In VZV infection in humans, VZV gE is the most abundantly produced viral glycoprotein during infection. VZV gE is a major antigenic determinant to which numerous humoral and cytolytic responses are observed (Arvin et al., *J. Immunol.*, 137:1346–1351 (198); Bergen et al., *Viral Immunol.*, 4:151–166 (1991); and Ito et al., *J. Virol.*, 54:98–103 (1985)). Recently, an immunodominant B-cell epitope was demarcated in the gE ectodomain; the epitope is defined by murine monoclonal antibody (MAb) 3B3 (Duus et al., *J. Virol.*, 70:8961–8971 (1996); Hatfield et al., *BioTechniques* 22:332–337 (1997); and Grose, U.S. Pat. No. 5,710,248).

It has long been believed that varicella zoster virus exists in nature as a single serotype (Rentier, *Neurol.*, 45(Suppl. 8), S8 (1995), and that all varicella zoster viruses had essentially the same immunological properties. The first strain of varicella zoster virus that was sequenced was VZV-Dumas. Following the publication of this sequence, it was further believed that all varicella zoster viruses had essentially the same genetic properties as VZV-Dumas.

Significant progress has been made in the diagnosis of and vaccination against the sole VZV serotype that is believed to exist and cause disease in the United States. However, the production of the reagents used in diagnosis and vaccination of VZV is time consuming and expensive due to the slow growth rate of the strain grown to produce antigens for diagnostic and vaccine use.

SUMMARY OF THE INVENTION

The present invention represents a significant advance in the art of detecting and preventing varicella zoster virus infection and disease. During the characterization of a varicella zoster virus isolated from a patient, the surprising and unexpected observation was made that the virus had a different serotype. This strain was designated VZV-MSP. The molecular basis of the different serotype was found to be a single nucleotide polymorphism in the genome between VZV-Dumas and VZV-MSP. It was also determined that this single nucleotide polymorphism resulted in the loss of an epitope that is the epitope to which most protective antibody is produced upon vaccination with most currently used vaccines.

Typically, varicella zoster virus isolates can be divided into two groups with respect to growth rate in tissue culture cells. Some isolates, for instance VZV-Oka and VZV-Ellen, grow at a rate that results in complete lysis of a monolayer in about 5 to 7 days. Clinical isolates typically grow at a rate that results in complete lysis of a monolayer in about 4 to 5 days. Further investigation revealed that the new strain, VZV-MSP, unexpectedly and surprisingly had by in vitro tissue culture a growth rate that was significantly higher than previously characterized isolates, and was able to lyse a monolayer in about 2 days.

The present invention provides a method for detecting antibodies that specifically bind to a varicella zoster polypeptide. A biological sample that includes an antibody is contacted with a preparation that includes a varicella zoster polypeptide, for instance an isolated varicella zoster polypeptide or fragment thereof, to form a mixture. The varicella zoster polypeptide includes a polymorphism and can encoded by a polymorphism of ORF37. The polymorphism in the polypeptide encoded by the polymorphic ORF37 can be due to a single amino acid polymorphism, which can be present in the polypeptide as a leucine at amino acid 269. Alternatively, the varicella zoster polypeptide includes a polymorphism and can encoded by a polymorphism of ORF68. The polymorphism in the polypeptide encoded by the polymorphic ORF68 can be due to a single amino acid polymorphism, which can be present in the polypeptide as an asparagine at amino acid 150. The mixture is incubated under conditions to allow the antibody to specifically bind the polypeptide to form a polypeptide:antibody complex. The presence or absence of the polypeptide:antibody complex is then detected. Detecting the polypeptide:antibody complex indicates the presence of antibodies that specifically bind to a varicella zoster polypeptide.

The preparation can include whole varicella zoster virus, for instance VZV-MSP or a modified varicella zoster virus, where the modified virus has the ATCC designation VR-795 wherein the nucleotide sequence of the virus has been modified to comprise the polymorphism of ORF37 or ORF68. The biological sample can be blood, vesicle fluid, bone marrow, brain tissue, or combinations thereof. Also provided are kits for detecting antibodies that specifically bind to a varicella zoster polypeptide. This kits include a whole varicella zoster virus.

In another aspect, the present invention provides a method for detecting the presence of a varicella zoster virus in an animal. The method includes detecting the presence of an antibody to a varicella zoster virus polypeptide encoded by a polymorphic ORF of GenBank X04370. The ORF can be ORF37 or ORF68, where the encoded polypeptide includes a single amino acid polymorphism. When the polypeptide is encoded by ORF37, the single amino acid polymorphism present in the polypeptide can be a leucine at amino acid 269. When the polypeptide is encoded by ORF68, the single amino acid polymorphism present in the polypeptide can be an asparagine at amino acid 150. Optionally, the antibody that is detected does not specifically bind to the varicella zoster polypeptide encoded by ORF37 of GenBank Accession X04370 or ORF68 of GenBank Accession X04370.

The present invention is also directed to a method for diagnosing a disease, for instance chicken pox and shingles, caused by varicella zoster virus. The method includes contacting a polynucleotide, optionally an isolated polynucleotide, of a subject suspected of having a disease caused by varicella zoster virus with a primer pair. This is incubated under conditions suitable to form a detectable amplification product, and the primer pair will not form a detectable amplification product when incubated with a polynucleotide having the nucleotide sequence of GenBank Accession X04370. An amplification product is detected, where the detection indicates that the subject has a disease caused by varicella zoster virus. The polynucleotide of the subject can be present in a biological sample, including blood, vesicle fluid, bone marrow, brain tissue, or combinations thereof.

The polynucleotide that is amplified to result in a detectable amplification product can include a single nucleotide polymorphism relative to the nucleotide sequence of GenBank Accession X04370 (SEQ ID NO:76). The primer pair can include a first primer that includes nucleotides that hybridize with a polynucleotide of GenBank Accession X04370, and a second primer comprising nucleotides that hybridize with a polynucleotide of GenBank Accession X04370, with the proviso that the 3' nucleotide of the second primer hybridizes to the single nucleotide polymorphism relative to the nucleotide sequence of GenBank Accession X04370 and does not hybridize with the corresponding nucleotide present in the nucleotide sequence of GenBank Accession X04370. The single nucleotide polymorphism can be present in ORF37, and the single nucleotide polymorphism can be present at nucleotide 806 of ORF37. The nucleotide at nucleotide 806 can be a thymine. The single nucleotide polymorphism can be present in ORF68, and the single nucleotide polymorphism can be present at nucleotide 448 of ORF68. The nucleotide at nucleotide 448 can be an adenine. An example of a primer pair is CGATGACAGACATAAAATTGTAAATGTGA (SEQ ID NO: 1) and CACCCAAGTATTGTTTTTCTGTCCG (SEQ ID NO:2).

The present invention further provides a method for detecting a varicella zoster virus, for instance VZV-MSP, having a single nucleotide polymorphism in ORF68. The method includes contacting a polynucleotide with a primer pair and incubating under conditions suitable to form a detectable amplification product. The primer pair amplifies a portion of ORF68 of GenBank Accession X04370 and/or a polymorphism thereof, that includes nucleotide 448 of RF68. The amplification product is exposed to a restriction endonuclease having nucleotide 448 in its recognition sequence. Examples of restriction endonuclease include AflII, AsuI, AvaII, Cfr13I, Eco47I, NspIV, PshAI, Sau96I, and SinI. The amplification product is then detected. The presence of an amplification product that is not cleaved by the restriction endonuclease indicates the presence of a varicella zoster virus having a single nucleotide polymorphism in ORF68. The polynucleotide can be present in a biological sample, including, for instance, blood, vesicle fluid, bone marrow, brain tissue, or combinations thereof. Optionally, the polynucleotid can be isolated. An example of a primer pair is GGCATACTACCAATGACACG (SEQ D NO:12) and AAGCTCCAAGTCTCGGTGTACC (SEQ ID NO:71).

The present invention is directed to a vaccine composition that includes a modified attenuated varicella zoster virus. The modified attenuated virus has the ATCC designation VR-795, and the nucleotide sequence of the virus has been modified to contain a single nucleotide polymorphism. The single nucleotide polymorphism can be present in the coding sequence encoding glycoprotein H. For instance, the single nucleotide polymorphism in the virus can be present at nucleotide 806 of the coding sequence encoding glycoprotein H. The nucleotide present at nucleotide 806 can be a thymine. The single nucleotide polymorphism can be present in the coding sequence encoding glycoprotein E. For instance, the single nucleotide polymorphism in the virus is present at nucleotide 448 of the coding sequence encoding glycoprotein E. The nucleotide present at nucleotide 448 can be an adenine.

Also provided by the present invention is a method for producing a modified attenuated varicella zoster virus. The method includes growing the virus in a tissue culture preparation. The virus has the ATCC designation VR-795, and the nucleotide sequence of the virus has been modified to contain a single nucleotide polymorphism. The single nucleotide polymorphism can be present in the coding sequence encoding glycoprotein H. For instance, the single nucleotide polymorphism in the virus can be present at nucleotide 806 of the coding sequence encoding glycoprotein H. The nucleotide present at nucleotide 806 can be a thymine. The single nucleotide polymorphism can be present in the coding sequence encoding glycoprotein E. The single nucleotide polymorphism in the virus can be present at nucleotide 448 of the coding sequence encoding glycoprotein E. The nucleotide present at nucleotide 448 can be an adenine. The modified attenuated virus can have an in vitro growth rate that is greater than the in vitro growth rate of a second varicella zoster virus. The second varicella zoster virus can be, for instance, VZV-32, ATCC VR-586, ATCC VR-1367, or ATCC VR-795. The growth rate of the modified varicella virus can be at least about 4-fold greater than the second varicella zoster virus at 48 hours postinfection. Optionally, the modified varicella virus can be isolated.

The present invention further provides isolated polynucleotides, including an isolated polynucleotide having the nucleotide sequence of nucleotides 66,074 to 68,599 of GenBank Accession X04370, with the proviso that nucleotide 66,879 is a thymine; and an isolated polynucleotide having the nucleotide sequence of nucleotides 115,808 to 117,679 of GenBank Accession X04370, with the proviso that nucleotide 116,255 is an adenine. Also provided are the isolated polypeptides encoded by each of the above two polynucleotides. The polynucleotide can be isolated from a varicella zoster virus.

Also provided are viruses having the designation VZV-MSP, VZV-VSD, VZV-VIA, or VZV-Iceland.

Definitions

As used herein, an antibody that can "specifically bind" a polypeptide is an antibody that interacts only with the epitope of the antigen that induced the synthesis of the antibody, or interacts with a structurally related epitope. "Epitope" refers to the site on an antigen to which specific B cells and/or T cells respond so that antibody is produced. As used herein, the term "polypeptide:antibody complex" refers to the complex that results when an antibody specifically binds to a polypeptide.

"Polypeptide" as used herein refers to a polymer of amino acids and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations and the like. Coding sequence, coding region, and open reading frame are used interchangeably and refer to a polynucleotide that encodes a polypeptide, usually via mRNA, when placed under the control of appropriate regulatory sequences. The boundaries of the coding region are generally determined by a translation start codon at its 5' end and a translation stop codon at its 3' end.

An "ORF" followed immediately by a number, for instance ORF37 or ORF68, refers to a specific open reading frame of varicella zoster virus. The approximately 70 individual open reading frames of varicella zoster virus are known to the art, and are described in Davison et al. (*J. Gen. Virol.*, 7:1759–1816 (1986)) and at GenBank Accession X04370. GenBank Accession X04370 is also referred to herein as SEQ ID NO:76. For instance, ORF37 is the open reading frame encoded by nucleotides 66,074 to 68,599 of the nucleotide sequence at GenBank Accession X04370, and ORF68 is the open reading frame encoded by nucleotides 115,808 to 117,679 of the nucleotide sequence at GenBank Accession X04370. A "polymorphic ORF" followed immediately by a number, for instance polymorphic ORF37 or polymorphic ORF68, refers to an open reading frame of varicella zoster virus that has a nucleotide sequence similar to the appropriate nucleotide sequence of GenBank X04370, but includes a single nucleotide polymorphism. Moreover, a polymorphic ORF may contain an insertion or deletion of nucleotides, preferably an insertion of 3 nucleotides or a deletion of 3 nucleotides. When referring to a specific nucleotide of an ORF, the first nucleotide of the start codon is considered to be nucleotide 1, with the following amino acids labeled consecutively. When referring herein to a specific amino acid of a polypeptide encoded by an ORF, the first methionine (prior to any post-translational modification that may occur) is considered to be amino acid 1, with the following amino acids labeled consecutively.

As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including for instance coding sequences, and non-coding sequences. A polynucleotide can be obtained directly from a natural source, for instance from a virus, or can be prepared with the aid of recombinant, enzymatic, or chemical techniques. A polynucleotide can be linear or circular in topology. A polynucleotide can be, for example, a portion of a vector, such as an expression or cloning vector, or a fragment.

An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities. An "isolated" varicella zoster virus means a varicella zoster virus has been removed from its natural environment, e.g, the cell that produced the virus.

As used herein, the term "whole varicella zoster virus" refers to a varicella zoster virus particle or virion. The particle can be infective, i.e., be able to reproduce when introduced to an appropriate tissue culture cell under the appropriate conditions, or the particle can be inactive, i.e., incapable of reproducing.

As used herein, a "biological sample" refers to a sample of tissue or fluid isolated from a subject, including but not limited to, for example, blood, plasma, serum, lymph tissue and lymph fluid, cerebrospinal fluid, bone marrow, brain tissue, samples of the skin, external secretions of the skin including vesicle fluid from a pox, organs, biopsies and also samples of in vitro cell culture constituents including but not limited to conditioned media resulting from the growth of cells and tissues in culture medium, and cell components, or combinations thereof. A "subject" is an animal, including, for instance, a mouse or a human, preferably a human.

As used herein, the term "whole varicella zoster virus particle" refers to an intact varicella zoster virus, for instance a varicella zoster virus that has been produced by a cell and not manipulated to cause the polypeptides that make up the envelop to disassociate from one another.

As used herein, a "primer pair" refers to two single stranded polynucleotides that can be used together to amplify a region of a polynucleotide, preferably by a polymerase chain reaction (PCR). The polynucleotide that results from amplifying a region of a polynucleotide is referred to as an "amplification product." The phrase "under conditions suitable to form a detectable amplification product" refers to the reactions conditions that result in an amplification product. For instance, in the case of a PCR, the conditions suitable to form a detectable amplification product include the appropriate temperatures, ions, and enzyme.

As used herein, the term "hybridize" refers to the ability of two complementary single stranded polynucleotides to base pair with each other, where an adenine of one polynucleotide will base pair to a thymine of a second polynucleotide and a cytosine of one polynucleotide will base pair to a guanine of a second polynucleotide. When the term "hybridize" is used to describe the interaction between a primer and a polynucleotide, hybridization requires that the 3' nucleotide of a primer be able to base pair with the corresponding nucleotide of the polynucleotide that is to be amplified. Typically, the inability of the 3' nucleotide of a primer to base pair with the polynucleotide that is to be amplified results in no amplification (see Newton et al., U.S. Pat. No. 5,595,890).

As used herein, the term "in vitro growth rate" refers to the rate at which a varicella zoster virus spreads from an infected tissue culture cell to an adjacent uninfected tissue culture cell. A tissue culture cell is a cell that replicate in vitro in a nutritive media. The in vitro growth rate of a varicella zoster virus can be measured as described herein.

As used herein, the term "vaccine composition" refers to a pharmaceutical composition containing an antigen, where the composition can be used to prevent or treat a disease or condition in a subject. "Vaccine composition" thus encompasses both subunit vaccines, as described below, as well as compositions containing whole killed, attenuated or inactivated virus. "Subunit vaccine composition" refers to a composition containing at least one immunogenic polypeptide, but not all antigens, derived from a varicella zoster virus. Such a subunit vaccine composition is substantially free of intact virus particles. Thus, a "subunit vaccine composition" is prepared from an isolated, preferably purified, immunogenic polypeptide from the virus. A subunit vaccine composition can comprise the subunit antigen or antigens of interest isolated from other antigens or polypeptides from the pathogen.

As used herein, an "attenuated varicella zoster virus" refers to a varicella zoster virus that is less virulent in humans and preferably, when introduced to a human in the appropriate manner, causes a protective immunological response such that resistance to infection will be enhanced and/or the clinical severity of the disease reduced.

As used herein, a "single nucleotide polymorphism" and a "single amino acid polymorphism" refers to a specific type of polymorphism in a polynucleotide and a polypeptide, respectively, and are described in greater detail herein.

As used herein, the term "recognition sequence" refers to the site on a polynucleotide to which a restriction endonuclease binds prior to cleaving the polynucleotide.

Unless otherwise specified, "a," "an," "the," and "at least one" are used interchangeably and mean one or more than one.

BRIEF DESCRIPTION OF THE FIGURES

FIG. 1. Sequence of the ectodomain of VZV gE. (A) The deduced amino acid sequence of the N-terminal 400 of 623 codons of wild-type VZV gE. The previously defined MAb 3B3 epitope is underlined. The aspartic acid residue altered in VZV-MSP is designated by an arrowhead at codon 150. The silent mutation is indicated by an arrowhead at codon 341. (B) Nucleotides 149–161 and deduced amino acid sequence of the MAb 3B3 epitope in the wild type VZV-32 strain (designated VZVgE) and the mutant VZV-MSP strain gE gene (designated VZVgE-D150N). The altered nucleotides (G to A) and amino acids (D to N) are underlined and marked with the arrow. The two additional codons inserted into the expression plasmid described in FIG. 4 are designated 3B3.2, while the original 3B3 epitope is designated 3B3.11.

FIG. 4. Infectious center assays of VZV-MSP and VZV-32.

FIG. 5. Summary of genetic analysis of VZV-MSP (A) Schematic diagram showing regions of the VZV-MSP genome where the nucleotide, sequence has been determined. ORFs 31, 37, 47, 60, 61, 62, 66, 67, and 68 are shown. The polypeptide encoded by the ORF is shown in parentheses under the appropriate ORF. The horizontal arrows above the schematic of the VZV-MSP genome represent the location of the ORFs and the direction of transcription. $U_L$, unique long; IRs, internal repeat short; $U_S$, unique short; TRs, terminal repeat short; shaded boxes, regions of the VZV-MSP that have been sequenced; hatched boxes, repeat sequences. (B) Summary of results of sequence analysis of amplified fragments. All mutations discovered are listed by the nucleotide number of the Dumas strain. Any substitutions within open reading frames are followed by the predicted amino acid expressed by VZV-MSP. Nucleotides, nucleotides that were sequenced (the numbering system used is that described in Davison et al., (J. Gen. Virol., 67:1759–1816 (1986))); Size of Region, number of nucleotides sequenced; ORF(s), the ORF or region near an ORF that was sequenced; Substitutions, locations and nature of single nucleotide polymorphism. If the single nucleotide polymorphism encodes a mutation in the resulting polypeptide, the location and nature of the mutation is shown in parentheses. For instance, at position 269 of glycoprotein gH, the proline has been replaced with a leucine.

FIG. 6. Comparative sequence analysis of the VZV gE. VZV ORF 68 was amplified from the viral DNA of eight VZV strains, including VZV-MSP. Each sequence was compared to the prototype VZV-Dumas genotype. The location of each detected polymorphism is designated by nucleotide number (bp) of the gE gene. Any resulting single amino acid polymorphism that results in gE (e.g., T>1) is noted below the location of the appropriate detected polymorphism. Silent, the single nucleotide polymorphism did not result in a single amino acid polymorphism; asterisk, location of the single nucleotide polymorphism.

FIG. 7. Comparative sequence analysis of VZV gI. VZV ORF 67 was amplified from viral DNA of eight VZV strains. Each sequence was compared to prototype VZV-Dumas genotype. Any resulting single amino acid polymorphism that results in gI (e.g., Q>H) is noted below the location of the appropriate detected polymorphism. Silent, the single nucleotide polymorphism did not result in a single amino acid polymorphism.

FIG. 8. Comparative sequence analysis of VZV gH. VZV ORF 37 was amplified from viral DNA of eight VZV strains. Each DNA sequence was compared to the prototype VZV-Dumas genotype. Nucleotide variations from the VZV-Dumas genotype were tabulated. The P269L mutation originally discovered in VZV-MSP was also present in six other VZV strains, including VZV-32. A total of nine polymorphisms within ORF 37 were discovered among the eight tested strains. Any resulting single amino acid polymorphism that results in gH (e.g., R>K) is noted below the location of the appropriate detected polymorphism. Silent, the single nucleotide polymorphism did not result in a single amino acid polymorphism.

FIG. 9. Comparative sequence analysis of VZV gL. VZV ORF 60 was amplified from eight VZV strains. Each sequence was compared to the VZV Dumas genotype. Only the gL gene of VZV Oka differed from the gL sequence of VZV Dumas.

FIG. 10. Comparative sequence analysis of the VZV IE 62 regulatory gene. VZV ORF 62 was amplified from eight VZV strains. Each sequence was compared to the VZV-Dumas genotype. A total of 38 polymorphisms were detected among the eight VZV strains. VZV-MSP contained only a silent substitution within codon 30 when compared to the VZV-Dumas gene. Any resulting single amino acid polymorphism that results in IE 62 (e.g., S>A) is noted below the location of the appropriate detected polymorphism. Asterisk, location of single nucleotide polymorphism that did not result in a single amino acid polymorphism

DETAILED DESCRIPTION OF THE INVENTION

Polynucleotides

The present invention provides polynucleotides, preferably isolated polynucleotides, having a (at least one) single nucleotide polymorphism. An isolated polynucleotide has a nucleotide sequence that is identical to a nucleotide sequence present in VZV-Dumas, but there is a nucleotide that is polymorphic between the isolated polynucleotide of the present invention and the corresponding polynucleotide present in VZV-Dumas. The nucleotide sequence of VZV-Dumas is present at GenBank Accession X04370. The term "polymorphism" refers to the coexistence of at least two different forms (i.e., at least two different nucleotide sequences or at least two different amino acid sequences) of a polynucleotide or a polypeptide in members of Varicella zoster. The polymorphism can be due to a single nucleotide that is different (a single nucleotide polymorphism). In contrast, a polymorphism can be due to several consecutive nucleotides, for instance 2, 3, or 4 consecutive nucleotides, that are different, which is not within the scope of the present definition of "single nucleotide polymorphism." In the isolated polynucleotides of the present invention, a polymorphism is due to, in increasing order of preference, the presence of 1 single nucleotide polymorphism, at least 1, at least 2, at least 3, most preferably at least 4 single nucleotide polymorphisms in the polynucleotide. Preferably, the isolated polynucleotides of the present invention include no greater than 4 single nucleotide polymorphisms. A single nucleotide polymorphism could be separated from another single nucleotide polymorphism by only one nucleotide.

An example of a polynucleotide of the present invention is a polymorphic ORF37 or the complement thereof, where a polymorphism is at nucleotide 806 of ORF37 (see FIG. 8). The nucleotide at nucleotide 806 can be a guanine, adenine, or thymine, preferably a thymine.

Another example of a polynucleotide of the present invention has the nucleotide sequence of nucleotides 101,650 to 103,081 (i.e., the region upstream of ORF60) of GenBank Accession X04370 or the complement thereof, but contains a single nucleotide polymorphism at nucleotide 102,203, or a single nucleotide polymorphism at nucleotide 102,575, or a single nucleotide polymorphism at nucleotide 102,617, or a single nucleotide polymorphism at nucleotide 102,969. The nucleotide at nucleotide 102,203 can be a guanine, cytosine, or thymine, preferably a guanine. The nucleotide at nucleotide 102,575 can be a guanine, cytosine, or thymine, preferably a guanine. The nucleotide at nucleotide 102,617 can be a guanine, adenine, or thymine, preferably a thymine. The nucleotide at nucleotide 102,969 can be a guanine, cytosine, or thymine, preferably a guanine.

A further example of a polynucleotide of the present invention has the nucleotide sequence of nucleotides 104,468 to 104,936 (i.e., the region upstream of ORF61) of GenBank Accession X04370 or the complement thereof, but contains a single nucleotide polymorphism at nucleotide 104,898. The nucleotide at nucleotide 104,898 can be a guanine, cytosine, or thymine, preferably a guanine.

Another example of a polynucleotide of the present invention is a polymorphic ORF62 or the complement thereof, where a polymorphism is at nucleotide 90 of ORF62 (see FIG. 10). The nucleotide at nucleotide 90 can be a guanine, adenine, or thymine, preferably a guanine.

Another example of a polynucleotide of the present invention is a polymorphic ORF66 or the complement thereof, where a polymorphism is at nucleotide 1,104 of ORF66. The nucleotide at nucleotide 1,104 can be a guanine, cytosine, or thymine, preferably a guanine.

Another example of a polynucleotide of the present invention is a polymorphic ORF68 or the complement thereof, where a polymorphism is at nucleotide 448 of ORF68 (see FIG. 6). The nucleotide at nucleotide 448 can be an adenine, cytosine, or thymine, preferably an adenine.

Other examples of polynucleotides of the present invention are shown in FIGS. 5–10.

The polynucleotides of the present invention can be obtained by recombinant techniques known to the art including, for instance, cloning from a member of varicella zoster or mutagenizing a polynucleotide so that it has the nucleotide sequence of a polynucleotide of the present invention. Alternatively, a polynucleotide of the present invention can be chemically or enzymatically synthesized by, for instance, an oligonucleotide synthesizer or PCR.

The present invention further includes polynucleotides that are similar to polynucleotides of the present invention as described above, including nucleotides of a polymorphic ORF37 or a polymorphic ORF68, or the complements thereof. The similarity is referred to as structural similarity and is determined by aligning the residues of the two polynucleotides (i.e., the nucleotide sequence of the candidate polynucleotide and the nucleotide sequence of a preferred polynucleotide of the invention) to optimize the number of identical nucleotides along the lengths of their sequences; gaps in either or both sequences are permitted in making the alignment in order to optimize the number of shared nucleotides, although the nucleotides in each sequence must nonetheless remain in their proper order. Moreover, the nucleotide at the position of the single nucleotide polymorphism (e.g., the thymine at nucleotide 806 in a polymorphic ORF37) is invariant in the candidate polynucleotide. A candidate polynucleotide is the polynucleotide being compared to a preferred polynucleotide of the present invention. Preferably, two nucleotide sequences are compared using the Blastn program, version 2.0.14, of the BLAST 2 search algorithm, as described by Tatusova, et al. (*FEMS Microbiol Lett* 1999, 174:247–250), and available at http://www.ncbi.nlm.nih.gov/gorf/b12.html. Preferably, the default values for all BLAST 2 search parameters are used, including reward for match=1, penalty for mismatch=−2, open gap penalty=5, extension gap penalty=2, gap x_dropoff=50, expect=10, wordsize=11, and filter on. In the comparison of two nucleotide sequences using the BLAST search algorithm, structural similarity is referred to as "identities." Preferably, a polynucleotide includes a nucleotide sequence having a structural similarity with a preferred polynucleotide of the present invention of at least about 98%, more preferably at least about 99%, most preferably at least about 99.5% identity.

Figure 2:
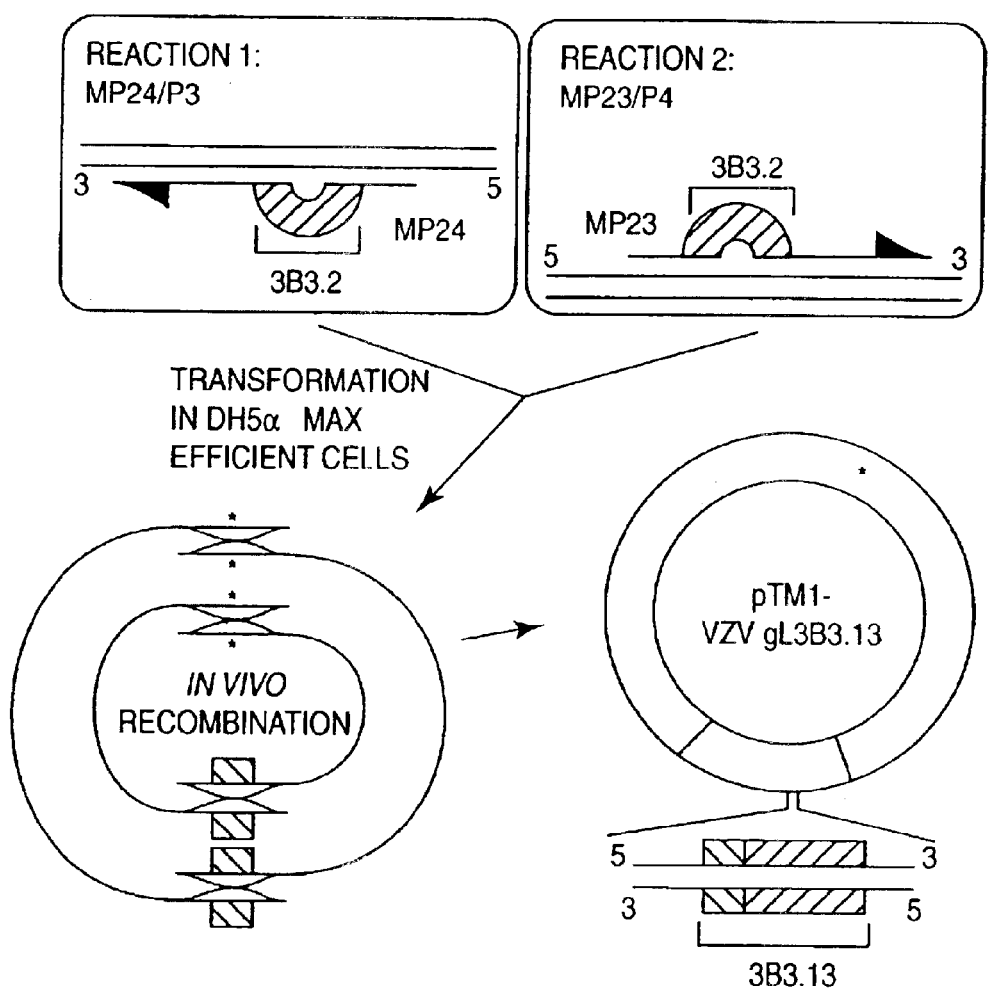
FIG. 2. Recombination PCR mutagenesis. Two additional codons (3B3.2) were inserted into the MAb 3B3 epitope to produce plasmid gL 3B3.13 from plasmid gL 3B3.11.
Figure 3:
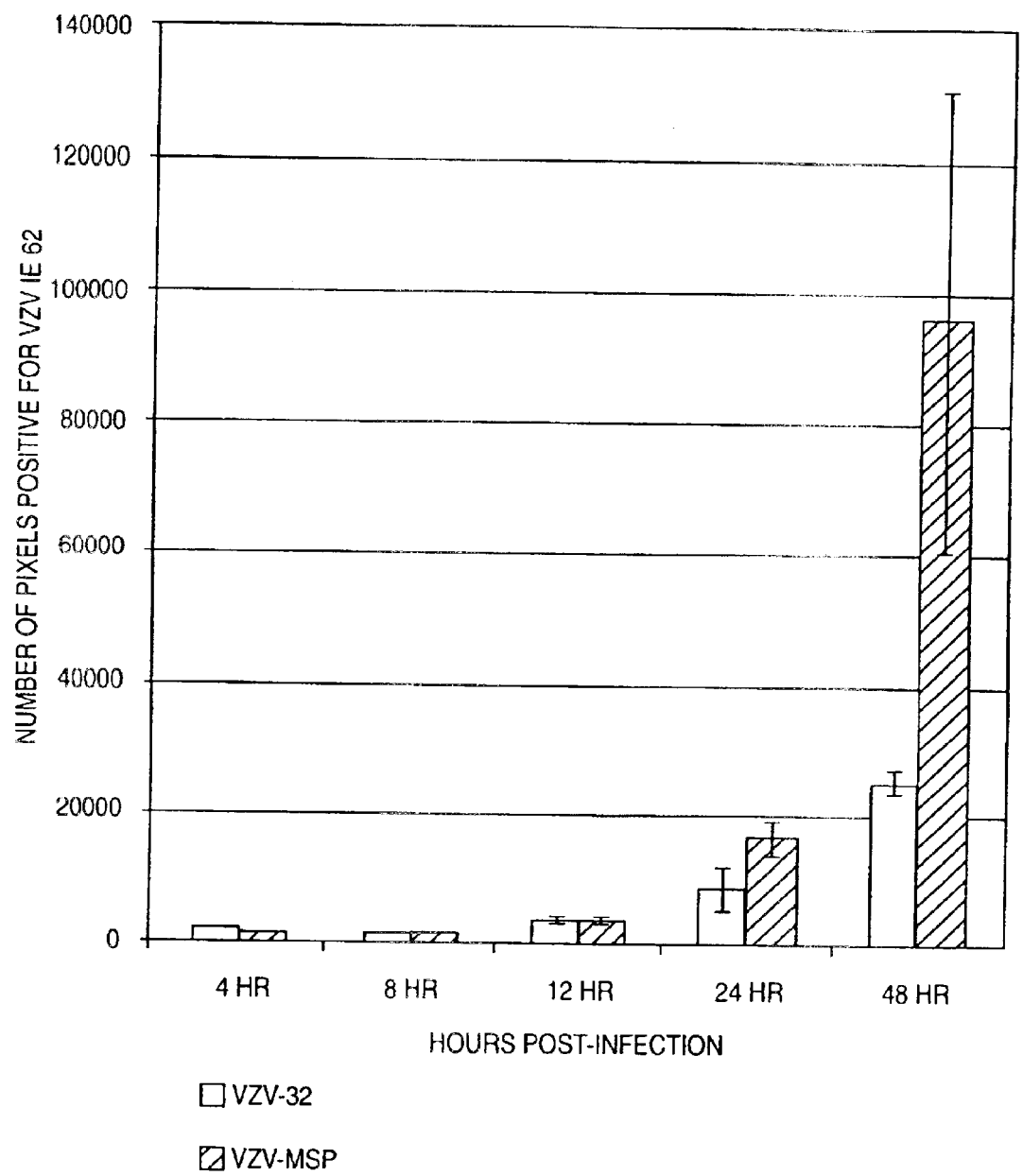
FIG. 3. Quantitative analysis of VZV IE 62 by confocal microscopy. VZV-MSP or VZV-32 infected monolayers were examined by confocal microscopy at increasing times post-infection at ×4 magnification. The total number of pixels positive for VZV IE 62 within each image was quantitated with the Brainvox tal_support programs (University of Iowa) as described herein. The graph summarizes the results from four separate images. Error bars: +/−1 S.D.

The present invention further includes isolated polynucleotide fragments. A polynucleotide fragment is a portion of an isolated polynucleotide as described herein, where the portion is preferably at least about 15, more preferably at least about 20, most preferably at least about 25 consecutive nucleotides and includes at least one single nucleotide polymorphism. The single nucleotide polymorphism can be at any location in the polynucleotide fragment, and preferably is the nucleotide at one of the 3' ends of the fragment (when the polynucleotide fragment is double stranded) or the nucleotide at the 3' end of the fragment (when the polynucleotide fragment is single stranded).

A polynucleotide of the invention can be inserted in a vector. Construction of vectors containing a polynucleotide of the invention employs standard ligation techniques known in the art. See, for instance, Sambrook et al, *Molecular Cloning: A Laboratory Manual.*, Cold Spring Harbor Laboratory Press (1989). A vector can provide for further cloning (amplification of the polynucleotide), i.e., a cloning vector, or for expression of the polypeptide encoded by the coding sequence, i.e., an expression vector. The term vector includes, but is not limited to, plasmid vectors, viral vectors, cosmid vectors, or artificial chromosome vectors. Typically, a vector is capable of replication in a bacterial host, for instance *E. coli*. Preferably the vector is a plasmid.

Selection of a vector depends upon a variety of desired characteristics in the resulting construct, such as a selection marker, vector replication rate, and the like. Suitable host cells for cloning or expressing the vectors herein are prokaryote or eukaryotic cells. Preferably the host cell secretes minimal amounts of proteolytic enzymes. Suitable prokaryotes include eubacteria, such as gram-negative or gram-positive organisms. Preferably, *E. coli* is used.

Suitable host cells for the expression of the polypeptides of the invention, preferably encoded by a polymorphic ORF37 or a polymorphic ORF68 as described herein and containing a single amino acid polymorphism can be derived from multicellular organisms. Such host cells are capable of complex processing and glycosylation activities. Vertebrate or invertebrate culture can be used. Numerous baculoviral strains and variants and corresponding permissive insect host cells from hosts such as *Spodoptera frugiperda, Aedes aegypti, Aedes albopictus, Drosophila melanogaster, Trichoplusia ni,* and *Bombyx mori* are known to the art.

Vertebrate cells can also be used as hosts. Examples of useful mammalian host cell lines are monkey kidney CV1 line transformed by SV40 (CAS-7, ATCC CRL-1651); human embryonic kidney line (293 or 293 cells subcloned for growth in suspension culture, Graham et al., *J. Gen. Virol.*, 36:59 (1977)); baby hamster kidney cells (BHK, ATCC CCL 10); Chinese hamster ovary cells/−DHFR (CHO); CHO-K1 (ATCC CCL-61); CHO-D; mouse sertoli cells (TM4); monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (WI 38, ATCC CCL 75); human liver cells (Hep G2, HB 8065); mouse mammary tumor (MMT 060562, ATCC CCL 51); TRI cells; MRC 5 cells; FS4 cells; and a human hepatoma line (Hep G2).

Suitable plasmids for expression in *E. coli*, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, N.H.) or Sigma Chemical Co. (St. Louis, Mo.). pKK233-3, pKK233-2 and pTrc99A can be obtained from Pharmacia Biotech. pET-(X) vectors can be obtained from Promega (Madison, Wis.) Stratagene (La Jolla, Calif.) and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli*.

Suitable plasmids for expression in eukaryotic cells, for example, include the EPITAG vectors available from Invitrogen (Carlsbad, Calif.) for mammalian cells. Examples of suitable EPITAG vectors include pcDNA3.1/myc-His and pEF1/myc-His. Other plasmids that can be used in mammalian cells include, for example, pRc/RSV (Invitrogen) and pSecTag2 (Invitrogen). Suitable plasmids for expression in insect cells include, for instance, pIZ/V5-His (Invitrogen), and pBlueBac4.5 (Invitrogen).

An expression vector optionally includes regulatory sequences operably linked to the coding sequence. The invention is not limited by the use of any particular promoter, and a wide variety are known. Promoters act as regulatory signals that bind RNA polymerase in a cell to initiate transcription of a downstream (3' direction) coding sequence. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

Promoter sequences are known for eukaryotes. Most eukaryotic coding sequences have an AT-rich region located approximately 25 to 30 bases upstream from the site where transcription is initiated. Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors.

Transcription of a coding sequence encoding a polypeptide of the present invention in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, and Hepatitis-B virus.

Transcription of a coding sequence encoding a polypeptide of the present invention by eukaryotes can be increased by inserting an enhancer sequence into the vector. Enhancers are cis-acting elements of DNA, usually having about 10 to 300 bp, that act on a promoter to increase its transcription. Enhancers are relatively orientation- and position-independent, having been found 5' and 3' to coding sequences, within an intron as well as within the coding sequence itself. Many enhancer sequences are now known from mammalian genes (globin, elastase, albumin, alpha-fetoprotein, and insulin). Enhancers from eukaryotic cell viruses are also known and include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the coding sequence encoding a polypeptide of the present invention, but is preferably located at a site 5' of the promoter.

An expression vector can optionally include a ribosome binding site (a Shine Dalgarno site for prokaryotic systems or a Kozak site for eukaryotic systems) and a start site (e.g., the codon ATG) to initiate translation of the transcribed message to produce the enzyme. It can also include a termination sequence to end translation. A termination sequence is typically a codon for which there exists no corresponding aminoacetyl-tRNA, thus ending polypeptide synthesis. The polynucleotide used to transform the host cell can optionally further include a transcription termination sequence. The rrnB terminators, which is a stretch of DNA that contains two terminators, T1 and T2, is an often used terminator that is incorporated into bacterial expression systems. Transcription termination sequences in vectors for eukaryotic cells typically include a polyadenylation signal 3' of the coding sequence.

The polynucleotide used to transform the host cell optionally includes one or more marker sequences, which typically encode a molecule that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol, tetracycline, neomycin, and formulations of phleomycin D1 including, for example, the formulation available under the trade-name ZEOCIN (Invitrogen).

Polypeptides

The present invention is also directed to polypeptides, preferably isolated polypeptides, encoded by polynucleotides of the present invention. A polypeptide has an amino acid sequence that is identical to an amino acid sequence encoded by a coding sequence present in VZV-Dumas, but there is an amino acid that is polymorphic between the polypeptide of the present invention and the corresponding polypeptide encoded by VZV-Dumas. The polymorphism can be due to a single amino acid that is different (a single amino acid polymorphism). In contrast, a polymorphism can be due to several consecutive amino acids, for instance 2, 3, or 4 consecutive amino acids, that are polymorphic, which is not within the scope of the present definition of "single amino acid polymorphism." In the polypeptides of the present invention, a polymorphism is due to, in increasing order of preferance, the presence of 1 single amino acid polymorphism, at least 1, at least 2, at least 3, most preferably at least 4 single amino acid polymorphisms in the polypeptide. Preferably, the isolated polypeptides of the present invention include no greater than 4 single amino acid polymorphisms. A single amino acid polymorphism could be separated from another single amino acid polymorphism by only one amino acid.

Preferably, a polypeptide of the present invention has immunogenic activity. "Immunogenic activity" refers to an amino acid sequence which elicits an immunological response in a subject. An immunological response to a polypeptide is the development in a subject of a cellular and/or antibody-mediated immune response to the polypeptide fragment. Usually, an immunological response includes but is not limited to one or more of the following effects: the production of antibodies, B cells, helper T cells, suppressor T cells, and/or cytotoxic T cells, directed specifically to an epitope or epitopes of the polypeptide fragment.

The polypeptides of the present invention can be obtained from, for instance, a biological sample from a subject infected with a varicella zoster virus that encodes the polypeptide. The polypeptide can be obtained from tissue culture cells that have, for instance, been infected with a varicella zoster virus that encodes the polypeptide or contain a recombinant polynucleotide, preferably a polynucleotide of the invention, that encodes the polypeptide of the invention. Alternatively, the polypeptide can be obtained from a prokaryotic cell, for instance *Eschericia coli*, that contains a recombinant polynucleotide, preferably a polynucleotide of the invention, that encodes the polypeptide of the invention. The polypeptides of the present invention can also be obtained by chemical synthesis.

An example of a polypeptide of the present invention is encoded by a polymorphic ORF37, where a polymorphism is at amino acid 269 (see FIG. 8). When referring herein to a specific amino acid of a polypeptide encoded by an open reading frame, the first methionine is considered to be amino acid 1, with the following amino acids labeled consecutively. The polypeptide encoded by ORF37 is referred to in the art as glycoprotein H, gH, and gpIII. Preferably, the amino acid at position 269 in the polypeptide encoded by a polymorphic ORF37 is an amino acid other than proline, more preferably, the amino acid is a nonpolar (hydrophobic) amino acid, for instance alanine, leucine, isoleucine, valine, phenylalanine, tryptophan, or tyrosine, most preferably, the amino acid is leucine.

An example of a polypeptide of the present invention is encoded by a polymorphic ORF68, where a polymorphism is at amino acid 150 (see FIG. 6). The polypeptide encoded by nucleotides ORF68 is referred to in the art as glycoprotein E, gE, and gpI. Preferably, the amino acid at position 150 in the polypeptide encoded by a polymorphic ORF68 is an amino acid other than aspartic acid, more preferably, the amino acid is asparagine, lysine, histidine, or glutamic acid, most preferably, the amino acid is asparagine.

Other examples of polypeptides of the present invention are shown in FIGS. 5–10.

The present invention further includes polypeptides having similarity with the polypeptides of the present invention as described above, including the polypeptide encoded by a polymorphic ORF37 or a polymorphic ORF68. The similarity is referred to as structural similarity and is generally determined by aligning the residues of the two amino acid sequences (i.e., a candidate amino acid sequence and the amino acid sequence of a preferred polypeptide of the present invention) to optimize the number of identical amino acids along the lengths of their sequences; gaps in either or both sequences are permitted in making the alignment in order to optimize the number of identical amino acids, although the amino acids in each sequence must nonetheless remain in their proper order. Moreover, the amino acid at the position of the single amino acid polymorphism (e.g., the leucine at amino acid 269 in the polypeptide encoded by a polymorphic ORF37) is invariant in the candidate polypeptide. A candidate amino acid sequence is the amino acid sequence being compared to an amino acid sequence present in a preferred polypeptide of the present invention.

Preferably, two amino acid sequences are compared using the Blastp program, version 2.0.14, of the BLAST 2 search algorithm, as described by Tatusova et al. (*FEMS Microbiol. Lett.*, 174:247–250 (1999)), and available at http://www.ncbi.nlm.nih.gov/gorf/bl2.html. Preferably, the default values for all BLAST 2 search parameters are used, including matrix BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identities." Preferably, a polypeptide includes an amino acid sequence having a structural similarity with a preferred polypeptide of the present invention of, in increasing order of preference, at least about 96%, at least about 97%, at least about 98%, and most preferably, at least about 99% identity.

The present invention further includes polypeptide fragments. A polypeptide fragment is a portion of a polypeptide as described herein, where the portion includes at least one single amino acid polymorphism. Preferably, the polypeptide fragment has immunogenic activity. Preferably, a polypeptide fragment is at least about 8, more preferably at least about 12, most preferably at least about 20 amino acids in length.

Viruses

The present invention further provides isolated varicella zoster viruses. Preferably, the genome of an isolated varicella zoster virus of the present invention includes, in increasing order of preference, 1, at least 1, at least 2, at least 3, most preferably at least 4 single nucleotide polymorphisms when compared to the nucleotide sequence of GenBank Accession X04370. Preferably, the genome of an isolated varicella zoster virus of the present invention includes no greater than 4 single nucleotide polymorphisms. Examples of isolated varicella zoster viruses of the present invention include VZV-MSP, VZV-VSD, VZV-VIA, VZV-Iceland. Alternatively, the isolated varicella zoster virus can be a modified varicella zoster virus, preferably a modified attenuated varicella zoster virus. Modified varicella zoster viruses are described in greater detail herein.

A single nucleotide polymorphism can be present in a coding sequence where it can result in the encoded polypeptide containing a single amino acid polymorphism when compared to the polypeptides encoded by the nucleotide sequence of GenBank X04370. Alternatively, a single nucleotide polymorphism can be silent, i.e., not alter the amino acid sequence of a polypeptide encoded by a coding sequence. A single nucleotide polymorphism can be present in a region of the genome that is not a coding sequence. In an isolated varicella zoster virus of the present invention that encodes a polypeptide having a single amino acid polymorphism, the varicella virus may have a serotype that is different than the serotype known to the art. Preferably, the serotype of an isolated varicella zoster virus of the invention is one that does not contain the epitope to which the monoclonal antibody 3B3 binds. Monoclonal antibody is available from the ATCC (accession number HB-12377). An example of a varicella zoster virus having this serotype is VZV-MSP.

Preferably, the isolated varicella zoster viruses of the present invention have the ability to spread from one cell to another at a rate that is greater than previously characterized varicella zoster viruses. This phenotype, which is also referred to herein as in vitro growth rate and cell-to-cell spread, can be measured by methods that are known to the art, including, for instance, the methods described in Example 2 (i.e., laser scanning confocal microscopy combined with pixel intensity measurement, infectious center assays, and replication in the SCID-hu mouse). Examples of previously characterized varicella zoster viruses that can be used as a baseline for measuring the in vitro growth rate of an isolated varicella virus of the present invention include VZV-32, Oka strain (see Kubo, U.S. Pat. No. 3,985,615), or the varicella zoster viruses having the designations ATCC VR-586, ATCC VR-1367, or ATCC VR-795. Examples of tissue culture cells that can be used include human melanoma cells (including, for instance, MeWo cells), lung fibroblasts (including, for instance, MRC-5 cells, which have the ATCC designation CCL-171), cells derived from human embryos, simian cells, or guinea pig cells.

Preferably, when the infectious center assay is used to measure the in vitro growth rate of a varicella zoster virus, tissue culture cells are added to the well of a 35-mm tissue culture plate and grown until they form a substantially confluent monolayer. The well is inoculated with between about 300 infectious centers to about 700 infectious centers, preferably about 500 infectious centers, i.e., an aliquot of the appropriate varicella zoster virus to result in the initial infection of about 500 cells. The resulting number of infectious centers in the well is measured at 24 hours after inoculation and at 48 hours after inoculation. Preferably, the number of infectious centers of a varicella zoster virus at 48 hours after inoculation is at least about 1.5-fold greater, more preferably at least about 2-fold greater, most preferably at least about 3-fold greater than a previously characterized varicella zoster virus.

Preferably, when laser scanning confocal microscopy combined with pixel intensity measurement is used to measure the in vitro growth rate of a varicella zoster virus, tissue culture cells are inoculated with the varicella zoster virus to be measured. These infected cells are then used to inoculate uninfected cells at a 1:8 ratio of infected to uninfected cells. The spread of the varicella zoster virus is then determined at 24 hours after inoculation at the 1:8 ratio and at 48 hours after inoculation at the 1:8 ratio. The spread of the varicella zoster virus away from a single cell that initially contained the virus can be measured by assaying for evidence of virus in adjacent cells. For instance, the presence of viral nucleic acid or a viral encoded polypeptide can be measured. Preferably, the presence of a viral encoded polypeptide is measured. Preferably, the viral encoded polypeptide is IE62. Preferably, the spread of a varicella zoster virus at 24 hours after inoculation at the 1:8 ratio is at least about 1.5-fold greater, more preferably at least about 2-fold greater than a previously characterized varicella zoster virus. Preferably, the spread of a varicella zoster virus at 48 hours after inoculation at the 1:8 ratio is at least about 2-fold greater, more preferably at least about 4-fold greater than a previously characterized varicella zoster virus.

The present invention is also directed at modifying a varicella zoster virus so that it has an in vitro growth rate that is greater than the in vitro growth rate prior to modification. A varicella zoster virus can be modified by altering the genome of the varicella zoster virus. Preferably, the genome is modified to contain, in increasing order of preference, 1 single nucleotide polymorphism, at least 1, at least 2, at least 3, most preferably, at least 4 single nucleotide polymorphisms. Preferably, the genome is modified to include no greater than 4 single nucleotide polymorphisms. The single nucleotide polymorphisms that could be incorporated into the genome of a varicella zoster virus are described herein. Methods of modifying a genome of a varicella zoster virus are known to the art (see, for instance, Cohen et al., *Proc. Natl. Acad. Sci. USA*, 90:7376–7380 (1993)). Preferably, recombinant DNA techniques are used to make the modification. Preferably, the single nucleotide polymorphisms that could be incorporated into a varicella zoster virus include nucleotide 806 of ORF37, where the single nucleotide polymorphism is a thymine, and/or nucleotide 448 of ORF68, where the single nucleotide polymorphism is an adenine. Examples of varicella zoster viruses that could be modified include a clinical isolate, Oka strain (see Kubo, U.S. Pat. No. 3,985,615), ATCC VR-586, ATCC VR-1367, or ATCC VR-795, preferably ATCC VR-795. It is expected that varicella zoster virus that is presently used to produce, for instance, antigen for diagnostic assays or whole virus for use in vaccine compositions, can be modified by this method. Diagnostic assays and vaccine compositions are described in greater detail herein. The modified virus will grow at a faster rate and result in lowered production costs.

Another aspect of the present invention is directed to methods for producing a varicella zoster virus that has a high in vitro growth rate. Preferably, the varicella zoster virus has an in vitro growth rate that is greater than the in vitro growth rate of a second varicella zoster virus, including, for instance, a clinical isolate, Oka strain (see Kubo, U.S. Pat. No. 3,985,615), VZV-32, ATCC VR-586, ATCC VR-1367, or ATCC VR-795. The method can further include isolation of the varicella virus that has the high in vitro growth rate.

Methods of use

The present invention provides methods for detecting a varicella zoster virus. These methods are useful in, for instance, detecting a varicella zoster virus in an animal, diagnosing a disease caused by a varicella zoster virus, and detecting a varicella zoster virus having a single nucleotide polyporphism. Preferably, such diagnostic systems are in kit form. Kits are described in greater detail herein. In some aspects of the invention, preferably the varicella zoster virus detected is one having a serotype that is different than VZV-32, or the varicella zoster viruses having the designations ATCC VR-586, ATCC VR-1367, or ATCC VR-795, or having a single nucleotide polymorphism when compared to the nucleotide sequence of GenBank Accession X04370. Preferably, the varicella zoster virus detected is one to which the monoclonal antibody 3B3 does not bind. In some aspects of the invention, detecting a varicella zoster virus includes detecting antibodies that specifically bind to a varicella zoster polypeptide. Whether an antibody specifically binds a polypeptide or non-specifically binds a polypeptide can be determined using methods that are known in the art. Preferably, the polypeptide is gE, gH, gB, or IE62, most preferably gE. The methods include contacting an antibody with a preparation that includes a varicella zoster polypeptide to result in a mixture. Preferably, the antibody is present in a biological sample, more preferably blood, vesicle fluid, bone marrow, or brain tissue.

In this aspect of the invention the varicella zoster virus polypeptide contains a polymorphism. Such polypeptides are described herein. Preferably, the varicella zoster virus polypeptide is encoded by a polymorphic ORF68, and the encoded polypeptide includes an asparagine at amino acid 150. Alternatively and optionally, the varicella zoster virus polypeptide is encoded by a polymorphism of ORF37, and the encoded polypeptide includes a leucine at amino acid 269. The varicella zoster polypeptide in the preparation can be an isolated varicella zoster polypeptide or fragment thereof. Alternatively, preparation can further include whole varicella zoster virus, preferably VZV-MSP, VZV-VSD, VZV-VIA, or VZV-Iceland, more preferably, VZV-MSP.

The method further includes incubating the mixture under conditions to allow the antibody to specifically bind the polypeptide to form a polypeptide:antibody complex. The preparation that includes the varicella zoster virus may also includes reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase.

The methods for detecting the presence of antibodies that specifically bind to a varicella zoster polypeptide can be used in various formats that have been used to detect antibody to varicella zoster virus, including complement fixation, indirect fluorescent antibody, fluorescent antibody to membrane antigen, neutralization, indirect hemagglutination, immune adherence hemagglutination, radioimmunoassay, latex agglutination, and enzyme-linked immunosorbent assay.

Other methods for detecting a varicella zoster virus include the amplification of a polynucleotide, preferably by PCR. The polynucleotide can be one that is, for instance, isolated from a subject, preferably a subject suspected of having a disease caused by varicella zoster virus. Preferably, the polynucleotide is from a subject, for instance a biological sample, preferably blood, vesicle fluid, bone marrow, or brain tissue. In some aspects of the invention, the method includes contacting a polynucleotide, preferably an isolated polynucleotide, with a primer pair, incubating under conditions suitable to form a detectable amplification product, and detecting the amplification product. Detection indicates that the subject has a disease caused by varicella zoster virus.

The primer pair is one that will not form a detectable amplification product when incubated with a polynucleotide having the nucleotide sequence of GenBank Accession X04370, and preferably will form a detectable amplification product with a polynucleotide containing a single nucleotide polymorphism described herein. Preferably, one of the primers of the primer pair has a nucleotide sequence that hybridizes to a nucleotide sequence of GenBank Accession X04370; however, the 3' nucleotide of the primer corresponds to a single nucleotide polymorphism present in the varicella zoster virus that is to be detected. This method is known to the art as amplification refractory mutation system (ARMS; see Newton et al, U.S. Pat. No. 5,595,890). For instance, a primer pair could be CGATGACAGACAT-AAAATTGTAAATGTGA (SEQ ID NO: 1), where the underlined nucleotide corresponds to the single nucleotide polymorphism present in VZV-MS in the coding sequence of nucleotides 115,808 to 117,679 (i.e., the polymorphic ORF68 coding sequence), and CACCCAAGTAT-TGTTTTCTGTCCG (SEQ ID NO:2). Optionally, an additional amplification can be done to detect a varicella zoster virus that does not have the single nucleotide polymorphism by using, for instance, a primer pair that will form a detectable amplification product when incubated with a polynucleotide having the nucleotide sequence of GenBank Accession X04370. An example of such a primer pair is CGATGACAGACATAAAATTGTAAATGTGG (SEQ ID NO:3), and CACCCAAGTATTTGTTTTTCTCTGTCCG (SEQ ID NO:2). Other primer pairs can be designed using methods known to the art to detect other single nucleotide polymorphisms described herein.

In another aspect of the invention that involves detecting a varicella zoster virus by amplification of a polynucleotide, preferably by PCR, the method is directed to detecting a varicella zoster virus having a single nucleotide polymorphism, preferably at nucleotide 448 of ORF68. Preferably, in the varicella zoster virus to be detected, nucleotide 448 of ORF68 is a cytosine, thymine, or adenine, more preferably an adenine. The method includes contacting a polynucleotide with a primer pair and incubating under conditions suitable to form a detectable amplification product. The amplification product is then exposed to a restriction endonuclease, preferably one that has the recognition sequence that includes nucleotide 448 and is no longer able to cleave when that nucleotide of the recognition sequence is not a guanine. Examples of such restriction endonuclease are AflII, AsuI, AvaII, Cfr13I, Eco47I, NspIV, PshAI, Sau96I, and SinI. In VZV-Dumas and other varicella zoster viruses, the nucleotide at position 448 of ORF68 in the viral genome is a guanine, and is cleaved by the above-identified restriction endonucleases. When the nucleotide at position 448 of a polymorphic ORF68 is a cytosine, thymine, or adenine, more preferably an adenine, the restriction endonuclease is no longer able to cleave the amplification product. Thus, the method further includes detecting the amplification product after exposure to the restriction endonuclease. The presence of an amplification product that is not cleaved by, for instance, AvaII, indicates the presence of a varicella zoster virus having a single nucleotide polymorphism at nucleotide 448.

The primer pair that is used in this aspect of the invention must amplify a region of varicella zoster virus genomic DNA that includes nucleotide 116,255. With out intending to be limiting, an example of a primer pair includes GGCAT-ACTACCAATGACACG (SEQ ID NO:12) and AAGCTC-CAAGTCTCGGTGTACC (SEQ ID NO:71), as well as some of the primers listed in Table 1. Other primers can be designed using methods known in the art.

The methods that involve detecting a varicella zoster virus by amplification of a polynucleotide, preferably by PCR, can also be used to determine the percentage of a population that has a particular single nucleotide polymorphism. Methods of screening populations for the presence of a single nucleotide polymorphism are known to the art. For instance, PCR is sensitive enough to allow samples from a large number of subjects to be pooled and assayed for the presence of a varicella zoster virus having a single nucleotide polymorphism.

The present invention also provides a kit for detecting a varicella zoster virus. The kit includes a varicella zoster polypeptide as described herein (when detecting antibody to varicella zoster virus) or a primer pair as described herein (when amplifying a polynucleotide) in a suitable packaging material in an amount sufficient for at least one assay. Optionally, other reagents such as buffers and solutions needed to practice the invention are also included. Instructions for use of the packaged polypeptide or primer pair are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polypeptide or primer pair can be used for detecting a varicella zoster virus. In addition, the packaging material contains instructions indicating how the materials within the kit are employed to detect a varicella zoster virus. As used herein, the term "package" refers to a solid matrix or material such as glass, plastic, paper, foil, and the like, capable of holding within fixed limits a polypeptide or a primer pair. Thus, for example, a package can be a glass vial used to contain milligram quantities of a primer pair, or it can be a microtiter plate well to which microgram quantities of a polypeptide have been affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is also directed to vaccines. In one aspect, the present invention is directed to vaccine compositions. Preferably, the subject receiving the vaccine composition will display a protective immunological response such that resistance to infection will be enhanced and/or the clinical severity of the disease reduced. A vaccine composition can include a modified varicella zoster virus, more preferably a modified attenuated varicella zoster virus. A varicella zoster virus can be modified as described above under "Viruses." In other alphaherpesviruses, for instance, pseudorabies virus (PRV), it has been found that spread of the virus in an infected animal is facilitated by gE mutations that reduce virulence (Yang et al., *J. Virol.*, 73:4350 (1999)), it has been found that increasing the in vitro growth rate does not result in an increased virulence of the virus. It is expected that the varicella zoster viruses used as a source of viral antigen for vaccination can be modified to have an increased in vitro growth rate, and not have a increase in virulence. Preferably, the varicella zoster virus that is modified to have an increased in vitro growth rate is Oka strain (see Kubo, U.S. Pat. No. 3,985,615), or ATCC VR-795. The modified varicella zoster virus of the vaccine composition can a live virus, or an inactivated whole virus preparation. The virulence of a varicella zoster virus modified to have a higher in vitro growth rate can be determined using methods known in the art, for instance by using human volunteers.

In another aspect, the vaccine composition can include an isolated varicella zoster virus polypeptide of the present invention or a fragment thereof. Varicella zoster virus polypeptides of the present invention are described herein.

The vaccine composition includes polypeptide or modified varicella zoster viruses having immunogenic acivity. Immunogenic carriers can be used to enhance the immunogenicity of the polypeptide or modified varicella zoster viruses. Such carriers include but are not limited to other polypeptides, polysaccharides, liposomes, and bacterial cells and membranes. Polypeptide carriers may be joined to the polypeptides or modified varicella zoster viruses of the present invention to form fusion polypeptides by recombinant or synthetic means or by chemical coupling. Useful carriers and means of coupling such carriers to polypeptide antigens are known in the art.

The vaccine compositions may be formulated by means known in the art. The formulations include those suitable for parental (including subcutaneous, intramuscular, intraperitoneal, and intravenous administration. They are typically prepared as injectables, either as liquid solutions or suspensions. Solid forms suitable for solution in, or suspension in, liquid prior to injection may also be prepared. The composition may also, for example, be emulsified, or the polypeptide or modified varicella zoster virus encapsulated in liposomes. Where mucosal immunity is desired and the vaccine includes a polypeptide or an inactivated varicella virus, the vaccine compositions may advantageously contain an adjuvant such as the nontoxic cholera toxin B subunit (see, e.g., U.S. Pat. No. 5,462,734). Cholera toxin B subunit is commerically available, for example, from Sigma Chemical Company, St. Louis, Mo. Other, suitable adjuvants are available and may be substituted therefor.

The polypeptide or modified varicella zoster virus can be mixed with pharmaceutically acceptable excipients or carriers. Suitable excipients include but are not limited to water, saline, dextrose, glycerol, ethanol, or the like and combinations thereof. In addition, if desired, the vaccine compositions may contain minor amounts of auxiliary substances such as wetting or emulsifying agents, pH buffering agents, and/or adjuvants which enhance the effectiveness of the vaccine. Such additional formulations and modes of administration as are known in the art may also be used.

The present invention is illustrated by the following examples. It is to be understood that the particular examples, materials, amounts, and procedures are to be interpreted broadly in accordance with the scope and spirit of the invention as set forth herein.

EXAMPLE 1

Identification of Single Nucleotide Polymorphisms in ORF 68 (the gE Gene) of VZV-MSP This example demonstrates the presence of a single nucleotide polymorphism in gE. Because of the important functions of gE, this discovery was completely unexpected. This example provides a more complete characterization of the altered biological properties and genetic composition of this contemporary variant in VZV evolution. For the first time, a VZV variant virus has been discovered which has a cell-to-cell spread phenotype clearly distinguishable from previously characterized VZV strains.

Materials and Methods

Viruses and Cells

The mutant VZV was isolated from a 6 year old boy with leukemia, who contracted chickenpox and was hospitalized for intravenous acyclovir treatment in late 1995. The child's illness responded to treatment and no unusual sequelae were observed. The child's vesicle fluid was inoculated onto MRC-5 cells in glass tubes. The isolate was designated VZV-MSP because the child lived in Minnesota. The VZV-32 laboratory strain was isolated in Texas in 1976 from an otherwise healthy child with chickenpox (Grose, *Virology*, 101:1–9 (1980)). This virus has never been passaged more than 20 times. The VZV Oka strain was isolated from a Japanese child with chickenpox and attenuated by M. Takahashi in Japan in the 1970s (Takahashi hi et al., *Biken J.*, 18:25–33 (1975)). All viruses were subcultured in either MRC-5 cells or human melanoma cells (MeWo strain, available from C. Grose, University of Iowa, Iowa). MeWo cells are highly permissive for VZV replication but no infectious virus is released into the culture medium (Grose, *Virology*, 101:1–9 (1980)). Therefore, transfer of infectivity is carried out by trypsin dispersion of infected cells and relayering of infected cells onto an uninfect monolayer at a ratio of 1:8 (infected to uninfected cells). The HSV-1 Miyama strain was propagated in the FL line derived from human amnion cells (Padilla et al, *J. Elect. Microscopy.* 46:171–180 (1997)).

Antibodies and Immunodetection by Confocal Microscopy

MAb 3B3 was produced in this laboratory (Grose et al., *Infect. Immun.*, 40:381–388 (1983)). The antigen for mouse immunization was VZV-32 infected cells. MAb 3B3 attaches to VZV gE even under stringent conditions of buffers containing 1% SDS. Other monoclonal antibodies to VZV gE (MAb 711), VZV gI (MAb 6B5) and VZV gH (MAb 206) were also produced and characterized in this laboratory and are described in Grose (*Annu. Rev. Microbiol*, 44: 59–80 (1990). Conditions for immunodetection of VZV proteins by laser scanning confocal microscopy have been outlined by Duus et al., (*J. Virol.*, 70:8961–8971 (1996)). Immunoblotting was performed with the above antibodies as described (Grose, *Annu. Rev. Microbiol*, 44:59–80 (1990)).

Epitope Mapping by Recombination PCR Mutagenesis

The technique of recombination PCR mutagenesis has been adapted to investigate epitope mapping and tagging (Yao et al., *J. Virol.*, 67:305–314(1993), Hatfield et al., *BioTechniques*, 22:332–337 (1997)). By this methodology, the epitope of MAb 3B3 was initially defined between amino acids 151–161 in the ectodomain of the 623-amino acid gE glycoprotein. The methodology for producing plasmid pTM1-VZV gL 3B3.11 is described in detail by Hatfield et al., (*BioTechniques*, 22:332–337 (1997)). As part of the investigation in Results (FIG. 2), an additional two codons were inserted at the N-terminus of the 11-amino acid 3B3 epitope, to produce a 13-amino acid epitope tag in the VZV gL protein. The mutating primers included the following: MP23 (sense) CAT ACT GTG TCG ACC AAA GGC AAT ACG TG ACG TG (SEQ ID NQ:4) and MP24 (antisense) TTG TG CCT TIG GTC GAC ACA GTA TGC GAT TGT GAT AG (SEQ ID NO:5). PCR amplification was performed under the following parameters: 94° C. denaturation for 30 seconds, 50° C. annealing for 30 seconds, 72° C. extension for 5 minutes; after 25 cycles, there was a final extension at 72° C. for 7 minutes. PCR products ere combined and transformed into cells where the overlapping regions underwent recombination to yield a plasmid containing the mutagenized insert. Plasmid purification was performed with a Qiagen Maxi Kit. The newly designated pTM1-VZV gL 3B3.13 plasmid was partially sequenced at the University of Iowa DNA Core Facility to confirm the authenticity of the insertional mutagenesis. This PCR mutagenesis protocol is very reliable with a error frequency of less than 0.25% (Jones et al., *Biotechniques*, 8:178–183 (1990)).

Subcloning of VZV-MSP gE

The subcloning of wild type VZV gE has been described previously (Yao et al., *J. Virol.*, 67:305–314 (1993)). Briefly, two flanking PCR primers were utilized which amplified the VZV-MSP gE ORF directly from VZV-MSP infected melanoma cells. These primers also created a Sac I and a Spe I restriction enzyme site at the 5' and 3' ends, respectively. The primers were the following: Nco gpl (sense) CGA CCC GGG GAG CTC CCA TGG GGA CAG TTA ATA AAC C (SEQ ID NO:6) and IP2 (anti-sense) CGC TCT AGA ACT AGT GGA TCC CCC GGG GAA TTT GTC ACA GGC TTT T (SEQ ID NO:7). PCR amplification was performed using AmpliTaq (Applied Biosystems, Foster City, Calif.) under the following conditions: 94° C. denaturation for 40 seconds, 50° C. annealing for 40 seconds, 72° C. extension for 4 minutes; after 35 cycles, there was a final extension at 72° C. for 7 minutes. After amplification, the PCR fragment was digested with Sac I and Spe I before cloning into the multiple cloning site of the expression vector pTM1.

Imaging of Viral Particles

Clean coverslips were coated with carbon, hydrophilized, irradiated with ultraviolet light for 12 hours, followed by a glow discharge for a few seconds and then sterilization by dry heat (160° C. overnight). MeWo cells were cultivated on the glass coverslips. When the cells became confluent, they were co-cultivated with either VZV-32 or VZV-MSP infected cells at a 1:8 ratio and incubated at 32° C. At the designated times after infection, the cells were prefixed with 1% glutaradehyde in PBS at 4° C. for 1 hour, rinsed in chilled PBS followed by postfixation with 1% osmium tetraoxide in PBS at 4° C. for 1 hour, and then dehydrated in a graded ethanol series. Finally, after two changes in 100% ethanol, the specimens were subjected to a critical point drying method. In the case of HSV-1 samples, FL cells prepared on coverslips were inoculated with HSV-1 Miyama strain at an MOI of 10. Twenty four hours after virus inoculation, coverslips were washed with PBS and processed as described for VZV. Subsequently, the specimens were mounted onto aluminum plates and observed with either a Hitachi S-4000 or a Hitachi S-900 SEM. Imaging was performed at the University of Iowa Central Microscopy Research Facility and the University of Wisconsin-Madison Integrated Microscopy Facility.

Results

Analysis of the VZV Isolate by Confocal Microscopy

The virus designated VZV-MSP was initially isolated in human fibroblast monolayers. The cytopathic effect (CPE) was compatible with VZV, but the isolate was poorly reactive with antibodies in a commercial VZV diagnostic kit. Since the isolate did not stain with antibodies to herpes simplex virus (HSV) types 1 and 2 nor did its CPE resemble that of HSV, the virus isolate was further analyzed. When the isolate (VZV passage 1) was received, the infected cell monolayer was trypsin-dispersed and inoculated onto human melanoma cells (VZV passage 2). When CPE was apparent in 5 days, the infected cell monolayer was trypsin-dispersed one more time and inoculated onto 35 mm monolayers for examination by laser scanning confocal microscopy (VZV passage 3). The low passage VZV-32 strain was included in separate dishes as a control virus. When CPE covered about 70% of each monolayer, the infected monolayers were probed with MAb 3B3 against gE and MAb 6B5 against gI and examined by confocal microscopy. In prior studies, it has been shown that these two MAbs do not cross-react with other viral or cellular proteins (Grose, *Annu. Rev. Microbiol.*, 44:59–80 (1990)). As expected from numerous published experiments, MAb 3B3 and MAb 6B5 reacted with the laboratory strain VZV-32. In marked contrast, the anti-gE MAb 3B3 did not attach to cells infected with the VZV-MSP strain, even though MAb 6B5 did bind the infected cells strongly. As an additional control, the anti-gH MAb 206 was added to cultures individually infected with both VZV strains; all VZV-infected cultures were positive in this assay.

The next question addressed was whether the VZV-MSP strain failed to express the entire glycoprotein or whether it has lost an epitope on the glycoprotein. Monoclonal antibodies produced in the epitope-mapping of gE were used. It was previously established that the 3B3 epitope consisted of at least 11 amino acids 151–161 of gE (Duus et al., *J. Virol.*, 70:8961–8971 (1996)). Another monoclonal antibody, MAb 711, attaches to another as yet undefined epitope on the ectodomain of gE. This epitope does not overlap with the 3B3 epitope. Therefore, the above experiment was repeated with MAb 711 as the immunoprobe of VZV-32 and VZV-MSP infected monolayers. Both monolayers stained positively, a result which indicated that gE was expressed in VZV-MSP infected cells but appeared to have lost either a small segment of its ectodomain or just the 3B3 epitope.

Sequence Analysis of VZV-MSP gE

To further investigate the nature of the gE mutation, we used PCR amplification techniques to first determine whether a full-length gE gene (VZV ORF 68) was present in the mutant strain. The full length gene was amplified. Thereafter, primers were used to amplify overlapping portions of the gE gene, each overlapping portion about 300 bases in size, beginning at the upstream region of ORF 68. Each fragment was subjected to DNA sequencing and each sequence was compared with the published Davison and Scott (Davison et al., *J. Gen. Virol.*, 67:1759–1816 (1986)) sequence of the Dumas strain (FIG. 1A; Genbank Accession number X04370). After analysis of the first 337 codons of VZV-MSP gE ORF, we found the first and most important base change in codon 150 (FIG. 1B, arrow); the substitution involved a replacement of a guanine by an adenine. Of great interest, this point mutation led to a change in amino acid from aspartic acid to asparagine (FIG. 1B). Since this alteration in gE occurred one amino acid away from the deduced 3B3 epitope, which is underlined in FIG. 1A, the sequence data strongly suggested that amino acid 150 was a previously unrecognized contributor to the 3B3 epitope. Further sequencing of VZV-MSP gE revealed one silent mutation in codon 341 of VZV-MSP gE. All other codons were identical to those in the gE sequence of the Dumas strain.

Epitope Mapping of VZV-MSP gE

In an earlier experiment, we had evaluated the 3B3 epitope by inserting the 11-amino-acid sequence into the unrelated VZV ORF 60, namely, the gL glycoprotein (Duus et al., *J. Virol.*, 70:8961–8971 (1996)). The epitope tag within gL was recognized by MAb 3B3 when observed by laser scanning confocal microscopy. To evaluate the contribution of the aspartic acid residue to formation of the epitope, the gL epitope mapping and tagging experiment was repeated in order to insert the aspartic acid residue in its correct location at the N-terminus of the 3B3 epitope. In order to obtain the proper parameters for the mutagenesis primers, one additional codon was inserted along with an aspartic acid (FIG. 1B). The pTM-1 expression plasmids, including gL-3B3.11 and gL-3B3.13, were transfected into HeLa cells and observed by confocal microscopy after labeling with MAb 3B3. Cells transfected with the gL-3B3.11 plasmid were positive in a restricted cytoplasmic pattern, as previously described by Duus et al., (*J. Virol.*, 70:8961–8971 (1996)). Cells transfected with the gL-3B3.13 were not only more intensely stained, the pattern was more widely distributed throughout the cytoplasm. Cells transfected with the pTM-1 gL plasmid alone were negative.

Subcloning the VZV-MSP gE ORF

After completion of the above experiment, we sought to confirm the epitope experiments by amplifying the entire gE gene from VZV-MSP DNA and inserting it into a pTM-1 expression vector. We had previously cloned wild-type gE into the same expression vector; the same primers were used for the second cloning experiment (Yao et al., *J. Virol.*, 67:305–314 (1993)). After transient transfection with these two forms of VZV gE as well as the pTM-1 vector as a control, the cell lysates were solubilized and subjected to electrophoresis followed by transfer to membranes. Additional control samples for the transfection immunoblotting experiments included Mewo cell monolayers infected with three VZV strains: VZV-32, VZV-Oka and VZV-MSP. Uninfected Mewo cells served as a negative control. All samples were blotted with MAb 3B3 followed by detection using chemiluminesence. The MAb attached to VZV-32, VZV Oka and VZV gE wild type, but not to VZV-MSP, VZV MSP gE or the vector and uninfected cell controls. When VZV-MSP gE was subsequently immunoblotted with a polyclonal monospecific antibody to gE, the result was positive. Thus, these results confirmed that VZV-MSP gE by itself was expressed but lacked the 3B3 epitope.

Alterations in Topography of Egress of Viral Particles

In previously published studies, it was shown that the egress of wild type VZV particles onto the surface of infected cells occurs in a distinctive pattern which was termed "viral highways" (Harson et al., *J. Virol.*, 69:4994–5010 (1995)). The viral highways are composed of thousands of viral particles which emerge in long rows across the surface of the syncytia. When the distribution of VZV-32 and VZV-MSP particles were compared at a low magnification level by scanning electron microscopy (SEM), wild type virions were again arranged in a pattern consistent with viral highways. Cells infected with the VZV-Oka strain show a similar pattern of viral highways (Grose, Infect. Dis. Clinics NA, 10: 489–505 (1996)). In contrast, no such topographical pattern was observed on samples infected with VZV-MSP; instead, viral particles were distributed more uniformly over the cell surface. After observation of numerous monolayers by SEM, it appeared that the number of VZV wild type virions present on the cell surface was less than those of VZV-MSP. The topographical arrangement of VZV-MSP particles also exhibited a high degree of similarity with that of HSV-1, in which thousands of particles covered the cell surface.

In a VZV-infected monolayer, cytopathic effect follows the longitudinal axis of the cells. In VZV-infected human melanoma cell cultures, individual syncytial foci enlarge and eventually merge until the entire monolayer has become a single syncytium. Virions only emerge after syncytia are formed but the virions are never released into the culture medium. If syncytial formation is blocked by adding anti-gH antibody into the culture medium, virions do not egress until the antibody is removed. Based on the imaging studies in this as well as previous reports, it is postulated that virions exit at the leading edge of syncytial foci which are merging. Further, VZV egress (gE/gI mediated) and VZV-induced cell-to-cell fusion (gH/gL mediated) are separate but interdependent events. The mutation on VZV-MSP gE appears to lessen that interdependence.

EXAMPLE 2

Identification of Single Nucleotide Polymorphisms in Other ORFs of VZV-MSP and Assessment of Cell-to-cell Spread This example provides a more complete characterization of the altered biological properties and genetic composition of this contemporary variant in VZV evolution. For the first time, a varicella zoster virus variant is described which has a cell-to-cell spread phenotype clearly distinguishable from previously characterized varicella zoster virus strains.

Cells, viruses and transfer of infectivity. VZV-MSP was isolated in Minnesota in late 1995. VZV-32 was isolated in Texas in the 1970s (Grose et al., Infect. Immun., 19:199–203 (1978)). Reserve stocks of VZV-32 and VZV-MSP were prepared; thus low passages (<20) were used in all experiments in this report. VZV-Oka was isolated in Japan and attenuated in the 1970s (Takahashi et al., Biken J. 18:25–33 (1975)). VZV-Dumas was isolated in Holland and sequenced in its entirety by Davison et al., (Davison et al., J. Gen. Virol., 67:1759–816 (1986)). All strains were propagated in human melanoma cells (MeWo strain). MeWo cells are highly permissive for VZV replication with no release of infectious virus into the culture medium (Grose, Virology 101:1–9 (1980)). Transfer of infectivity was carried out by inoculation of trypsin-dispersed infected cells onto an uninfected monolayer at a 1:8 ratio of infected: uninfected cells unless otherwise noted. Similarly, infectious center assays were carried out by described methods; these assays included both melanoma cell and human neonatal foreskin cell substrates (Cole et al., J. Virol. Methods, 36:111–8 (1992), Grose et al., Infect. Immun., 19:199–203 (1978)).

Imaging by confocal microscopy. Replicate 35-mm monolayers of MeWo cells were overlaid with VZV-infected cells at a 1:8 ratio of infected:uninfected cells. At 4, 8, 12, 24, and 48 hours post-infection, the monolayers were fixed and permeabilized with 0.5 ml 2% paraformaldehyde with 0.05% Triton X-100. Cells were probed with an anti-IE 62 mouse monoclonal ascites (MAb 5C6, available from C. Grose, University of Iowa, Iowa) at a dilution of 1:1,000 (Ng et al., J. Virol., 68:1350–1359 (1994)). The secondary antibody was goat anti-mouse IgG F(ab')$_2$ conjugated to Alexa 488 at a dilution of 1:2,500 (Molecular Probes, Eugene, Oreg.). Cell nuclei were stained with TOTO-3 (Molecular Probes), a dimeric cyanine nucleic acid stain, at a dilution of 1:10,000. Samples were examined with a BioRad 1024 laser scanning confocal microscope, as described (Duus et al., Virology 210:429–440 (1995)).

Quantitative Analysis of Confocal Images. Confocal images were converted to TIFF format images (Confocal Assistant, v. 4.02, Bio-Rad Laboratories (Hercules, Calif.), available from ftp://ftp.genetics.bio-rad.com/Public/confocal/cas) and transferred to a Silicon Graphics Indy workstation in order to produce the color prints by Showcase software program (Silicon Graphics, Mountain View, Calif.)). Confocal images also were analyzed with the Brainvox tal_support programs (Frank et al., Neuroimage, 5:13–30 (1997)). Similar analyses can be performed with the public domain NIH Image program, which was developed at the U.S. National Institutes of Health (http://rsb.info.nih.gov/nih-image/).

Replication in the SCID-hu mouse. The SCID-hu mouse has been established as an animal model for VZV replication (Moffat et al., J. Virol., 69:5236–42 (1995)). In this model, C.B-17 scid/scid mice were implanted with fetal skin tissue subcutaneously as full thickness dermal grafts. Human fetal tissues were obtained with informed consent according to federal and state regulations and were screened for human immunodeficiency virus. The general care of the experimental animals used for this study was in accordance with the National Institutes of Health guidelines for laboratory animals and in compliance with the Animal Welfare Act (Public Law 94–279) as well as the Stanford University Administrative Panel on Laboratory Animal Care. Animal inoculations were performed according to the previously described protocol (Moffat et al., J. Virol., 69:5236–42 (1995)), viz., an aliquot of infected cell suspension containing $10^5$ infectious centers was injected into each implant. Mock-infected implants were injected with human cells alone. Skin implants were harvested at 7, 14 and 21 days post-inoculation. The implants were fixed in 4% paraformaldehyde, paraffin-embedded, cut into 3-$\mu$m sections, and stained with hematoxylin and eosin. Tissue sections were examined on a Leitz Diaplan light microscope, and digital images were acquired with an Optronics DEI 750 digital camera (Optronics Engineering, Goleta, Calif.). Digital images were formatted as described above.

Isolation of viral DNA. For all viral strains, a 25 cm$^2$ monolayer of MeWo cells was infected as described above. After development of 80–100% cytopathology, the infected monolayer was washed thrice with 0.5 ml of 0.01M phosphate buffered saline (PBS), pH 7.4. Infected cells were then harvested by dislodging into 0.5 ml of PBS. Viral DNA was collected with a DNAeasy Kit following the Blood and Body Fluid Protocol (Qiagen Inc, Valencia, Calif.). Following DNAeasy protocol, DNA was placed onto a Microcon 50 filter (Millipore, Bedford, Mass.) and washed twice with 0.5 ml of Nanopure water (Barnstead/Thermolyne, Dubuque, Iowa). Viral DNA was resuspended in 100 $\mu$L of Nanopure water. DNA concentration was assessed visually after 1% agarose gel electrophoresis.

PCR amplification and sequencing of VZV genes. For each ORF, a pair of flanking primers was designed to amplify the gene of interest. PCR amplifications were performed with the Expand High-Fidelity PCR System (Boehringer Mannheim, Indianapolis, Ind.). This system utilizes both Taq DNA and Pwo DNA polymerases, with the 3'–5' proofreading activity of Pwo DNA polymerase allowing increased fidelity ($8.5 \times 10^{-6}$ per bp error rate) (Boehringer Mannheim). After amplification, the PCR product was sequenced by using the dye terminator cycle sequencing chemistry with AmpliTaq DNA polymerase, FS enzyme (Perkin Elmer Applied Biosystems, Foster City, Calif.). Sequencing reactions were performed on and analyzed with an Applied Biosystems Model 373A stretch fluorescent automated sequencer (Perkin Elmer) at the University of Iowa DNA facility. All genes were PCR amplified twice and each PCR fragment was sequenced at least twice to confirm reported mutations. Each DNA sequence was compared to the prototype VZV-Dumas sequence. The accession number for the complete VZV-Dumas sequence is X04370. The primers used for amplification and/or sequencing the amplified fragments are shown in Table 1.

TABLE 1

VZV sequencing and amplification primers

| Protein[1] | Primer[2] | bp[3] | Seq/Amp[4] | Sequence[5] | |
|---|---|---|---|---|---|
| gB | | | | | |
| (ORF 31) | Scp 1 (S) | -163 to -136 | Seq/Amp | GGCGTTTTCATAACCTCCGTTACGGGGG | (SEQ ID NO:8) |
| | Scp 2 (AS) | 2685 to 2658 | Seq/Amp | CCCTGTGATGCGTAATGGAGACACATGA | (SEQ ID NO:9) |
| | Sp 1 (A) | 309 to 328 | Seq | CTTTGTAATATACCGTCGCC | (SEQ ID NO:10) |
| | Sp 2 (S) | 201 to 220 | Seq | CGTACGATTAGAACCAACTC | (SEQ ID NO:11) |
| | Sp 3 (S) | 569 to 588 | Seq | GGCATACTACCAATGACACG | (SEQ ID NO:12) |
| | Sp 4 (S) | 929 to 948 | Seq | AGTGGCGTGAGGTTGAAGAC | (SEQ ID NO:13) |
| | Sp 5 (S) | 1264 to 1283 | Seq | CACCCGACTCGAAATACCAG | (SEQ ID NO:14) |
| | Sp 6 (S) | 1615 to 1634 | Seq | TCTGGTAGTACTACGCGTTG | (SEQ ID NO:15) |
| | Sp 7 (S) | 1948 to 1970 | Seq | GACTACAGTGAAATTCAACGCCG | (SEQ ID NO:16) |
| | Sp 8 (S) | 2259 to 2279 | Seq | CCCGATGAAGGCATTATATCC | (SEQ ID NO:17) |
| | Sp 9 (A) | 1418 to 1437 | Amp | TAGCTGGCACCACGACGAGG | (SEQ ID NO:18) |
| | Sp 10 (A) | 2565 to 2584 | Amp | TGCGAACACGGGAGTATCCT | (SEQ ID NO:19) |
| gH | | | | | |
| (ORF 37) | Sp 2 (S) | 104 to 131 | Seq | CTGCTCTTCTACGAGAATATTCCGACCG | (SEQ ID NO:20) |
| | Sp 3 (A) | 223 to 199 | Seq | CGTGTTTTCTATCATTTCCCCAGTG | (SEQ ID NO:21) |
| | Sp 4 (S) | 448 to 471 | Seq | ACTACGTTCCCACCAAACCCCCTTG | (SEQ ID NO:22) |
| | Sp 5 (S) | 850 to 873 | Seq | GCGGTTACAAGCGACACCACATGG | (SEQ ID NO:23) |
| | Sp 6 (S) | 1165 to 1191 | Seq | CTGTTAGATGAGATCGTAGATGTTCAG | (SEQ ID NO:24) |
| | Sp 7 (S) | 1498 to 1514 | Seq | GCTACAGAGAGGCAGGCT | (SEQ ID NO:25) |
| | Sp 8 (S) | 1816 to 1840 | Seq | TTGCATACCCAACTAGACGAATCTG | (SEQ ID NO:26) |
| | Sp 9 (S) | 2129 to 2152 | Seq | TAGAGACGGTCGCACTGCCCCATC | (SEQ ID NO:27) |
| | Sp 10 (S) | -32 to -5 | Seq/Amp | CGGTGATATTGTAGCGCAAGTAACAGC | (SEQ ID NO:28) |
| | Sp 11 (A) | 2605 to 2580 | Seq/Amp | CCCAAAGGTAGTGTGTATTATTCGCG | (SEQ ID NO:29) |
| | Sp 13 (A) | 223 to 198 | Seq | CGTCTCCTTCGTGTGTTG | (SEQ ID NO:30) |
| | Sp 14 (A) | 1005 to 988 | Seq | ATCCAAACTCTCTTCGGG | (SEQ ID NO:31) |
| | Sp 15 (A) | 2218 to 2199 | Seq | TCGCCCCCGTGGTTAGATAC | (SEQ ID NO:32) |
| gE | | | | | |
| (ORF 68) | Ip2 (A) | 2061 to 2039 | Seq/Amp | CGCTCTAGAACTAGTGGATCCCCCGGGGAATTTGTCACAGGC TTTT | (SEQ ID NO:7) |
| | NcogpI (S) | 1 to 11 | Amp | CGACCCGGGGAGCTCCCATGGGGACAGTTAATAAACC | (SEQ ID NO:6) |
| | Sp 1 (S) | 1452 to 1470 | Seq | GCATGTTGAAGCCGTAGCA | (SEQ ID NO:33) |
| | Sp 3 (S) | 199 to 217 | Seq | ATGCGCGGCTCCGATGGTA | (SEQ ID NO:34) |
| | Sp 4 (A) | 505 to 486 | Seq | GGCCTTGGGGTTTTGGATTA | (SEQ ID NO:35) |
| | Sp 6 (S) | -70 to -48 | Seq | GTCCATGGTTTTAGACCTCGGG | (SEQ ID NO:36) |
| | Sp 7 (S) | 543 to 561 | Seq | GTTTACTTTACGCGCACCG | (SEQ ID NO:37) |
| | Sp 8 (S) | 823 to 840 | Seq | GAATTAGACCCCCCCGAG | (SEQ ID NO:38) |
| | Sp 9 (S) | 1127 to 1146 | Seq | TAGAGTGGTTGTATGTCCCC | (SEQ ID NO:39) |
| | Sp 10 (S) | 1601 to 1619 | Seq | CACTTCTACGATATGCCGC | (SEQ ID NO:40) |
| | Sp 12 (A) | 846 to 827 | Seq | TTCAATCTCGGGGGGGTCTA | (SEQ ID NO:41) |
| | Sp 13 (A) | 1790 to 1772 | Seq | TCCGTAGATTCCGAGTCCT | (SEQ ID NO:42) |
| gL | | | | | |
| (ORF 60) | P1 (S) | -1 to 16 | Seq/Amp | CAAGCGCCATGGCATCACATAAAT | (SEQ ID NO:43) |
| | P2 (A) | 913 to 886 | Amp | AAACACTAGTCCATGTGCATGTCCCGC | (SEQ ID NO:44) |
| | Sp 1 (A) | 548 to 530 | Seq | GCTTGCGGGTTTTTTTGGT | (SEQ ID NO:45) |
| | Sp 2 (A) | 320 to 302 | Seq | GCCAGCCCCTTTAAGGTGA | (SEQ ID NO:46) |
| | Sp 4 (S) | 473 to 494 | Seq | GCCAATGAAATGAAACTATCGG | (SEQ ID NO:47) |
| gI | | | | | |
| (ORF 67) | Scp 1 (S) | -60 to -33 | Seq/Amp | CGGCTCACAGAGCTGCTCTTCGGTGTAG | (SEQ ID NO:48) |
| | Scp 2 (A) | 1154 to 1137 | Seq/Amp | TAATCCTTCCCCTCATATCACAACGCGT | (SEQ ID NO:49) |
| | Sp 1 (A) | 995 to 978 | Seq | GCGGCCTCCAACATCACA | (SEQ ID NO:50) |
| | Sp 2 (A) | 383 to 365 | Seq | CCAGCATCCGGCTCTGTTG | (SEQ ID NO:51) |
| | Sp 4 (S) | 314 to 337 | Seq | CGTGTAGGTACAAACATTCGTGGC | (SEQ ID NO:52) |
| ORF 47 | ScP 1 (S) | -349 to -320 | Amp | ATCTAATCCGTGGGGGTGCGAGTGTACAAG | (SEQ ID NO:53) |
| | ScP 2 (A) | 103 to 132 | Amp | TCCATGTTCGGTGATGTCTTCTGTAGGCGTG | (SEQ ID NO:54) |
| | Sp 1 (S) | 3 to 22 | Seq | GGATGCTGACGACACACCCC | (SEQ ID NO:55) |
| | Sp 2 (A) | 163 to 182 | Seq | GTTGCAGTTGACGGATTGGC | (SEQ ID NO:56) |
| | Sp 3 (S) | 341 to 360 | Seq | TTGTACCCATCTTCACGCTC | (SEQ ID NO:57) |
| | Sp 4 (S) | 743 to 762 | Seq | ATCGAACGTGCGGCCTGACC | (SEQ ID NO:58) |
| | Sp 5 (S) | 1135 to 1154 | Seq | CTTCCCGGACAACTGCCCAT | (SEQ ID NO:59) |

TABLE 1-continued VZV sequencing and amplification primers

| Protein[1] | Primer[2] | | bp[3] | Seq/Amp[4] | Sequence[5] | |
|---|---|---|---|---|---|---|
| IE62 (ORF 62) | Scp 1 | (S) | −79 to −50 | Seq/Amp | CACCAACCGCAATCGCAATCCTTTGAAGGC | (SEQ ID NO:60) |
| | Scp 2 | (AS) | 3990 to 3961 | Seq/Amp | TATTAACAACAAACAGTCCGCGCGCCAGTG | (SEQ ID NO:61) |
| | Sp 1 | (S) | 318 to 342 | Seq | GCCGAGGTCTTCCACACCCGATTCT | (SEQ ID NO:62) |
| | Sp 2 | (S) | 749 to 773 | Seq | TTTGAAGGTTAAGGTCCCACTCCCG | (SEQ ID NO:63) |
| | Sp 3 | (S) | 1142 to 1166 | Seq | TACAGGCAGCAGGTCCGGACGCGAA | (SEQ ID NO:64) |
| | Sp 4 | (S) | 1511 to 1535 | Seq | TTACGAGGCCTCAACGGAACCCGTG | (SEQ ID NO:65) |
| | Sp 5 | (S) | 1925 to 1949 | Seq | GATCTCCCGCGGTCACCCTTCTCCA | (SEQ ID NO:66) |
| | Sp 6 | (S) | 2309 to 2333 | Seq | CAAGGCGTACTGTACCCCCGAAACC | (SEQ ID NO:67) |
| | Sp 7 | (S) | 2685 to 2709 | Seq | ACTCATGCCTGGGCCGGGAACTGGA | (SEQ ID NO:68) |
| | Sp 8 | (S) | 3098 to 3122 | Seq | CGTCGCATACACCGTGTGTACCCGC | (SEQ ID NO:69) |
| | Sp 9 | (S) | 3500 to 3524 | Seq | TGCCCTCCCCCCGATTCCCAGAGTA | (SEQ ID NO:70) |

[1]The protein that is encoded by the listed ORF.
[2]The designation of the primer.
[3]The base pairs to which the primer hybridizes. The numbering used denotes the transcriptional start site as +1.
[4]Seq, the primer was used as a primer in a sequencing reaction; Amp, the primer was used as a primer in PCR. Some primers were used in both sequencing and amplification.
[5]The nucleotide sequence of the primer, listed 5' to 3'.

Results

Cell-to-cell spread phenotype of VZV-MSP. During the initial assessment of VZV-MSP, it was observed that the egress of VZV-MSP particles in cell culture differed from that of other typical VZV laboratory strains, such as VZV-32 and VZV-Oka. Like other VZV strains, however, infectious virus was not released into the culture medium. The fact that greater numbers of VZV-MSP particles were present on the surface suggested that cell-to-cell spread may be increased. Cell-to-cell spread has been assessed in both herpes simplex virus type 1 (HSV-1) and pseudorabies virus (PRV) through measurement of plaque size in permissive cells or number of cells infected within a typical plaque. Neither technique is easily applicable in the VZV system given the formation of irregularly shaped syncytia by VZV in cell culture and the absence of cell-free virus in tissue culture. Therefore, a technique was developed to assess cell-to-cell spread through confocal microscopic examination.

The spread of low-passage VZV-MSP was compared to the low-passage laboratory strain VZV-32. Human melanoma cells were inoculated with either VZV-32 or VZV-MSP at a 1:8 ratio of infected: uninfected cells. At increasing intervals post-infection, the infected monolayers were probed with an antibody against the VZV immediate early protein 62 (IE 62). The number of cells expressing IE 62 and the intracellular localization of the protein were determined. This assay was based on the observation by Kinchington et al., (*J. Infect. Dis*., 178 Suppl 1:S16–21 (1998)) that VZV IE 62 is present in the nuclei of infected cells during early stages of infection, but then appears in the cytoplasm during later stages.

At the time point of four hours post-infection, comparing VZV-32 and VZV-MSP by confocal microscopy represents the number of infected cells originally overlaid onto each monolayer. Both monolayers contained similar levels of IE 62 positive cells. At twenty-four hours post-infection the difference in extent of spread between VZV-MSP and VZV-32 was apparent. For VZV-32 at 24 hours, 6–8 cells with advanced infection were present in each focus; IE 62 was present in both nucleus and cytoplasm. A few scattered cells adjacent to the infectious focus contained nuclei with IE 62 concentrated near the membrane; these cells represented a recent transfer of infectivity from the central focus. When the VZV-MSP culture was examined at 24 hours, large syncytia had already formed. A typical syncytium contained 20–30 nuclei, an infectious focus 3 to 4 fold larger than that seen with VZV-32. This experiment was repeated four times with equivalent results.

Quantitative analysis of confocal images of VZV IE 62. To quantify the difference in cell-to-cell spread, multiple confocal images were analyzed with the image analysis programs called Brainvox tal_support programs. Each confocal image is made up of 512×512 pixels, for a total of 262,144 pixels. The green fluorescence channel representing the presence of VZV IE 62 within each confocal image was analyzed. The image analysis program initially assigns a relative signal intensity within each pixel of the confocal image. Then, a threshold of signal intensity is calculated to remove background signals. This analysis facilitated quantification of all pixels within each confocal image that contained IE 62. Thus, confocal microscopy of IE 62 coupled with image analysis facilitated a comparison of the extent of viral spread between two different VZV strains.

The results for this analysis are shown in FIG. 3. There was no major difference between the extent of IE 62 spread for VZV-32 and VZV-MSP at 4, 8, and 12 hours post-infection. The results at both 4 and 8 hours, in particular, demonstrated that each monolayer was infected with a similar inoculum of infected cells. Also, the lack of a difference between the three time points (4 hours–12 hours) confirmed that the replication cycle for both VZV strains was greater than 12 hours, in agreement with previous studies. However, at twenty-four hours post-infection, there was a noticeable difference between spread of VZV-MSP and VZV-32. The extent of VZV-MSP spread was at least two-fold greater than VZV-32. At forty-eight hours post-infection, this difference increased further, as VZV-MSP spread was four-fold greater than VZV-32. Thus, image analysis provided a new method by which to measure differences in cell-to-cell spread between VZV strains. Again, this methodology is particularly suited for VZV because cell free virus is not released spontaneously from infected cell cultures; even after sonic disruption of infected monolayers, most viral particles remain attached to remnants of outer cellular membranes.

VZV infectious center assays. Because the results in the previous experiments represented a new application of confocal microscopy, a traditional method was also used to confirm the differences in VZV cell-to-cell spread, namely, infectious center assays. For these titrations, the initial virus inocula were replicate samples of VZV-infected cells frozen and stored in liquid nitrogen. After freezing, one aliquot was thawed and titrated from each lot. The inoculum for each 35-mm tissue culture dish was 500 infectious centers. Two dishes were harvested and assayed at each of the following time points: immediately after inoculation (0 hour), 24 hours, and 48 hours post-inoculation (FIG. 4). When comparing the average fold increase of VZV-MSP infectious centers to VZV-32 infectious centers, the spread of VZV-MSP was consistently greater than the spread of VZV-32 over both the first 24 hour period (24 hr pi) and the second 24 hr period (48 hr pi). Otherwise stated, at 48 hours post-infection, the cytopathic effect of VZV-MSP was complete, while numerous infectious center titrations with VZV-32 demonstrated that a 60–72 hr interval was required for similar spread (Grose et al., *Infect. Immun.*, 19:199–203 (1978)). Furthermore, the rapidity of VZV-32 spread was not altered over the initial 20 passages. VZV-Oka and VZV-Ellen titrations exhibited a time course similar to that of VZV-32. Therefore, results from both quantitative confocal microscopic image analyses and infectious center assays documented that the spread of VZV-MSP was 3–4 fold greater than the spread of VZV-32.

Growth of VZV-MSP in the SCID-hu mouse. The SCID-hu mouse has provided the first reproducible animal model of VZV pathogenesis. Published studies have documented the pathology of viral infection in human thymus/liver and skin implants after inoculation with parental and vaccine Oka strains as well as low passage wild type virus (Moffat et al., *J. Virol.*, 69:5236–42 (1995), Moffat et al., *J. Virol.*, 72:965–974 (1998)). To assess whether VZV-MSP showed enhanced pathology in the SCID-hu mouse model, skin implants infected with VZV-MSP were harvested at 7, 14, and 21 days after infection. At 7 days post-infection, numerous foci of infection were visible in the epidermis of the human skin implant. By 14 days the foci coalesced into large necrotic lesions with histopathology typical of varicella vesicles. These vesicles were characterized by epidermal hyperplasia, balloon cells, and the separation of the keratin roof from the epidermis. After 21 days, the infection had spread into the dermis and destroyed the entire implant. Samples of the implants also were examined by previously described electron microscopy methods; the virion formation closely resembled that shown in FIG. 2 of the report by Moffat et al., (*J. Virol.*, 72:965–974 (1998)). Mock infected skin implants showed normal skin structure consisting of a thin layer of keratinocytes above the dermis and hair follicles.

Prior published studies had not shown such a rapid progression of pathology in the SCID-hu mouse infected with VZV. To further assess this aspect of VZV infection in the animal model, another experiment was performed with a clinical isolate passaged even fewer times than VZV-32; in addition, the low passage parent VZV-Oka strain was included. Again, the skin samples were collected and examined at days 7, 14, and 21 post-inoculation. When all the specimens were reviewed, the histopathology of the clinical isolate and parental VZV-Oka at 21 days post-inoculation were similar, and for both strains the histopathology was approaching that caused by VZV-MSP at 14 days post-inoculation. Even at 21 days, however, the former two viral strains never caused the total destruction seen after VZV-MSP infection. In short, the progression of VZV-MSP through the skin implant was noticeably more extensive than seen with other viral strains tested in the SCID-hu animal model.

Genetic analysis of other major glycoproteins of VZV-MSP. After documenting the enhanced cell-to-cell spread of VZV-MSP, it was determined whether mutations were present in ORFs other than gE that may be contributing to this phenotype. Specifically, ORFs 31, 37, 60, and 67 coding for VZV gB, gH, gL, and gI, respectively, were analyzed. The ORFs were amplified from the VZV-MSP viral genome and sequenced, then compared to the published VZV-Dumas sequence. Neither gI nor gL gene contained any nucleotide differences when compared to the nucleotide sequences of VZV-Dumas. Further, the gB sequence was identical to that of VZV-Dumas. However, VZV-MSP gH contained a single point mutation within codon 269 (CC̲A→CT̲A), converting a proline residue in the predicted VZV-Dumas peptide sequence to a leucine residue in VZV-MSP gH.

Given the presence of mutations within VZV-MSP gE and gH, a similar genetic analyses of VZV-32 was performed. As expected, VZV-32 lacked the D150N mutation within gE. VZV-32 gH, however, revealed the identical point mutation found within codon 269 of VZV-MSP gH. Thus, the mutation within VZV-MSP gH cannot account for the VZV-MSP cell-spread phenotype. VZV-32 contained one additional mutation within ORF 67 (gI) which would lead to a Q5H substitution (CA̲A̲→CA̲T̲). This substitution was within the probable leader sequence of VZV gI and thus would not be present in mature gI (Davison et al., *J. Gen. Virol.*, 67:1759–816 (1986)). Altogether, within five major glycoprotein ORFs, VZV-MSP contained two point mutations which caused amino acid substitutions when compared to VZV-Dumas: D150N in gE, and P269L in gH (FIG. 5).

In addition to 5 ORFs, we sequenced major portions of the 5' untranslated regions of ORFs 31, 60, 67 and 68. All regions were identical to VZV-Dumas except for that of ORF 60. The latter region contained four polymorphisms; these ranged from 554 to 1320 nucleotides from the ORF 60 initiation codon (FIG. 5). It is very unlikely that these polymorphisms will alter the expression of gL since they are located over 500 nucleotides upstream of the gL start site.

Genetic analysis of VZV-MSP regulatory proteins and kinases. Although viral glycoproteins are the most likely candidates for mediating the cell-to-cell spread phenotype of VZV-MSP, we considered the possibility that an alteration in immediate early (IE) regulatory events may contribute to this enhanced cell-to-cell spread phenotype. VZV expresses one predominant species, IE 62, which acts as the major regulatory protein for viral gene expression. This protein contains a potent acidic activation domain at its N-terminus and is a component of the virus particle. Therefore, the IE 62 gene of VZV-MSP was sequenced, but detected only one silent polymorphism within codon 30 when compared to the Dumas strain (GCG̲→GCC̲) (FIG. 5). Thus, the peptide sequence of VZV-MSP IE 62 was identical to the predicted VZV-Dumas sequence. Further, we sequenced the 5' untranslated region containing 525 nucleotides and this region was identical to VZV-Dumas. In addition, we sequenced the adjacent VZV-MSP ORF 61, which encodes the functional homolog of HSV-1 ICP0. Again, the nucleotide sequence was identical to VZV-Dumas.

Previous studies have shown that the viral protein kinase VZV ORF 47 can phosphorylate IE 62 (Ng, et al., 1994). Also, VZV ORF 66 encodes a protein kinase which has been shown to affect the intracellular localization and transactivation function of IE 62. Based upon these results, we wanted to determine whether mutations in these viral kinases could affect the function of IE 62 within VZV-MSP infected cells. Therefore, we sequenced both protein kinase genes within the VZV-MSP genome and found both to be identical to the prototype VZV-Dumas sequence (FIG. 5). Thus, there was no genetic evidence of polymorphisms within either of two regulatory ORFs or either of two viral protein kinase ORFs. In short, after sequence analysis of over 15% of the VZV-MSP genome, the main impression was a striking similarity with VZV-Dumas except for the notable exceptions mentioned earlier.

EXAMPLE 3

Single Nucleotide Polymorphisms in Major Open Reading Frames of Other Varicella Zoster Viruses Materials and Methods Viruses. VZV-MSP was isolated in Minnesota in late 1995. VZV-32 was isolated in Texas in the 1970s. VZV-Oka was isolated in Japan and attenuated in the 1970s. VZV-VSD was a wildtype virus collected in South Dakota in the 1980s. VZV-VIA was isolated in Iowa from a child with chickenpox in the 1990s. VZV-Iceland was isolated in Iceland from vesicle fluid of a child with chickenpox in the 1990s. VZV-Ellen was originally isolated in Georgia from a child with chickenpox in the 1960s and obtained from the American Type Culture Collection. VZV 80-2 was originally isolated in Pennsylvania from an adult with herpes zoster in the 1980s.

Propagation of viruses. All viral strains except VZV 80-2 virus were propagated in human melanoma cells (MeWo strain). Transfer of infectivity was performed by inoculation of trypsin dispersed infected cells onto an uninfected monolayer at a 1:8 ratio. Each 25 cm$^2$ VZV-infected monolayer was allowed to incubate until cytopathology reached 80%. The monolayer was then washed thrice with 5 ml of 0.01M phosphate buffered saline (PBS) of pH 7.4. Cells were dislodged by scraping into 0.5 ml PBS. Viral DNA was collected from the cells using the DNeasy Tissue Kit following the DNeasy Protocol for Cultured Animal Cells (Qiagen Inc). Collected DNA was cleaned by placing on a Microcon 50 filter and washing twice with 0.5 ml of Nanopure water. (Barnstead/Thermolyne). Viral DNA was resuspended in 100 µl of Nanopure water. The VZV 80-2 viral genome DNA was present in two cloned restriction enzyme libraries prepared by Ecker et al., (*Proc. Natl. Acad. Sci. USA*, 79:156–160 (1982)).

PCR amplification and sequencing of viral DNA. PCR amplification was performed with primers flanking the region of interest (Table 1). The Expand High Fidelity PCR System was used in the PCR amplification procedure (Roche Molecular Biochemicals). This system includes Taq DNA and Pwo DNA polymerases, with the 3'–5' proofreading activity of the Pwo DNA polymerase to increase the fidelity (Roche Molecular Biochemicals). Electrophoresis of each sample was carried out in a 1% agarose gel to determine concentration. The DNA sequencing reactions were performed using dye terminator cycle sequencing chemistry with AmpliTaq DNA polymerase, FS enzyme (PE Applied Biosystems, Foster City, Calif.). Reactions were run and subsequently analyzed with an Applied Biosystems Model 373A stretch fluorescent automated sequencer at the University of Iowa DNA Facility. Sequences were further analyzed using the program DNASIS V2.0 (Hitachi Software Engineering Co.). Any region of a VZV genome which differed in sequence from that of the prototypic VZV Dumas was re-amplified in a second PCR step and subjected to a second sequencing analysis.

Results

Polymorphisms in the VZV gE Gene

The VZV gE gene was of greatest interest because of the discovery of the gE mutant strain VZV-MSP. Surprisingly, six gE polymorphisms were found among the eight tested strains and isolates, four of which caused amino acid substitutions (FIG. 6). However, none of the tested strains contained the D150N mutation within the 3B3 epitope of VZV-MSP. VZV-Ellen, VZV-Iceland, and VZV 80-2 had three identical polymorphisms. One was a synonymous mutation within codon 220. Two non-synonymous mutations in these three strains caused amino acid substitutions within codons 40 (T→I) and 536 (L→I). The vaccine strain VZV-Oka also contained the mutation within codon 40, but lacked the other two mutations found within VZV-Ellen, VZV-Iceland, and VZV 80-2. VZV-VSD was the only strain tested which contained a polymorphism within the gE cytoplasmic domain of gE. Interestingly, this change within codon 603 (G→D) inserted an additional acidic amino acid adjacent to the acidic casein kinase II phosphorylation site of gE. VZV-32 and VZV-VIA were the only strains tested that did not contain gE substitutions when compared to the Dumas strain. Since the mutations previously found in VZV-MSP gE were not discovered in any other strain, VZV-MSP gE retained a unique sequence among all currently tested strains and isolates.

Polymorphisms in the VZV gI Gene

The discovery of several polymorphisms in the gE gene of the 8 strains was unexpected. Since VZV gE and gI proteins are commonly found in a complex in the infected cell culture, the gI gene was the next obvious candidate for further genetic analysis. Sequencing of ORF 67 led to the discovery of two changes from the published Dumas sequence (FIG. 7). VZV-32 had an A to C substitution at bp 15 of the ORF that resulted in a glutamine to histidine substitution. VZV Oka also had a silent change of G to A at bp 546. The number of gI sequence variants was less than that seen with gE and may suggest that gI function requires a more rigid amino acid sequence.

Polymorphisms in the VZV gH Gene

Next to the VZV gE:gI complex, the gH:gI complex has been most extensively studied because of its role in cell-to-cell fusion. Overall, the eight strains contained nine polymorphisms, three of which caused amino acid substitutions (FIG. 8). Again, VZV-Ellen, VZV-Iceland, and VZV 80-2 were remarkably similar, with identical changes within codons 76 (R→K) and 700 (R→K) as well as silent substitutions within codons 13, 676 and 727. VZV-Ellen possessed a unique polymorphism within codon 418 that allowed differentiation from VZV-Iceland and VZV 80-2. VZV-32 and VZV-VIA both contained a silent change within codon 815 not present in any other tested strain. VZV-MSP contained only the P269L polymorphism shared by seven strains, including VZV-32.

Polymorphisms in the VZV gL Gene

In a manner similar to gE and gI, gL is invariably linked with the gH protein in VZV-infected cultures. For this reason, the gL ORF was a another candidate gene for sequence analysis. The result was striking: only VZV-Oka gL gene differed from prototype Dumas gL gene (FIG. 9). The first change included the insertion of a methionine codon between amino acids 9 and 10. Secondly, there was a G to A substitution at bp 320 of VZV-Dumas that resulted in a glycine to aspartic acid change in the protein. The fact that the gL genes from the 7 other strains were identical to the prototype gL gene may suggest, as with the gI protein, that gL function requires a protein that is restricted in its genetic variability.

Polymorphisms in the VZV gB Gene

The gB gene is one of the most conserved genes among all herpesviruses. In the case of VZV, this protein is important in the infectious cycle of the virus, based on the previous evidence that addition of anti-gB monoclonal antibody to an infected culture inhibits the progression of infection (Montalvo et al., *J. Virol.*, 61:2877–2884 (1987)). Of the eight strains in which gB was sequenced, 7 were identical to the prototype Dumas gB gene. As with the gL gene, only the Oka gB gene was different from Dumas. The Oka gB had three alterations: an A to C change at bp 217, which led to an amino acid substitution of a threonine to a proline at residue 73; a G to T change at bp 391 resulting in a aspartic acid to a tyrosine substitution at amino acid 131; finally, a silent change of A to C at bp 294. In short, the sequence of gB was highly constrained.

Polymorphisms in the VZV IE62 Gene

The fact that polymorphisms were easily discernible in the major glycoprotein structural genes led to examining whether a similar situation existed in the major VZV regulatory gene called IE62. Overall, 38 polymorphisms were found in the IE 62 gene of the eight tested strains, when compared to the VZV-Dumas IE 62 gene (FIG. 10). As was the case with the gE and gH gene sequences, VZV-Ellen, VZV-Iceland, and VZV 80-2 showed remarkable similarity in their IE 62 genes. Identical silent substitutions within IE 62 were present in these strains at codons 61, 129, and 1071. Also, these three strains contained an identical polymorphism at codon 703 (V→A). VZV-Oka was similar to these three strains, as it shared the silent IE 62 substitutions within codons 61 and 129, but lacked the change at codon 1071. VZV-Oka shared additional polymorphisms with VZV-Ellen at codons 341 and 958 (R→G) that were not present in VZV-Iceland and VZV 80-2. VZV-Ellen revealed nine unique substitutions in addition to those shared with VZV-Iceland, VZV 80-2 and VZV-Oka.

VZV-32 and VZV-VIA both contained identical polymorphisms within IE 62 at codons 516, 1057 (Q→R), 1072 (Q→R), 1080, and 1241. VZV-32 also contained five unique changes as well as containing the R958G mutation found in VZV-Ellen and VZV-Oka. VZV-VIA revealed four unique polymorphisms, which combined with the unique changes within VZV-32 allow differentiation of VZV-32 and VZV-VIA. VZV-VSD contained one unique substitution (A→V at codon 602) but otherwise was identical to the Dumas strain. Overall, numerous mutations were found within IE 62 among the tested VZV strains. However, VZV-MSP IE 62 contained no polymorphisms, other than the synonymous substitution found within codon 30, when compared to the Dumas strain. Thus, there was no genetic evidence that IE62 contributed to the VZV-MSP phenotype Polymorphisms in the VZV Protein Kinase Gene The VZV genome encodes at least two putative protein kinases, one in the UL region (ORF 47) and the second in the US region of the genome (ORF 66). The ORF 47 kinase is known to phosphorylate the IE62 gene product. Sequencing of the ORF47 protein revealed two variations from Dumas. VZV Ellen, Oka and Iceland shared a silent A to G transition at nucleotide 1449. VZV Ellen had a unique transversion of T to C at nucleotide 913, which caused an amino acid change from serine to proline. The VZV 80-2 gene 47 was not sequenced because neither cloned VZV DNA library contained a complete ORF (Ecker et al., *Proc. Natl. Acad. Sci. USA*, 79:156–160 (1982)).

Transitions Versus Transversions

Mutations that result in the substitution of a pyrimidine for a pyrimidine or a purine for a purine are called transitions. Substitutions of a purine for a pyrimidine and vice versa are transversions. Transversions are much less common than transitions in the human genome. When the number of transitions and transversions were counted for the sequenced VZV genes, 78% were transitions. Interestingly, all three substitutions in gB were transversions. This result was in contrast with the other genes. The gE gene had 1 transversion and 5 transitions. The gH gene had 3 transversions and 6 transitions. The gI gene had 1 transversion and 1 transition. The gL gene had 6 transitions. The ORF 47 gene had 2 transitions. The IE62 gene had 5 transversions and 33 transitions. Even though there were many polymorphisms in some IE62 genes, the fact that the IE62 gene of the VZV-MSP strain differed by only one transversion from VZV-Dumas should be noted.

The complete disclosure of all patents, patent applications, and publications, and electronically available material (e.g., GenBank amino acid and nucleotide sequence submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

| Sequence Listing Free Text | |
|---|---|
| SEQ ID NOs:1–71 | Oligonucleotide primer |
| SEQ ID NO:75 | Portion of polypeptide encoded by VZV-MSP ORF68 |

What is claimed is:

1. A method for detecting antibodies that specifically bind to a varicella zoster polypeptide, the method comprising:

contacting a biological sample with a preparation to form a mixture, wherein the biological sample comprises an antibody and the preparation comprises a varicella zoster polypeptide that is encoded by a polymorphism of ORF68 and that is not bound by monoclonal antibody 3B3;

incubating the mixture under conditions to allow the antibody to specifically bind the polypeptide to form a polypeptide:antibody complex; and detecting the presence or absence of the polypeptide:antibody complex, wherein detecting the polypeptide:antibody complex indicates the presence of antibodies that specifically bind to a varicella zoster polypeptide.

2. The method of claim 1 wherein the preparation comprises whole varicella zoster virus that expresses the varicella zoster polypeptide.

3. The method of claim 2 wherein the whole varicella zoster virus is VZV-MSP.

4. The method of claim 1 wherein the varicella zoster polypeptide in the preparation is an isolated varicella zoster polypeptide or fragment thereof.

5. The method of claim 1 wherein the biological sample is selected from the group consisting of blood, vesicle fluid, bone marrow, brain tissue, and combinations thereof.

6. The method of claim 1 wherein the varicella zoster polypeptide is encoded by a nucleotide sequence corresponding to nucleotides 115,808 to 117,679 of SEQ ID NO: 76, wherein the nucleotide at position 116,255 is an adenine.

7. The method of claim 2 wherein the whole varicella zoster virus is a modified varicella zoster virus, the virus having the ATCC designation VR-795 wherein the nucleotide sequence of the virus comprises a polymorphism of ORF68.

8. A kit for detecting antibodies that specifically bind to a varicella zoster polypeptide comprising a whole varicella zoster virus of claim 2.

* * * * *

UNITED STATES PATENT AND TRADEMARK OFFICE
CERTIFICATE OF CORRECTION

| | | |
|---|---|---|
| PATENT NO. | : 6,843,997 B2 | Page 1 of 2 |
| APPLICATION NO. | : 10/288823 | |
| DATED | : January 18, 2005 | |
| INVENTOR(S) | : Charles F. Grose et al. | |

It is certified that error appears in the above-identified patent and that said Letters Patent is hereby corrected as shown below:

On The Title Page Item (56), delete "6,087,170 A 7/2000 Kemble" and insert -- 6,087,170 A 6/2000 Kemble --; and On The Title Page Item (56) Other Publications (first column), delete "ATCC CCL-171, "Homo sapiens (human," [online]. Retrieved on May 16, 2001. Retrieved from the Internet; <URL:http://phage.atcc.org/cgi-bin/searchengine/longview.cgi!view=ce, 317407, CCL-171&ctext-CCL.-1,3 pages." and insert -- ATCC CCL-171, "Homo sapiens (human," [online]. Retrieved on May 16, 2001. Retrieved from the Internet; <URL:http://phage.atcc.org/cgi-bin/searchengine/longview.cgi?view=ce, 317407, CCL-171&text-CCL.-1,3 pages. --; and On The Title Page Item (56), under Other Publications (second column), delete "ATCC VR-586, "Variella-Zoster," [online]. Retrieved on June 5, 2001. Retrieved from the Internet <URL:http//phage.atcc.org/cgi-bin/searchengine/longview.cgi!view-av, 343894, VR-586&text=VR-586>, 2 pages." and insert -- ATCC VR-586, "Varicella-Zoster," [online]. Retrieved on June 5, 2001. Retrieved from the Internet <URL:http//phage.atcc.org/cgi-bin/searchengine/longview.cgi?view-av, 343894, VR-586&text=VR-586>, 2 pages. --; and On The Title Page Item (56), under Other Publications (second column), delete "ATCC VR-785, "Varicella-Zoster deposited as Varicella," [online]. Retrieved on May 16, 2001. Retrieved from the Internet:<URL:Http://phage.atcc.org/cgi-bin/searchengine/longview.cgi!view-av,476976, VR-795&text=VR-7.9>, 2 pages." and insert -- ATCC VR-785, "Varicella-Zoster deposited as Varicella," [online]. Retrieved on May 16, 2001. Retrieved from the Internet:<URL:Http://phage.atcc.org/cgi-bin/searchengine/longview.cgi?view-av,476976,VR-795&text=VR-7.9>, 2 pages. --; and On The Title Page, Item (56) under Other Publications (second column), delete "ATCC VR-916, "Varicella-Zoster deposited as Varicella," [online]. Retrieved on Sept. 6, 200. Retrieved from the Internet:<URL:Http://phage.atcc.org/cgi-bin/searchengine/longview.cgi!view-av,554286&text=varicella>, 1 page." and insert -- ATCC VR-916, "Varicella-Zoster deposited as Varicella," [online]. Retrieved on Sept. 6, 200. Retrieved from the Internet:<URL:Http://phage.atcc.org/cgi-bin/searchengine/longview.cgi?view-av,554286&text=varicella>, 1 page. -- and

UNITED STATES PATENT AND TRADEMARK OFFICE
CERTIFICATE OF CORRECTION

PATENT NO. : 6,843,997 B2
APPLICATION NO. : 10/288823
DATED : January 18, 2005
INVENTOR(S) : Charles F. Grose et al.

It is certified that error appears in the above-identified patent and that said Letters Patent is hereby corrected as shown below:

On The Title Page Item (56) under Other Publications (second column), delete "ATCC VR-1367, "Varicella-Zoster," [online]. Retrieved on June 5, 2001. Retrieved from the Internet: <URL:http://phage/atcc/org/cgi-bin/searchengine/longview.cgi!view=av, 871705, VR1367&text= VR-1367>, 2 pages." and insert -- ATCC VR-1367, "Varicella-Zoster," [online]. Retrieved on June 5, 2001. Retrieved from the Internet: <URL:http://phage/atcc/org/cgi-bin/searchengine/longview.cgi?view=av, 871705, VR-1367&text= VR-1367>, 2 pages. --; and On The Title Page, Item (56) Pg 2 under Other Publications (first column), delete "P. LaRussa et al., "Restriction fragment length polymorphism of polymerase chain reaction products from vaccine and wild-type varicella-zoster virus isolates," *J. Virol. 66*, 1016-1020 (1922)." and insert -- P. LaRussa et al., "Restriction fragment length polymorphism of polymerase chain reaction products from vaccine and wild-type varicella-zoster virus isolates," *J. Virol. 66*, 1016-1020 (1992). --; and On The Title Page Pg 2 Item (56) Other Publications (second column), delete "National Center for Biotechnology Information, National Library of Medicine, National Institutes of Health, Genbank X04370. Accession Number X04370 M14891 M16612, "The complete DNA sequence of varicella-zoster virus," [online]. J. Gen. Virol. 67(Pt 9) 1759-1816 (1986), [retrieved on May 29, 2001]. Retrieved from the Internet:<URL:http://www.ncbi.nlm.nih.gov/entrez/query.fgci!cmd=Retrieve&db=Nuceloti de&list uids=599.8=Genbank>, 39 pages." and insert -- National Center for Biotechnology Information, National Library of Medicine, National Institutes of Health, Genbank X04370. Accession Number X04370 M14891 M16612, "The complete DNA sequence of varicella-zoster virus," [online]. J. Gen. Virol. 67(Pt 9) 1759-1816 (1986), [retrieved on May 29, 2001]. Retrieved from the Internet<URL:http://www.ncbi.nlm.nih.gov/entrez/query.fgci?cmd=Retrieve&db=Nucelot ide&list uids=599.8=Genbank>, 39 pages. --.

Signed and Sealed this

Twentieth Day of November, 2007

JON W. DUDAS
*Director of the United States Patent and Trademark Office*

SEQUENCE LISTING

<160> NUMBER OF SEQ ID NOS: 80

<210> SEQ ID NO 1
<211> LENGTH: 29
<212> TYPE: DNA
<213> ORGANISM: ARTIFICIAL
<220> FEATURE:
<223> OTHER INFORMATION: Oligonucleotide primer

```
-continued

<400> SEQUENCE: 1
cgatgacaga cataaaattg taaatgtga                                29

<210> SEQ ID NO 2
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 2
cacccaagta ttgtttttct gtccg                                    25

<210> SEQ ID NO 3
<211> LENGTH: 29
<212> TYPE: DNA
<213> ORGANISM: ARTIFICIAL
<220> FEATURE:
<223> OTHER INFORMATION: Oligonucleotide primer

<400> SEQUENCE: 3
cgatgacaga cataaaattg taaatgtgg                                29

<210> SEQ ID NO 4
<211> LENGTH: 35
<212> TYPE: DNA
<213> ORGANISM: ARTIFICIAL
<220> FEATURE:
<223> OTHER INFORMATION: Oligonucleotide primer

<400> SEQUENCE: 4
catactgtgt cgaccaaagg caatacggtg acgtg                         35

<210> SEQ ID NO 5
<211> LENGTH: 35
<212> TYPE: DNA
<213> ORGANISM: ARTIFICIAL
<220> FEATURE:
<223> OTHER INFORMATION: Oligonucleotide primer

<400> SEQUENCE: 5
ttgcctttgg tcgacacagt atgcgattgt gatag                         35

<210> SEQ ID NO 6
<211> LENGTH: 37
<212> TYPE: DNA
<213> ORGANISM: ARTIFICIAL
<220> FEATURE:
<223> OTHER INFORMATION: Oligonucleotide primer

<400> SEQUENCE: 6
cgacccgggg agctcccatg gggacagtta ataaacc                       37

<210> SEQ ID NO 7
<211> LENGTH: 46
<212> TYPE: DNA
<213> ORGANISM: ARTIFICIAL
<220> FEATURE:
<223> OTHER INFORMATION: Oligonucleotide primer

<400> SEQUENCE: 7
cgctctagaa ctagtggatc ccccggggaa tttgtcacag gctttt             46

<210> SEQ ID NO 8
<211> LENGTH: 28
```

```
<212> TYPE: DNA
<213> ORGANISM: ARTIFICIAL
<220> FEATURE:
<223> OTHER INFORMATION: Oligonucleotide primer

<400> SEQUENCE: 8
ggcgttttca taacctccgt tacgggggg                                          28

<210> SEQ ID NO 9
<211> LENGTH: 28
<212> TYPE: DNA
<213> ORGANISM: ARTIFICIAL
<220> FEATURE:
<223> OTHER INFORMATION: Oligonucleotide primer

<400> SEQUENCE: 9
ccctgtgatg cgtaatggag acacatga                                           28

<210> SEQ ID NO 10
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 10
ctttgtaata taccgtcgcc                                                    20

<210> SEQ ID NO 11
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 11
cgtacgatta gaaccaactc                                                    20

<210> SEQ ID NO 12
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 12
ggcatactac caatgacacg                                                    20

<210> SEQ ID NO 13
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 13
agtggcgtga ggttgaagac                                                    20

<210> SEQ ID NO 14
<211> LENGTH: 20
<212> TYPE: DNA
<213> ORGANISM: ARTIFICIAL
<220> FEATURE:
<223> OTHER INFORMATION: Oligonucleotide primer
```

```
<400> SEQUENCE: 14
cacccgactc gaaataccag                                            20

<210> SEQ ID NO 15
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 15
tctggtagta ctacgcgttg                                            20

<210> SEQ ID NO 16
<211> LENGTH: 23
<212> TYPE: DNA
<213> ORGANISM: ARTIFICIAL
<220> FEATURE:
<223> OTHER INFORMATION: Oligonucleotide primer

<400> SEQUENCE: 16
gactacagtg aaattcaacg ccg                                        23

<210> SEQ ID NO 17
<211> LENGTH: 21
<212> TYPE: DNA
<213> ORGANISM: ARTIFICIAL
<220> FEATURE:
<223> OTHER INFORMATION: Oligonucleotide primer

<400> SEQUENCE: 17
cccgatgaag gcattatatc c                                          21

<210> SEQ ID NO 18
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 18
tagctggcac cacgacgagg                                            20

<210> SEQ ID NO 19
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 19
tgcgaacacg ggagtatcct                                            20

<210> SEQ ID NO 20
<211> LENGTH: 28
<212> TYPE: DNA
<213> ORGANISM: ARTIFICIAL
<220> FEATURE:
<223> OTHER INFORMATION: Oligonucleotide primer

<400> SEQUENCE: 20
ctgctcttct acgagaatat tccgaccg                                   28

<210> SEQ ID NO 21
<211> LENGTH: 25
```

-continued

<210> SEQ ID NO 21
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 21
cgtgttttct atcatttccc cagtg					25

<210> SEQ ID NO 22
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 22
actacgttcc caccaaaccc ccttg					25

<210> SEQ ID NO 23
<211> LENGTH: 24
<212> TYPE: DNA
<213> ORGANISM: ARTIFICIAL
<220> FEATURE:
<223> OTHER INFORMATION: Oligonucleotide primer

<400> SEQUENCE: 23
gcggttacaa gcgacaccac atgg					24

<210> SEQ ID NO 24
<211> LENGTH: 27
<212> TYPE: DNA
<213> ORGANISM: ARTIFICIAL
<220> FEATURE:
<223> OTHER INFORMATION: Oligonucleotide primer

<400> SEQUENCE: 24
ctgttagatg agatcgtaga tgttcag					27

<210> SEQ ID NO 25
<211> LENGTH: 18
<212> TYPE: DNA
<213> ORGANISM: ARTIFICIAL
<220> FEATURE:
<223> OTHER INFORMATION: Oligonucleotide primer

<400> SEQUENCE: 25
gctacagaga ggcaggct					18

<210> SEQ ID NO 26
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 26
ttgcataccc aactagacga atctg					25

<210> SEQ ID NO 27
<211> LENGTH: 24
<212> TYPE: DNA
<213> ORGANISM: ARTIFICIAL
<220> FEATURE:
<223> OTHER INFORMATION: Oligonucleotide primer

```
<400> SEQUENCE: 27
tagagacggt cgcactgccc catc                                      24

<210> SEQ ID NO 28
<211> LENGTH: 27
<212> TYPE: DNA
<213> ORGANISM: ARTIFICIAL
<220> FEATURE:
<223> OTHER INFORMATION: Oligonucleotide primer

<400> SEQUENCE: 28
cggtgatatt gtagcgcaag taacagc                                   27

<210> SEQ ID NO 29
<211> LENGTH: 26
<212> TYPE: DNA
<213> ORGANISM: ARTIFICIAL
<220> FEATURE:
<223> OTHER INFORMATION: Oligonucleotide primer

<400> SEQUENCE: 29
cccaaaggta gtgtgtatta ttcgcg                                    26

<210> SEQ ID NO 30
<211> LENGTH: 18
<212> TYPE: DNA
<213> ORGANISM: ARTIFICIAL
<220> FEATURE:
<223> OTHER INFORMATION: Oligonucleotide primer

<400> SEQUENCE: 30
cgtctccttc gtgtgttg                                             18

<210> SEQ ID NO 31
<211> LENGTH: 18
<212> TYPE: DNA
<213> ORGANISM: ARTIFICIAL
<220> FEATURE:
<223> OTHER INFORMATION: Oligonucleotide primer

<400> SEQUENCE: 31
atccaaactc tcttcggg                                             18

<210> SEQ ID NO 32
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 32
tcgcccccgt ggttagatac                                           20

<210> SEQ ID NO 33
<211> LENGTH: 19
<212> TYPE: DNA
<213> ORGANISM: ARTIFICIAL
<220> FEATURE:
<223> OTHER INFORMATION: Oligonucleotide primer

<400> SEQUENCE: 33
gcatgttgaa gccgtagca                                            19

<210> SEQ ID NO 34
<211> LENGTH: 19
```

```
<212> TYPE: DNA
<213> ORGANISM: ARTIFICIAL
<220> FEATURE:
<223> OTHER INFORMATION: Oligonucleotide primer

<400> SEQUENCE: 34
atgcgcggct ccgatggta                                              19

<210> SEQ ID NO 35
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 35
ggccttgggg ttttggatta                                             20

<210> SEQ ID NO 36
<211> LENGTH: 22
<212> TYPE: DNA
<213> ORGANISM: ARTIFICIAL
<220> FEATURE:
<223> OTHER INFORMATION: Oligonucleotide primer

<400> SEQUENCE: 36
gtccatggtt ttagacctcg gg                                          22

<210> SEQ ID NO 37
<211> LENGTH: 19
<212> TYPE: DNA
<213> ORGANISM: ARTIFICIAL
<220> FEATURE:
<223> OTHER INFORMATION: Oligonucleotide primer

<400> SEQUENCE: 37
gtttacttta cgcgcaccg                                              19

<210> SEQ ID NO 38
<211> LENGTH: 18
<212> TYPE: DNA
<213> ORGANISM: ARTIFICIAL
<220> FEATURE:
<223> OTHER INFORMATION: Oligonucleotide primer

<400> SEQUENCE: 38
gaattagacc cccccgag                                               18

<210> SEQ ID NO 39
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 39
tagagtggtt gtatgtcccc                                             20

<210> SEQ ID NO 40
<211> LENGTH: 19
<212> TYPE: DNA
<213> ORGANISM: ARTIFICIAL
<220> FEATURE:
<223> OTHER INFORMATION: Oligonucleotide primer
```

```
<400> SEQUENCE: 40
cacttctacg atatgccgc                                              19

<210> SEQ ID NO 41
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 41
ttcaatctcg gggggtcta                                              20

<210> SEQ ID NO 42
<211> LENGTH: 19
<212> TYPE: DNA
<213> ORGANISM: ARTIFICIAL
<220> FEATURE:
<223> OTHER INFORMATION: Oligonucleotide primer

<400> SEQUENCE: 42
tccgtagatt ccgagtcct                                              19

<210> SEQ ID NO 43
<211> LENGTH: 24
<212> TYPE: DNA
<213> ORGANISM: ARTIFICIAL
<220> FEATURE:
<223> OTHER INFORMATION: Oligonucleotide primer

<400> SEQUENCE: 43
caagcgccat ggcatcacat aaat                                        24

<210> SEQ ID NO 44
<211> LENGTH: 27
<212> TYPE: DNA
<213> ORGANISM: ARTIFICIAL
<220> FEATURE:
<223> OTHER INFORMATION: Oligonucleotide primer

<400> SEQUENCE: 44
aaacactagt ccatgtgcat gtcccgc                                     27

<210> SEQ ID NO 45
<211> LENGTH: 19
<212> TYPE: DNA
<213> ORGANISM: ARTIFICIAL
<220> FEATURE:
<223> OTHER INFORMATION: Oligonucleotide primer

<400> SEQUENCE: 45
gcttgcgggt tttttggt                                               19

<210> SEQ ID NO 46
<211> LENGTH: 19
<212> TYPE: DNA
<213> ORGANISM: ARTIFICIAL
<220> FEATURE:
<223> OTHER INFORMATION: Oligonucleotide primer

<400> SEQUENCE: 46
gccagcccct ttaaggtga                                              19

<210> SEQ ID NO 47
<211> LENGTH: 22
```

-continued

<210> SEQ ID NO 47
<211> LENGTH: 22
<212> TYPE: DNA
<213> ORGANISM: ARTIFICIAL
<220> FEATURE:
<223> OTHER INFORMATION: Oligonucleotide primer

<400> SEQUENCE: 47
gccaatgaaa tgaaactatc gg                                    22

<210> SEQ ID NO 48
<211> LENGTH: 28
<212> TYPE: DNA
<213> ORGANISM: ARTIFICIAL
<220> FEATURE:
<223> OTHER INFORMATION: Oligonucleotide primer

<400> SEQUENCE: 48
cggctcacag agctgctctt cggtgtag                              28

<210> SEQ ID NO 49
<211> LENGTH: 28
<212> TYPE: DNA
<213> ORGANISM: ARTIFICIAL
<220> FEATURE:
<223> OTHER INFORMATION: Oligonucleotide primer

<400> SEQUENCE: 49
taatccttcc cctcatatca caacgcgt                              28

<210> SEQ ID NO 50
<211> LENGTH: 18
<212> TYPE: DNA
<213> ORGANISM: ARTIFICIAL
<220> FEATURE:
<223> OTHER INFORMATION: Oligonucleotide primer

<400> SEQUENCE: 50
gcggcctcca acatcaca                                         18

<210> SEQ ID NO 51
<211> LENGTH: 19
<212> TYPE: DNA
<213> ORGANISM: ARTIFICIAL
<220> FEATURE:
<223> OTHER INFORMATION: Oligonucleotide primer

<400> SEQUENCE: 51
ccagcatccg gctctgttg                                        19

<210> SEQ ID NO 52
<211> LENGTH: 24
<212> TYPE: DNA
<213> ORGANISM: ARTIFICIAL
<220> FEATURE:
<223> OTHER INFORMATION: Oligonucleotide primer

<400> SEQUENCE: 52
cgtgtaggta caaacattcg tggc                                  24

<210> SEQ ID NO 53
<211> LENGTH: 30
<212> TYPE: DNA
<213> ORGANISM: ARTIFICIAL
<220> FEATURE:
<223> OTHER INFORMATION: Oligonucleotide primer

```
<400> SEQUENCE: 53
atctaatccg tggggtgcg agtgtacaag                                30

<210> SEQ ID NO 54
<211> LENGTH: 31
<212> TYPE: DNA
<213> ORGANISM: ARTIFICIAL
<220> FEATURE:
<223> OTHER INFORMATION: Oligonucleotide primer

<400> SEQUENCE: 54
tccatgttcg gtgatgtctt ctgtaggcgt g                             31

<210> SEQ ID NO 55
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 55
ggatgctgac gacacacccc                                          20

<210> SEQ ID NO 56
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 56
gttgcagttg acggattggc                                          20

<210> SEQ ID NO 57
<211> LENGTH: 20
<212> TYPE: DNA
<213> ORGANISM: ARTIFICIAL
<220> FEATURE:
<223> OTHER INFORMATION: Oligonucleotide primer
<400> SEQUENCE: 57
ttgtacccat cttcacgctc                                          20

<210> SEQ ID NO 58
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 58
atcgaacgtg cggcctgacc                                          20

<210> SEQ ID NO 59
<211> LENGTH: 20
<212> TYPE: DNA
<213> ORGANISM: ARTIFICIAL
<220> FEATURE:
<223> OTHER INFORMATION: Oligonucleotide primer

<400> SEQUENCE: 59
cttcccggac aactgcccat                                          20

<210> SEQ ID NO 60
<211> LENGTH: 30
```

-continued

<210> SEQ ID NO 60
<211> LENGTH: 30
<212> TYPE: DNA
<213> ORGANISM: ARTIFICIAL
<220> FEATURE:
<223> OTHER INFORMATION: Oligonucleotide primer

<400> SEQUENCE: 60
caccaaccgc aatcgcaatc ctttgaaggc                              30

<210> SEQ ID NO 61
<211> LENGTH: 30
<212> TYPE: DNA
<213> ORGANISM: ARTIFICIAL
<220> FEATURE:
<223> OTHER INFORMATION: Oligonucleotide primer

<400> SEQUENCE: 61
tattaacaac aaacagtccg cgcgccagtg                              30

<210> SEQ ID NO 62
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 62
gccgaggtct tccacacccg attct                                   25

<210> SEQ ID NO 63
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 63
tttgaaggtt aaggtcccac tcccg                                   25

<210> SEQ ID NO 64
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 64
tacaggcagc aggtccggac gcgaa                                   25

<210> SEQ ID NO 65
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 65
ttacgaggcc tcaacggaac ccgtg                                   25

<210> SEQ ID NO 66
<211> LENGTH: 25
<212> TYPE: DNA
<213> ORGANISM: ARTIFICIAL
<220> FEATURE:
<223> OTHER INFORMATION: Oligonucleotide primer -continued

```
<210> SEQ ID NO 67
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 67
caaggcgtac tgtaccccccg aaacc                                        25

<210> SEQ ID NO 68
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 68
actcatgcct gggccgggaa ctgga                                         25

<210> SEQ ID NO 69
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 69
cgtcgcatac accgtgtgta cccgc                                         25

<210> SEQ ID NO 70
<211> LENGTH: 25
<212> TYPE: DNA
<213> ORGANISM: ARTIFICIAL
<220> FEATURE:
<223> OTHER INFORMATION: Oligonucleotide primer

<400> SEQUENCE: 70
tgccctcccc ccgattccca gagta                                         25

<210> SEQ ID NO 71
<211> LENGTH: 22
<212> TYPE: DNA
<213> ORGANISM: ARTIFICIAL
<220> FEATURE:
<223> OTHER INFORMATION: Oligonucleotide primer

<400> SEQUENCE: 71
aagctccaag tctcggtgta cc                                            22

<210> SEQ ID NO 72
<211> LENGTH: 350
<212> TYPE: PRT
<213> ORGANISM: VARICELLA ZOSTER

<400> SEQUENCE: 72

Met Gly Thr Val Asn Lys Pro Val Val Gly Val Leu Met Gly Phe Gly
 1               5                  10                  15

Ile Ile Thr Gly Thr Leu Arg Ile Thr Asn Pro Val Arg Ala Ser Val
            20                  25                  30
```

-continued

```
Leu Arg Tyr Asp Asp Phe His Thr Asp Glu Asp Lys Leu Asp Thr Asn
        35                  40                  45
Ser Val Tyr Glu Pro Tyr Tyr His Ser Asp His Ala Glu Ser Ser Trp
 50                  55                  60
Val Asn Arg Gly Glu Ser Ser Arg Lys Ala Tyr Asp His Asn Ser Pro
 65                  70                  75                  80
Tyr Ile Trp Pro Arg Asn Asp Tyr Asp Gly Phe Leu Glu Asn Ala His
                 85                  90                  95
Glu His His Gly Val Tyr Asn Gln Gly Arg Gly Ile Asp Ser Gly Glu
            100                 105                 110
Arg Leu Met Gln Pro Thr Gln Met Ser Ala Gln Glu Asp Leu Gly Asp
            115                 120                 125
Asp Thr Gly Ile His Val Ile Pro Thr Leu Asn Gly Asp Asp Arg His
130                 135                 140
Lys Ile Val Asn Val Asp Gln Arg Gln Tyr Gly Asp Val Phe Lys Gly
145                 150                 155                 160
Asp Leu Asn Pro Lys Pro Gln Gly Gln Arg Leu Ile Glu Val Ser Val
                165                 170                 175
Glu Glu Asn His Pro Phe Thr Leu Arg Ala Pro Ile Gln Arg Ile Tyr
            180                 185                 190
Gly Val Arg Tyr Thr Glu Thr Trp Ser Phe Leu Pro Ser Leu Thr Cys
            195                 200                 205
Thr Gly Asp Ala Ala Pro Ala Ile Gln His Ile Cys Leu Lys His Thr
            210                 215                 220
Thr Cys Phe Gln Asp Val Val Val Asp Val Asp Cys Ala Glu Asn Thr
225                 230                 235                 240
Lys Glu Asp Gln Leu Ala Glu Ile Ser Tyr Arg Phe Gln Gly Lys Lys
                245                 250                 255
Glu Ala Asp Gln Pro Trp Ile Val Val Asn Thr Ser Thr Leu Phe Asp
            260                 265                 270
Glu Leu Glu Leu Asp Pro Pro Glu Ile Glu Pro Gly Val Leu Lys Val
            275                 280                 285
Leu Arg Thr Glu Lys Gln Tyr Leu Gly Val Tyr Ile Trp Asn Met Arg
            290                 295                 300
Gly Ser Asp Gly Thr Ser Thr Tyr Ala Thr Phe Leu Val Thr Trp Lys
305                 310                 315                 320
Gly Asp Glu Lys Thr Arg Asn Pro Thr Pro Ala Val Thr Pro Gln Pro
                325                 330                 335
Arg Gly Ala Glu Phe His Met Trp Asn Tyr His Ser His Val
            340                 345                 350

<210> SEQ ID NO 73
<211> LENGTH: 13
<212> TYPE: PRT
<213> ORGANISM: VARICELLA ZOSTER

<400> SEQUENCE: 73

Val Asp Gln Arg Gln Tyr Gly Asp Val Phe Lys Gly Asp
1               5                   10

<210> SEQ ID NO 74
<211> LENGTH: 39
<212> TYPE: DNA
<213> ORGANISM: VARICELLA ZOSTER
```

```
<400> SEQUENCE: 74
gtggaccaac gtcaatacgg tgacgtgttt aaaggagat                              39

<210> SEQ ID NO 75
<211> LENGTH: 39
<212> TYPE: DNA
<213> ORGANISM: VARICELLA ZOSTER

<400> SEQUENCE: 75
gtgaaccaac gtcaatacgg tgacgtgttt aaaggagat                              39

<210> SEQ ID NO 76
<211> LENGTH: 124884
<212> TYPE: DNA
<213> ORGANISM: Varicella zoster

<400> SEQUENCE: 76
aggccagccc tctcgcggcc ccctcgagag agaaaaaaaa aagcgacccc acctccccgc       60
gcgtttgcgg ggcgaccatc gggggggatg ggatttttg ccgggaaacc ccccccgcc        120
agcctttaac aaaacccgcg ccttttgcgt ccaccctcg tttactgctc ggatggcgac       180
cgtgcactac tcccgccgac ctgggacccc gccggtcacc ctcacgtcgt cccccagcat      240
ggatgacgtt gcgaccccca tccctacct acccacatac gccgaggccg tgcagacgc        300
gccccccct tacagaagcc gcgagagtct ggtgttctcc ccgcctcttt ttcctcacgt       360
ggagaatggc accacccaac agtcttacga ttgcctagac tgcgcttatg atggaatcca      420
cagacttcag ctggctttc taagaattcg caaatgctgt gtaccggctt ttttaattct      480
ttttggtatt ctcacccta ctgctgtcgt ggtcgccatt gttgccgttt ttcccgagga      540
acctcccaac tcaactacat gaaactactg tccggaaggg gaaggtattt attctcgctt      600
gcagcttgtc gcgcgtgtat gcacaacaaa agctatatat gtcaccaaag ccaacgtcgc      660
catctggagt actacaccca gtacgttgca taacctgtcc atttgcattt tcagttgcgc      720
ggacgccttt ctccgggatc gtggccttgg gacatcaacc agtggaataa gaaccgccgg      780
tggtcttgtt tgaacgacga gtggcgacgc gttgttctgc ataagctctg tatgctgata      840
cataaacaca gagtctgtat cgctatcaga ttcccgaaca ccttccggta ccccatactc      900
cgatacactg gacattgcgg atcccaaaaa tataatatta acaggattg cttatacttt       960
gctacagctt atataaattt atgtgcgata catcttaagt gcatccgtac gttatttata     1020
cattgcctgt cacgtgaaaa gactgtgtta cccaataaag gttctacaaa aaatgcttta     1080
ttgggtgttt gtttaatagc tattatcgta acccacccc gtaaaatcat aaaatgcatg      1140
taatttctga cacttgca tatgggcatg ttcccgcatt tattatgggc tccactctgg       1200
tgcgtcccag tttaaacgcc accgccgagg aaaatcccgc gtcagaaacg cgatgtttat     1260
tacgagtgct tgcggggaga actgtagacc tgccaggcgg aggaacgtta cacattacct     1320
gtaccaaaac ctatgtaatt attggcaaat atagcaaacc cggcgaacgt cttagccttg     1380
cccgtctaat agggcgtgca atgacgcctg gaggtgcaag gacatttatt attttggcga     1440
tgaaggaaaa gcgatccaca acgcttgggt atgaatgtgg tacgggcttg catttactgg     1500
ctccatctat gggtacattt tccgcacac acgttaag taacagagat ctctgtttat        1560
ggcggggtaa tatttatgat atgcatatgc aacgtcttat gttttgggag aatatcgcgc     1620
aaaataccac tgaaacacct tgtataacgt cgacgttaac atgcaacttg acagaagact     1680
ctggtgaagc cgcacttacc acgtcagacc gacccactct cccaacccta acagcccaag     1740
```

```
gaagaccaac agtttccaac attcgtggaa tattgaaagg atccccccgt caacagccgg    1800
tctgtcaccg ggttagattt gccgaaccta cggagggcgt attgatgtaa tcactaaata    1860
aaatacacct tttttcgatt gtacgtattt ttatttaaat gtgtagttca tagtccgccg    1920
acagccgctc gggcttttcc cccacataca acatgatcgt atgcctcgga tgcaccggtc    1980
caacactccg ccgagaaggg ggatttacaa tgacagtgat acccaatagc cgccagatgt    2040
acacccagct gtccggactc cagcatcatc tgctgagttg cggcgctgaa gggtgcatcg    2100 cataggggtgt tataattagc catttccggt aacagtcgtt gggaatttag gaggctgcaa    2160
aacggctgta ggtcaacata cattgggggat tcagatggtt tatctcgacg tccaagtcca    2220
atcaaaaaag cgtgtaaatc atcagcccgg ccgcatgttg ctcgaagagc ataaccctc    2280 ttaacaccgt acagagggga tggcgtcggt gcatgtgagt tggcagggca tgtccacgtt    2340
gtttccaacg ccagtggcgg tataacttgt gtaaacgacg ccaacgggtc aggtttaaga    2400
ttcactcgga tgggttgact gctttcggaa gctcccgttg tatccattaa ttaaacgttc    2460
ggtacacgtc tggtgtgtgt tttacccgaa tcagagacgg aattgcaaag atattggttt    2520
gaaagcaatg taatcccgcc catatatccc caacgtcgcc ttaaaaactc ccacaatatt    2580
acatttttat tagtctttta ttaatataga atcacataaa caattgataa aatcaagggg    2640
tggtgtataa tgattaaaaa tataaattga tatgttttac aagcatgaaa taggtattta    2700
ctattctaac aggtaaatat gcttaatgat taaaaataca aattagtatg ttttgacaag    2760
catgaaaaag gtattttta ttttagcagt taaaggtact acacttaaaa tatttaccgt    2820
atggacgggc gtcagaaaga tgcccggccc aagttgagag ggtacattca acacgaccac    2880
actcgcgttg gtgggtgatt agggcctcta aaacaccggc cagacatgac ccgggtgtat    2940
attcttgtaa cacttgaacg ttacaactga tatcatcata ttccacaaat ttagagccac    3000
ggacaactat attagcaatg cgggcaatca taacaaacat ataagtagta atacacgtga    3060
tatcactaaa acgttgctgg cgcaacagtt cggggagagt acgagacccc aaatcgttgt    3120
ccctgtttag aagaagacat cttacaaaag gccccagctt taactttaaa ttctccaaaa    3180
gtgacttcga ggttgcaaca atgggattat ttgtgtagat gggcaagttt tttgccgcta    3240 acatttaat ccacgttaac agttcatccg cagactccaa cgcttcaatc aaagattctc    3300
cacgtatgac tctctcacgc aacgcgcggg caatacgtga gtccatttta tatgactcaa    3360
aggtacgata agttcatgt ccgtacaaca tcaactccgg ccaagatgtg ttttgtttta    3420
tccccggaaa acatccaccg gaagcccatg aatcaccctc ttgtattgtg gcatatcgga    3480
ctaccagttt ttcaattgtt tcatctaaat ggcgtaccga gtcaatggtc acgctggctc    3540
ccgcggtgga gacgacttca atagcacggc ccgtaattcg atcgaccggg atatcatact    3600
cttttcgaat acgctctcgg cgggcgtctc tcttggaaaa tcgcaacctg tacgattcgt    3660
catgtgtctg atcatttctt tctcccgtgg tcattgcagg aggcgttgta ggacgccgtc    3720
ttcgatttga cagggatcga tcacggtgtt ttcttgaact ttgagtgtta aagatctgg    3780 atgatcgtcg atgtccccgt tcgatgcgtg catatccagt ctccacgtct cttcctccat    3840
gatggtttga tcgggtaat acaacaacca aagttttcgg gcgattgtgg tggtagcttt    3900
cacgccttcc gtgccttcgt ttggaatacc gtggattata tgctgtatct gcagtacgct    3960
ccacatacac agttctagac gttgtggagt cctcgcctgg agtggagcca atagcttcat    4020
catttgccca atcggtgact tccaatgcaa agtcatccga aggttcgtct ggtagcaaat    4080
tcataaagtc ttcacaaata gtagacacgt ctgggtcggt tggaattgaa gcagaggcca    4140
```

```
tggctgcaaa atatctgaca attgcgtgtt tgcagttgcc tgtatcttcc gccaatgttg      4200
tagaatttat aggctcaccc aacccgcaa tgggcgtgtt tagtcacatg attaatgctt       4260
ctggagtttt tcactttccc caaacaagct tacctgcacc ctttgttcgt aatgcataaa      4320
aataaccact gctatagcaa atatgacgat ataaaaacat tttatagcaa ggccggacat      4380
tactgtagcg caacatgttg tgcatatacc acgtattccc cccgtattga tatgatttaa     4440
atgattatcc ttggttggtt ttggtctaac ataagatata agctctacta tagcgagcgt     4500
gcatacaaca acccaggcca gaatccgaat gtatgtgggg tataataacg cgcatggtgt     4560
atatgcaacg ccaagcgtta aaagcacaat acatccagat gatatatgag cgataacctc     4620
caaaagcatc aataacgtaa cacctttatg catatataaa aaacttatag ggtcagcatt     4680
aaatacttta ctcataccat cccgtcgcat ggaaacatca cataacaacc ttgccaactt     4740
tgtatatggg taaccaagaa gaatgttcga ataacccgt gttacgtaat tcagtgaata      4800
tgatgtgggg gatattaact cacaggatga tcggaatggc ccaaacatac gacgtattcg     4860
tcgaaattgt aaatacatac catatacaaa ccatgcaaaa aaaatcattt ttagctgcac     4920
gcaccaaaaa taagcgtgac aattacgtgt tcccagaaca attcgaattt tgtcatgcaa     4980
aggtgtagaa atagcggttt ttaccatagt atctcctgat aatagatttt cccggcagct     5040
gtaatcgtat ccagataggc catccaaaaa cgttgagtgg tttacaaacg ttacatatat     5100
aagagagttg ttataagacc cccatacaac cggtccacca ttaatcaccg tggttgcata     5160
cacacactca tgttcaaact ttacacgagc ggtataccat agggtaaaaa cagcatgtcc     5220
gctaagtaga cacataatta taaaatgttc tgtcttgatt cctaaagcct gcatgacccg     5280
tggaagatgg caattcaagc acgatgtagt atcacacggt tggtgttaac tcgaagttaa     5340
atttggataa ttaggtactt ctagagtaaa gattgtatgc atgcgattgc tatcgcactt     5400
tgtagcaaaa cattgttgtg caagcgaaat acacaaacgg ttgtgatgat ccactcgcag     5460
agacacaaat gtccggggag ccgttcttcc tccgcgatgg ggatatcgaa gacaagtgaa     5520
cccttttgtt ccgcatatga gctgaaataa cacccagtcc cttttgatgg cgatacactt     5580
tgatgatgtt aaggtatatt cgcgatcacg cccggggaaa tgaacagcaa tatgctccac     5640
aatagattct aatattgtgc tgtcgacaaa ggcctccagt gtaaatgcgt ccagacaagt     5700
taccccgcgc tcttttagag cctttgttaa agatatttgc ggggagctaa atatttgttt     5760
attacgcgca accttacgtt caaaaaactc tgcgtattcc cccccaaggt tatgtaaaat     5820
aaattgcact ggaacattcg actgcggtct tgaatgaaaa tgaaagtttg ccgggtttct     5880
atgtgatgtc acaaacgcta atatatcaat acactgctca ggtacaacat aaaatgggag     5940
tagttgtcca accgccgtcc ctgtggttgt tactttggag aaaaaaggca gtcttaaact     6000
atgtccgtgg ctataaacac cagtatctat aaacgaaaag tcccgtaaat acggaccaat     6060
atattcaaca aattcccgtt ccagcaacac cgcttgctgt aatatttgtg caaaccccctt    6120 taaagtggaa gaccccacta acgcataggg atttgggatt ggtacgcata ccctgaaacc     6180
tattttctct ttacagttac agggtagagt ttcatgcaag ttttcattgt ttgatacatc     6240
ggcgtgtgta tggacttcag acgttgtctg tgtatcaaaa aaccatacat cctctgtata     6300
attctcttct acacacgtgt ataattcgcc attttctatg taaaaatcga tgtcagaatg     6360
gctggttata tccaataaat tatcatcatc caacacctca acggtaggtt caggacatgc     6420
agttttataa aaataacatg ggtctttgtt agggtttacc acggcctttg gaaaagtaa      6480 ttgcatggcc gttaaaatac catgacgaaa tgctcgcatg ccggcatgta aaatacccaa     6540
```

-continued

| | |
|---|---|
| tgggatgggt tttcttatat gaaagtctac atcaagtatg aggtttgtga ttataagatt | 6600 |
| tgtattaaat agctcattcc tgtttatata aagctgatct ttgggtatgt ttgatgaaat | 6660 |
| tttagaaacg tttttaacag acgtagataa tagtaaagtc aactgcatat ctcgtagtga | 6720 |
| agcggcaaca aaattacatg gattaatttg tttaaggtcc tccgcaatta atcgagcctc | 6780 |
| gtgcggtaaa gtgtaacggt ttgttattga tgaccacgta tcattagcaa taacagcaaa | 6840 |
| tgcttgggcg ccgtgaggca aggctacccg atatacaggc attggtccag ttacctcaga | 6900 |
| atggccgatg agggcttcta atggagtttt ataactcagg atggatacat catgtgtggc | 6960 |
| tatcccagtg gcagcagaga aaaacagtaa tagttttgta atccccgggc tcgtatcaaa | 7020 |
| accagtacga ccactttggt taggtgtatc gtttgcaaag ttggctgctc gtaacgcctc | 7080 |
| cgcggaaaca cccgaatcct caaaattaga caattcgtca aaaccgggtg gatttgaggg | 7140 |
| aatagtggag gaccatccat atggactaaa ttgttttttca atgttttcca cacgacgagt | 7200 |
| tagcgttgta gctaggtcac atacgccat aaacttgcta ggttttgcgg catacgtaag | 7260 |
| acttaaagta tatgttttag taattgtata tttatgtcca atctcaggtc caagttcagt | 7320 |
| gacatcacaa attacgttct ttttttatata gtcacgcatg ttgagacgag aacgtacatg | 7380 |
| attaaaaaaa ttagcagtag ctcttttttcc caggttggat gattttaaga ggaccggttt | 7440 |
| attcacaaaa tctgagtatg taaccgcttg taggtggtct gcgatctgtt tccgattgaa | 7500 |
| acattcaaaa tgtgccagat aaatataatc aacaaattca cggtctggaa ctttaaggcc | 7560 |
| ttttctatcg ttggtaatat actccgatac tgcgtgtatt tccgttgtgt ctgtatgtat | 7620 |
| tcgctgtaaa atgtacgata gagcattttt ggctgtcaaa cctcgtgtat atgttgagga | 7680 |
| acaacaaaac atggaaagtt tatcaaaaga caacaagtcc gaaatattgt acccactaca | 7740 |
| attaggtaat gccgggactt ggtaagttaa aaacaaatct ttaattgcct gtaagtcata | 7800 |
| taaggggggtt tccaacgtat tgtaacttgt gtccgtttgt aacaagtaat agcgtgtagc | 7860 |
| caacactagc gttttttcag agggtccaaa tcgaacaata taccaaaacg gcgagcatcc | 7920 |
| ataccccccag tagagtcgtc gatatgcagc caatacttga cgttcgtaat gggcatataa | 7980 |
| tgatgttagc tcctgacgac caacggattt tttaactaac ttgcagagtg ttgcctctgt | 8040 |
| gatgcatagg ccgttgtccg ataatcccctt tcggtttaaa tggtgtgttg ttaccatcag | 8100 |
| agtttgtata acttccgagt gaatgtcaaa cgtctccgat atacataggg tatcagatat | 8160 |
| tatatgcgga tttaggggtg ctccatacca taacgcctta tataaagctt taaaatcagt | 8220 |
| ttgggtttta aaacaacaaa aaaatatagg ccagacccgg gatcgtacat ctccagttga | 8280 |
| aaatccacca attaaataaa aaataacgtt gacgtcccta ctacaaaata aatgcattat | 8340 |
| ttggtttttct tcatcgtttt cagttacttc acgtgggcgt ttagttggga ttacttgcgt | 8400 |
| gatctcttcc ctcccatttt tgacaaagac gtcatctaag tcgggagtcc aagtataact | 8460 |
| caccacatac agaggttctg tgcttatctg cccggtaagc aacaacagcg agtgggagat | 8520 |
| tgcacatccc tttgtggcaa ataataaccg aatcgtcggt ttggaggatt tatccatagt | 8580 |
| tcaatacgtt ggaaagccag tcaatcatgc agacggtgtg tgccagctta tgtggatatg | 8640 |
| ctcgaatacc aactgaagag ccatcttatg aagaggtgcg tgtaaacacg cacccccaag | 8700 |
| gagccgccct gctccgcctc caagaggctt taaccgctgt gaatggatta ttgcctgcac | 8760 |
| ctctaacgtt agaagacgta gtcgcttctg cagataatac ccgtcgtttg gtccgcgccc | 8820 |
| aggctttggc gcgaacttac gctgcatgtt ctcgtaacat tgaatgttta aaacagcacc | 8880 |
| attttactga agataacccc ggtcttaacg ccgtggtccg ttcacacatg gaaaactcaa | 8940 |

```
aacggcttgc tgatatgtgt ttagctgcaa ttacccattt gtatttatcg gttggcgcgg    9000
tggatgttac tacggatgat attgtcgatc aaaccctgag aatgaccgct gaaagtgaag    9060
tggtcatgtc tgatgttgtt cttttggaga aaactcttgg ggtcgttgct aaacctcagg    9120
catcgtttga tgtttcccac aaccatgaat tatctatagc taaagggaa aatgtgggtt    9180 taaaaacatc acctattaaa tcggaggcga cacaattatc tgaaattaaa cccccactta    9240
tagaagtatc ggataataac acatctaacc taacaaaaaa aacgtatccg acagaaactc    9300
ttcagcccgt gttgacccca aaacagacga agatgtaca acgcacaacc cccgcgatca    9360
agaaatccca tgttatgctt gtataaatat tgaaataaaa actaaaaacg tttctggtgt    9420
atgtttttat tttgtatata aaattaaaac attgctggct ggcgtggtta ttacatttaa    9480
tgttttagta gaaaatcgac atcgtttgtt tctttatcag ttgaaccaaa tccacgcgtt    9540
ccccgttcgc tgggtgtggc tattagatct aacgttttag taaaatacca ttgtacaccc    9600
ggtatgccac atttaccgcg gatagcataa ggaaatgcaa tattacttaa aacgttgtgt    9660
tttaagtgta tttgggtgtt gtgatctatt aacaggacct gtgcaagacg atctcccgtt    9720
tttatacgta tgtcatcacc cgtgagatta tacgtaga atttacagtg ttctcctgca    9780
ggccatgccg ttggacacac gataatgcct gatcggcttt tcgatgatct tccaaaaata    9840
taagcgttta tactcggatg ttgtaagtcc cagtctctta taatcggtaa gacaattttt    9900
ataaattcat tccttttaa atataggtta tatggtacac aaatatcata tcccgcgtct    9960
tcttggcgtt ttggattgat gatatgtttg taggttaagg gaacatcgat atggtattct   10020
gcagaatccc tatgtaaagg ttgcccctgc tgtaccgtgg aaatatcagc aaattcaggt   10080
ataacgggtt tttcataatt tgacggcgag tttgataagg gttgaacttg tatcgattta   10140
aaaattggat ccagatgttt aagaacgttt tttgggagaa ggcgactttg tcttaatttt   10200
accgggaaca agtagattgt taaatgtccg ggtaaaataa cggttactcc tggccggtaa   10260
tacaaagggg ctgaaattac tcctctgtaa cccgcatcaa taactccgtt ggcgacaaaa   10320
aaattgtctt catcagcaag ggcagtatct ttgcattgaa ttaacaacag tgcgtattca   10380 tgggaggcg ccgacttaac caacagctcc aactgctgca tataaaaacc gccccgtgtt   10440
acagattttt cagatggcag ttcgagtttc ttgtggttcc ggagtaacaa cggttgatgt   10500
cgacttactt tatcgtctaa cacgcattgc agcgtatctg cacattcagg ttgaacttct   10560
attaaaattg tatcttttaa acaccgattc ggaatagttt ggctacaaaa catatcacct   10620
gtatttactg ccgtttccaa gatgggatca attaccgctt cgttcatatt aataacgatg   10680
caaattttat ttttttgtga agacagcagt ggggagccaa actttgcaga acggaatttt   10740
tggcatgcca gctgttcggc tcgtggagtt tatatcgacg gatcaatgat caccacccctt   10800 ttcttctacg catccctttt gggggtgtgt gtagcccctta tttcgttagc ttatcatgcg   10860
tgtttccggt tatttactcg ttctgtatta cgcagcacgt ggtaaacccg tttgcctata   10920
aaaggggcag gcgtgtataa gagggcccct gtttaatacg cggtctgccg tgtttggata   10980
tttcacgacc ctatcgttta tttacgtaat ggcatcttcc gacggtgaca gactttgtcg   11040
ctctaatgca gtgcgtcgta aaacaacgcc tagttattcc ggacaatatc gaaccgcgcg   11100
gcgaagtgtg gtcgtaggac cccccgatga ttcagacgac tcgttgggtt acattaccac   11160
agttggggcc gattctcctt ctccagtgta cgcggatctt tattttgaac ataaaaatac   11220
gacccctcgc gtacatcaac caaacgactc cagcggatcg gaagatgact ttgaagacat   11280
cgatgaagta gtggccgcct ttcgggaggc ccgtttgaga catgaactgg ttgaagatgc   11340
```

```
tgtatatgaa acccgctaa gtgtagaaaa accatctaga tcttttacta aaaatgcggc   11400
ggttaaacct aaattagagg attcaccgaa gcgagctccc ccgggagcag gcgcaattgc   11460
cagcgggaga ccaatttcct tcagcactgc accaaaaacc gcaacaagct cgtggtgcgg   11520
tcctacgcca tcatataaca aacgcgtctt ttgtgaagcg gtccggcgcg tagccgccat   11580
gcaggcacaa aaggctgccg aagcggcttg aatagtaat cccccaagga ataacgccga   11640
attagaccgt tgttaaccg gagccgttat tcgtattacg gtgcatgagg gtttaaattt   11700
aatacaagcc gctaatgaag cagacctagg tgaaggagca tcggtatcca aacgtggaca   11760
taatcgaaaa actggagatt tacagggggg catgggtaat gaacctatgt acgcacaagt   11820
tcgtaagcca aaaagtcgaa cggatacaca aacgactggg cgtataacta atcgaagtag   11880
ggcccgttct gcatcaagaa ctgatacgcg aaaataggga tataattacg cagtaacggt   11940
ttacccggta ttatgtataa taaataaacg tataaaagac agtcgtggtt tgtgtttatt   12000
ataaatgtgt attatatgtc acatattata aactgtttaa atagtaccac gtggtattat   12060
gaacagttta taatcagttg ctaccaaaca aaccccatta gacggcgggt tttgataaag   12120
ggaatcgctt atttaaacta aagattttac tctataagta tggagtgtaa tttaggaacc   12180
gaacatccta gtacagatac gtggaatcgt agtaaaacgg aacaagcggt tgtggacgca   12240
tttgatgaat cgttgtttgg tgatgtagca tcggatattg gatttgaaac gtcgttatat   12300
tcacatgcag ttaaaactgc tccgtctccg ccttgggtag ctagccctaa aattttatat   12360
caacagttaa tacgggatct tgattttcta gaagggccgc gtttactatc atgtcttgaa   12420
acctggaacg aggatttatt ctcatgtttt cctattaatg aggacctata ttccgatatg   12480
atggttttat ccccggatcc agatgacgtt atctcaaccg tttcaaccaa agaccatgtt   12540
gaaatgttta atttaacaac ccggggttcc gttcgattgc ctagtccacc aaagcaaccg   12600
acggggcttc cagcttacgt tcaggaggtc caggattcgt ttaccgtaga actacgcgcc   12660
cgggaagaag catacacaaa actactagtt acttattgta aatcgattat acgttatctc   12720
caaggaacgg cgaaaaggac gacaataggt cttaatatac aaaaccctga ccagaaagct   12780
tacacgcaac tcaggcaaag tattctactt agatattatc gtgaggtggc aagtttggcg   12840
cgtcttctgt acctacattt atatttaacc gtaacgcgtg aattttcctg gcgtttgtac   12900
gccagtcaat ctgcacaccc ggacgtgttt gcggctttaa aattcacctg gaccgaacgt   12960
cgacagttca cgtgtgcgtt tcatcctgta ttatgcaacc acggcattgt gttattagaa   13020
gggaaaccac taacagcgtc tgccttgagg gaaataaatt accgccgccg agaactggga   13080
ctgcctctag ttagatgtgg tcttgttgaa gaaaacaaat ctccgttggt tcaacaaccc   13140
tcatttttcgg ttcatttacc acggtcggtg ggttttctta cccaccacat taagcgtaag   13200
ttagacgcat atgcggtcaa acatcctcaa gaaccgagac atgtacgagc ggatcatcct   13260
tacgcaaaag ttgttgaaaa tagaaactac ggtagtagca tcgaagctat gattttagca   13320
cctccgtccc catccgagat cctgccgggg gacccaccac gcccacccac gtgtgggttt   13380
ttaacgcgtt aaacgtcatt ggggtagagg gtgtaaataa attacgaaaa cgtgcatgcg   13440
ttttttatt ttacaatgcg ccgtatatgg tatgtctgtc atgtgctcta aagtcccata   13500
tataaaagaa gccccaacga gtgtatgcgt attgcgtacc gcgaccctgg gatgttttac   13560
aggcgcgttt gtttgtctcg gttataagta tgcagtcggg tcattataac cggaggcaat   13620
cccgccgaca gcggatatcg tctaatacca cagactcccc ccgtcacaca cacgaacac   13680
gttatcggtc aaccaattgg tatacacacc caccccagat attgtccaat tcagaaacat   13740
```

```
tagttgcggt tcaagaacta ctgaactccg agatggatca ggacagcagt tctgacgcat    13800
cggatgattt tccgggatac gccttacatc attctacata taatggatcc gaacaaaata    13860
catcaacttc cagacatgaa aatcgcatat ttaaattaac ggagagggaa gctaatgagg    13920
aaatcaacat caatacggac gcgatcgacg acgagggaga ggcggaggag ggagaggcgg    13980
aggaggacgc gatcgacgac gagggagagg cggaggaggg agaggcggag gaggacgcga    14040
ttgacgacga gggagaggcg gaggagggag aggcggagga ggacgcgatt gacgacgagg    14100
gagaggcgga ggagggagag gcggaggagg gagaggcgga ggagggagag gcggaggagg    14160
acgcgatcga cgacgaggga gaggcggagg aggacgcggc ggaggaggac gcgatcgacg    14220
acgagggaga ggcggaggag gattattttt ctgtaagtca gtttgcagt cgagacgcgg    14280 atgaggttta ttttacgtta gacccggaaa taagttacag taccgatctt cgcattgcaa    14340
aggttatgga gcctgcggta tcaaaggaac ttaatgtatc aaaacgttgt gttgaacctg    14400
ttaccctaac aggctctatg ttagcgcata atgggtttga tgagtcctgg tttgctatgc    14460
gcgaatgtac ccgtcgcgaa tatattacgg tccaaggatt atacgaccca attcatttac    14520
ggtatcagtt tgatacttcc cggatgcaca ccccacagat tttgagaact ataccagccc    14580
ttcctaacat gacacttggt gaactttat tgattttcc tattgaattt atggcccagc    14640
caatttctat agaacgtatt ttagttgaag atgtattttt agataggcgg gcttccagta    14700
aaacacataa atacggcccg cgttggaatt ccgtctacgc acttccatat aatgcgggta    14760
aaatgtatgt acaacacatt cctgggtttt atgacgtgtc cttacgtgct gtgggccaag    14820
gaacggccat ttggcatcac atgatattat ccacagcagc atgcgctatt tctaatcgca    14880
tttcacatgg agatggatta ggattttgt tagacgcggc aattcgtatt agcgcaaact    14940 gtatttttt gggacgtaac gataatttg gcgtggggga tccatgttgg ttagaagacc    15000
atcttgccgg attaccacga gaagccgtac ccgacgtact ccaagtgaca cagttggttt    15060
tgccaaatcg gggtccaacg gttgccatta tgcgtggttt ttttgggcg ttggcatatt    15120 ggccccgaact aagaattgct ataagtgaac catctcacatc tttggtgcga tatgctaccg    15180
gtcacatgga acttgccgaa tggttttat tttcacgtac acatagttta aagccacaat    15240
ttaccccaac ggaacgggaa atgttagcgt catttttac gttgtatgtt actcttggtg    15300
gaggaatgtt gaactggatc tgtagagcaa ctgcaatgta tttagctgct ccttaccatt    15360
cccgttcggc ttcatcgcg gtctgtgaat ctctgcccta ttactatatc ccggttaata    15420
gtgacctgtt atgtgattta gaggtattac tgttaggcga ggtcgacctc ccaactgttt    15480
gtgaatccta cgcaactatt gcacacgaat taaccggata tgaggctgtt cgcacagcag    15540
ccacaaattt tatgatagag tttgccgatt gttataagga aagtgagacc gatttaatgg    15600
taagcgcgta cctgggggcc gttttattgt tacaacgggt gttgggtcat gcaaatcttc    15660
ttttgttgct tctctccggt gctgcgttgt acgaggatg ttcaatttac atcccccgag    15720 gtatttaga tgcatataat actttaatgt tggcagcaag tcctctttac gctcaccaaa    15780
ctttaacatc cttttggaaa gaccgcgatg atgcaatgca aactttgggg attcgaccga    15840
caacggacgt tttacccaaa gagcaagaca ggatagttca ggcatcacct atagagatga    15900
acttccgttt tgtgggattg gagaccatct atccccgaga acagcccatt ccctccgtgg    15960
acctagccga aaatcttatg caatacagga atgaaattct gggtttggat tggaaaagcg    16020
tagccatgca tttactacga aaatattaag ggttgtgatt ttttttcatta ggatgaaaag    16080 aacgtttcct agccacaccc acaaaggagt ttgtaaaata aaatctctgt ttagaccta    16140
```

```
aaatttgttg tgtgtgttgt gtggggggtc cgtgaggatc gacctttaca agatataatt    16200
tgtccatatc gcaatgtttt ctcggtttgc gcgttccttt tccagcgatg atagaacgcg    16260
taaatcttat gatggtagtt accaaagttt taatgccggc gaacgtgatt tgcccacacc    16320
tacccgggac tggtgttcta tttcccaacg cataaccagc gagcgcgtga gggatggatg    16380
tcttattcca acgcccggcg aggctttgga gacggcggta aaggcttat ctgaaaagac    16440 cgacagccta acatcgccgg ttttacaaag taccgaaaga cacagtgttc tgcttggatt    16500
acaccataat aatgttcctg aatcgttggt ggtctcgtgt atgtctaacg atgttcatga    16560
cgggtttatg cagcgttata tggaaacaat tcaaagatgt ttggatgacc tgaaactttc    16620
tggggatgga ctttggtggg tttatgaaaa tacatattgg cagtatctca aatacaccac    16680
aggagccgag gtaccggtga cttcagaaa ggtaaataaa aagtctaaat ccacggtttt    16740
gttgttttca tccgtagttg ccaataaacc aatatccaga catccttttta aatctaaagt    16800 tataaattcg gattaccggg gaatatgtca ggagctacgt gaggcgttag gagctgtgca    16860
aaagtatatg tattttatgc gtccagatga tcctacaaac cccagcccgg atacaagaat    16920
acgtgtacaa gaaattgcgg cttacacggc tactggctac gggtggatgt tatggttctt    16980
ggacgttgtg gacgccaggg tatgtcgcca tctcaaactt caatttcgac ggattcgagg    17040
gccgcgcgcg tctgttattc cagatgattt gcttagacga catttaaaaa cgggtcctgc    17100
ggtctcagcg ggcacaggag ttgcgtttat tttagcagca caactgcca gcgctcttac    17160 tgcgcttttg cgtattagtg tattatggcg aaaggaagag tggcgggatg gtttaaatgg    17220
aaccgcagct gcaattgttg cggcggttga acttattacg cttttgcacc accattttca    17280
atacttaatt aatatgatgc ttattggata tgcatgttgg ggggatgggg gattaaacga    17340
tccttatata ttaaaggcgc tacgtgccca gggacggttt ttatattttg cgggtcagtt    17400
ggtcagaaca atgtcaacac acagttgggt tgtgttagag accagcaccc atatgtggtt    17460
ttcccgggcc gtggcgcaga gtattttagc acatgggggt aaacccacaa agtattatgc    17520
tcaggttctt gccgccagta aacggtatac tccgttacat ttaagacgta tatccgaacc    17580
atcgagtgtg tctgatcagc cgtatattcg ttttaatcga ctgggatctc caatagggac    17640
aggtataggg aatttggaat gtgtctgttt aacgggaaat tatttatctg acgacgtaaa    17700
tgcaagttcg catgtaatta atacagaagc accgttaaac agtatagcac ccgatacaaa    17760
tagacagcgg acttctcgcg ttttagttcg tccagacacg ggtttggatg taactgtccg    17820
aaaaaaccac tgtctggaca taggccatac ggacggtagt ccagttgacc caacgtatcc    17880
tgatcattac acccgaataa aggcggaata tgaaggtccg gttcgggatg aatcaaacac    17940
aatgtttgac caaagatcgg atttacgtca catagaaacc caagcatctt taaatgatca    18000
cgtatatgaa aatataccac ccaaggaagt gggttttaac tcatcttcag acctggatgt    18060
ggatagcctt aacgggtaca cctccggaga catgcataca gacgatgact tatcaccaga    18120
ttttataccc aacgacgttc ccgttagatg taaaccacg gttacgttta ggaaaaatac    18180
gcctaagagt catcattaag tacagcggtt aatagatagt tatggactag cactttggc    18240 ggtcatttcc acaaccaggt taaaattggg ggatttggga gaaaatagtc tattgcgtat    18300
tttctgttca ataattggac tgcgttattt aaaggtctga ttggttgatt gggttataaa    18360
aggaattact ccttttaaatt ttacttaatg tacccacaat atcaagtggt cgtttgtatt    18420
taacgattat taccggtacc atgggagact tgtcatgttg gacaaaggtg ccgggtttta    18480
cgttaaccgg cgaacttcag tacttaaaac aagtggatga tattttaagg tatggagttc    18540
```

```
ggaaacgcga tcgaacagga atcggaacgt tatctttatt tggaatgcaa gctcgataca    18600
atttgcgaaa tgaatttcct cttttaacta caaagcgtgt tttttggagg gccgtcgtgg    18660
aagagttgtt atggtttatc cgcgggtcaa ccgattccaa agaactcgcc gctaaagata    18720
tacacatatg ggatatatac ggatcgagca aatttctaaa taggaatggc ttccataaaa    18780
gacacacggg ggaccttggc cccatttacg gcttccagtg gagacatttt ggagcggaat    18840
ataaagactg tcaatcaaac tatttacagc aaggaatcga tcagctgcaa actgttatag    18900
atacaattaa aacaaaccca gaaagccgac gaatgattat atcgtcttgg aatccaaagg    18960
atatccccctt aatggtacta cctccatgtc acacgttatg tcagttttac gttgcaaacg    19020
gtgaattatc ctgccaagta taccagagat cggggatat gggccttggg gtaccgttca     19080
acattgctgg atatgcactt cttacctaca tagtagcgca tgttacagga cttaaaaccg    19140
gagatttaat tcatacaatg ggggatgcac atatttactt gaatcatata gatgctttaa    19200
aagtgcagct agctcgatcc ccaaaacctt ttccttgcct taaaattatt cgaaatgtaa    19260
cagatataaa cgactttaaa tgggacgatt ttcagcttga tggatataat ccacaccccc    19320
ccctaaaaat ggaaatggct ctttaatgga ttttaaatg ttgtcaagac agtagatgtg      19380
ttgcgaatgt aataaaatga tatacacaga cgcgtttggt tggtttctgt ttatgaacag    19440
caacggatgc ataggttgc gataactgcg ataagaccca atgtcccaag gatagatatc      19500
acaccaatta taactgctac aacggaaaat gtagtggcgt aggtagatgc atcgtaggta    19560
taaacggccg aaaacggagg gaatttttta gggtaaccat ctagatgaca cgaataggtg    19620
ataggtccgt cgagttccga tgttggacaa gaactttgca tgtttacaaa ccgtttgttt    19680
tgatcacaca ccccagtaat ctcactgttt tcgtggttaa tgggagaatc gttaacccac    19740
catacgaaat gtacaacgcc acgtggcaca cattttgccg tacatactat gtgtccatca    19800
ataaccta tagacacgtt gggaaatgga tagacgtcag gggtaacgac agcagaaat       19860
ttcatattag agacgccatc ccgaatccat aaaacattac attggatggc tgggggtggg    19920
taatccattt gtttttgctg tggaattcgt accgccgaaa cataactaaa taatccattg    19980
gcatattctt gtattgcatc ggttataaaa ttttttccga tgttaccaaa ccttgaagtc    20040
caccgaacac gtaccgagtg cggtggataa tactttgata cgttacagta ggctgcgtat    20100
gtctgtccgg ttaagactgg atcgccgaca acggtaatat ttggacgata atacgttgta    20160
actgtaatac tgtgttccga tatgacgttc ttagtttttg tattaacgac tcgccaaata    20220
tacgttccct ccgtggtagc atccatagat aaaattgtta cagaaaaatc agacgttgtt    20280
ttaacatctg gtattacata attttcctta gcgtgtgtaa atatctcagg gttgtttatt    20340
aagtttaaat cggcactgtt gctatataac ataaccggta aatctggcat gcgtattaac    20400
gcattgccca gttgacggtg cggatctata aggtgacgcg taaaccaaac ttcaatatga    20460
agatcggggc gtataagcga cttccacctt gttatatttg aaccttccgg atctaaagaa    20520
tattgttcat atgttttttg ttgctgctta aaggccgcct gttgtccggt cgttagacgc    20580
atgtaacaag gcatgataaa tgtgtgaaaa tagggtatgg attgtattcc gccgtgaacg    20640
cattgtatat tttcatatag aaaaggtggt tgtgaatgtt gggtgttggc tgcgggatcg    20700
ggctttcggg aagcggccga ggtgggcgcg acgcgggat cgggctttcg ggtagcggcc     20760
gaggtgggcg cgacggcggg atcgggcttt cgggaagcgg ccgaggtggg cgcgacggcg    20820
ggatcgggct tcgggtagc ggccgaggtg gcgcgacgg cgggatcggg ctttcggaa        20880
gcggccgagg tgggcgcgac ggcgggatcg ggctttcggg aagcggccga ggtgggcgcg    20940
```

-continued

```
acggcgggat cgggctttcg ggaagcggcc gaggtgggcg cgacggcggg atcgggcttt    21000
cgggtagcgg ccgaggtata taattcagtt atacttacgg gtgtgggttg agattcagtc    21060
gataattgta tacacgcgat cgttaaaatt aaatttattt gtatccgctt catcctggtt    21120
tttattgaca catccacgct ccccttaaat aaaagattaa acacccacc gcggaattta     21180 aatgatggaa acgttttttt cgacattggg aataataaaa acggcttttg caactttaaa    21240 aactttatt atctcgatta cgatacatat gtaccacata gatagcatag atttattata     21300
atataaacac acacgtgata tactttagtg atatgagatg ccataaaaca gtcaataggt    21360
ttaacgctta gtctcatcat ctgaatacac gtcaaacccg ccgcaactgt tgatgttaga    21420
attataatag ctccccatga aatgccggca aatgttacag ctatacccgt caccgaggtc    21480
gttgtatata atacaattac ccataggttt ttttttcctt gatataaaac ggcaaaaccc    21540
tgtaacccaa atgctataat atgacctcct attgaaactg ctaacgttac ttgtgtaagt    21600
ttgataaaat gatttaattt aattatatgt gagattgccc acattaatgg ggtaactata    21660
tataacaccg ggggtataac agacattata cgaattcctt taaacacgcg tttaagggtc    21720 cgggaactt ctcgatggtc acatactctc ccgcggtcat tttgtgtata tacaacggca    21780
aaacctaaat ctgtataagt gtttaattgc ttatggcgat ttttacgata tatacacgta    21840
tcttgcaaat cggtggcggc atcgacaatt gaaactagtg tgacaataga tatacacaat    21900
ccaataagaa cctcatattt actgacatac atatataaaa taacggttag taaacctccc    21960
aacccagttc ccaacatcat aacataaaaa taaatatgcg gtccattgaa tgtcgtaaca    22020
aagttgtagt aatggatatg cacagcagcc actgttccgg taatcgcgga tatggaaatt    22080
cccagtaatt ctacaaatgg aagatcccgg gatattgggc aaccaaccgc ccataacaca    22140
gcaaaaccca acacgaccac cgtctgcaaa catcgtccca attttgctaa tgtgcgtaga    22200
aatttcacgg atgttggcca taaccccgaa acgacgatca accccataat agttgcattg    22260
acggcagctt cgcagacgtg atattgtaaa attaacccgg acgtgataac gcttgcttgt    22320
agtcccacga gaaacaaccg cgatgctgag gttattgcac acgaattaca ttcttgaggg    22380
tttccgacac atccttggat tgattgagcg cggattaatt ctctgtctaa cacacccagg    22440
ttttcatcat ggacagctct ttcaccattc acggccatgt cttaagttta ataattcaaa    22500
acaaataaaa atgtgttcat ctatggtaca cacaagtttg tatgtaaaat ataagcaaaa    22560
gttgcactta tttaactgta catattacgt cagattcacg tgataattca gaataatcca    22620
gggttcctgc agggtccact ggaggagcca cacaatattc gcgaattccg attccctcct    22680
gccatgtggt ttcggggagt ttcccccca tttattttcc ggtatttttt tcgtttcttt     22740
ttgttaataa attgcgtctt ttttttaatg gtggttcatc cttcacagat tccatgttcg    22800
caaataattg catcgaggtt aattttctt taaggtcttt gggacttaag aacgttgcat     22860 aaaaaaaga atgcacgggt gcggaacgtt ggatatacaa tccaaccatg ggggagttag     22920
ttaaggcgag ataaaaatta atataacacg tctcatcccg tgttaactta agattttgta    22980
cggcagaacg gaatccactg tgtgtttcca ataatactcc aaattcacgc atactcccgc    23040
tgccataaac aacattatta aggatccttt ttgaatttgt gattgagcgt attaaattat    23100
atggtgtagg cttgcttccg tttatatcca aggaaacatt aaatgagata aaaccacccc    23160
cggcggtctg gatgtacata tccgtggctg ttagaatgaa gcatgttgta aacccaaaag    23220
ttttaagtag tcgctgtaaa cgggtgaatt gatcgcgttt taagcaaatg cttatatctg    23280
gagttagatt tggaaacatc attgtataac aagcgagttc acgttttaca acttgttgt     23340
```

```
aacattgtac ttgatcatct ggaccacaat cacccgggcg ttgccatacc atcgtttgga   23400
taatactccg ctcgggggt tgtccggtaa atttaaaata taaccgtgtt ggggtcgacg    23460
gatcttttgt atggcgaaac gcgtcaataa gcgaggaccg tccctccgtt gccgcgagta   23520
caaccattct cggcccagtc caattatact ggtcaaacat atttgccggt ataggaatat   23580
acagttgttc tgtttccaaa ctacagtgaa taattaatcc ttcgtcgctg aatattaaaa   23640
tagaatccct tagtctatta accagaggtg atatagacga aattaaacca gtaagcgttt   23700
tttccgttaa aacagctctg gcgatttctg gggcgtcaaa acccgcatgc aattccatgt   23760
ccaaagcatc gtctgtacgc gacctcaaat ccataattta ctacttaaaa tgtttactat   23820
agaaaaagta atcatatgta aacacacgag tttcgttaat atgtttgttt aacccgatcc   23880
ggtgacttaa gtacataaac aggcatgata tttgaatagt acggcccatg ggagggaaca   23940
tttccacgtg ttccaataca gggggtgttc cttaataggg actgtgcaat aaaatacgta   24000
agaagttacc agatttgatg taatgtttgt cataaaaaat atgtacatca ttatatacgt   24060
ctgtaattaa cacaagatca catcgaagaa ttactgaagc cgctgtgaaa cctttcacaa   24120
gacgatataa acttggttaa gtgtattgat ggggctcttt ggactgacac gctttatcca   24180
tgaacataaa ctggttaaac ccagcatcat ttcaacgcca cccggagttt taaccccgt    24240 ggcggtagac gtatgaacg tcatgtacac attgttggaa cgtttatacc ctgtgggtaa    24300
acgcgagaat ttacacggac catctgtaac gatacattgt cttggagtct tattgcggct   24360
attaacacaa cggtcatact atccgatatt tgtattggaa cgttgtacag acggcccatt   24420
atcacgtgga gccaaggcaa ttatgtcacg ggccatgaac cacgatgaaa ggggaacctc   24480
ggacttaacc cgtgttctac tatcatccaa cacatcatgt tctatcaagt ataacaaaac   24540
atcggaaaca tatgacagtg tgtttcgaaa ctcttccacg agttgtattc ctagcgaaga   24600
aaacaaatcc caggatatgt ttttggacgg ttgtccacga caaactgaca agacgatctg   24660
cctgcgcgac caaaacgtat gcagtcttac ctctacaatg ccatcccgag gacatcctaa   24720
ccatcgatta tatcacaaat tgtgtgcaag tcttattaga tggatggggt atgcatacgt   24780
cgaggcggtt gacattgagg cggacgaggc atgtgcaaac ttatttcata cgcgtacagt   24840
ggctttggtt tatacgacag atactgattt actcttcatg ggctgtgata ttttgttaga   24900
tgcaattcct atgtttgctc cagtagtacg atgtcgcgat ttgcttcaat atttaggaat   24960 tacatacct gaattttgg ttgcctttgt tcgctgtcag accgatttgc atacaagtga     25020
caacctaaaa tctgttcagc aagttattca ggataccggc ctgaaagttc cacatcaaat   25080
ggacacttca acgcgctccc ccacttacga ctcgtggaga catggcgagg ttttcaaaag   25140
tcttaccgta gccacgtcgg gtaaaacaga aaacggagtg tccgtttcca aatatgcatc   25200
taaccgatcg gaggtgacag tagacgccag ttgggcttta aaccttctgc caccctcatc   25260
ctccccattg gataatttgg aacgcgcatt tgttgaacat ataatcgccg tggtaactcc   25320
attgacccgc ggtcgcctaa agttaatgaa acgtgtaaat attatgcaaa atacggcaga   25380
cccatatatg gttattaaca ccttatatca taacttaaag ggggaaaaaa tggctcgcca   25440
atacgcacgt attttaaac agtttattcc tactccactc ccactaaaca ctgtattaac    25500
aaaatattgg aattaaaaca cacataagag cgacttaatg gttcattgtt ttatttttgct  25560 cgtatataca tgttataaat cgtttatcac tgtgcccgca taagatgtac tgtgtctctc   25620
aaaaaaattt gtgtttttat ctgcaatcat aaatgcaagt ggaaagtccg aatcgggagg   25680
tggggtgtta aatagttttg gtacattaat cgctgataaa agcctgtccg cgctgaattt   25740
```

```
cacgtattgt gtaattgcat cgacgttcac caaacgggtt ttgggtgcat gggattttaa    25800
aaacgcacac tcgatttcaa cggcttccga aaacagttga tgtattctgg tgatagcggg    25860
tttttcgggt acatagttat tgtatataca acacgatgcg ctggtatgta tggcttcatc    25920
tcggcttata aggtcgttaa attgacaagt tacaacaaat agtccgttat tgcgtaaata    25980
tgcaatagcc gcgaacgatg atacaaaaaa aatgccctct ataagaatca ttagtatata    26040
tttttctgca acgatgggt tgtcccgtac cttttcttcc aaccattgta cttttttgttg    26100 gatcgacgga ttattaatag tgacatttac gtattgtacc cgcaacgatt catccctct    26160 gaacaacatt agttgaattt gactatagac acgcgcgtgg acaacctcga tgcactcttg    26220
ttcaatgtag taatggtgaa tatccttttg ggaaagagt tgggttagag agcccaaatt    26280
aacatttacc agatcatctg ccgccgataa aaatgtaaaa ataaatctgt agaatattag    26340
ttcatcttcc gttaaacagt ccaagtattg ataatcatct tcaatgataa aatcgctttc    26400
taaccaacga ttcgaaatgc tcagggcacg taaattgttt atatctggac actccggcct    26460
gtaaaaaaaa tgactgcaat ctttctgatc cattttggaa tagtttcccg tgtaaattta    26520
taaagcacaa ctggtacagg ttaattcgcc tcccgcaaac agtccgctgt tcgtagcttt    26580
acgaatttta cagtagtaca tacccgtttt aaggccggct ttataggcac gtataagcaa    26640
attcattatt ttggaggcgg gaattgtccc gtctgggcgt tcctcaataa ataaagtcat    26700
tgattgactt tggtcaataa atggcgccct ttctgcacac atatcaacga gatcctcttg    26760
ctcatattca aacgctgttt tatatttaa gagtgggtga ctattagata aacagccaaa    26820
cgaacgtatt actgaccatt ggttttctc aagtatgttt ataacttcca gtcgttttc    26880 ttcacatgaa tacatatctc ttagttcgtc cataaggtct aagttgggtc taagtaactc    26940
acccgaggtg gtgaccttac taaacatatt attataaatt ggagagaaac cctcactgca    27000
ctccgttacc tgtgcagatg aaactgtggg cattaacgct aagaactgcg agttgtataa    27060
cccataagcg caaatatcat ctcgcagggt acaccatggt aaatctaaat aacttatcgt    27120
agaaaaccca tcttggtgta accatcccct agcatattta ctttcggtaa aacccttaaa    27180
cggggctaag ccgccaatct tacacatttc catgcttgtt ttcattgtct catacaacat    27240
taactccgct atttgtacat ttaaccgtct agctggttgg gaagttaaat caaatcctaa    27300
gcggagacaa gttgtatgta acccttgtat gccaatgcca agtgatcggt tgttttttac    27360
acctttacat gattttttac atggaaagtt cccagccgcc aggacccccgt ttaaaaaaat    27420 aacagtcgtt cttgctgtca attgaaggtc gtttaaatta aatgacactg gcctttgga    27480 taagcacgtt gtaagatta tgctggcaag attacatacg ccatgttgat gagcgtctgc    27540
cttttgaaca atttccgtac acaaatttga ccccgtgata gcatttcctt gggtattcat    27600
atgataatta cgattacagg catctttgaa cattaaaaag gggcttcctg ttacagcagc    27660
actgcgtatg attgtgaatg cgatatcttg aatgggaaca gaagaaacgc ctaatccttc    27720
tctctctaaa cgtaaatagg ttgaagtgaa tgcctccccg tgtaatgttc gaaggatatc    27780
ggctctgtta tcaaaagag tccactgaac attactagcc cctttagat agcttaggta    27840 tcttcaaaa ataaatctg gggtccataa acaacaaat atgttatcac atcgaaatat    27900
ttcatcacga accaacattc cacgtgtggc caaaacagtt tgtagatcga cgtgccatgg    27960
ttctatgtaa acacaaactc cagttggtcg ttcacaatca ctgttaattg ccataaccat    28020
gcaatctaaa agttttaaaa ctgcaagaag acctttcgtt tgattttccg taggtattaa    28080
attcagactc tgtagagaaa ttcccactcc acctcgactt tgtaataccg ttcccacatc    28140
```

```
gcctgtgata gctcgaacag ctctcccaac agtgatggat tccgggtcca ttaaataaca   28200
actggccgtt gccccggtct ctcgacctaa aaacatcata accggtgtag ccgggacaat   28260
tttctgacat gccaacgctg tgaaaaatac ccgacagaca tcagtccatg tataaccatc   28320
atttattccg ggaataagag ttgcgatttt aggcaggttt acgatttctg ttgtcacggt   28380
ggccgccagt cttaaaaaga attggcaaag cgactctaat ttaccttcct ctaacttagt   28440
taaataaaag tcttcgtact ttaaagcaga ctgtagtcca agggtagcta aagcggggta   28500
ttgatctttc aaaaacggtt ctaatatagc ccgacgaatt tcgtccctcc gcccttcaat   28560
tgcttggcgg actcggggag ttaaacagag aattggggaa gtcaaccacg tttccatgga   28620
aacggatcgt aggttaatac ggcaatggat aagttctcca caacatcggt acactcgctc   28680
atcttgtcgc gtcaccgcct taagttttga gacgatagtg ctaatatact ccattaattc   28740
caccggtgtg gttgattcgg gcggaatgat gtattccttg tagccatgtt gacataatcg   28800
gtttataatg tcatgaaccg tattaaaaat tcttttgaac tccataacgg ataacgtatt   28860
taggctccgg aataaacctt taaaccctaa actcacagct gagttagttc tacaatattg   28920
tagactccct tatatatggt tacgtacagc ctgcccctcc ccagtatata atatcacgca   28980
aaacccacgc tatgttaaat tcagtttatt ttacatacat gctttaataa taacattcgt   29040
tccatgtatt tgtaccccccc cacacaaccc cctctaacca aatagttggc acgttataac   29100
ctccgaaccg ttccatgcgt cttgtataac gcacagactc tgatggaatt gttccaatta   29160
acgtatatgc cgcatacatg caggataatt gtgtgggaag tccccgaaaa tcgccggtcc   29220
attgatacaa tcgctgtcta gccaagttcc aatttactcc tgtaatttcg ccaatactac   29280
atcgagggct tgtcgggtca ttggataact gcacaagcgg caacgccctt gtgttatatg   29340
gctggtgggt atttgcaacc ccttcagtcc cccaggcggc atttttcagct cgtatgcgtc   29400 ctaacaggaa gccaatacca cgaccaaaac attgttcgtt tagttggctt aatgcaagat   29460
gcagtcttac accttctcgt tggcgtcgct gtgtatatac aaaaaccaag aacacatgct   29520
tcagtccgtc cgcggaaaga tgtaaatctt tgtcaacgtc ccaaaatacg caggccggga   29580
tgttggctgt gaccctgcga gttgaagttt tgtctgtacg tgcagcttct tggggacctt   29640
tggccacggc ggttatattg cataaattat cctgaatggt atattccagc agggacccaa   29700
aaaaacttat aaatcgatgt ggaaatacat gacattgtac catcgcacgt aaacactccg   29760
aaaaccttat gagccgcgtt tccatacgac tgcatccata ggcagaaaca attgctgttc   29820
tgttggcatc cgctgcctgt ttatccgtat attcttctgc ccggcatgcg gcgatgaaac   29880
ttaatgacgt tacatatgct ctaagccccc caccttctcc aacggtccaa ggagccgtgc   29940
aggcattgaa taggtttcgt aaaccctcta gtagtacatc ggggtcacgt ccagcctgtg   30000
taagtgtatt agcttctcca atcatgtcag atggatgacg aaggattaag acgattgacc   30060
cagcatgctc aatgtccgga cgaaaaaaat cggttaatga cacttgttgg attagctgtg   30120
tcgttgattt aaaattattt aacgggagtc taatggtaac ttgcgggtta ccaattgaag   30180
ttggatttat ttgaatgttg ttcatacgat taataacaat tgaacggggg gttacttgaa   30240
tagacgcggt ttctgtacgt tttggtggta catgtatcgg ttgtttgttc agacctccaa   30300
agcgagggcc aattgttaaa tcgcgactcc aatttccgaa gaagcccgga gcataagtca   30360
tatgaagccc gttccctatt tgaataaaac ggttatttcc taaaagactg atattagttc   30420
cacatagcgt ttgttcgttt aaagtaaaat gcgagttggt tggttgactc cccatagctg   30480 agggggttaaa ttcacacaat gcaatcgtga cgtggtacta tctgaaatgt tgcctgggt   30540
```

-continued

```
atgtgtacac attatacagt cgtagtaccg tttatataat gttaggtagg aggagcctat    30600
aaaaatattt tgattggcgt taaaaggttc ttcaacttac cgtgacgtcc tttttattaa    30660
catgcgtttt tattgatgtt acatttatgt cttttcattc cggacggatg tagctttttc    30720
atatcacgtt ataaagttaa gtcagcgtag aatataccat ggaagaacca atttgttatg    30780
atacacaaaa acttttggat gatttaagta acttgaaagt acaagaagcg acaacgaaa     30840 gaccatggtc accagagaaa acagaaatcg ccagagttaa ggtagttaag tttttacgat    30900
ctacccagaa aattccagct aaacatttta ttcagatatg ggaaccctg cattctaata     30960 tctgttttgt atattccaat acatttttgg cggaggctgc tttcacggcc gaaaatttac    31020
ccggactgtt gttttggaga ctagatctag actggacgat agaggagcca ggtaatagct    31080
taaaaatttt aacccagcta tcaagtgtag tacaagattc cgagacgtta catcgtttat    31140
cggccaataa attacgaacc tcgtctaaat ttggacccgt ttcgatacac ttcattataa    31200
cggactggat aaatatgtac gaggtcgcct taaaggatgc aacaacagcc attgaatcac    31260
cattcactca cgctcgtatt ggaatgttgg aaagcgccat tgcagcttta acacaacata    31320
aatttgcgat catttacgat atgccatttg ttcaagaggg gattcgtgtt ttaacacaat    31380
atgcaggatg gcttcttccg tttaatgtta tgtggaatca gattcaaaat agctcactca    31440
ctcctctaac acgagccctt tttataatct gtatgattga tgaatatctc acggaaacgc    31500
cagtacatag catatcagaa ttatttgcag atactgtaaa tttaattaaa gatgaggcgt    31560
tcgtatccat cgaagaagcg gtaacgaatc cacgaacggt gcacgagtca cgaatttcct    31620
cagctctggc ttatcgagac ccttatgttt ttgagacatc cccgggaatg cttgctagga    31680
gacttagatt agacaatggt atatgggaaa gcaacctctt atcgttgtcc acccccggaa    31740
ttcatattga ggcgctgtta catttactaa actccgaccc ggaagcggaa accacatctg    31800
gaagtaatgt agcagaacac acccgtggca tttgggaaaa ggttcaggct agtacatcgc    31860
ctagtatgtt aataagcacc cttgccgaat ccgggtttac aagattttca tgcaaattgc    31920
tacgtcggtt tattgctcac cacacactcg ccggttttat tcacggaagc gttgtagcag    31980
acgagcatat tacagatttc caacaaacac taggatgtct cgctttagtg ggtggactgg    32040
cataccaatt agtggaaacg tacgctccta ctaccgagta tgtgttaaca tatacacgga    32100
cagtaaacga gaccgaaaaa cggtatgaaa cgctattacc cgccttagga ttaccaccgg    32160
gaggcctggg acaaattatg cggcgctgtt ttgctccacg acccttatt gaaagtatac     32220 aagcgacacg cgtaatacta cttaatgaaa tttcacatgc agaagctaga gagacaacat    32280
attttaagca aacacataat caatcctcag gtgcgttatt accacaagca ggacaaagtg    32340
ccgtacgcga agccgtacta acctggtttg acctacgtat ggattcaaga tgggtatta    32400 ctcccccggt ggatgtgggt atgacacctc ctatttgtgt tgatccaccg gctacagggt    32460
tggaagctgt catgataaca gaagcactaa agattgcata tcctaccgaa tataatcgct    32520
ctagcgtgtt tgtggaaccg tcgtttgtgc cttatattat tgcaacaagc acgcttgatg    32580 cccctttcggc aacaatagct ttgtcttttg atacacgggg aatacagcaa gccttgtcta    32640
ttcttcagtg ggctcgcgat tatggatccg gaaccgtgcc caatgcagat ggatatcgca    32700
caaaactatc tgctccttata acaatattag aaccttttac ccgtacacac cccccagtac    32760
ttttaccatc tcacgtttct actatagatt cccttatatg cgaacttcat cggactgttg    32820
gcattgccgt tgacctgctt ccccagcacg tccgtccttt ggttcctgac cgtccttcta    32880
ttacaaatag cgttttttta gcaactctct attatgatga actttacggt cgttggaccc    32940
```

```
gactggataa aacatcgcag gcgttggttg aaaattttac atccaacgcg ttagtggttt    33000
ctcggtacat gttaatgtta caaaaatttt ttgcgtgtcg tttttatcca acgccagatc    33060
ttcaggctgt tggtatctgt aacccaaagg ttgaacgcga tgaacaattt ggggtatggc    33120
gtttaaacga tcttgctgat gcggttggtc atattgttgg gacaatacaa ggaatccgaa    33180
cgcaaatgag agtgggaata tccagcctgc gcacaattat ggccgatgct tcctcagccc    33240
ttagggaatg tgaaaattta atgactaaaa cctccacttc tgctattggg cctctttttt    33300
caacgatggc ttcccggtat gcacggttta cacaggatca aatggacatt ttaatgcgtg    33360
ttgacaaact aacaacagga gaaaatatac ccggtcttgc aaatgtagag atttttttaa    33420
ataggtggga acgaatagca acagcttgta ggcatgccac ggcagtcccg tcggccgaat    33480
ctattgcaac cgtgtgtaat gaattgaggc gcggtttaaa aaatatacaa gaggatcgtg    33540
taaatgcccc aacctcatat atgagtcacg cccgaaatct ggaagatcac aaggcagcag    33600
tttcattcgt tatggactcc aggcaacagt ttattgtgga ttctggacct cagatgggcg    33660
cggttttaac ttcacaatgt aatataggaa catgggagaa tgtaaatgca acgtttttac    33720
atgataatgt taaaataacg acaacggtca gagacgtaat ttcagaggct ccgacgctga    33780
taataggaca aagatggctt cgtccagatg agattttatc taatgtagat ttgcgtcttg    33840
gcgtacccgg gaatacaagt gggagtgacc cttaatataa aacaggcgtg tttatgtaca    33900
ttaaagtatt tgtggttttt attgactggg cgtttcgttt gtataacgct gttgttgcta    33960
gtattttcat aacctcctag gttttttggag ctacacgtgc ttattcaacg ctctttggaa    34020
tttgaatcat cgtaaacgta gcgtccctac cagttgagcg cgtaattttc gtaagcaata    34080
aaatggatat aattccgcct atagctgtca ctgttgcggg agtgggaagc cgtaatcaat    34140
ttgacggtgc cctgggaccg gcgtcaggtc tgtcatgttt aagaacatct ttatcgtttt    34200
tgcatatgac atatgcgcat ggaattaatg caaccctgtc atcagacatg attgatggat    34260
gtttacaaga gggtgcagca tggactacgg atctgtctaa tatggggagg ggtgtcccag    34320
atatgtgtgc tcttgttgat ctccccaatc gaatttcata tattaaactg ggggacacta    34380
ccagtacgtg ctgcgttttg tctagaatat acggcgatag ccatttttt accgttccag    34440 acgagggttt tatgtgcaca caaattcccg ctagagcgtt tttcgatgat gtgtggatgg    34500
gacgtgaaga gtcgtataca attataactg tagactcaac gggaatggcc atctatcgtc    34560
agggaaacat atcttttatt tttgatccac atggccatgg gactatagga caggctgtag    34620
ttgttcgggt gaataccacg gatgtgtact cttatatcgc atcggagtat acccaccgcc    34680
ccgataacgt agaatcccaa tgggccgctg cattagttttt ttttgtcacc gcaaacgacg    34740
gtcccgtaag cgaagaagcg ctatcttcgg cagtaacgct tatatacgga agctgtgata    34800
catattttac agatgaacaa tattgcgaaa aactggttac agctcaacat ccgttgcttc    34860
tttcacctcc taattccacg acaattgtgc ttaataaatc gtctatagta cctcttcacc    34920
aaaacgttgg tgaaagtgta tccttggaag caaccctaca ttcaacgtta accaacacgg    34980
ttgcactgga ccctagatgt agttacagcg aggttgatcc ttggcatgcg gttctagaaa    35040
caacctcgac tgggtctggc gttttggatt gtcgtcgtag acgccgtcct tcatggactc    35100
ctccttcaag cgaggaaaat ttagcttgta tcgacgatgg cttggtaaat aatacacatt    35160
ccacggataa tttacataaa cccgctaaaa aggttctcaa atttaaacca actgtagacg    35220
tgccggataa aacacaagtg gcacatgtat taccccgcct acgagaagtt gctaacaccc    35280
cagacgttgt gttaaatgta tccaatgtag atacgcctga atccagtccc acttttttcac    35340
```

```
ggaacatgaa tgtaggaagc agtttgaaag atcggaagcc atttctattt gaacagagtg    35400
gtgatgtcaa catggttgtc gaaaaactac tacaacatgg gcatgaaatt agcaatggat    35460
acgtacaaaa tgcggtgggt acgttggata ctgttattac cggtcataca aatgttccca    35520
tttgggtaac aaggcccttg gttatgccag acgaaaagga tccattggag cttttattta    35580
acctcaccat tttgcgttta acgggatttg tggtggaaaa tggaacacgt acacatcatg    35640
gtgctacaag cgttgtatca gactttatag gtccccttgg ggaaatttta acaggatttc    35700
cctccgccgc ggaacttata cgcgttacaa gtttgatatt aacaaacatg ccggggggcgg    35760 aatatgctat taaaactgtt ctccggaaaa aatgtacaat tggcatgctc attatcgcta    35820
agtttggtct agttgccatg cgggttcagg atacaaccgg cgctttacat gccgaactag    35880
atgtgttaga agcggatcta ggaggttcgt cgcccataga cctctattct agactgtcga    35940
caggtcttat aagtatacta aattcgccta ttatttctca tcccggactt tttgccgagc    36000
ttattccaac ccgtacaggg tccctgtctg aacgaatacg tcttctttgt gaattagtct    36060
cggcccggga gacacgctat atgcgtgaac acaccgcgct tgtttctagt gtaaaggctt    36120
tagagaatgc attacggtct acccgcaata aaattgatgc cattcaaata ccagaagttc    36180
cccaggaacc cccggaagaa accgacattc cacccgaaga gttaattcgg cgtgtatatg    36240
agatacgatc cgaagttaca atgctattga cctcggctgt tacagaatac ttcacccgcg    36300
gagtgttata tagcacacgg gccttgatcg ctgaacaatc ccctaggcgt tttcgggtcg    36360
cgaccgcaag tacggcaccc attcaacggc ttttagattc tcttccggaa ttcgacgcta    36420
aattaacggc aatcatatcg tccctgtcta tacaccctcc tcctgagact atacaaaatc    36480
tccccgtcgt atctctgtta aaagagctta ttaaagaagg ggaagattta aacacagaca    36540
cggctctcgt atcgtggtta tctgtagtcg gggaagctca aaccgcaggt tacttatcca    36600
gacgagagtt cgatgaatta tcacgtacaa ttaaaaccat taatacacgc gcaacgcaac    36660
gggcttccgc ggaagcagag ttgtcttgct ttaatacgct aagcgcggcc gtagaccaag    36720
ccgtaaagga ctatgaaaca tataacaatg gtgaggtcaa gtatcctgaa ataacacggg    36780
atgatttatt agcaacaatt gtacgtgcta cagacgattt ggtgcgacag ataaaaattt    36840
taagtgatcc aatgatccaa tccggtttac aaccttcgat taaaagacga ttggaaacaa    36900
ggcttaaaga ggttcagacg tatgcaaacg aggcccgaac cacacaggac acaataaaga    36960
gtcgaaaaca ggcggcatat aataaactcg gggggttact tcgcccggta accggttttg    37020
tgggacttag ggctgcagta gatttattac cggaacttgc ttctgagtta gatgtccaag    37080
gagccctggt aaatctcagg accaaagtct tagaggcgcc ggtagagatc cgttctcaac    37140
ttacgggtga tttctgggcg ttatttaacc aatatcgaga catttttagaa catcccggaa    37200 acgcacgcac atctgtctta ggaggactgg gagcttgttt tacagctatt atcgaaattg    37260
tgccgatacc tacggagtat agaccatcat tgcttgcgtt ttttggtgac gtggcagatg    37320
tgcttgcatc cgacatcgcg accgtatcta ctaacccgga aagtgagtcc gccataaacg    37380
ctgttgttgc aactcttagt aaagcgacgt tagtttcatc tacagtgcca gccttatcct    37440
ttgtgttgtc gttatataaa aaatatcagg ctttacaaca agaaattacg aatacccata    37500
agttgactga attacaaaaa caacttggag atgacttctc caccctagct gtctcatctg    37560
gacacttgaa gttatatatca tcttcaaatg tagatgatta tgaaataaac gatgcgatat    37620
tatcaataca aacaaatgtg cacgcccaa tggatacggt taaacttgtt gaagttgaac    37680
tgcaaaagct acccccccat tgtattgctg ggacatctac cttatctcga gtagtaaagg    37740
```

```
atcttcataa actcgtcaca atggcacatg agaagaagga acaggcaaaa gtgttaatta   37800
ccgattgtga acgtgcacat aaacaacaaa cgactcgggt tttgtatgag cgttggacac   37860
gtgatattat agcatgtctg gaggcaatgg aaacgcgcca tatatttaac gggacagaac   37920
tggcacggtt gcgagatatg gccgctgcgg gagggtttga tatacacgca gtttacccac   37980
aagcacgtca ggttgtagcg gcatgtgaaa ctacagccgt tacggcatta gatactgtgt   38040
ttcgccacaa tccatatacc cccgaaaata caaatattcc accacctttg gctttgttaa   38100
gagggttaac atggtttgat gatttttcga ttacggctcc cgtattcacc gttatgtttc   38160
caggtgttag tattgaggga ctccttctgc ttatgcgtat tcgcgcggtt gtgttattat   38220
ccgccgatac gtctattaat ggaataccta actaccgaga tatgatatta cgaacctcgg   38280
gggatctatt acaaataccc gcattggctg ggtatgttga tttttacaca cggtcttatg   38340
atcagtttat aaccgaaagt gtaacgttaa gtgaacttag agcagacatc agacaggctg   38400
ccggggctaa acttacagaa gcaaataagg ctttggagga agtaactcat gttcgggcac   38460
acgaaacggc taaacttgca cttaaagaag gtgtcttcat tacattacca agcgaaggtt   38520
tattgattcg ggctatagag tattttacaa ctttcgatca taaacgattt ataggaacgg   38580
catatgaaag agttttacaa acaatggtag accgcgatct aaaggaggcc aacgcagagc   38640
ttgcacagtt tcgtatggtg tgtcaggcaa caaagaaccg tgcaatacaa attttacaaa   38700
acattgttga tacggccaat gccactgagc aacaagaaga cgtggatttc actaacctga   38760
agacgttatt aaaactaacc cccctcccaa aacaattgc attggccatt gatagatcta    38820
cttccgttca ggacattgtc acgcagtttg cattgctgtt agggcgtctg gaagaagaaa   38880
ctggtacgtt ggacattcag gcggttgact ggatgtacca agctcgcaat attattgact   38940
cccatccact aagtgtgcgt atagacggta ccggcccccct gcatacttat aaagataggg  39000
tggataaact ttatgcgtta cgaactaaat tagatctcct acgacgacga atagaaaccg   39060
gtgaggttac gtgggacgat gcatggacaa catttaaaag agaaacgggg gatatgttgg   39120 catcgggga cacgtacgct acttccgtag atagtataaa ggcactccag gcatcggcgt    39180
ctgtggttga catgctttgt tccgaacccg aattttttt attgcctgtg gaaacgaaaa    39240
accgtctcca aaaaagcaa caggaacgta aaacggcgtt ggatgttgtg ttgcaaaaac    39300
aaagacagtt tgaagagacc gcgtctcgct tacgagcttt aattgaacgt attccaacgg   39360
agagtgacca tgacgttctt cgtatgttat tacgtgattt cgatcaattt acacatttgc   39420
ctatatggat aaaaacacag tatatgacat ttcgaaattt actcatggta cggttaggct   39480
tgtatgcaag ttatgctgag attttttccac ccgcgtctcc aaacggagta tttgctccta   39540
ttcccgccat gtcgggtgta tgtctagaag accaatcccg atgcattcgc gcgcgggtgg   39600
ccgcgtttat gggggaggcg tctgtggtgc aaacgtttag ggaagccaga tcttctatag   39660
acgctttgtt tggaaaaaat ttaaccttt acttggatac tgatgggggtt ccacttcgat   39720 atagagtgtg ttataaatca gttggggtta aacttggaac catgctatgc agtcagggtg   39780
gattatcttt cgaccggca cttcccgatg aaggtattgt ggaagaaact acactatcgg    39840
cattacgcgt ggccaatgag gtcaatgagc tacgcattga atacgaatcc gctataaaat   39900
ccgggttttc tgccttttcc acctttgtta ggcatcgcca cgccgaatgg ggtaaaacca   39960
acgcacgcag agccattgca gagatatacg ccggccttat aacaacaaca ttgacacgac   40020 aatacgggt tcattgggac aagcttattt attcttttga aaaacaccac ctaacttctg    40080
taatgggcaa tggactaact aaaccaatcc agagaagggg tgatgtacgc gtattagagt   40140
```

```
taaccctatc tgatattgta actattttgg ttgccacaac cccggtacat cttctcaatt    40200
ttgctagatt ggatttaatt aaacagcatg agtatatggc ccgtaccctc agacccgtaa    40260
tcgaggccgc atttagaggt cgtttactcg ttcgctcatt ggatggagac ccgaaaggca    40320
atgcccgggc cttttttaat gccgccccat ccaaacataa actcccgtta gctcttggat    40380
caaaccaaga tcctaccggc gggagaatat ttgcatttcg gatggcagat tggaaacttg    40440
ttaaaatgcc acagaaaata acggatcctt ttgcgccatg gcaactttcc ccccccccg     40500 gggtaaaggc caatgtcgat gcagttaccc gtataatggc aacagatcgt cttgcgacca    40560
ttactgtact tgggcgcatg tgtctcccgc caatttcctt agtgtcaatg tggaatacgc    40620
tgcaaccgga ggaattcgca tacagaacac aagatgatgt ggacattata gttgatgcga    40680
gactggattt gtcatccacg cttaatgcaa gatttgatac cgctcccagc aataccacgt    40740
tagagtggaa tacagaccgt aaagtaatta cagatgctta tattcaaacc ggggcaacga    40800
cagtttttac agtaacgggg gcggcaccaa ctcacgtttc taatgtaaca gcgtttgaca    40860
tagcaactac ggctatttta tttggggctc ctttggttat tgccatggaa cttacatccg    40920
ttttttcaca aaattccgga cttactttgg ggttaaaatt attcgattcc cggcatatgg    40980
ctacagattc gggtatatcc tcagccgtat ctcccgatat tgtttcttgg gggttacgtt    41040
tactgcatat ggatcctcac ccaattgaaa atgcatgttt aattgtccaa ctagaaaaac    41100
tgtccgcgct cattgcaaac aaacctctta caaacaatcc cccgtgttta ctgctattgg    41160
acgaacatat gaatccctct tatgttttat gggaacgaaa agactcgatt ccagctccgg    41220
attatgtggt cttttgggg ccagaatctc ttattgattt gccgtacatc gactccgatg    41280
aggactcttt cccctcgtgt cccgatgatc cattttactc gcaaattatt gccggttatg    41340
cgccccaagg cccccccaaac ctcgacacaa ctgattttta cccaacggag ccactattta    41400
agtctcccgt tcaagttgtt agaagttcca aatgtaaaaa aatgcccgtc cggcccgcgc    41460
agcccgcgca gcccgcgcag cccgcgcagc cgcgcagac cgtccagccc gcgcagccca    41520
tagaaccggg cacacaaata gtggtacaaa attttaagaa accccaaagc gtaaaaacaa    41580
cccttagcca aaaagatatt cccttgtatg tggaaaccga atcagaaacg gctgtgctta    41640
tacctaagca attaaccacc tccattaaaa caaccgtttg taaaagtatt accccaccaa    41700
ataaccaatt gtcggattgg aaaaataatc cacagcaaaa ccaaacgtta aaccaagcgt    41760
tcagtaaacc aatacttgag attacctcca ttccgacaga tgactcgata tcttaccgga    41820
cttggattga aaaatcaaat caaacacaaa acggcatca aaatgaccct cgaatgtata    41880
actccaaaac agtattccac cctgtaaata accaattacc ttcttgggtt gacacggcag    41940
ccgatgcccc ccaaacggac ctattgacaa actataaaac aagacagccg tcgccaaact    42000
ttccgcggga cgtacacaca tggggcgtat cttctaaccc gtttaactca ccgaacagag    42060
acctatatca aagtgatttt agtgaacctt ctgacggcta tagcagtgag agtgaaaatt    42120
ctatcgtact aagtctcgac gaacatcggt catgtcgcgt tcctaggcac gtacgcgttg    42180
ttaatgccga tgtagtcacc ggtcgacgtt atgtccgagg accgccttg ggagcactgg     42240 cactgttaag ccaggcatgt cggcgtatga tcgacaacgt tagatataca cgtaaacttt    42300
taatggacca cacggaagat atatttcaag gcctgggta tgttaaattg ttattagatg     42360
gaacatatat ataaagtagc gcctattaaa gaaaaaaaaa aaacaacgat tattttctgt    42420
gtatttttat ttcaccccta cgacttcttg aagcgtttcc agattgtccc gtgtgtgaca    42480
aggtctgtcc cttacccccc tgggggtat tttggttgg gggcggggta gactgtggca      42540
```

```
cgccttgggc cgcgggcggt gatccggttg ttggctggac agtgcttgac tgtgctccct   42600
gttgcggttg ttgtccagaa gaccccgaca ccacgtgttg ctgttgtcca acggatgccg   42660
acgtcgtttg aggtgggggg tgttgcgggg atgatcccga aaacgccaac gcggcgggct   42720
gttgtaaagc agactgatcg gcgctctgtg ttttttgcgg caatatagta ggccccgaga   42780
ttcccaaact catggatgga tttgggggtt gtggtcgtat aatacgcggg ttaaacgtac   42840
gttttaagcc aaccgttggt cttaaccatg tcatagggtc agtctcggca aacatggccg   42900
ttcggcgtat cgtatttgca ttatggttag cgcgtgcacg cgcggcactg gccgcggctc   42960
ccacggtgta aatgcttctg gcatcagcga tgtccacacg tgaccaggt tgcaaaggtc    43020 cactggcgtt taaaagtcgt attaaagcaa cggggtgta agccgcaatt gcttccaccg    43080
aaaatgtggt ggggttgctg ggatcaaaga ctacacgaga cgatgcgggt tgtgtcatcg   43140
tttattagtt tacgggacaa tcgataacag catacacgta catctgcgca ggatatgtac   43200
ggaaaggcaa tttatttcca gaaaagcacc gccctaata caactaccag tacaattaca    43260
atgaacaggg catatgtcac gttagctacg ggtagagcaa gtttccagac acgcgtagtt   43320
tgggtatcgg gtaacgcagg tttaatgtca ctttgcattt gaacagacgt gtttggactt   43380
ccgttctcgg gtggggatct gaatgaaggc cgccagcgta tatattcatc caaattattg   43440
ccagtttcct tatacatgta tgcatccgtg gcgcgggcca taagtttaat ggtgcgagat   43500
ggatcttccg gtcccataaa acgaaaggat aactgaacat atggcattcg cacaaagcag   43560
ttcacccaca ttaaagcctg gagaggtcgg cggtcaatac ccccacctcg tttaattgat   43620
tccaaagcag ataggttgat accggtactt aacgttgaac taagaatcac gttattactg   43680
tcaatggaca cttcagccac tggtgcgtta gtcggacgaa aaaaaaaacc ttgaaatagc   43740
acagacaccc ccgtattttg aattttatg taagggtcac aatctacttg cgcccaattc    43800
gccattaaac gcataatata ctctaccgga aaggcttcgg atacgttgtc ttcgccgtta   43860
aactgaaaaa cacaacgggc gggggggcgt tgtggatcaa atattggaag atccccatcg   43920
caacattgaa gagcgcttgg taccaccaac cgaatacgtt gtaaaagatt atctccgcaa   43980
cccctcctgc gttcactccg tacatacgtt ctccgtgaca tattgatcta aggttgcaaa   44040
ccaaggcaca cgcgtgaagt atttagacca tttatcgtgg gatataggag gagtttggag   44100
tgatccaccc cctgacgact tattaatgcg tttatttcc ccatgtatta agcatccttc    44160
aatatttcat gcaaatctag aaatttggcc atgactcccg caaagcgttc acggcgacgg   44220
gtcacgctgg cactatgttc acatggaaca acataagcag attttctga atcgttactt    44280 tctttatgtt ttaaaacgga cgccaggcga ctggtaaatg atatataatt taattgagcg   44340
tcagttgtag gtagaattgc ttctatttcc gggggaatta aattttcaaa ccaaacggaa   44400
agagtaaagg tgctatcagc aggaaaatac tttgactcca gtgcatcgat atttaataga   44460
ttaacatcgg tgtctgtaat taaatcgcgg gccctcatcc cagagatgga tcgggtagaa   44520
tcagaagaac ccatggatgg attcgaatcg cccgtattct ccgaaaatac atcttctaat   44580
tccggatggt gttccgacgc attttccgat tcgtacatcg cttataatcc agcccttctg   44640
ctaaaaaacg atttgttatt ttcagaattg ttatttgcct cccacttaat aaatgttccc   44700
cgtgcaatag aaaacaacgt cacttatgag gcctcttcgg cggtaggtgt ggataatgaa   44760
atgacctcaa gtaccactga atttatagaa gaaattggag acgttttggc gttagacaga   44820
gcctgtttgg tctgcagaac gcttgatttg tataaacgta aatttggact gacaccggaa   44880
tgggttgcgg actacgccat gttatgtatg aaaagtctgg catccccgcc ctgtgcagtt   44940
```

```
gtcactttta gcgctgcctt tgaatttgtg tatcttatgg atcgttacta cctgtgccgt    45000
tataacgtta ctttggttgg gtcctttgcc aggcgcacgc tttccctgtt agatatacaa    45060 agacatttt ttttgcatgt atgttttcgt accgatggag ggttaccagg tatacgaccg    45120
ccccccggta aggaaatggc caacaaagta agatattcca attactcctt ttttgtacag    45180
gcggtagtta gggctgcatt actatcgatc agcacgtctc gtttagacga aaccgaaacg    45240
cgtaagtcat tttactttaa tcaggacgga ctgactggag ccctcaacc tttagcggcc     45300 gccttggcta attggaaaga ttgcgcgcgg atggttgact gttcatcatc ggaacatcgc    45360
acaagtggga tgattacctg cgcggaacgt gcattaaaag aggatataga gtttgaagat    45420
atattaatag acaaacttaa aaaatcgtct tacgtagaag cagcttgggg ttacgcagac    45480
ttggctttat tattactgag tggggttgct acttggaatg tagacgagcg tacaaattgt    45540
gctatagaaa ctcgcgttgg atgtgttaaa tcatactggc aggcgaaccg gattgaaaac    45600
tccagggacg ttccaaaaca attttccaaa tttacgagcg aggatgcctg tcccgaagta    45660
gcatttgggc ctattttgtt aactaccta aaaaacgcaa agtgccgtgg tcgcacgaat     45720
accgaatgca tgttatgttg tttattaacc ataggcgcact attggatcgc tttgcggcag   45780
tttaaaaggg atatattagc atactcagca aataacacaa gtttatttga ctgtatcgaa    45840
cctgtaatca atgcatggag cctagataac cccattaaac ttaaatttcc atttaatgat    45900
gagggtcgat tcataaccat tgtaaaagca gcaggttccg aggccgtata taaacattta    45960
ttttgcgatc tcctatgcgc tctctcggaa ttacagacaa accctaaaat tttatttgcc    46020
catcctacaa ccgcggataa ggaagtgttg gagttatata aagcccaact ggctgcacaa    46080
aacagatttg aaggtcgtgt atgtgctggc ctgtggacat tggcgtatgc atttaaagcc    46140
taccagattt ttccacgcaa accaaccgcc aatgccgcat tcatacgaga tggaggactt    46200
atgcttcgac gacatgcaat atcgctggtc tccctcgaac acaccctatc gaagtatgtc    46260
taggcgatat aaatccgtat ctcggagcgg gccttcgatg cgtgtacgct ccagaacgcc    46320
atgccgccgt caaaccattc gaggaaaact tatgtcaaag gagcggtctg tgtaccgcca    46380
ttattttaat tacatcgcaa ggtccccccc agaagaacta gctaccgtta gaggcttaat    46440
cgtgccaatt attaagacga cccctgtcac ccttccgttt aacttgggtc agacagtggc    46500
ggataactgc ctgtcgttat ccggaatggg ttatcattta ggtctcggag gttattgtcc    46560
gacatgcact gcatctggag aaccgcgtct atgtcgaacc gatcgggcgg ctctgatact    46620
agcatatgtt cagcagctta acaacatata cgaatatcgt gtgtttcttg catccatttt    46680
ggcgctatca gaccgagcca acatgcaagc agcgtccgct gaaccccctat tgtcgagcgt    46740 attggcacaa ccggaattat tttttatgta tcatattatg agggaggggg gcatgcgaga    46800
tatacgcgta ctttttttatc gtgatggaga tgccggaggg tttatgatgt atgttatatt    46860
tccggggaaa tctgttcacc tccattacag actaatcgat catatacagg ccgcgtgtcg    46920
ggggtataaa atagtcgcac acgtttggca gacaacattt ttactgtcgg tatgtcgcaa    46980
cccagaacaa caaacagaga ctgtggtgcc atccattgga acatcggacg tttactgtaa    47040
aatgtgtgac cttaactttg atggagaatt gcttttggaa tacaaaagac tctacgcatt    47100
atttgatgac tttgttcctc ctcggtgatt tcagcttcag tgttcatttt attatcccag    47160
cacggggcgt gtatacaaac aaagcctgcc gcctgcaagc ggtttagcat tttaacgtta    47220
acaactcgtg tctctggaat aaaacgtttt aaaagccgtt ctgtgagttt agtgtcgttt    47280
ccaaataacg ccttaaaagt tacactcgcc gtcccaatga gatgagaaaa ataatagtca    47340
```

```
atgtttaaag acagcccgtg tgatgttacg tgaatgggat cttccgctaa gtcagatatt    47400
attaacttac gctttgcttc cccacaccgt ttacctgcgg tattctgtaa aggatctcca    47460
cgtagcaaag ctacactttt tgcatcagcc tccacttcgt ctgtggggc cacaataaca     47520
taagggatgc gttctcgaac gtttgggatt tgaccctgtc tcattactaa tttataatat    47580
actgttaagt gagccaagcg acggtttatg taggcggatg gtggacgact aagctcggcc    47640
gtcataacaa acttattaat atccaatttg ggtgatgtaa tctggcgatg tgcatctgca    47700
attatgcgtc caaacccggc catcccagac ggcatggccc gtctattcca ttcagcaatg    47760
gaaacacacg acgcctccgc cgcagcacgc gagacggtgt cgtcatataa caacagttct    47820
acaagtttgc gggcataatc gttaataaat tgacagttgt tttttctaac caagtcgact    47880
cccttcatta aaacctttcc gccgtaaatt accccaatgt actttttctt tgttataagc    47940
aaaagtttta taaagttttt ttcacactcc aactttatag gaggacaaaa cagagccgtt    48000
gaaattatat gtgccatttt ctcgccgatt ttagctatcc cctcaacact aacacccttg    48060
aatcggataa acacagaatc cgtatctcca tatataacct ttacctcgta cgcttttttgg   48120
gagagaacgc tactttcaat gtctggaaac gctgtaataa aacgttcaaa tgcggcccag    48180
ttattatgaa tataatctct ggtacttaat aacatttgac ggccaattgt agtgacagtg    48240
gccgctacgt ataaacatgg cagaaatccc tgcgcaactc cagtaaaacc gtacacggaa    48300
ttacaaacta ctttttatcgc ggcttgttgt ttgtctaata acactgcttc atctgaagaa   48360
cttccgggta tgcgcgctct aatagccttg cgcatagcca accagtcttt taaaagaaca    48420
cccagcagac tttctcgaac gttagagcgc acaaaaaaaa gacgttttcc tccaactgta    48480
aaggtggcat aatcggatgg attcaaacgt ttaaccgtct caaaatttaa cgttagcgtg    48540
gtaaaacata agttatgggc ctgaattata cttggatata aacttgcaaa atccaatacg    48600
accaccggat cgatataaaa tcccgtatca gggtcaaaaa ccctggctcc tttatatcct    48660
acatttcgcc cacttgacgt accagtggga gaaacgctct cgtcttcatc catctcttcc    48720
tcaacatccc cgacatcggg aataacatcc ttatattcaa aagtagctgg gtatcccccca   48780
tcgggtaaaa taaatcctcg agacgaagcc agtcctaata aacaggtgta aatcctaacc    48840
tgctgtccgt cgtaaatagc cttggttaaa gtaattctag ctagccttgc aaccgcggat    48900
aactcaaggt gtggtaaata tttaaaaaac agtttcccca caagagccga gtcttgtata    48960
caatattcac caataattcc tcgtgtattc ggtccactag cgtaatatcc cggaatgtct    49020
ttgtagggca aatctctctt ggactcattt agagcttcac gtgcaaccga atctaattta    49080
taactcgaga gtttttaattt ttcagttgca attgcataca tatccagaga tatgagaccg   49140
ttgatctttta ccttgcttcg tcgctgaaat ccggatttgc caacatccca tatcttaaac   49200
agaccccccac ggtttatact gccataacca tcaagcttga gactgtatat agaattaagt   49260
ttctccataa taaacgccca atcaaaatta acaatgttat aacctgtggc aaactcggga    49320
gcgtactgtt ttacgagggt cataaatgca attaatagct cgaattcact atcaaactcc    49380
agcacagtcg gctccggtaa ccccgcgtcc ttcatttctt gtacatacct ttgtggtaag    49440
tcacaagagc caagggaaaa cagtaaaatg tgttctaaag actgtcgagg gattgaatat    49500
aatagacaag aaatttggat tacaagatcc tccagatgtg ttgcatcggg aaacgccagc    49560
tcattagatc ctcctgattt acattcaata tcgaaacata acaacttgta gtcaggccat    49620
gagtcatcgt ttggtatagc ctgcagatta tccgacatgc agtcaatttc aacgtcgctt    49680
aacgttaatt ggcgacttgc cggtcgaact cgaacacgtt ccccatcaac tccaggtttt    49740
```

```
agttgatacc aaccaaaact aacaaagccg ggattatcca ttagaaaacg agtggtagcg   49800
tctacccgac cttcatactt tttcaactcc gggtgaaagt tatcacaaag ataatttgta   49860
aatttagatg agggagaata caccctgtaa aacgcacatg gctgtgtatc gtagtaataa   49920
acatctgtgc gctcaataac ctcaacgcga aagctttctg gagatgcgct tttaaacgag   49980
gtaccatgaa aagcgttctt gtctccattt aacgttgcat cattttgtgt tatcatagaa   50040
ctgcgtaaac actcggcaag taatacagat aactcgctac cggaacgtat gccacaagcg   50100
gtatccacct cggctttgtt tatataaaaa tattgacaga tgccgtatac atgaactgcc   50160 acccttttc cacatcggga catgccaagt aaagtaataa cggtaccaag cggtcgtgtt   50220
gcagttgcaa accgggatac atctccatta gacgcggctt ctgttgtttc gacaatatca   50280
tatacatgga atgtgttaaa gcgggggtca aacttatccc cacgaaagtc gatttccccc   50340
caaatattca cgcgtctagg ccaggggctg gaacaacgaa aatccagaat cggaacttct   50400
tttccattac agtaaacttt aggcggtcga ctaagtgtac cgacgtgaac cccctttcgt   50460
tcttccatgg gcacatcttc atctaaacat ttaggggcca aaaattgaaa cgatgacatg   50520
gtagttttgt aactatgaag aaattctctg ttactaccgc gcccggttct tgggttatat   50580
ttaatccctg atgcttgggt taaaaaggga ttacaaaacc ccgttctgat cgccatttta   50640
tgttaacgat tgataatctt gtaaaaagcc agtgttactg agtaacacaa ccccacgccc   50700
ttctaataca taaagtgtaa tcacgtgatt tgttgtggtt tccgcatatg taatacccgt   50760
ttaaaagcct ctcttcttaa tgtatcgaca gactgggttt tgggtggtca tttgaccctg   50820
ccaacaaccc cccattatta cgagtacttc accaaaatgg aaaatactca gaagactgtg   50880
acagtgccca cggggcccct gggttacgtt tatgcgtgcc gggttgaaga tttggatctg   50940
gaggaaattt cattttggc cgctcgtagc acggactctg atttggcttt attaccttg    51000 atgcgtaatt tgaccgtgga aaaaactttt acatccagcc tggcggtggt ttctggagca   51060
cgcactacgg gtcttgccgg agctggtatt accttaaaac tcactaccag tcatttctat   51120
ccatctgtct ttgtctttca cggaggcaaa cacgttttac ccagctccgc ggccccaaat   51180
ctcacacgcg cgtgtaacgc ggctcgagaa cggtttgggt tttcacgctg ccaagggcct   51240
cctgttgacg gtgctgttga gacgaccggc gctgagatat gcacccgcct tggattagag   51300
ccagaaaata caatattata cttggtggtc acggcattgt ttaaggaagc cgtatttatg   51360
tgcaacgtgt ttctgcatta tggaggactc gatattgttc atattaacca tggggatgtt   51420
atacgtatac cgttatttcc ggtacaactt ttcatgcccg atgttaaccg tctggtaccc   51480 gaccccattca acactcatca caggtctatc ggagagggtt ttgtataccc aacacccttt   51540
tataacaccg ggttgtgcca tttaatacat gactgtgtta ttgctcccat ggccgttgcc   51600
ttgcgcgtca gaaatgtaac tgccgtcgcc cgaggagcgg cccaccttgc ttttgatgaa   51660
aatcacgagg gggcagtact cccccctgac attacgtaca cgtatttca gtcctcttca   51720 agtggaacca ctaccgcccg tggagcgcgt cgaaacgatg tcaactccac gtctaagcct   51780
agcccatcgg gggggtttga aagacggttg gcgtctatta tggccgctga cacagccttg   51840
cacgcagaag ttatattcaa cactggaatt tacgaagaaa ctccaacaga tatcaaagaa   51900
tggccaatgt ttataggcat ggagggcact ttgccaaggc taaacgctct ggggtcatat   51960
accgctcgtg tggccggggt cattggtgcg atggttttca gcccaaattc tgcgttgtat   52020
ctaactgagg tggaggatag cgggatgacc gaagccaagg atgggggacc gggtccatca   52080
tttaatcgat tttaccagtt tgccggacct catttagctg cgaatcccca aacagatcga   52140
```

```
gatggccacg ttctatccag tcagtctacg ggttcatcaa acacagagtt tagcgtggat    52200
tatttggcac tcatttgtgg atttggagca cccctgttgg cgcgactgct tttttatcta    52260
gaacgctgtg acgctggtgc gtttacaggg ggtcacgggg atgcgttaaa atatgttacg    52320
gggacctttg actctgaaat tccatgtagt ttatgtgaaa acacacgcg gccggtatgc     52380 gctcacacaa cagtacaccg acttagacaa cgcatgccgc gatttggaca agccacccgt    52440
caacctattg gggtgtttgg aacaatgaac agccaatata gcgactgcga tcctctagga    52500
aactatgctc catatttaat ccttcgaaaa cccgggatc aaacggaagc agcaaaggca     52560
accatgcagg acacttatag ggctacacta gaacgcttgt ttatcgatct agaacaagag    52620
cgactactgg atcgcggtgc cccatgttct tccgagggac tatcgtctgt cattgtggat    52680
catccaacgt ttcgtcgcat attagacaca ctgcgtgcgc gtatagaaca gacaacaaca    52740
caatttatga aagtgttggt tgagacccgc gattataaga tccgtgaagg attatccgaa    52800
gccacccatt caatggcgtt aacgtttgat ccatactcag gagcattttg tcccattacc    52860
aattttttag ttaaacgaac acacctagcc gtggtacaag acttagcatt aagccaatgt    52920
cattgtgtat tttacggaca gcaagttgag gggcggaact tcgtaaccca attccaacct    52980
gttttgcggc ggcgttttgt tgacctgttt aatggggggt ttatatcaac acgctctata    53040
accgtaacat tatctgaagg tcctgtatcc gccccaaatc cgacattggg acaagacgcg    53100 cccgcgggc gtacctttga tggggattta gcgcgcgtaa gcgtggaagt tattcgggat     53160
atacgagtta aaaatagggt cgttttttca ggtaactgta caaatctctc tgaggcagcc    53220
cgggcaaggc ttgtaggcct tgcaagtgcg taccaacgcc aagaaaaaag agtggatatg    53280
ttacacgggg ccctagggtt tttgcttaaa cagtttcacg gcctgttatt tcctcggggt    53340
atgccaccaa acagtaaatc ccccaacccg cagtggtttt ggaccctgtt acaacgcaac    53400
cagatgccgg cagataaact tacacacgaa gagattacca ctattgcagc tgttaaacgg    53460
tttaccgagg aatatgcagc aataaacttt attaatctac ccccaacctg cataggagaa    53520
ttagcccagt tttatatggc aaatcttatt cttaaatact gcgatcattc acagtacctt    53580
ataaatacct taacttctat aattacgggt gccaggcgcc cgcgtgaccc atcatccgtt    53640
ttgcattgga ttcgtaaaga tgtcacgtcc gccgcggaca tagaaaccca agcaaaggcg    53700
cttcttgaaa aaacggaaaa cttaccggaa ttatggacta cggcttttac ttcaactcat    53760
ttagtccgcg cggccatgaa tcaacgtccc atggtcgttt taggaataag cattagtaaa    53820
tatcacggag cggcaggaaa caaccgcgtc tttcaggcag ggaattggag cggtttaaac    53880
gggggtaaaa atgtatgccc gctatttaca tttgatcgca ctcgccgttt tataatagca    53940
tgtcctagag gaggttttat ctgccccgta acaggtccct cgtcgggaaa tcgagaaacc    54000
accctatccg accaagttcg cggtataatt gtcagtggcg gggccatggt tcaattagcc    54060
atatacgcca cggttgtgcg tgcagtgggc gctcgagcac aacatatggc atttgacgac    54120
tggttaagtc ttacagacga tgagttttta gccagagact tggaggagtt acacgaccag    54180
attatccaaa ccctggaaac gccctggacc gtagaaggcg ctctagaagc agtaaagatt    54240
ctagatgaaa aaacgacagc gggagatggg gaaaccccca caaacctagc atttaatttt    54300
gattcttgtg aaccaagcca tgacaccaca tctaacgtat taaacatttc agggtcaaac    54360
atttcagggt caactgtccc tggtcttaaa cgaccccccg aagatgacga actctttgat    54420
cttagtggta ttcccataaa acatgggaac attacaatgg aaatgattta acctccctct    54480
ttatccaatt aaagcccaca cgcgggtgag tgtacgtaat aaacaagtca atattacata    54540
```

-continued

```
ttctgttgtg ttttcttttt ttgtgtgtag tccttaccca tatgacctgt aatatagtgt    54600
gtctccaacc attcagctta cagtccagtg gacagtaaca gcccgataac atggaattgg    54660
atattaatcg aacattgttg gttctactgg gtcaagttta tacgtacatc tttcaggttg    54720
aactgctacg tcgatgtgat ccaagggtgg cgtgtcgctt tttatatcgg ttagcggcta    54780
actgtttgac agttcgttat ttattaaagc tgtttctccg gggatttaat acccagctaa    54840
aatttggaaa cactcccacg gtttgtgcac tgcattgggc attatgttat gtaaagggag    54900
aaggtgagcg tttgtttgag ttgctacaac attttaaaac gcgttttgtt tatggtgaga    54960
ctaaagactc aaactgtatc aaagattact ttgtctcagc gtttaactta aaaacctgcc    55020
aatatcacca tgagctgtcg ttaacaacat acggaggtta cgtatcgagt gaaattcagt    55080
ttttacacga cattgagaat ttttttaaaac agcttaatta ctgctatatt atcacgtctt    55140
ctcgtgaggc gctaaacaca ttggaaaccg tgacgcggtt tatgacagat actataggaa    55200
gcggtctaat accaccgtg gagttgtttg atccggcgca tccatgtgct atatgttttg    55260
aagaattatg tataacagct aaccaaggtg agaccttaca tcgtagatta ttaggatgta    55320
tctgcgatca cgttactaag caagttcggg ttaacgtgga tgttgacgat attattcggt    55380
gtttaccata tatccctgat gtaccggata tcaaacgtca atccgccgtt gaagcgttac    55440
gaacacttca aaccaagacg gtagtcaatc ccatggagc aaagaacgat acgtttgacc    55500
aaacatacga aattgcgagc accatgcttg attcttataa tgttttaaa cctgcccctc    55560 ggtgtatgta cgccatcagc gagcttaaat tctggttaac gtctaattcc actgaaggac    55620
cccaacgtac tttagacgtg tttgttgata atttggatgt attaaacgaa catgaaaaac    55680
acgcagaact tacagccgta acggttgagt tggcgttatt tggaaaaact cccatacact    55740
ttgatagggc gttttctgaa gaactcggat ctctggatgc aattgatagt attttggttg    55800
gcaatcgctc atcctcacca gacagtcaga tagaagcatt aattaaagcc tgttatgccc    55860
atcatctatc gtcgcctctc atgcgtcaca tttctaaccc gagtcatgat aacgaagccg    55920
ccttacgcca acttttagaa agagttgggt gtgaggatga tttaaccaaa gaggcgagtg    55980
acagcgctac agcatccgaa tgtgatctga acgatgatag tagcataact tttgctgttc    56040
atggatggga aaacctgtta tccaaagcaa aaattgacgc tgcggaaaga aaacgagtat    56100
atcttgaaca tctgtctaag cgctctctaa ccagcctcgg tagatgtatc cgcgaacagc    56160
gccaagagct agaaaaaaca ctcagggtaa acgtttatgg agaggcctta ttgcagacat    56220
ttgtttcgat gcaaatgggg tttgggcac gaaacgtgtt tttagctaag gtttcccagg    56280
cagggtgtat tatcgacaat cgcattcagg aagcggcctt tgatgcacat agatttataa    56340
ggaatacctt agttcgacat acagtagatg cggctatgtt acctgcactt acacataaat    56400
tttttgagtt ggtcaacggc ccattgttta atcacgatga acaccgtttt gcacaacccc    56460
ctaacaccgc cttattttt accgtggaaa acgttggcct atttccgcac ttaaaagagg    56520
aattggcaaa gtttatgggc ggtgtcgttg gttccaactg gcttctcagt ccatttaggg    56580
gcttttattg cttttctggg gtagaaggcg ttacttttgc acagagactt gcctggaaat    56640
atattaggga gcttgtgttt gcaaccacac tattcacctc tgttttccat tgtggggagg    56700
tgcggttatg tcgcgttgac cgtctaggta aggatccacg cgggtgcacg tctcaaccta    56760
aaggtatagg cagttcccac ggacccttag acggcattta tttaacgtac gaagaaacat    56820
gtccccttgt ggctattatt caaagtggag aaacagggat cgaccagaat accgtcgtaa    56880
tctacgattc agacgttttt tctcttctat acaccctaat gcagcggctg gctccggatt    56940
```

```
caacggaccc ggcgttttca taacctccgt tacggggtg tggttatgct ttttatgcat    57000
attttctatg tttgttacgg cggttgtgtc ggtctctcca agctcgtttt atgagagttt    57060
acaagtagag cccacacaat cagaagatat aacccggtct gctcatctgg gcgatggtga    57120
tgaaatcaga gaagctatac acaagtccca ggacgccgaa acaaaaccca cgttttacgt    57180
ctgcccaccg ccaacaggct ccacaatcgt acgattagaa ccaactcgga catgtccgga    57240
ttatcacctt ggtaaaaact ttacagaggg tattgctgtt gtttataaag aaaacattgc    57300
agcgtacaag tttaaggcga cggtatatta caaagatgtt atcgttagca cggcgtgggc    57360
cggaagttct tatacgcaaa ttactaatag atatgcggat agggtaccaa ttcccgtttc    57420
agagatcacg gacaccattg ataagtttgg caagtgttct tctaaagcaa cgtacgtacg    57480
aaataaccac aaagttgaag cctttaatga ggataaaaat ccacaggata tgcctctaat    57540
cgcatcaaaa tataattctg tgggatccaa agcatggcat actaccaatg acacgtacat    57600
ggttgccgga accccggaa catataggac gggcacgtcg gtgaattgca tcattgagga    57660
agttgaagcc agatcaatat tcccttatga tagttttgga cttccacgg gagatataat    57720 atacatgtcc ccgttttttg gcctacggga tggtgcatac agagaacatt ccaattatgc    57780
aatggatcgt tttcaccagt ttgagggtta tagacaaagg gatcttgaca ctagagcatt    57840
actgaaacct gcagcgcgga acttttttagt cacgcctcat ttaacggttg gttgaaactg    57900
gaagccaaaa cgaacggaag tttgttcgct tgtcaagtgg cgtgaggttg aagacgtagt    57960
tcgcgatgag tatgcacaca attttcgctt tacaatgaaa acactttcta ccacgtttat    58020
aagtgaaaca aacgagttta atcttaacca aatccatctc agtcaatgtg taaaggagga    58080
agcccgggct attattaacc ggatctatac aaccagatac aactcatctc atgttagaac    58140 cgggatatc cagacctacc ttgccagagg ggggtttgtt gtggtgtttc aacccctgct    58200
gagcaattcc ctcgcccgtc tctatctcca agaattggtc cgtgaaaaca ctaatcattc    58260
accacaaaaa caccgactc gaaataccag atcccgacga agcgtgccag ttgagttgcg    58320
tgccaataga acaataacaa ccacctcatc ggtggaattt gctatgctcc agtttacata    58380
tgaccacatt caagagcatg ttaatgaaat gttggcacgt atctcctcgt cgtggtgcca    58440
gctacaaaat cgcgaacgcg ccctttggag cggactattt ccaattaacc caagtgcttt    58500
agcgagcacc attttggatc aacgtgttaa agctcgtatt ctcggcgacg ttatctccgt    58560
ttctaattgt ccagaactgg gatcagatac acgcattata cttcaaaact ctatgagggt    58620
atctggtagt actacgcgtt gttatagccg tcctttaatt tcaatagtta gtttaaatgg    58680
gtccgggacg gtggagggcc agcttggaac agataacgag ttaattatgt ccagagatct    58740
gttagaacca tgcgtggcta atcacaagcg atattttcta tttgggcatc actacgtata    58800
ttatgaggat tatcgttacg tccgtgaaat cgcagtccat gatgtgggaa tgattagcac    58860
ttacgtagat ttaaacttaa cacttcttaa agatagagag tttatgccgc tgcaagtata    58920
tacaagagac gagctgcggg atacaggatt actagactac agtgaaattc aacgccgaaa    58980
tcaaatgcat tcgctgcgtt tttatgacat agacaaggt gtgcaatatg atagcggaac    59040
ggccattatg cagggcatgg ctcagttttt ccagggactt gggaccgcgg gccaggccgt    59100
tggacatgtg gttcttgggg ccacgggagc gctgctttcc accgtacacg gatttaccac    59160 gttttttatct aacccatttg gggcattggc cgtgggatta ttggttttgg cgggactggt    59220
agcggccttt tttgcgtacc ggtacgtgct taaacttaaa acaagcccga tgaaggcatt    59280
atatccactc acaaccaagg ggttaaaaca gttaccggaa ggaatggatc cctttgccga    59340
```

```
gaaacccaac gctactgata ccccaataga agaaattggc gactcacaaa acactgaacc   59400
gtcggtaaat agcgggtttg atcccgataa atttcgagaa gcccaggaaa tgattaaata   59460
tatgacgtta gtatctgcgg ctgagcgcca agaatctaaa gcccgcaaaa aaataagac    59520
tagcgccctt ttaacttcac gtcttaccgg ccttgcttta cgaaatcgcc gaggatactc   59580
ccgtgttcgc accgagaatg taacgggggt gtaaatagcc aggggtttg ttttaattta    59640
ttaataaaaa tgtgtattac gttactcatg tgtctccatt acgcatcaca gggggtattt   59700
atacccgata atatacaaaa cgcgttttgt acctctaccg cacccgatat cttaacgggg   59760
ttattatgga atcgtctaac attaacgcgc tacaacaacc gtcgtctatc gcacatcatc   59820
cgtccaaaca gtgcgcttca agtctcaatg aaacagtaaa agattctccc cccgcgattt   59880
atgaagatag gttagaacac acgccggtac aattaccccg cgacggtaca ccccgagacg   59940
tatgttctgt gggacagcta acctgtcgag catgtgcaac gaaacctttt cgccttaacc   60000
gcgacagcca atacgactac ttaaacacat gtccaggggg ccgtcatatt tcactggcac   60060
tggagattat aacgggtcga tgggtttgca tcccgcgtgt gtttccggat accccagagg   60120
aaaaatggat ggcgccatat attattccag accgagaaca accatcatca ggggatgaag   60180
attctgacac cgattaaatt taacttaaat aaaaccttac cacccataaa aacgccttct   60240
gtttgtttaa cacgacaccg cttaacaaaa aaaaaaaaac caaacacgcc ttttatgaat   60300
gtaatacttt tatttgttgg ttaacaccgc cccaccatca tctgatttgc aaacatatcg   60360
gcgtcgtctg ccgtggaccc ctgtattaaa ggggccttgg aactcgcctc cactgcattt   60420
acatcttgtc caactgtatc tgtatgtggg gtgcttgttg tattttggga tgagcataga   60480
cccgaaacgc tttgaagctg ttttaataaa atcgatattc gaggatcccg tgtccctct    60540
ggtatatttg tatggtgcga caaaggcatt tgtgtcccat tttgtgattt tagctctgta   60600
acctcctgtt gcagttttgc cacaaccca gcaagctctt cgtgctgacc attagaaact    60660
ctgtgtctcc tctgccaata tgatggagaa actcgacgtc tccgatgcgt tatatacgtt   60720
ggttcaccgg gaaatatat atttgaggga aactctccgt ccatttgaga ctccccacta   60780
taaaagaat ccaattccct ttgatccatg ctcttgaaat cccgttttcc tggacgacgg     60840
acatcggttt tgtctggaaa atttacacac ggggtctgca agtcaatacc ccgttcggcg   60900
gccaatgcgt tcataaatgc ggacatttgc atttccaaac gattgggtgg tggatatccc   60960
ggaaacccgt acgtccccc gaagtgtccc ggagggcaac cataacccc tgtattaggt     61020
gggaaggcag gcgggtgtgg agatccatat ggcccgacga tatactgtcc gttatttgga   61080
gctccaattg atacctgcgg attttagtc tgcccggtta acagctgtga ataatacgcg    61140
gtaggtatca gtacaaattc ccctccggtt ggaacgcccg acggggggctg tggtgagata   61200
ttactagcgt tacctgctac agaagccata tcgctgtcgt tcctacacaa ctgcgtaacc   61260
tttaaatgcg gaacagtctt ttcacaatct tcatttgatt ccccaacacc caacgcgaga   61320
tcgtatatgg gcccgccggg gtggaatgtg gcgtttataa cacccgcgtt gggtaattta   61380
gactccaccc cattaacgtt ggttatccga gcaagtccat atccggtgct agcctgaaga   61440
taaacgtgac ccataattcc ggcttcgcgt ctacgtttg caaccacgtc ccatctatct    61500
cttaaaagca tattgttcac ggctgtggat aataacacct tggcgagttt atcttcgcta   61560
accttccata cttttattaa acccgcgtag tctttaacca gcgacaataa ccgcgcttta   61620
cttttccatcg ataaaacccg gaatggttca attgaagatt ccggggtaca gtcataattg   61680
accactgttc caacgcgtct tccaacaaca cataacgcaa catgggtaaa aaaattaccg   61740
```

```
tctggtatct cattcgggga caatcgtttt gaagacaggg atacggaggg taagtaattt    61800
gtgaccaagt ataacgcacg ttctagcgga gataatacag aatctctatt tccaaaaaaa    61860
ttcgaatggg ccgcttcaaa cagcaccgca tgtagttgag ggcatctaac gatacccaaa    61920
aaaaaaggtc cgcgtatgtc ctcaatgatt gcgattactt cacccacgac acagtctttt    61980
cgatgatcga tgtttattgg tattttacta gtaggcggca aagcggaccg cacaatctct    62040
ggggtaatat ttaattcccc ttcgtccttt gaatataagg ctaaatacccc agccacgtat    62100 aacgcttcac agttctcttc gtcagcttca gcagccatta taaacacccc acggaccgga    62160
tagtgaatac tcacggtgtg gaggcaaact gaggaatgac acccaaacag acaaaatata    62220
gaagatcata gtcactgtta acgttgaact gcgcaaggcg gcgactttct tccaatgccg    62280
cccttacacg cggttggtgc attaacattc caagtccccg ttcatattgc aacataacac    62340
tgtcatgtat tgataccacg gcggctatgg gtagggatgt aacattttgt cggcggtgtt    62400
ctaattccaa tgcaattaag cttatgagcc gatcttggta ctgtccagaa gaaatatcta    62460
ttacggttct tcctaaactt ccacgactaa gctgggtatg cgcgtctaaa caaagagcaa    62520
ctaatccagg aaacatttca gtcagctctg tggtccgatt taacgtatac agtggtgcta    62580
tatatcgttc acataaaaat tgaaagttat tattaccgct tttaaacttc ccatcaaacc    62640
ccgtcgctcc gcgcaagatt acattgttgg tagggggttcc tgttgcttct gacacaatca    62700
aacccagttg aaaattattt tttagtttat ctccgtatac gttcccgttc cataataagc    62760
gccttaataa taataacgcc gtaatcgtgt caattgttaa ccttaataga gtttggtctt    62820
ccataagaaa cacgttttgg gcccgttcta aatacgccgc ggccgcctgt tgaatcttgt    62880
ccacatatgc ggtatgattg cgatcaataa tgtcattaac cccaggatta aactgtccag    62940
gtgcaggcgg taggacctgc aaccgtataa gcgcatccat aacagaatgt gacgttaagg    63000
cgccttgatc ataccgcccc ccacgagcat gaaactggtc gcgtggtaga cgatcatagc    63060
aaaattgata actgttttta ttttcgtgtg ttgtcatata attcacaaat gtctcagtat    63120
attccggtag gtgctctata aggttcccga aggacgaaac ttgaggttcg tggacactat    63180
tagatgtcct atacattaaa tataaacata ataccgcaca ctcgaacgcg gagtacgctc    63240
tatctccaac atacattctc ccggcggact gtagacatgt taccgttgtg ttcataaacg    63300
tacgggaaat gcgcccgtct ttacaatcaa ctccgcgtgc agctacgggc ctatctaaca    63360
caagccgttc ctgcagagta cgataccatg gcccgaaaac aatccctgga gagttattgc    63420
cccttgccct tcccaagtac accagggtga taaaatccac ttgaaagttt gtatcgtact    63480
gcaacggtgc atcattttg gcaatctgta cctcggggtg tatagactca ttgcgtatta    63540
tttctgtacg tgtacattcc tcagattgtg catctgcttc ttccgcctcg gcagcagccg    63600
tctccaggga atccaaaacc ttggccatgc gcgttagttg ttcttcgagg ggctttaaac    63660
gacgatctat ttccgttggt aacgtaatcg tttccccgcg aaggttgtct aatgcggcaa    63720
cggccgccgc attttttaac gttaacgtat tttttccaa atcgggattc atacgccctc    63780
ttaactcaaa cgcgggagcc gtccagtagt gtatgggaa gttgggggct ataaagttct    63840
tagtggtaga caaaaatatc ccacatttat tcggaaacga gatagatccg aacccatatc    63900
tcgccgtcat ggtgtctgca gcaaacaaag tcaactggcg tgaatataaa ccggtactgc    63960
tttaaaagct gttttcttac ccatgggaaa acatcccggt tatactttgt aaaattccac    64020
cacaagcacc taaagaaggc cttctaaggg gtaaatccac cccacaagct gcatttcctt    64080
caaactttgt taaagcggaa cgatggcatg atttcgcacg cttttttcgca agagaacata    64140
```

```
cgtgaatttt cttttttgcat agacgtcttc gctctctaac ggaccttatc ggggggtat    64200 attccgctac attctccaaa tgcgacgcta gcataacaag gtttccatga atcacctttg    64260
ggggtaaccg agttacctgt aacaggttca gaccccgttg agatacaaac acaaggaggg    64320
gggtcaccat tatttcatca gatcccgtgg gtgtggtttc ctttattaaa gccatggtat    64380
ccctcagctg gcgcataccc tcgcaaaact ggtgatactt agtagggggta tgtatattag   64440 cgctaaaacg gcaagatttt aattccacta taaaacaaac ggtctttccg gcaccactgg    64500
attccgtttg tataatacaa acacaatcgg ggcgtcggcg tcccaaattt acttcaaacg    64560
acattgatat gcgtacagcc cttttgaacat ccacgtggga taacggcgac aggagttttg   64620
ccagcctcgg gttgaacgcg tccgcgaaac ctcgacgtac gttatcaata tccttttttga  64680 gtacatcgta aaaacgagtg tggcaacgtt gtcccaaacg aaaacacttg gcccgaattc    64740
gactagcgga catatttgaa gttccgtccc agaagataac ctaagacgcg tttgtctaca    64800
ataaacatgt caacggataa aaccgatgta aaaatgggcg ttttgcgtat ttatttggac    64860
ggggcgtatg gaattggaaa acaaccgcc gccgaagaat ttttacacca ctttgcaata    64920
acaccaaacc ggatcttact cattggggag cccctgtcgt attggcgtaa ccttgcaggg    64980
gaggacgcca tttgcggaat ttacggaaca caaactcgcc gtcttaatgg agacgtttcg    65040 cctgaagacac cacaacgcct cacggctcat tttcagagcc tgttctgttc tccgcatgca   65100
attatgcatg cgaaaatctc ggcattgatg gacacaagta catcggatct cgtacaagta    65160
aataaggagc cgtataaaat tatgttatcc gaccgacacc caatcgcctc aactatatgt    65220
tttcccttgt ccagatactt agtgggagat atgtccccag cggcgcttcc tgggttattg    65280
tttacgcttc ccgctgaacc ccccgggacc aacttggtag tttgtaccgt ttcactcccc    65340
agtcatttat ccagagtaag caaacgggcc agaccgggag aaacggttaa tctgccgttt    65400
gttatggttc tgagaaatgt atatataatg cttattaata caattatatt tcttaaaact    65460
aacaactggc acgcgggctg gaacacactg tcattttgta atgatgtatt taaacagaaa    65520
ttacaaaaat ccgagtgtat aaaactacgc gaagtacctg ggattgaaga cacgttattc    65580
gccgtgctta aacttccgga gctttgcgga gagtttggaa atattctgcc gttatgggca    65640
tggggaatgg agaccctttc aaactgctca cgaagcatgt ctccgttcgt attatcgtta    65700
gaacagacac cccagcatgc ggcacaagaa ctaaaaactc tgctaccca gatgaccccg    65760 gcaaacatgt cctccggtgc atggaatata ttgaaagagc ttgttaatgc cgttcaggac    65820
aacacttcct aaatataccct agtatttacg tatgtaccag taaaagatg atacacattg    65880 tcatactcgc gtgtacgtgt ttttcttttt tatatatgcg tcatttatta ccacatcctt    65940
taatcccgcc tttatctccc taaaacggag tggtaatatt aaaagccgcc aagcctgttg    66000
gtgggtgagg aggggtaaag gcacgctgtg tgcataacgt tgcggtgata ttgtagcgca    66060
agtaacagca actatgtttg cgctagtttt agcggtggta attcttcctc tttgaccac    66120 ggctaataaa tcttacgtaa caccaacccc tgcgactcgc tctatcggac atatgtctgc    66180
tcttctacga gaatattccg accgtaatat gtctctgaaa ttagaagcct tttatcctac    66240
tggtttcgat gaagaactca ttaaatcact tcactgggga aatgatagaa aacacgtttt    66300
cttggttatt gttaaggtta accctacaac acacgaagga gacgtcgggc tggttatatt    66360
tccaaaatac ttgttatcgc cataccattt caaagcagaa catcgagcac cgtttcctgc    66420
tggacgtttt ggatttctta gtcacccgtgt gacacccgac gtgagcttct ttgacagttc   66480
gtttgcgccg tatttaacta cgcaacatct tgttgcgttt actacgttcc caccaaaccc    66540
```

```
ccttgtatgg catttggaaa gagctgagac cgcagcaact gcagaaaggc cgtttggggt    66600
aagtctttta cccgctcgcc caacagtccc caagaatact attctggaac ataaagcgca    66660
ttttgctaca tgggatgccc ttgcccgaca tactttttt tctgccgaag caattatcac    66720
caactcaacg ttgagaatac acgttcccct ttttgggtcg gtatggccaa ttcgatactg    66780
ggccaccggt tcggtgcttc tcacaagcga ctcgggtcgt gtggaagtaa atattggtgt    66840
aggatttatg agctcgctca tttctttatc ctctggacca ccgatagaat taattgttgt    66900
accacataca gtaaaactga acgcggttac aagcgacacc acatggttcc agctaaatcc    66960
accgggtccg gatccgggc catcttatcg agtttattta cttggacgtg ggttggatat    67020
gaattttcca agcatgcta cggtcgatat atgcgcatat cccgaagaga gtttggatta    67080
ccgctatcat ttatccatgg cccacacgga ggctctgcgg atgacaacga aggcggatca    67140
acatgacata aacgaggaaa gctattacca tatcgccgca agaatagcca catcaatttt    67200
tgcgttgtcg gaaatgggcc gtaccacaga atatttctg ttagatgaga tcgtagatgt    67260
tcagtatcaa ttaaaattcc ttaattacat tttaatgcgg ataggagcag gagctcatcc    67320
caacactata tccggaacct cggatctgat ctttgccgat ccatcgcagc ttcatgacga    67380
actttcactt cttttggtc aggtaaaacc cgcaaatgtc gattatttta tttcatatga    67440
tgaagcccgt gatcaactaa agaccgcata cgcgctttcc cgtggtcaag accatgtgaa    67500
tgcactttct ctcgccaggc gtgttataat gagcatatac aaggggctgc ttgtgaagca    67560 aaattaaat gctacagaga ggcaggcttt atttttgcc tcaatgattt tattaaattt    67620
ccgcgaagga ctagaaaatt catctcgggt attagacggt cgcacaactt tgcttttaat    67680
gacatccatg tgtacggcag ctcacgccac gcaagcagca cttaacatac aagaaggcct    67740
ggcatactta aatccttcaa aacacatgtt tacaatacca aacgtataca gtccttgtat    67800 gggttcccctt cgtacagacc tcacggaaga gattcatgtt atgaatctcc tgtcggcaat    67860
accaacacgc ccaggactta acgaggtatt gcatacccaa ctagacgaat ctgaaatatt    67920
cgacgcggca tttaaaaacca tgatgatttt taccacatgg actgccaaag atttgcatat    67980
actccacacc catgtaccag aagtatttac gtgtcaagat gcagccgcgc gtaacggaga    68040
atatgtgctc attcttccag ctgtccaggg acacagttat gtgattacac gaaacaaacc    68100 tcaaagggt ttggtatatt ccctggcaga tgtggatgta tataaccca tatccgttgt    68160 ttatttaagc agggatactt gcgtgtctga acatggtgtc atagagacgg tcgcactgcc    68220
ccatccggac aatttaaaag aatgtttgta ttgcggaagt gtttttctta ggtatctaac    68280
cacgggggcg attatggata taattattat tgacagcaaa gatacagaac gacaactagc    68340
cgctatggga aactccacaa ttccaccct caatccagac atgcacgggg atgactctaa    68400
ggctgtgttg ttgttccaa acggaactgt ggtaacgctt ctaggattcg aacgacgaca    68460
agccatacga atgtcgggac aataccttgg ggcctcttta ggaggggcgt ttctggcggt    68520
agtgggtttt ggtattatcg gatggatgtt atgtggaaat tcccgccttc gagaatataa    68580 taaaataccct ctgacataaa aaacatgtat aataaaaagt cactataaac gtattctcta    68640
caatacttta ttcgcgaata atacacacta cctttggggtt tttttcccgt ccccaaatgg    68700
tgtttggtgc actctaccaa aaaatagagc gcctaaatat gctatataac gcctcccagc    68760
aaaatacggt tcaaaggcat tacccgatat tgtattgtag tacagggcaa tgggaattga    68820
tgatcccaat aaacggcata gacgcacagc gccgttatag caggggtctc cagagtacag    68880
ggtatctaag taccgggata tctcatactc atgcctttcc gtgacagaaa catcaaccgg    68940
```

```
aacagtatcc gataaaccaa ctcctgtttt tgcaaggcgt aaaattcgca caccttcctt    69000
ttttgcaaga tgtgacgttt ccttgtaaca gggaagctgg gggagtggta agaacaacaa    69060
agtttcagcc aacgtgccaa taaagcccac ttccctcaag aggctgtttg ctgtatccac    69120
aatggtccgt attaaatctt gagcaacttg atccgtgtca tcatcactgg gtaacgcgtt    69180
aacataacta cgcgttaaat cttcaataac ggcataacaa ttaaacgctt cccaccgaga    69240
cagtatatat tgaacaatca cgaaccgttg acaggacgtc agatcacgtc cgtaagcatg    69300
cccgaaaaat ggaagttccc cccgttcgcc ataccgcaca caactgcag tatatatcgt     69360 ctcacgggct tcattaagtt catcttcaag tccaggccat tttctggctt taaatataac    69420
ctcgtccgca aaaaaaaccg cacatgataa cgcgcggata caatgagtag tggctttatg    69480
gcgaggatcc caaatgtcca ttacccgggg gatggtccta atctgtacaa agttacttag    69540
tgtaatatga tcggacttct tacgccgtct aggctgtttc tcagaatacg gttcacccga    69600
aatcggcaca tcatctgctt ttacgtcttc cgtaaccaca tcagcagcgc gccgactaac    69660
aattatactt gttttttcat cgtcgttact tccgttaagc gcgtctcgta tctcgggcgt    69720
cccgtcgaat aatccactca ctagctcctg caaactttct ggtaactcca acatacgcat    69780
atacaccaat gaaaaactgg cttcgtttgg tacgtacata aagccatttg tggtattaat    69840
ggcggtgggt gttggaaaca attttagctt attctcgcgc gtaacatcta ccccgccac    69900 caatgttaaa tgcgtcacgg ggagggacac gagataatct gcgagcgtag ggtcctccac    69960
ttcaacatca aatgttccgc aaaggtcgcg atccaccgcc cccgatcccg ctgcaagtaa    70020
ggccactcga tccaaaaaca cgcagttatt attggatgat accgcccatg tcttcccggt    70080
gcgattgagc tcacttcgaa cgtaactggc aacagatctg tcaccgggtc cgaccccgcg    70140
aacaacatgt ccaaattttg cgatctcgcc tccatgtttg cggggtatgg aaattaagca    70200
tcccccgcat ataaaatacg ccctggtagc acgctcgtta aaataaaacg ttacgccgtt    70260
ataagatacg gttgaatgat atggaaattc catattaaag cgtttatcgg aacattaacc    70320
tcgaacttgc cgtcccgtga tcgtgtgatc gccaacctta ggtccacacc gaatatgaga    70380
aatatataac tacacgcaaa cattcaaaac accgtggtat cattaacgtc atatgaaaag    70440
atccaatcaa tccaatcaac cacacctcct accgtttagc acgtcagcta tgtgacatgc    70500
tccaaacata cgtaaacatt tagagagggt gttataacag tctgtcaggc ggggtatatt    70560
ctacataata caaggatcgg ctttaacttt gtcaacattt ttactttgga ctataaactg    70620
cgactgaacg ttatgaaccc accccaagcc cgcgtctcgg aacagacaaa ggacttgctt    70680
agcgttatgg ttaaccagca ccccgaagag gacgcaaaag tgtgtaaatc cagtgataat    70740
tcaccgcttt ataacaccat ggttatgtta tcgtatgggg gtgatacgga cttactatta    70800
agctctgcat gtacccgcac atctaccgta aacaggtcgg cgtttacgca acactccgtg    70860
ttttatatta tatccacggt gttgattcaa ccaatatgtt gtatcttctt tttttttac    70920 tataaagcga cacgctgtat gctcttattc acagccgggt tacttctgac gattctacat    70980
cactttcgac ttattattat gttattgtgt gtctacagaa atatacgatc agacctgcta    71040
cccttatcta catcccagca actgctgctt ggaattattg ttgtgactcg aacaatgcta    71100
ttttgtatta cggcgtatta tactcttttt atagacaccc gggtgttctt tttgattacc    71160
ggacacttgc aaagtgaggt tattttccca gatagcgttt caaaaatact tcctgtgtcg    71220
tggggtccaa gtccagccgt gttactggta atggcggcag ttatttacgc tatggactgt    71280
ttggtggaca cggtatcctt tattgggcca agggtgtggg tccgtgttat gttaaaaaca    71340
```

```
tctatttcgt tttagtccat ttcaataaat gtactataat tgttcagtct aaaaataatg    71400
ttgggtattt ataattaccg cccccgtgtt acttggaaac acccatacat atgttccact    71460
ctacatcaaa cttctcgcag tttcttgtt cccgcacacg tttacacgtc cggattcaag    71520
tcgcaacgct gctgacaaaa tgacaacggt ttcatgtccc gctaacgtga ttactacaac    71580
ggaatctgat cgtattgctg ggttatttaa catcccagcg gggatcattc caactggaaa    71640
tgtgctgtca accatagagg tgtgtgcaca ccgttgcatt tttgattttt ttaaacaaat    71700
acgatcagat gataacagcc tttactcggc tcaattcgat attcttttgg ggacatactg    71760
caatacatta aactttgtgc gttttctaga acttggactg tctgtcgctt gcatctgtac    71820
taaatttccg gagctggctt acgtgcgaga tggcgttatt caatttgagg tacaacaacc    71880
catgatagca cgtgatggcc cacatcccgt cgatcagcct gttcataatt atatggttaa    71940
gcggatacac aagcgttcgt taagcgctgc gtttgcaatt gcatcggaag cgttgagttt    72000
gttaagtaac acatatgtcg atgggacaga gattgactca tcgttacgta taagagctat    72060
ccaacagatg gctcgtaatt tacgcaccgt tttggactca tttgaacgag gcactgccga    72120
tcaacttctt ggtgttctat tggagaaagc cccaccgcta tcgctgcttt caccaattaa    72180
taaattccaa cccgagggac atctaaatcg tgttgcacgc gcggccctac tttcggacct    72240
caaacgtaga gtctgtgcgg atatgttttt tatgacccga cacgccaggg aacctaggct    72300
gatctctgcg tatctgtcgg atatggtttc gtgcacccaa ccatcggtga tggtatcacg    72360
aataactcat acaaacactc gcggacggca ggttgacggt gtgttggtaa caacagcaac    72420
cttaaaacgg caactattac agggaatttt acaaattgac gacaccgccg ctgacgtacc    72480
agtaacatat ggcgaaatgg ttctacaggg gacaaacttg gtaaccgccc ttgtgatggg    72540
aaaggccgtc cgcggaatgg atgatgtagc ccgccatctc cttgatataa ccgaccctaa    72600
cacgttaaac ataccgtcta tacccccaca atccaactcc gattaacga cagctgggct    72660 tccggttaac gcccgtgttc ctgcggattt agtgattgtt ggggataaac ttgtattctt    72720
agaagcatta gaacggcggg tctaccaagc tacgcgcgtt gcctaccctc ttattggaaa    72780
tatagatatt acgtttatca tgccaatggg agtgtttcag gcaaactcca tggacagata    72840
tacacgacac gccggcgatt tttcaactgt atccgaacag gatccacgtc aatttccacc    72900
ccaagggatt ttttttata ataaagatgg gatattaaca cagttgactc ttcgtgatgc    72960
aatgggtacc atctgccaca gttcattgct tgatgtcgag gccacacttg ttgccctccg    73020
ccaacaacat ttagatcgtc agtgttattt tggtgtatac gtggccgagg gtacagagga    73080
cacattggat gttcaaatgg ggaggtttat ggaaacgtgg gcagatatga tgcctcatca    73140
ccctcattgg gtaaacgaac atttaacaat tctacagttt atagctccga gcaacccgcg    73200
tctaaggttt gaattaaacc ccgcctttga ttttttgtt gcaccggggg acgtagacct    73260
tcccggaccg cagcgtcccc cggaagccat gccaaccgtt aacgcaacat tacgattat     73320 caacggaaac attcccgtgc ctctatgtcc catttcattt cgagactgtc gcggaaccca    73380
actcggtttg ggaagacata caatgacccc ggcaaccatt aaagccgtaa aggatacatt    73440
tgaagaccgc gcatacccaa ctattttcta catgctagag gctgttattc atggaaacga    73500
aagaaacttc tgtgcgttac tgcgactgtt aacacagtgt attcgcgggt attgggagca    73560
atcccacagg gtggcatttg taaataactt tcacatgtta atgtacataa ctacatatct    73620
cggaaacggt gagcttcccg aagtctgtat taatatatat cgggatttac tgcagcatgt    73680
aagagcatta cgccaaacta taaccgattt tacaatacaa ggagagggcc ataacggcga    73740
```

```
gacctcggaa gcgctaaata acatccttac ggatgacacg tttattgcac ctattctatg   73800
ggattgtgat gcgttaatat accgtgatga agccgcccga gaccgactcc ccgcaattcg   73860
tgtaagcggg cgaaacggat accaagccct tcactttgtg gatatggccg ggcataactt   73920
ccaacgacgc gataatgtgt taatccacgg gagacccgtt cggggagaca cgggtcaggg   73980
tattcccatt actccacacc atgaccgtga atggggtatt ctctccaaga tttactacta   74040
tattgtcatt cctgcatttt cccgcggttc ctgttgtaca atgggcgtgc gttatgatcg   74100
cctatacccT gcgttacagg cagttatcgt tccggaaatt cccgctgatg aagaagcccc   74160
aactacccca gaagatccaa gacaccctct tcacgcacac caactcgttc cgaactctct   74220
taacgtttac ttccataatg cacacctaac cgttgatggt gatgcattgc tcacactaca   74280
agagttaatg ggagatatgg ctgaacgaac gacggccatt ttagtatcaa gcgcccccga   74340
tgcgggagcc gccacggcaa caaccagaaa tatgagaata tatgacggag cgctttacca   74400
tggccttatt atgatggcat atcaggcgta cgatgaaacc attgcaacgg gtacttttt    74460 ttatcccgtt ccggtcaacc ctctgtttgc atgtccggaa catttggcat cattgcgtgg   74520
aatgacaaat gctaggcggg ttttggcaaa aatggtacca ccaatccctc cttttctggg   74580
agccaaccac cacgcaacta tacgccaacc cgttgcctac catgtaacgc atagtaagtc   74640
ggattttaat actcttacat attctcttct tggaggtat tttaagttta caccaatatc    74700
tcttacacat caactacgaa cgggatttca ccccgggatt gcctttaccg tagtgcgcca   74760
ggatcgcttt gccacagagc aacttttata tgccgagcgt gcttctgaat cgtactttgt   74820
cggacaaatc caagtacacc atcatgatgc tattgggggg gtaaacttta ccctaaccca   74880
acccagagct cacgtggacc tgggagtcgg gtatacagct gtatgtgcca cagcagccct   74940
gcgatgccct ctcacggata tgggcaatac tgcccaaaat cttttttttt cacgaggagg   75000
agtgccaatg ttacatgata acgttaccga atcgttgcgt cgtataacag catcgggggg   75060
tcgcttaaat cccaccgaac ccctacccat cttcggcgga ctacgtcctg ctacatcggc   75120
aggaattgca cgagggcaag cctctgtgtg tgagtttgtg gccatgccgg tgtccactga   75180
cctacaatat tttagaactg catgcaatcc tagaggtcga gcatctggaa tgttatatat   75240
gggtgaccgt gacgccgaca tagaggctat aatgtttgat cacacacaat cggatgttgc   75300
ttatacagat cgagcaactc ttaacccatg ggcatcacaa aaacattcat acggtgacag   75360
gctatacaac ggaacataca accttacagg cgcttctcct atctacagcc catgcttta    75420 gttttttaca ccagcggagg ttaacactaa ttgtaataca ctggatcggc ttctaatgga   75480
ggcaaaggct gtggcgtcgc aaagctccac cgacactgaa tatcaattta aacgccctcc   75540
cggttctacc gaaatgacac aggatccgtg tggccttttt caagaagcat atccaccact   75600
atgctcaagc gatgcggcca tgttacgaac ggctcacgcg ggagaaaccg gggcagatga   75660
agttcactta gcccaatatc tgattcgaga cgcgtcgccc cttagggat gtcttcctct     75720 tccgcgataa tttcaccacg cccacatacc cactcccaat aaaagccctg tagagcgcat   75780
tggcatctta cttgagattt ggatacgctc ggccgacttg gtctgtttca cgcttcctta   75840
aacaacatgg ctatgccatt tgagatagag gtattgttac caggagaact atccccggcg   75900
gaaacatctg cattacagaa atgtgaggga aaaattatta ccttctcaac cctgcgtcat   75960
cgagcttcac tggtggatat agcgctgtcg tcatattaca ttaacggtgc tccaccagac   76020
acgctctcgc tgttagaggc ataccgaatg cgattcgcgg cagttataac acgggtcatc   76080
ccgggaaagt tgttggcgca tgccattggc gtgggtactc ctacacccgg gttgtttatt   76140
```

-continued

```
caaaatacat cccccgttga tctttgtaat ggcgattaca tctgcttact tcctccggtt    76200
ttcgggtccg cagactcaat tcgcttggac tctgtaggac tggaaattgt tttcccttta    76260
accatccccc agaccttaat gcgagaaatc atcgccaaag tggttgcacg ggccgttgag    76320
cgcacggccg cgggtgctca aatttacccc cacgaagttc tacgaggcgc ggatgtcatt    76380
tgttacaatg gaaggcgtta tgaactcgaa acaaatttac aacatcggga cggatcggat    76440
gcggctattc gcacattggt tttaaatcta atgttttcca taaacgaggg atgtctgctt    76500
ttattggcgc tgattccaac tttgttagtc caaggagcac acgacggtta tgtaaattta    76560
ttgatacaaa cggccaattg cgttagagaa accggccagt taattaatat accgccaatg    76620
ccgcggattc aagacggcca tcgccgattt cccatatatg aaactatttc atcttggata    76680
tcaacatcat ctagactggg ggataccttg ggaactcgcg caattttacg cgtctgtgtg    76740
tttgatggac cctctactgt tcatccggga gaccgcacgg ccgtgattca agtgtaaaca    76800
ggtgttaata aaaacacaac cagtctagtt acatttcacg cgtcttgttt ttatttaata    76860
ggcataaaca cggaatccgg tatacatgaa ctgccaatat acacggacat aattaatgca    76920
accatcagat catctgacat tgttcccgtg gtacctttac ccgtgtaagt ttttgtgtct    76980
agattaccca taccgccttt aattacctct gtcaggttat ccaactgttt acatagatac    77040
tccacggggt ctacacctaa ctttactgtt agggatacaa gctcctgtga ggctattata    77100
tttccggagt taaatcgttt aacaaaatag tctacggccg gcgttttttg tttttgtaat    77160
aaaaaaaaag ggtacgccac gctacatccg ggaggtatgg aatgataaaa cagtaacact    77220
ggagcggaag atagcacgtt tcccttttcg aggacagcaa actgttgtgc tatagccaac    77280 gatatgcaa ctgcagaatc ctggctgctg tttccctcta tagaaacgtg tacgtttgta    77340
aatgtattgg ggtgtaaagc gagtatgtgg cctaagcatt gagtaacgca acgccctatc    77400
tcactggaag acgtgccagt taagctcta agaaaaaagt gctccaatcc aaatataatc    77460
caatccgact tataacgacc aacaatcgct acaccagtac cagacgctcg tgtatttgag    77520
gtaaatgcag ggtctacgta aacgtacaac actgacgata atatagcaca attcgcaacg    77580
gttgacggcc gatataaaat aaacctctca cgggcagttt ttgtaaataa tggccggtca    77640
aaccccacac ccccagaatt ctgtttacgc ccacctacaa tttcctgcac gaaggagtcg    77700
gccataaata aatctgcagt gcgccgcatg gctccatcca ttgtgatgaa aaccggctta    77760
tttaatacat aacacgaaca agctgtgaca tcgctatgtg ctaaaacacg cggcatgtga    77820
tcgtcgcata catatgtaac aacgtttaac aactgatccg acgatccacg taagttatac    77880
aaaaaacttg tacttgcttt tccggtattt gttgatgaaa caaaaataat tttacaattg    77940
gtttgattta aaaatccgac tatagtttgt acagcatcag gtcgaataaa attagcttca    78000
tccacaaaca gaagattaaa atcttgacct cggatacct ggaacgatag aaagatatat    78060 agttaccca ccaaagttta aatgtatcct taaataccac gtacgtaaaa aatgtttgaa    78120
tacgtacata tttctttttt ttttccagta caaccatatc cggtgtataa tggaagccca    78180
tttggcaaat gaaaccaaac atgcactttg gcataatgat cacacaaaag gattactaca    78240
cgttgtgata cctaacgcgg ggcttattgc ggccggaata gatcccgcat tactgatttt    78300
aaagaaaccc ggacaacgct tcaaggttga agtacaaaca agatatcatg ctacaggtca    78360
atgcgaaccg tggtgtcaag ttttcgccgc gtacattccc gataacgcct taacaaatct    78420
cttaatacca aaaacggaac catttgtttc acacgttttt tcggccacgc ataattcagg    78480
gggattgatt ttatcattgc ctgtttatct tagccccggt ttattctttg atgcatttaa    78540
```

-continued

```
cgttgtagcg atacgaataa atactggaaa ccgcaagcac cgtgatattt gtattatgta   78600
tgcagaacta atcccaaacg gaacgcgtta ttttgctgat ggacaacggg tacttttatt   78660
atgcaaacag ctgattgcgt atatccgatg cacccctcgt cttgcatcgt ctataaaaat   78720
atacgcagag catatggtgg cagccatggg tgaatcacac acgtcaaatg gggacaatat   78780
tggacccgtt tcatccataa tcgatcttga tcgacagtta acttctggag gtattgatga   78840
ctcccctgct gaaacacgca tacaggaaaa taatcgggac gtccttgagc taataaaacg   78900
ggccgtaaac attgttaact ccaggcaccc cgtccgacct tctagttccc gcgttgcatc   78960
tgggttgctt caaagtgcaa agggccacgg agcgcaaact tccaacacag atccgatcaa   79020
taacggttcc tttgatggcg tccttgagcc gcctggacaa gggcgattta cgggaaagaa   79080
aaacaattcg tccgccagca tcccaccttt acaagacgtt ctattgttta ccccagcttc   79140
gacagaaccc caaagtctta tggaatggtt cgacatctgt tatgcccaat tagttagcgg   79200
ggacactcca gcagatttct ggaaacgcg tcccctatca attgtaccgc gacattacgc   79260
agaatccccc agtccgttga ttgtagtatc ttacaacgga tcctctgcct ggggaggacg   79320
tattaccgga agtccaattt tatatcactc tgcacaggct attattgatg ctgcgtgtat   79380
aaatgcccgg gttgacaatc cccaaagcct acatgtgaca gctcgccaag agctagtcgc   79440
gcgtttaccg ttttggcta acgtcctaaa taatcaaacc cccttacccg cctttaaacc   79500
aggcgccgaa atgtttttaa accaggtatt taaacaagcg tgtgtgacat cgctaaccca   79560
aggtcttata acggagttac aaacgaaccc gactctacaa caactcatgg aatatgatat   79620
tgcagattct cccaaacgg ttattgatga aattgtagcc cgcacaccag acctgattca   79680
gactatagtt tcggtgttaa cggaaatgtc aatggatgcg ttttataaca gctccttgat   79740
gtatgcggtt ttggcgtatc tgtcatctgt atatacacga ccacaaggtg gggggtatat   79800
accctacctt cacgcttcct tcccatgctg gttaggtaat cgttctatat atttatttga   79860
ctattataat tcaggagggg aaatacttaa gctttccaag gtccccgttc ccgtagcctt   79920
agaaaaggtt ggtattggta attccacaca actgagggt aaattatac gcagcgcgga   79980 tattgttgat attggaattt gttctaagta tttacccggt caatgttacg cgtacatttg   80040
tctaggattt aaccagcaat tacaatccat tttagtttta ccgggggat ttgcggcatg   80100 tttttgtatt accgataccc tacaggcagc actacctgca tcgttaatcg gacctattct   80160
agacagattc tgcttctcta ttcccaaccc ccataaataa attagtgtca ctataaaaac   80220
ataacaccag aatctcttca tatgtaattt tacgtcattt ctcccgtttc caccccctct   80280
taaaatataa aataaccggg tgggtggcat taaacccaca agtacccggg cggcaatccg   80340
ctagactgtt tttctgctca tggaattaca acgcatattt ccgctgtaca ccgctacggg   80400
tgcagcgcgc aaattaaccc ccgaggcagt tcagagactc tgcgatgcat taacgctgga   80460
tatgggatta tggaagtcca tcctgaccga tccccgggtg aaaataatgc gatcaactgc   80520
ttttataact ttaaggatcg ctccgtttat ccccttcaa acggatacta ctaatattgc   80580
cgttgttgta gccacaattt acatcacgcg cccacgtcag atgaacttac ctccgaagac   80640
ttttcatgta attgtaaatt ttaattacga ggtctcgtac gcaatgacgg cgactttaag   80700
aatttatccg gttgaaaaca tagaccatgt ttttggagca acgtttaaga acccgatcgc   80760
gtaccccctt ccaacatcta ttccggatcc tcgagcagat cccaccccg cagatcttac   80820 accaacgcca aacttaagca actacttaca accccgcgg cttccgaaaa atccatacgc   80880
atgtaaagtt atttctccgg gagtgtggtg gtcagacgaa cgaaggcgtt tatatgtact   80940
```

```
ggctatggaa cctaatttaa tagggctatg tcccgccgga tggcatgctc ggatacttgg    81000
ctctgtatta aatcgactcc tcagccatgc ggacggatgt gatgaatgta atcatagagt    81060
tcacgtgggg gcactgtatg cgttacccca tgtcacaaat catgcggaag gttgtgtgtg    81120
ttgggctccg tgtatgtgga gaaaggccgg tcagcgggaa ttaaaagtgg aggtagacat    81180
tggcgccacg caggttcttt ttgtagatgt caccacctgc attcgaatta cgagtactaa    81240
aaatcctcgc attaccgcaa atcttggcga cgttatagcg ggaaccaacg ccagtggtct    81300
ctctgtacca gtaaattcat ctgggtggca gctttatatg tttggagaaa cattaagccg    81360
ggctattatt aacggctgtg gtctgcttca gcgaatttgc ttccccgaga cacaaagatt    81420
atcgggtgaa ccggaaccta caaccaccta gtataccttta actcaaccgc cgttgtggaa    81480
aggtatatgt caacatttac agtaatatat taaaggttaa atttataaaa cactcacgtt    81540
tgtgttgtga cttgacgcga acaccgctgt gctgtaagac ccgtcggtaa atgaaaacgt    81600
aatagattcg cctttttacat gatccacgta atttgcccca aaccactgtt ccaggcgaga    81660
cttgataccc tcaaacacgg gttccgttgc tttgcgtata tgagccgtat aacccacttt    81720
aattcctcta aacgtggcca ttactaaagc tattaatggt acaagaaacc atgttttccc    81780
atgtctacgt ggtaccaaaa acacagttga ttttttgtttg aagtgttcta aaacactgtc    81840
agaaacactt ggcgtgttaa acactgtacg cagaaagcag tcaactctgt cggcatgatc    81900
gcccaatagc accgatgaaa taaaatgcgt ggtgtgcatg aggatcattt tttgaaacag    81960
ttccaacgtc cccttatatc tgccatagat tggaacgtca acctttgcgc gtttgccatg    82020
acttccacac tcttcaatac tctcaaaaga tgtttccaca aggtacgaaa accgttgtgt    82080
aaaggtagac aactgacaga aactatccga cagagaaaac gcgcgaaatg tgttcataac    82140
accgctatac gcatttcgat gaggtgctgc ttcttccggt gaatattcat aaaactgtac    82200
actactgaca gccttttttta attcagggct tacgtttgca tttaccgaat atcgccatgg    82260
tttcaaaact acattggggg tacagttgta ccctgttgac gatagaaacg cgccaaacat    82320
tgcccgtcga gcagtagccg agaacagtgg aatatattca caacagttgt gaagcgttcc    82380
aattccggga ataacggcct gatgacgtcg ggttacatct atagcaaaat tcagaaacgg    82440
gatttgggtt gcgtttccca gagacccttg ccgcgtggaa cacggggtag gggactccaa    82500
cgtcccaaag cgttcatccc tacgacgctt tagacgttca aaatatctta cagattcttc    82560
accaagcgta cgaccaaaca ttatcaatga catttaacat caattcacgg aatccgcctc    82620
atctcttgta agcagtaaaa caggaagccg cgtcatctta cgtactcgtt acgtatatat    82680
cataaacatt ttcagggccg cattcattca ctttggtcat gtcaggccac actccaacct    82740
acgcttctca taggcgtaac cgtgtcaaac tagttgaggc gcataaccgc gcggggttat    82800
ttaaagaacg gaccctcgat ctaatccgtg ggggtgcgag tgtacaagat ccagcatttg    82860
tgtatgcctt tactgctgca aaagaggcct gcgccgattt aaataaccag ctccgctctg    82920
cagctcgcat agcttcagtt gaacagaaga ttcgtgatat acaatccaag gttgaggaac    82980
aaacaagtat tcaacagatt ttaaatacaa acagacgcta tatagcaccc gattttattc    83040
gcggtttgga taaaacagaa gacgataata ccgataatat agacagactg gaagacgcgg    83100
taggaccgaa catcgaacac gaaaatcata cttggtttgg agaagacgac gaagcgttac    83160
ttacacaatg gatgctgacg acacaccccc caacctccaa atatctccaa ctgcaggacc    83220
tttgcgttcc caccacaata ccgacggaca tgaaccaaat gcaaccgcag ccgatcagca    83280
agaacgagaa tccaccaacc ccacacacgg atgtgtaaat catccatggg ccaatccgtc    83340
```

```
aactgcaaca tgcatggaat caccagaacg atcacaacag acaagcttat ttttattaaa   83400
gcacggctta acgagagatc caatacatca acgcgaaagg gtggacgttt ttccacaatt   83460
taacaaaccc ccatgggttt ttagaatttc caaattatcc cgtttaattg tacccatctt   83520
cacgctcaat gaacagttat gttttctaa attacagatt cgagatagac ccaggtttgc    83580
gggacgggga acgtatgggc gtgttcatat atacccatcg tcaaaaatag ctgtaaaaac   83640
catggacagt cgtgttttta atagagagtt aattaacgcg attttagcga gtgagggttc   83700
tatacgagca ggggaaaggc taggtatttc tagcatagtt tgccttttag gttttcgtt    83760
acaaaccaaa cagctactgt ttccggcata cgacatggat atggatgaat acattgttcg   83820
cctgtccaga cggttgacaa tacctgatca catagacaga aaaattgccc atgtatttt    83880
agatttggct caagcgttga cgttttaaa tcgaacgtgc ggcctgaccc acctagatgt    83940
gaaatgtggc aatattttc ttaacgtcga caactttgcc tcgttggaaa taaccacagc    84000
agtaatcgga gactatagcc tagtaacatt aaatacgtat tcccttttgta ctcgagcgat  84060
atttgaagtt ggaaatccat cccacccgga gcacgtacta cgcgtacccc gggatgcatc   84120
gcagatgtca tttcgtttgg tgttgagtca tggaacaaac caaccccctg aaatcttgct   84180
tgattatatt aatggaacgg gccttactaa atatactgga accttgcccc aaagagttgg   84240
acttgcgatt gatctttatg cattgggcca agcactctta gaagtctacc tgctaggacg   84300
tcttcccgga caactgccca tttcagtaca tcggaccccg cattatcact actacggtca   84360
taagttatca ccagatttgg cgcttgatac gctggcatat cgatgtgtcc tggcgccata   84420
tatactccca tctgacatcc ccggggactt aaattataat cccttatac acgccggaga    84480
gctgaacacc cgtatttccc ggaattcttt acgccggata ttccagtgtc acgcagtgcg   84540
ttacggcgta acgcactcaa agcttttcga aggcatacgc attccggcct cattataccc   84600
agccactgtt gttacatcgt tgttgtgtca cgataattca gaaatacgct cggatcaccc   84660
tttattatgg cacgatcggg attggatagg atcgacataa gcccccagcc agccaaaaaa   84720
attgcccgtg tgggaggtct acagcaccct tttgtaaaaa cggatattaa cacgattaac   84780
gttgaacacc atttttataga cacgctacag aagacatcac cgaacatgga ctgtcgcggg   84840
atgacagcgg gtattttttat tcgtttatcc cacatgtata aaattctaac aactctggag   84900
tctccaaatg atgtaaccta cacaacaccc ggttctacca acgcactgtt ctttaagacg   84960
tccacacagc ctcaggagcc gcgtccggaa gagttagcat ccaaattaac ccaagacgac   85020
attaaacgta ttctattaac aatagaatcg gagactcgtg gtcagggcga caatgccatt   85080
tggacactac tcagacgaaa tttaatcacc gcatcaactc ttaaatggag tgtatctgga   85140
cccgtcattc cacctcagtg gttttaccac cataacacta cagacacata cggtgatgcg   85200
gcggcaatgg cgtttggaaa aaccaacgaa ccggcggcac gagcgatagt tgaagcattg   85260
tttatagatc cggctgatat ccgtactcct gatcatttaa cgccagaagc tacaactaag   85320
ttttttaatt ttgacatgct caataccaaa tctccaagtc tccttgtggg tacaccaaga   85380
atcggaacgt atgaatgtgg acttttaatc gacgttcgaa cgggacttat aggcgcgtcg   85440
ttggacgttc ttgtatgtga cagggaccct ttaactggca ccctaaatcc ccaccctgca   85500
gaaaccgaca tttcattttt tgaaattaaa tgtcgtgcta ataccctctt tgatccagat   85560
gacaaaaata acccgctcgg tcggacgtac accacgttaa taaatagacc tacaatggca   85620
aatctacggg acttttttata tactataaaa aacccatgtg taagcttctt tggaccctca   85680
gcaaacccaa gtacacgcga ggccttaata acggatcacg ttgaatggaa acgtttagga   85740
```

-continued

```
tttaaaggtg ggagggccct tacagaactc gacgcccatc atttgggcct caatcggaca    85800
atctcatccc gagtgtgggt atttaatgat ccggacatac aaaaggggac aattacaacc    85860
attgcatggg ccactggaga tacggctctt caaattcctg tatttgccaa tccgcggcac    85920
gctaacttta aacaaattgc cgtacaaacc tatgtattat ccggttactt tccagcgcta    85980
aaactacggc ccttccttgt caccttttata ggacgtgtgc gccgaccaca cgaggtggga   86040
gtcccattgc gcgtcgatac acaagcggct gccatttacg aatataactg gccgactatc    86100
ccacccact gtgcggttcc ggttatagcc gttctaacgc ctatcgaagt tgatgtgcct     86160
agagtgacac aaatacttaa agacacagga aacaacgcga ttcatcagc attgcggtca     86220
ttgcgatggg acaatcttca tccagcggtc gaggaggaat ctgtggattg tgcaaacggt    86280
acaacgagct tgttacgtgc aacggagaaa ccgttgcttt gaactcagag ttctttgaag    86340
actttgactt tgatgagaat gtaacagagg acgccgataa atccacacaa cgccgcccac   86400
gagtgatcga tgtaacacca aaacgaaaac cttcgggaaa gagctcccat tccaaatgcg    86460
caaaatgtta aaccctgata aaccctgata aacgttctaa taaaaacatc aaatcatggt    86520
tggttactgt gaatgtttgt tttattgctt gggggtttac aagtacaacc cacgctactc    86580
ccacccactg tttgatcgct cgtataacag ctcatcctcg cggtccgttt catatgttga    86640
gtcattttca tagacgtagc cgtagccttg tgatgggtaa tttgtgcggc gagaatttct    86700
atgtgcaggt tttactttttc gtatgtatcc ccgtacccgc tcgggtactc ttcttacggc    86760
accgtagaac cgactgcgtt tctgtcgatg atacacatat gcacgcatca atctgagaag    86820
caacatgaca acggaaaaca cggccaggca agccaaggtt ccccgagttg tgggaattaa    86880
ccgtggagat tgaaccgata tagggtcata taatcggtcc atatacgagt gcgcggcggt    86940
tcccaacgta gcacaggcca cgagcgttcc cagggacggt cctattaaca cgtgtatata    87000
atgcgccaaa attaattctg atactataag atatacaact gacaatgtac taaatgtaga    87060
catggccacg gacaccgatg accacagtcc cgtatgtaga tgattcgcca ccacaagttc    87120
cagcattaat gatacaaata ggatacatat cgccatcaac gcagccatca aattcacgaa    87180
cactgcgcgc gtaggccccg caaggcgata taaaaagacg ctctgctgtc gtaaatttgc    87240
gaccgctttt atgttcgttt cgtccaattt tccgcgtcca caaaaatacg ttgtaaatat    87300
tacacttgtc gcaaaatgtc caagatataa tgtagcagcc acgccgattt gcttgtaagc    87360
taataataac acaacggcgt ttaataacca caatgacaaa agaccccaaa aaagtgttgt    87420
gggatctaca actaaccatg caacaccgga gctttgccgg acacgttgat ttttcgtttc    87480
tcggtgtata atcgcggccg tgatcagtgt atataccgcc atggccattg ccgttaaagc    87540
cgtgtagtaa gtaaatgcca caacgctatg tggttccaaa acaaaaccg gggcgctgta    87600
tccacctcta tttccggacc ataccccccc atctagggtg gcgttaaata actcataatc    87660
aactacggca gcataaaaac aagggatccc ggtatattca gaagaggcgg caattaacgt    87720
agccaggagc attaccgcac ccaaagtgaa catcatcacc tgaattatcc aaattcgcca    87780
attaagcgta tccatttgat gatctaacgc ttccacctcg ggtgtcgtgg tgtcgtacgg    87840
cgagactttt tcagaacgcg gccccttctt ttgagttccc atgtctccca acaccgggga    87900
gagcaacgcc gccgtctatg cgtccagtac acagctcgcg cgggcgttat atggagggga    87960
tctggtttcg tggattaaac acacccaccc gggaattagc ctggaactgc aattggatgt    88020
tccagtaaaa ctaataaaac ctggtatgtc acaaactcgc ccggtaaccg tcgtacgtgc    88080
ccctatgggc tctggtaaaa caacagcctt gcttgagtgg cttcaacacg cgttaaaggc    88140
```

-continued

```
agatattagc gtactggttg tctcatgtcg ccgtagcttt acccagacgt tgattcaacg    88200
gtttaacgat gcaggcctct ccggattcgt aacatatttg acatccgaga catatattat    88260
gggttttaaa cgtttgattg tgcaacttga aagcctacac cgcgtatcca gcgaagctat    88320
cgacagctac gacgtattaa tactggatga ggtaatgtca gtgattggac aattatactc    88380
ccccacaatg agacgtcttt ccgcggttga tagcctatta tatcgtcttt taaatcgctg    88440
ttctcaaatt atcgcgatgg atgctacagt aaactcgcag tttattgatt taatctccgg    88500
attgcgtgga gatgaaaaca tacacacaat tgtgtgtaca tacgcgggag ttgggttctc    88560
cggaagaact tgcacgatcc tgcgtgatat gggcatcgac acgcttgtgc gagtcattaa    88620
acgatctcct gaacacgagg atgtacgtac catacaccaa ctacgtggaa catttttttga   88680
cgaactagca ctacgattac aatgtgggca taacatctgt atatttttcat caactttatc   88740
gttttcggag ctagttgctc agttttgtgc aatatttaca gactctattc ttattttaaa    88800
ctcaactcgg cccctatgta atgtaaacga atggaaacat tttcgcgtgt tggtgtacac    88860
taccgtcgtg accgttggat tgagttttga catggctcat tttcatagca tgtttgctta    88920
cataaagcca atgtcatatg ggccggatat ggtatcggtc taccagtcat tagggcgtgt    88980
acgtttattg ctacttaatg aagttttgat gtacgtcgat ggctcaagga ccagatgcgg    89040
accccctgttc tcgccaatgt tactaaactt taccatcgca aataaatttc aatggtttcc    89100
tacacacacc caaataacta acaaactgtg ctgtgcattt aggcaacgat gtgcaaatgc    89160
atttacacgc tcgaacaccc atctcttctc aagatttaaa tacaaacacc ttttcgagag    89220
atgctctctt tggagtttag ccgatagcat taatatctta caaactcttt tggcctctaa    89280
ccaaattttg gttgtattgg atggcatggg tccaataacg gacgtttccc cagttcaatt    89340
ttgtgcattt atacacgatc tcagacatag cgctaacgcc gtagcttcct gtatgcgttc    89400
tcttagacag gacaatgaca gctgcttgac cgattttggc ccttccggat ttatggccga    89460
taacattacc gcgtttatgg aaaagtatct tatggagtca attaataccg aagaacaaat    89520
taaagtatt aaagcccttg catgtccaat agaacagcct agactagtca atacggcaat    89580
attggggcg tgtatacgaa tacctgaagc gttggaagca tttgacgtat ttcaaaaaat    89640
atacacgcac tacgcttccg gttggttttcc cgtcctggac aaaaccgggg aatttagcat    89700
cgcgactata actaccgccc caaatttaac cacacattgg gagctgtttc gccgttgtgc    89760
ctatattgca aaaacactca agtggaatcc gtccaccgaa ggctgtgtaa cacaagtttt    89820
ggatacggac attaatacac ttttcaatca acacgggat tcgctggctc aactaatatt    89880
tgaggttatg cgctgtaacg ttactgacgc taagattata ttaaaccgcc cggtttggcg    89940
aacaaccgga ttcttagatg gatgccataa tcaatgcttc cgtccaatcc ctacaaaaca    90000
cgaatataac attgctctat ttcgtttaat ttgggaacaa ttatttggcg cccgcgtaac    90060
taaaagtacc cagacctttc cgggaagtac tcgtgtgaaa aacctaaaaa aaaagatct    90120
agaaacttta cttgattcaa ttaacgtgga tcgttctgca tgtcgtacct accgccagtt    90180
gtataacctg cttatgagcc agcgccattc gttctctcaa cagcgttaca aaattactgc    90240
ccccgcttgg gcacgccacg tgtatttttca agcacatcaa atgcacttgg ccccgcatgc    90300
cgaagccatg ctacaattag cgctatcgga actgtcccg ggatcgtggc cgcggataaa    90360
cggggcggta aattttgaaa gtttataacc cgttaatacc atatatggac atccataggg    90420
ggggttacat aaaatactaag cctctgtaca acacaagggg cctctaacaa tgcactgaac    90480
cacaaccaag ctatggacgc aacgcagatt accttggtta gagaaagcgg acacatttgt    90540
```

```
gccgcaagca tatacacatc ctggacacag tccggacaat taacacagaa cggtctttcc   90600
gtgttatact acttattatg caaaaactca tgtgggaaat acgtccctaa gtttgccgaa   90660
attaccgtac aacaagagga tttatgtcgc tactccaggc atgggggggag tgtttctgcg   90720
gcaacgtttg cgtctatctg cagggcggcg tcctcggctg cgttagacgc ctggccccctt   90780
gaaccactgg gtaacgcaga cacctggcgt tgtctccatg gcactgccct ggccacttta   90840
cggcgcgtat tagggtttaa atcgttttat tcgccagtaa cattcgagac tgatacgaat   90900
acaggtcttc tgttaaaaac aatccccgat gaacacgcgt tgaataatga caacacgcca   90960
tctaccggag tattgagggc taattttccc gtggccattg atgtttcagc agtcagcgca   91020
tgtaacgccc acacgcaagg tacgtcgcta gcctacgccc gcctgaccgc acttaaatct   91080
aacggtgaca cccagcaaca aacaccttta gacgtggagg taattacacc aaaggcctac   91140
atacgtcgga aatataagtc tacgttttcc cccctatag agcgggaagg ccaaacctcc   91200
gatttgttta accttgaaga acgccgcttg gttcttagtg gcaatcgcgc aattgtggta   91260
agggtactct taccgtgtta ttttgactgt ttaacaacgg attccaccgt tacatcttcc   91320
cttttcaatat tagcaacata tagactgtgg tacgcggcgg cgtttggaaa acccgggggtt   91380
gtccgtccaa tctttgcgta tttaggcccg gaactcaatc cgaagggtga agacagagac   91440
tacttttgta ctgtcggatt tcccggatgg accactcttc ggacacaaac tccagccgtc   91500
gaatctattc gcacggctac ggagatgtac atggaaacgg atgggttgtg ccagtaacc    91560
ggtattcagg cctttcatta tctagccccc tggggacagc atccccccctt acctccgcgg   91620
gtgcaggatc ttattgggca aatccctcaa gatactggac atgcagatgc aactgtcaat   91680
tgggacgcgg gccggatatc taccgtcttc aaacagcctg tacaactaca agatcgttgg   91740
atggcaaagt ttgatttcag cgccttttttt cccacgatat actgcgctat gttccccatg   91800
cattttagat taggcaaaat cgtcctggct agaatgcgtc gaggaatggg gtgcctaaaa   91860
cccgcgttgg tgtcttttttt tgggggggtta cggcacatac tcccgagtat atacaaagct   91920
attattttta tagccaatga aattagcctt tgcgtcgaac aaacggcctt ggaacagggc   91980
tttgctatat gtacttatat aaaagatgga ttttggggaa tcttcaccga tttacatacg   92040
cgcaatgtat gttcagatca ggcacgttgt tcggccttaa atttagcggc cacctgcgaa   92100
agagcagtca cgggcttatt acgaattcaa ctaggtctta actttacacc cgccatggaa   92160
ccggtactcc gggtcgaggg tgtgtacact cacgcattta cctggtgtac cacgggaagc   92220
tggctgtgga atttacaaac aaacacgcct ccggatttag ttggcgtgcc atggcgaagt   92280
caggcggcgc gagatttaaa ggagcgtctt tcaggactcc tatgtaccgc aacaaaaatt   92340
cgagaacgga tacaggaaaa ttgcatatgg gaccatgtcc tatacgacat atgggccgga   92400
caagttgtgg aggctgccag aaaaacatac gtcgattttt ttgaacatgt ttttgatcgc   92460
cgttatactc cggtatactg gagtcttcag gagcaaaatt cggaaacaaa agcaataccg   92520
gcatcttatc tgacatacgg acacatgcaa gataaggatt ataaaccaag acagataatt   92580
atggttcgta atcccaaccc acatggacct cctactgttg tttactggga attgctacca   92640
tcgtgtgcct gtattccccc catagactgc gctgctcatc tcaagcccct tatacacacg   92700
tttgtcacta ttattaacca tcttctagat gctcataatg attttttcaag tccatcattg   92760
aaatttactg acgatcccct tgcttcatat aacttcttgt ttttatgaca aaaaaacacg   92820
ccgcaacaac ccatccttaa aataaaaggt ttatttactt tacaacccgt ggtgaatttt   92880
tatacgtttc aaataactga acattttttcg gtgttaccat ggtgcgattt aaccaccaaa   92940
```

```
aatatacgct cttctgatat tccgaatctc gtaaaggtcc atttaacaat cccgggggta    93000
cttgcaccac accatctgga caggggggggg ttccgtgggg caggtcaaaa cgctgaccca    93060
ccccacatga atatatagcc tttataatat tgggggccgt tccaggctga gggttcagta    93120
acttaacaaa catataatgc ggcaatacgc gggttttttgt aaagggggttg ttatcaacga    93180 catacattag agtgtttaac aaccataaaa ctccctcata taaaaaccga cgcatttttt    93240
ccaaaggtcc tatttgacac tcaacgcgtc taagatatac agacaattgt acaaacagcg    93300
atggagatgc cccggagggc ccaatgcctt ccagatacat taaataaca cataaggtaa    93360 aatctaggac attatccggg cggaatagag tcatccgata gattaacagg cgcggaggca    93420
cccccaccgt atacaccctca tcttcaaccg cagttaatac ggaaaaaata aatccgcgga    93480
acgctggttg agtaacacac tccatgtagt aacgatcaca ggacacctca cttgaatcac    93540
cattcaacac tactaaaacg gtctcttggt gttccggttt tacgcgcagt gatacaacag    93600
agtttgccaa aaagcgtggc ttcaaaccgg ttacctcccg cgcctcgcat acgaatcttg    93660
gtattgcttg tattctaaga tcttcgatca cgtcgctcac atccaacccc tcttcggctc    93720
gtgttagtaa gttgtcgatc gttacgctgc aacctaaaat gctgggtata tttattccgg    93780
acatcccatc ggccatcccc gcgcctccgg tttgctcgaa ttttatccag taaggtcgaa    93840
tccgctgcat ttaccttgtg tacccgtaac ctctcagggg ggtgtccttt cataaaatgg    93900
gataggtttt tatatccaac atgcatgtat tggttattta ttttattggg ttccgggatt    93960 cttcgtcat cttctgtagg gtcaggcaaa ccccaggaag gacttggtgt tctccgtggg    94020 ccccgttta ttacctctgc gcgaacctgc atttcatata atattcggat ttgggataaa    94080
taggactctg ttctcgcctt tttaaaaata gcctggcata actcttcctc tgacctatgt    94140
acctcgcttt gagttaccaa gaatcctaat cgggtggccc gtaatatgaa tgaaaaatac    94200
ggcgcaacta gtaatgagat tgacgcattt gaatatgata cagaaatttc ctggccttga    94260
ttattgttta cccggtgaag cttaaaacag cgaacaagtt cctgtttcca tagctcagac    94320
aaacgtttta tatcatctcc ataagggggg atataacgag attgaaaact attggcaata    94380
tatgcatcat cccctattat gccggtaaga tctataacct cgtgatttaa atcggcaata    94440
cgtgtttctt ctgccattgt aatatgtgac cctttagatg gctttatttt taccctctct    94500
tcccgtaacc gtttcagctc tccttctttg aactggagcc tttcggtcag atcgctgttc    94560
acatccttga gaccctcaat ggttttgaat aaattattca cataaccctc gagcatgccg    94620
ttgatactgt taaccaccga agttttaaac gcactttgaa cgtttgttgt tccggacatt    94680 gccccccgt taaaggattg gttggccttg ccaaaccccg gttgtgatgt gtccaccgat    94740
ccacttcctt ccagaatgtg attgcccgtt tcttctagat aggaacgtac ggtttcggta    94800
atatctccaa catgtctcat gttttttaag ttaactatta gctttacaag tctagacgcg    94860
gccgatccag cccgtgttgt atcgttctcg cccattatac gatcaaccgc acgtgtgctg    94920
tgagatctat catcttcatt ccggcgacct attaacacgc gcaagggggc tgtatttaaa    94980
acttggcaga cgcgagcatg ttcacgtaat gcataacagg ccaacacctc cccagaaagc    95040
cgctgtaagg gtgagtcaaa tactacaccc tccccacata caacgggcgg ccacacgacc    95100
aaacactctc ccttcatgcc cgttacatca tcctttgcca taattaatct tcggttataa    95160
ttataataaa gacgcgtcct atcataatcc ataatagcaa cattttgcat acactcaact    95220
aggcttgtga caaccgccgc tcctctggcc aacgttgcat cggcaacttt taacatctgg    95280
gacagttctg ccgcttgacc catatacgta tttaatggtg caggggttcc attctgttct    95340
```

```
gatcgtacct ttcttacaac gggcacaata cctacacagg ctatccagtc cacgtatttg   95400
gcaaaaccga cccttccatt taaaccactg gtatagagac aaccggttat tccacgcaga   95460
aactcaagta acgatgactg taatgtttga cgccaggttt caaaaacctg atgtgcaagc   95520
cgtacggctt ctgattctcc acatagccca taacgttccg ctagagcccc ggcatgcagg   95580
ttacattgtt ggatgtggtg ttcccaatct gctgctaggt cctcataccg agttgcatcc   95640
aacgcgttca tcaaaacggt tgcctgaact tggcgaatta cagtttccgt agaccgtaca   95700
gcgctatata tgccttgtcc atcggtatat ccaaagtcac cggctaggat ttttcgaaac   95760
aacatacttt gcgtggttgg gtgtattaac atccagccat cttcctccgg aaatgtacaa   95820
aaccctatat ccggggcgta ctcattccag tatatatcga acatgttctt gtattggtca   95880
tttgggttac ttccattcaa gccctggtca atagaaacag aacttgctat cctttttttct  95940 tcactaccgg aactgttatt aaaagagac gttatttcgg ccattgaaaa ccacgatgaa    96000
aagatcaatt tctgtagaca gttcttcacc caaaaacgtt tttaatccag agacgcccaa   96060
tggatttgat gacagtgtat atttaaactt cacctctatg catagcattc aacctatcct   96120
ctcacggatt cgagaacttg ccgcaattac gattccaaaa gaacgtgttc cgcggttgtg   96180 ttggttttaaa cagttactcg aactgcaagc gcctcctgaa atgcagagga atgagctccc   96240
cttctccgtt tatttaatta gcggaaatgc cggctccgga aaaagcacgt gtatccaaac   96300
gcttaacgaa gctatcgatt gcattattac cggatccacc agggttgctg cccaaaatgt   96360
tcatgctaag ttatcaacgg cttatgcgag tcgtccgata aacacaatct ttcatgaatt   96420
tggttttcgc ggaaatcaca ttcaggctca gctgggccgt tacgcatata actggactac   96480 gacccccct tctattgagg acctgcaaaa aagagatatt gtatactact gggaagtttt     96540
aattgatata acaaaacgag tgtttcaaat ggggacgac ggtcgcggag gaacatcgac     96600
atttaaaacc ctgtgggcaa ttgaacgttt gcttaataaa cctacaggct caatgtccgg   96660
aaccgcgttt atcgcatgcg gttccctccc ggcttttacc cggagcaacg ttattgttat   96720
tgatgaagca ggattgctag gcgtcatat tctcacggcc gttgtttact gttggtggct    96780
tttgaatgct atatatcaaa gccctcagta cataaacggt cgaaaccgg tcatagtatg    96840 cgtcggttcg cccacccaaa ctgactcgtt agaatctcat tttcaacatg acatgcagcg   96900
ttcacacgta actcctagtg aaaatatact cacgtatata atctgcaatc aaactctgcg   96960
tcaatatact aacatctcac ataactgggc aatctttatt aataacaaac gatgtcaaga   97020
ggacgatttt ggaaatcttt taaaaacgct tgagtacggg ctacctatta ccgaagcaca   97080
tgcgcgtctg gtcgatacat tgttgtacc tgcatcctat attaacaatc ctgctaatct    97140
tcccggatgg acgcgtctgt attcgtcgca taaggaggtg agcgcgtata tgagtaagtt    97200
acacgcgcat ttaaaactat cgaaaaatga ccattttct gtgtttgcct taccgactta    97260
tacattcatc cggctaacgg catttgatga ataccgcaaa ttaacgggac aacccggact   97320
ttctgttgaa cattggatac gggcaaactc cggtcgtttg cacaattatt cccaaagccg    97380
agatcatgac atgggaacag ttaaatacga aacacattca aatcgcgact taattgtagc   97440
ccgtacagac atcacttacg tgctaaatag tctcgtagtt gtaaccacaa gactacgtaa    97500
gttagttatt ggattcagtg gtacatttca atcgtttgca aaggtttac gtgacgactc     97560 ctttgtgaag gctcgaggag agacatccat cgaatatgct taccggtttc tgtcaaacct    97620
aatctttgga ggcttgatta acttttacaa tttttttgtta aataaaaaacc tacatcccga   97680 taaggtatcg ttagcataca aacggttagc tgccttaacc ctggagttat tgtctggaac   97740
```

```
aaacaaagcc cccttacacg aagcagcggt taatggggcg ggtgccggga ttgactgtga    97800
tggtgcagct acttctgccg ataaagcctt ctgctttacc aaagcccccg agtccaaagt    97860
aacggcctcc atacccgaag acccggatga tgtaattttt acggcactta acgacgaggt    97920
tattgacttg gtatactgcc agtacgaatt ttcctatccc aaatcatcca atgaggtcca    97980
tgctcagttt ctgttaatga aagctattta cgatggtcga tatgccatat tagcagagct    98040
tttcgaaagc agctttacaa ccgcccccttt tagcgcgtat gtcgataatg ttaatttcaa    98100
cggaagcgag cttttgatcg gcaatgtgcg ggggggctg ttatctttgg cattacaaac    98160
agatacgtat acccttttgg ggtatacttt tgcacccgtg ccagtctttg tagaggaact    98220
gacccgaaaa aagctgtacc gcgaaactac cgaaatgtta tatgctctac acgtacctct    98280
tatggtctta caggatcaac atgggtttgt gtccatcgta aacgctaacg tatgtgaatt    98340
taccgagtct atagaggatg cagaattggc aatggccacc acggtggact atggccttag    98400
ttctaaacta gccatgacaa ttgcacgctc acagggtctg agtttagaga aggtagctat    98460
ctgttttacg gcggataaac tgcgcctaaa tagtgtgtat gttgccatgt cgcgtacggt    98520
ctcctctagg ttcttaaaaa tgaatctaaa ccctctacgg gaacgatatg aaaaatccgc    98580
agaaattagc gatcacattc ttgccgctct acgtgatccc aacgtacacg ttgtgtatta    98640
aagcattgta taaaaacacg catgcgggct tgctgttctc atttctaggt tttgtcttaa    98700
atacacccgc catgagcatc tctggaccccc caacgacgtt tatttatat aggttacatg    98760 gggttaggcg ggttcttcac tggactttac cggatcatga acaaacactc tacgcattta    98820
cgggtgggtc aagatcaatg gcggtgaaga cggacgctcg atgtgataca atgagcggtg    98880
gtatgatcgt ccttcaacac acccatacag tgacctgct aaccatagac tgttctactg    98940
acttttcatc atacgcattt acgcaccggg atttccactt acaggacaaa ccccacgcaa    99000
catttgcgat gccgttatg tcctgggtcg gttctgaccc aacatctcag ctgtacagta    99060
atgtgggggg ggtactatcc gtaataacgg aagatgacct atccatgtgt atctcaattg    99120
ttatatacgg tttacgggta aacagacctg acgatcagac cacaccaaca ccaacccgc    99180 accagtatac atcgcaaagg cggcagcctg aaaccaactg tccttcttca ccacaaccgg    99240
cctttttcac atcagacgac gacgttcttt cgttaatatt acgggacgcc gcaaacgcgt    99300
aaagacagat tcaagactaa catttatccc aactgattac atttcatacg cgaataaacg    99360
acacaaaaaa tttatattta acggcttta atttgaagac acctatcctc ttaacgttga    99420
tgagccttgc aggttgggtg ccgcgcttca ccggtattat acataaccga tttaccgtgt    99480
ttacggcagt ctgaccatt accagtgtat gtctgtaata cgacgttgtt gtgtcccgac    99540
aaaattaact cgcgtacaaa tttctgatgt tcccccggcg tggcaacgct ggcatttcca    99600
aacacattac gttctcgtac gtccatgacc gctattttca gtattaattg gttggtcgt    99660 caaagtattt tccttatgta aaaggacacg atctaaagcc gtaaactcat acacaaacac    99720
tggtaccaac ggacgcgatt ttccgtccgt tgagcgggtg taatatcggc gaggtcttct    99780
tgcacgaata ctctcgtaca gtaggtttct gacacgggt gcatgggttt tttgacacaa    99840
cacaaacatt tgcaggctct tatgactgga tggattgaat ttattttag atagggtcac    99900 gtgttttgt cgtgacacgc ctcgaccaga aaaggctgcg gtttcgtac acgcgaccgt    99960 tatttcacag gcgttcataa ccaagctgcg gcggatggtg tcggttaatt gtctccgccc   100020
aagttcgtca atagatgata ccatgaacaa cgtatcaaat ggtacatagt cgtctttggt   100080
tttctcaata cagcccgcgt gcccaatcgg aaattttca tttgcatcaa cgctattttc   100140
```

```
tgtaaaatcg ttctgaacac tgtgttggct ggctacctgt ttaaaatttg ggatcgaaca 100200
cggtccacga tgcaatcccc aaccccattg aagcaatgcc gtcggtacgg aaggaggcaa 100260
ctccgaaaac attatggtac gcaagagggt cgattggagt gttatataac actccaatcg 100320
atctcgggtt cgcctttacg cgtaaaatac tcattggctt gaacgaaatg tcgacaattc 100380
cgaaatggaa cacgggacaa tggcgacgga tgcgcgtgtg ttagcaccag atgacatctt 100440
gaattcggtt gggttgtctt ctgtgcatgc gcacccaca gcataaaaac taaccctgta 100500
cggttctcgc ataacctctg tagcacgcgt tgcaccagcc gccccagcc taagtataca 100560 tgcgaccccg gagtccgcg acgaaccgta agcgtggtat tcagcaataa cacccccctgc 100620 cttgcccaac tctccaggca tccgtgagtg ggcggagtca tatttgggta tgattccatg 100680
agggccgcaa aaatattttt aagactagac ggtggtgtta tgccacgttt tacactaaac 100740
gctagcccat gtgcatgtcc cgcggtaggg tatggatctt gaccaataat tacaacgcga 100800
atgctctggg gtccgcaaaa tcgcgtccat gcaaaaatat cgcctgtaga tggaagtatt 100860
tcttcccctg aatttaaaag acgattgtat tctaaaaaaa tacctttcgc gtacggctct 100920
ttaagttcgt ccgacaacag gtcataccac tcagggaaa tgttaaactt gctgaaaact 100980
tcaaccgaat ccagttgcga agagacgggg gtgaacgttt ccgtgtcgta atgatgtgac 101040
atgttattta acttgaaggt tgggggggtct agcttaaccc ccaaaggcag cccgcgggt 101100 cgcttgcggg tttttttggt aaccggatgg gccaaaacat aaatgtcctt tgaatccgat 101160
agtttcattt cattggcata cgcgttggaa caaacggtcg gctccccaga cacatccatt 101220
ttccgggata tttgtggaag atggagtaga gtctacccat acaccggaaa gggcatccaa 101280
caaagcatcg cgtatgtccc cgcttttatg ttcttcacca acagattgtg ccagccccctt 101340 taaggtgacg tatggatttg tccagtacgc catttgtttg tctttaaacc aaagtataac 101400
ttccggtact ggacattttg tcttaaccac gattcccgat agcgcctcgc tgaggtttga 101460
taccgggggt gccgcatagt cccacgcctc atataccgat gacacgcacg gttccgttat 101520
aatcaaactc acatccgata gcggtttggc tccaaaaaac aacggagtgt cgtcttggag 101580
atgaagacaa tacgcgattg tgatagtttt taaaaaaact atctgcagta accatttatg 101640
tgatgccatg acgcttgtgt tttcccttca ctacgacgtt gtcgtatcct ttgaaaaact 101700
tgaccactct aatggaagca tggacaagta tgagttttat atatacagtt ggcctttagt 101760
taaactcttg gtgtcatatc tcatttttcct aaaaagggcg atcttaatat gtcaaacgtc 101820
acggcgtgcc gacaaagcga atttccatgc aagatttgga tgtagtattt atacacccaa 101880
tcacatgtca cgtattaagc tttacagtcc cccgttatct gatataatca cttttcttaa 101940
cacgtcatcg ggaaaacaga tgtttatatt atacctctcg cggtcattta cggcaaatac 102000
ttagaccgtt ttcaagcgga ctgaaaacgc tcaaattgcc ttttggaggc ctgcccaacg 102060
gccattatcc cttggatcta agattgattt gcggtaacgt ttgccaatca gcttttaaaa 102120
acgtacccca aacttaaaac gctcaaattg cctttttggag gcctgcccaa cggccattat 102180
cccttggatc tgagattgat ttacggtaac gtttgccaaa cccacgcatt tcagtttaaa 102240
tatttctaag cattcttagt gcgtacttgg cagcgtgctt aaaatatcaa ccaatatcca 102300
ttatgctaca cgtttccttc tatccgtttc aatccattaa aagtccatta acaaaaatga 102360
tgcatcatac ctaattcacc taaaaacctg actcattgca gcagcgtttc ctccttgcag 102420
actatccagt tggcatttta aacgggtccg gctgcctaaa ccgaaaacac cgttgccttt 102480
actgtaagta caaaactaaa atttatattt gcgtgcgtat tttgtaacat atatgccttt 102540
```

```
tatcccccg caagtttgct ttaccctcgc cttcaccacc cccgccacct tccggccatt 102600
ttaataactt taattgctat aagacatacc caaaccggat gattttttgcc gctggaaaaa 102660 cagcttctaa ttttcccgtc tcaactcggc cttggttgca tctccaagta tacctttagt 102720
ttgctcccgt agaggtgtat aaatacaaac ggtgacaagt attgagcgta atctcaaatt 102780
tttgtaattt agggcggagc gcttacgaca gcacatgcgt actgttagac tgttatgttt 102840
attgtatttg cagagcagga tgccccggtt actccgagac cggattgcgg gcattccgaa 102900
tcgtgtacgg acttaccagg gggcagtatt tacaccttgg gttccagata taccaaccct 102960
tacgaccaat agcaacactc aggtattttt aaaatgcacg tttaatgatc ataatttaca 103020
tacagttggt aataaagcag actgtggatg tttaaggcat ttccttcccc ctcccaacaa 103080
actaggactt cttcatcttg tttggaatac ctttacccgc tttaccggca gagcttttt 103140 tggtaaggtg tttcagtgaa cctgatgttg atccggaggt ggagggggta ttggactccc 103200
cctgtggaga ggcaactttg cgggttttac ttcccttaca tgccgaatca gactcagatg 103260
tcaggtctat tgttaagcat cgtttaacgt ctctgccggt atgaaataaa cggcgcttag 103320 cacccctttgc gcttcccggt ttaatccccg gtaacacaga aaaagcctg acttttttggg 103380 gtgtatttac caatcgggta tcccttcat cgccacgaga ggtctccccg gttgaggtgg 103440
tttctggtct tacaattgga cctgtaatta gttggatggc tgtatcttc caggtccagg 103500 tttgcatggt taggcgggtt ggatcggtac atcgatccaa caagaataac atgtttgtta 103560
caaacggtcc tgttgaatca tgcaaaagac aacgcaggga tgtttttaat cccgcctcat 103620
cacgcccgta aatacctata tagtttaata tcaacatttt tgtaggctct acaatttcgg 103680
gttgatacag ttccgcaagt tgatcatcaa gccatccgag taaaggttgc atgtaacacg 103740
ggaatctcgc gtttccctct gttcctctat ccgtggctcg aaaaggcagt ctgtccatgg 103800
ttcgtgggtc ttgattaatt cccacagata ctggacgatc acggtagtcc tgccccccgg 103860
tccggggttg ctgtgcagat tcaatcgagc catacaccac cggggtcgcc gatcgaacag 103920
caggttggtc tttaaaaaat accttccgta aaaatgatgc ggtagagcat gttttggtta 103980
caccagggct cgagtctcgg gtcggtggtt gtatagaatc ctgttgagag tcacttggtg 104040
actctgctgt gggctctcta gccgacgatt gaaggggccc agggtttggt gattgaatgg 104100
gctcccgact cgatcttgat gttggctgtt ggatggactc ccgactcggt cctgggcttg 104160
gtggcagaag atctatgaca tctcccggta ggatgtcgat ggaatcttca aatgacggct 104220
cagaaaaacc atcgtcgtcg gatgggtgca cttcatattc cttgtaactt gtatcactta 104280
cgatcttatg caggatggat tgcactggac accggcagag aggacactgg acgctggtgg 104340
aggtccatgc ccgaatacaa acaaagcaga agtcgtgcaa acacggcatg gtttttccga 104400
gatcggaaac ggtgctcatg catatggtgc aggtattatc cgaagcgtcg gaggtgccgc 104460
taccgcccgc taatatggta tccatggtaa caactggctg tattctaatg tccgggcatc 104520
caaacacgta gcagaactgc catgcgttct aaattgtgag ttgtggcgag tacatttta 104580 taattggtac caacgaagac acaccccctat atccctccac ccatttcttt taagtcccac 104640
ccactaaaac gtgggtataa aatgtgtatt ggggtaggcg gacagtccca acaaacaggg 104700
aagttgattg gtataacctt gggccgggta tacagctaag tgcattttta gattctgtct 104760
ttatttagat aaagagcgat acgaagacat ttctccaccc ccctgtaata cccgtaaata 104820
aaggtaagtc cacaaacaaa agcactgtat ataggaagtc gggtgtattg ggacagttac 104880
tccattagag gcgtacaaac aatactggga tagggtaatg caagtccccc ccgatggtcg 104940
```

-continued

```
ccccgcaaac gcgcggggag gtggggtcgc tttttttttt ctctctcgag ggggccgcga  105000
gagggctggc ctcctctccc ggggtccgcc gggcgcccag aaaccggggg ggggttattt  105060 tcggggggg gtccgaccag cccgcccgtc gcccgcccgc acagacagac agacactttt  105120
ttcataaaaa ccgttccgct tttattaaca acaaacagtc cgcgcgccag tggcgctcac  105180
gagaaaagga ggggactccg tcaccccga ctctgcgggg ggctcctccc cccgcgccct  105240
ccccacacat cgtcctcgtc ctcggaggac gaggacgagg acaacagctc caccttgacc  105300
gccgggcgca aacccacccg gcggtctcgc agcacacccg gggccaccga cacgatgctc  105360
accccaaagg atgaccccgg tgcgtccccg tcgtccccgc cccctcctc gctgtcccac  105420 gcgtcttcac accccacctc ccaatcgtcc agctccaaag cgtgttctct gtcgtctgcg  105480
gtgcgccgct gtcgccccgc ctgggtttct gacggccgtt ccgagccccc gtggtgtccg  105540
aacacgaacc gtgttccgtc gctcccctcc aacaccgtct ccgcggcccc aaaaccgggc  105600
ggccacatta ctctgggaat cggggggagg gcattccgag cctcgtccgc cgacgcatac  105660
agcgccaccg accgaccggc cacgggtgga agcacgagtg gttctgcggc agggtcgggt  105720
tccagcaggg cgtggcggca aaacaccctc gcccaggtgg gtacgtcgcc ggcctccggc  105780
ccggcggccc ccggtctccg tccctcggga aggaagacgg gtcgaagcgc ggcacccagg  105840
ccccatcggt ttgctgcgcg gtggctatgt gccgcctcgt ccacaaagtc ggctgccccg  105900
agccccagac cccgagactg tcgcgcgagg tccttgcaac cgtcaaaacc cggcagcacg  105960
tactgccggt attcacgggg cgacaggggg acgcgggtct tggggcccgc gcgggtacac  106020
acggtgtatg cgacgttccc accgcggcac aaacacaggg gttgttcgcc cgggtacagg  106080
ttggcaaacg cagtctcgat acgagcaaaa ctcgctggcc caaggtgcg cgacgatgca  106140 aacacggccc gggcgagtcc ttctgtgacc gccgagtctg gccatcggac gacggcctgg  106200
gcgtccggtc gcgccgggc ccggacgtac acgtgatact gagacaaagc gggtccatcc  106260
ctgggccacc tctcgagggc caccgcgtcc aacaccagca accggcgccg ggcagaggcc  106320
aaccgcgagc ctagatactc gacgcccccg gcaaaggcca ggtctcgggt cgacagtaat  106380
aaaacgcccc gggcgttcaa agcggacacg tccggcgggc cggtccagtt cccggcccag  106440
gcatgagtgc tcggcaggca caaccggtta ctcagggctg ccaggaccac agacagtccc  106500
cctcgggatg gactccatga cggtcccgga tctgtcgcga gggtgctctc gagggggccg  106560
ttgatgtcct ctccgggcaa cggatcgtag atgatcagaa gcctcacatc ctccgggtct  106620
gggatctgcc gcatccaggc gcacctccgt cgcagcgcct ccactccgct gggtggacca  106680
aaccgtcggt ctcctccgcc cggacgccga gcggcgattt ccgccaaggc gccgggatca  106740
aagcttagcg cagggcgcca ggccgtggga acaatgggt cgtcgaccag acgggcgatg  106800
gtttcggggg tacagtacgc cttgcgagcc tggtccgacg ggaccggggt atgcagggcc  106860
ccccggggaa tacgccgaaa tccccgtttt ggggccggtc cgtcaagtgg catcgttatt  106920
acggcggggg gatccaccac agggcccgag gtgatggtca cgggctcgga taccgcctc  106980 ttggccttgg aaaccacatg atcgtctgca acccgggcgt ccgcgacggg tgtctcccta  107040
atcttgtcga ggaggcttct gctctcgact ggctgggact tgcgcttgcg cggagttcgt  107100
aaacgatcat ccggtggaca cacagaaaga gagcgtgcgg cggccgacgg ctgagggtcg  107160
ggagcctgtg tggccggggt tgttggagaa gggtgaccgc gggagatccg cgccgccgga  107220
ctggagcccg ttgcctcggg gtatgccatg ctggcaaagg ctctgcggag actctgtagg  107280
ataaagtgtt tttgggcccg gtcgtatcga cggctcatag ccacggccgc ggccgcgtgg  107340
```

```
gggagagccc agagggcctc ccccgtggcc atggcttcgc ctacatgcgg aacgggagac   107400
gctacgctcc ccgtaacggc ggtacccgcc cgtcccggtg gcaacagctt ttggtagaac   107460
tggttcaggg ccgagttgac accggtcagc ttggggttct ggagccatgc tatagggtct   107520
ctgtctggac agtagatcag gttaatcagc gcgcggtact gtctagccgg atctcccaac   107580
tccggcacgt aaagcggcac gggttccgtt gaggcctcgt aacgagcccg cgccgctctc   107640
acagcctcat cctcccagtg accctctctg gtctccccgg acggtccaaa ccgcaccctg   107700
ttggatggga ggggtgccga tccgggccaa gggcttccgt cgggcatcat gagcggcccc   107760
gacaccgggg gaattatcgg ggttctggat cgcggcaggg aaaatgattt ctgtctctgg   107820
cgccccggtt cccccgcaag acgtttggtc ttacgaatcc tcggatcggg accgctgatg   107880
gatcgatatc ccgttggat atttttgttc gtcgacccac catcatttga gtccgaatca    107940
tccgaatttg acggggaagg ggcgtgttcg cgtccggacc tgctgcctgt agtttcactt   108000
cccaccgaaa cgcgccgggg ttcatcgtct tcatcctccg atgacgatcc ccacgacgag   108060
gaagaggatg aagacgaaac aaactcacga ctctttggct ttttctccac tgggctgtca   108120
tcctcaatcg ggtctggtgc gtgggatctt cccggcaggg ccaaaaacgc tctaggtttg   108180
ccccccgacg aacgtccagg gacgcgaggt gttataccc gggcatcatg tttccttggg   108240
cgggtatcat cggtctcaaa cggcaggtcc gcctttgccc ccttagcggg aacgctgtcc    108300
gaaaggacgt ggtacaattg ctcaaccggg ccgggtacag gtccaccggg tttccgcgcc   108360
gggagtggga ccttaacctt caaagtcttt ttcttcgggc tctttccctg agcgggccgt   108420
tgagttttct ggagaactac tccgtccccc gatgcatgcg catgacccgc ttgctcatcg   108480
cccggctttt tacccgagat ggactgagtt tgtctgtctc gatggaccac cgacggcaaa   108540
cctggtgaat ttcctctcgt cgtttgtcgg ggtatagacc gctggtcttc ccgttgatcg   108600
ttcccggcgg cgtctccaac aggagacgcg ggggatacag gggagaaggc ctgcgggaac   108660
ggagggtcg tacctctgcc cgtttcccca tcgttcatcg gtggttttgg agacctagca     108720
agcttcgttc cgagagagac tgtctcaagg gagcgatcgg ctcctgttgg ttctcgcgcg   108780
ccggcctccg agaatcgggt gtggaagacc tcggccagcg ggattacagg cgagcccatt   108840
agatcctgac cgtcctcgca tacgtagtcg tcttgtgtta gctcttcgcc aacatcttcc    108900
gttctgggtt ctggttgaag tcccgatacg gagggaattg aaacgatctc gtgttcccgt   108960
cccaccatga cccgttctc tccaaatagt agatcgtcag gctgactcga ggtgaccacc     109020
cgggccctgt gttcggcggc cgccgcgcc gcgtccaaca ggtccattaa ctccaaagta   109080
tcaggcgacc ccgcgcgttg gggtgtagag cgctgcatcg gcggcgtatc catcgcactg   109140
gggtgaattt agacgtaccc gagttttcca aacgctctcg cagccttcaa aggattgcga   109200
ttgcggttgg tgagggagtt ccaacagtac ttaaaacgtg ttgtgccccc cctcgaccg    109260
catatttcct ccccgtgtcg tcaccgtgta aatattctta atgataagac gatgtagtga   109320
ttggacgaga ctcgaggcgg gaagttcatg gaccatagta tgcgtttaag gagagaccgc   109380
tggttggcga tgtacgcccg gtgtctattt ccgcatacct tacaacatca taacaaggga   109440
taccagacat gtgaatttca tttacatatg tttaaataac aaccaatcat cgtgtgtcta   109500
cagacgtat ataatataca taaacacaat tggggttgtc tcacatgcaa aacatcttat    109560
ataacacggg ttgtttccac ccatccggca tctagttaat caaatgcacg tcgacggtgt   109620
gtttgggtcc ctctccgtcg tcattacgtt cgcgcaatca acaagcgtat acaccaccac    109680
ccctcccaac gattatgtca ggcggcacga agcccgcgat aacccataaa atacacacgg   109740
```

```
ggttgtggtg ttcacgtaac cccccgccga tggggagggg gcgcggtacc ccgccgatgg 109800 ggaggggggcg cggtacccccg ccgatgggga ggggcgcgg taccccgccg atggggaggg 109860
ggcgcggtac cccgccgatg gggaggggggc gcggtacccc gccgatgttt ataaccataa 109920
ttctctaaac cgttgtagaa aatcacaaaa aaatttattc aaaaacaagt cgaagaactt 109980
catatctgag gcatgtaaac ccgttcgcac ttcctgggggt ggaatgggggt gggggtgggggg 110040 ggtgaaaaag ggggggggtt aaattgggcg tccgcatgtc tgtggtgtac gccaatcgga 110100
tacactcttt tgatctgcat tcgcacttcc cgttttttca ctgtatgggt tttcatgttt 110160
tggcatgtgt ccaaccaccg ttcgcacttt cttttctatat atatatatat atatatatat 110220
atatatagag aaagagagag agtttcttgt tcgcgcgtgt tcccgcgatg tcgcggtttt 110280 atgggggtgtg ggcgggcttt tcacagaata tatatattcc aaatgagcg gcaggctttt 110340 taaaatcgat ttgacgtgat aaaaaaaaac acacgggggcc cccccctttt tttggtgtta 110400
taaaggcaac ccaatcgaag gtctccccgcc ccggaatccc ccattgccat tttacccaag 110460
tagccttatt catagatgta aacgtttggg tgtgtgttttt ttgtgcagg gttcgtccga 110520 ttcataacgc gacagcgtcg agtcggtttt aagggaaaag gttactacgg ccccaaggac 110580
atgttttgca cctcaccggc tacgcgggggc gactcgtccg agtcaaaacc cggggcatcg 110640
gttgatgtta acgaaagat ggaatatgga tctgcaccag gacccctgaa cggccgggat 110700
acgtcgcggg ggccccggcgc gttttgtact ccgggttggg agatccaccc ggccaggctc 110760
gttgaggaca tcaaccgtgt tttttttatgt attgcacagt cgtcgggacg cgtcacgcga 110820
gattcacgaa gattgcggcg catatgcctc gactttatc taatgggtcg caccagacag 110880
cgtcccacgt tagcgtgctg ggaggaattg ttacagcttc aacccaccca gacgcagtgc 110940
ttacgcgcta ctttaatgga agtgtcccat cgaccccctc gggggggaaga cgggttcatt 111000 gaggcgccga atgttccttt gcataggagc gcactggaat gtgacgtatc tgatgatggt 111060
ggtgaagacg atagcgacga tgatgggtct acgccatcgg atgtaattga atttcgggat 111120
tccgacgcgg aatcatcgga cggggaagac tttatagtgg aagaagaatc agaggagagc 111180
accgattctt gtgaaccaga cggggtaccc ggcgattgtt atcgagacgg ggatgggtgc 111240
aacaccccgt ccccaaagag accccagcgt gccatcgagc gatacgcggg tgcagaaacc 111300
gcggaatata cagccgcgaa agcgctcacc gcgttgggcg agggggggtgt agattggaag 111360 cgacgtcgac acgaagcccc cgccggcat gatataccgc ccccccatgg cgtgtagtct 111420
ttataaataa atacaatggt ttggctcgtg tcttttttttg atgtctgtct gtgggggagt 111480
ggggtgttgt ggatattaga gggtagaggg tgctggtttg aacgtctcca ttaacccacg 111540
gggtccccac acgggccgtg tggtatgaat ctctgcggat cccgcggtga gcacccggggc 111600 ggtgaatatg ccggactta ctgcacacga cacgatacccc ccgcgcacca ggctctcatg 111660
aacgacgccg aacggtactt cgccgccgcg ctatgcgcca tatctaccga ggcctacgag 111720
gcttttatac acagcccctc cgagagaccg tgcgcgagtt tgtgggggag ggcaaaggac 111780
gccttcggac ggatgtgcgg ggagctcgca gcggatagac aacgtccacc ctcggttccg 111840
ccgatccgca gagcggtgtt atcgttatta cgcgagcaat gcatgccgga tccacaatcg 111900
catctggagc tcagcgagcg gctgatattg atggcatatt ggtgctgttt gggacacgcc 111960
ggacttccga ctattggatt gtcgcccgat aataaatgca tccgcgccga attatatgac 112020
cgccccgggg gaatttgtca caggcttttt gacgcgtacc tgggctgcgg gtcccttgga 112080
gtcccaagaa cctacgagag atcctgacac cccatcccctt tatatagaaa aaaaaaataa 112140
```

```
atttaaaaca tacaccggat aaaagcgtac tgtttttat ttaaatttac acgctcggcg    112200
ttgccccggt tcggtgatca ccgggtctta tctatataca ccgtgtaact cgaacccccg   112260
tgactccctc caatcgcgtt accaaactct tcttccgtat ccgtagattc cgagtcctcg   112320
aaatcgtcca cttatccaac aaattgtgac gttatatatc ccaaggcaaa ggccgctccc   112380
gtcatagcaa atacaaagac aattattagc gtaatataac agaatttttt acgatgatat   112440
attttatgtt gatattttcc aattcgacgc aaaaattcat ctgccgtttc attttcgcta   112500
tcactataat aacactttc agccgaacgg ctcggttgta tggctgttat cgttgtatta    112560
tttggttgcg ctcgcggggt taccaccgct tccatcagta aggccacggc ctcaccctcc   112620
atggtgtttt gtccggccat agaaatccag attgtaaggc cagcaggcta gtttaaaagt   112680
gtttaatacc acacctttg atatttatat acatgcaaga ttctagatta ttcatcaata    112740
ggtcgtttaa agcgcgtttt cataaacgtt gtcagctata ccgacattct cacaaagagg   112800
taaagttacc ttacgttatt attaaataaa acatgtagac attattaata atcctaggaa   112860
caatcaaatc catatttgta agttatgttt aacccctccc cttttgtca ttatctccgc    112920
cctcttataa tcggatcact ttataagtgt gtcggtgagt atattttgta cagttgttgg   112980
acaacaggtt tttggttcat taacactatc aacataagtc ggggtataca agtataatga   113040
acgacgttga tgcaacagac acctttgttg acaaggaaa gttccgtggc gccatctcaa    113100
catcaccgtc acatattatg caaacatgtg ggtttataca acagatgttt ccagttgaaa   113160
tgtcgcccgg catagaatct gaggatgatc ccaattatga cgttaacatg gatatacagt   113220
cttttaatat atttgatggt gtacacgaaa ctgaagccga agcctctgtg gcattgtgcg   113280
cagaagcacg cgttggaatt aataaagcgg gatttgtaat attaaaaacg tttacaccag   113340
gggcggaagg ttttgcgttt gcgtgtatgg acagtaaaac atgtgaacat gtggtcatta   113400
aagcgggtca acgtcaagga acggccaccg aggcaaccgt gttaagagcg ttaacccacc   113460
catccgttgt acagcttaaa ggaacgttta cgtataacaa aatgacatgt cttatattac   113520
cacgttaccg aacagattta tactgctatc tagctgcaaa gcgcaacctc cccatatgtg   113580
acattttagc aattcagcga tctgtattac gcgcgttaca gtatcttcat aataacagta   113640
ttattcaccg tgatataaaa tctgaaaata tatttattaa ccacccaggt gatgtttgtg   113700
tgggagactt tggagcagcg tgtttccccg tggatattaa tgccaacagg tattatggct   113760
gggctggaac aatcgccaca aactctcctg agttattggc tagagatcca tatggacctg   113820
ccgtggacat atggagtgcc gggattgtat tatttgaaat ggctacagga cagaactcgt   113880
tatttgaacg agacggttta gatggcaatt gtgacagtga gcgtcaaatt aaacttatta   113940
tacgacgatc tggaactcat cccaatgaat ttcccattaa ccctacatca aatcttcgtc   114000
gacaatacat tggtttggca aaacggtctt ctcgaaaacc cggatccagg ccattgtgga   114060
caaatctata tgagttgcca attgatttgg agtatttgat atgtaagatg ttatcgtttg   114120
acgcacgtca tcgaccatca gcagaggtgt tgcttaacca ctctgttttc caaactcttc   114180
ccgatccata tccaaatcca atggaagttg gagattaaaa ttcattaagc ctgttaataa   114240
aatattgtat aaattgtgtt tataacgtat aacccgttaa ggcaaatagg gtacaaacgc   114300
gcaatgtttt gaaatactaa tataaataac ataaccaata gaaacttaat acagagtcac   114360
gccccattac aacaaggata aaacacggga tcattttctt aacattgtag tagcgctgaa   114420
aagcgtcccc tccccggct cacagagctg ctcttcggtg tagttgggta tactggtgcg    114480
cctcatttaa tcgcgatgtt tttaatccaa tgtttgatat cggccgttat attttacata   114540
```

```
caagtgacca acgctttgat cttcaagggc gaccacgtga gcttgcaagt taacagcagt 114600
ctcacgtcta tccttattcc catgcaaaat gataattata cagagataaa aggacagctt 114660
gtctttattg gagagcaact acctaccggg acaaactata gcggaacact ggaactgtta 114720
tacgcggata cggtggcgtt ttgtttccgg tcagtacaag taataagata cgacggatgt 114780
ccccggatta gaacgagcgc ttttatttcg tgtaggtaca acattcgtg gcattatggt 114840
aactcaacgg atcggatatc aacagagccg gatgctggtg taatgttgaa aattaccaaa 114900
ccgggaataa atgatgctgg tgtgtatgta cttcttgttc ggttagacca tagcagatcc 114960
accgatggtt tcattcttgg tgtaaatgta tatacagcgg gctcgcatca caacattcac 115020
ggggttatct acacttctcc gtctctacag aatggatatt ctacaagagc ccttttttcaa 115080
caagctcgtt tgtgtgattt acccgcgaca cccaaagggt ccggtacctc cctgtttcaa 115140
catatgcttg atcttcgtgc cggtaaatcg ttagaggata acccttggtt acatgaggac 115200
gttgttacga cagaaactaa gtccgttgtt aaggagggga tagaaaatca cgtatatcca 115260
acggatatgt ccacgttacc cgaaaagtcc cttaatgatc ctccagaaaa tctacttata 115320
attattccta tagtagcgtc tgtcatgatc ctcaccgcca tggttattgt tattgtaata 115380
agcgttaagc gacgtagaat taaaaaacat ccaatttatc gcccaaatac aaaaacaaga 115440
aggggcatac aaaatgcgac accagaatcc gatgtgatgt tggaggccgc cattgcacaa 115500
ctagcaacga ttcgcgaaga atccccccca cattccgttg taaacccgtt tgttaaatag 115560
aactaattat cccggatttt atattaaata aactatatgc gtttttattta gcgttttgat 115620
tacgcgttgt gatatgaggg gaaggattaa gaatctccta actataagtt aacacgccca 115680
catttgggcg gggatgtttt atgaagcctt aaaggccgag ctggtataca cgagagcagt 115740
ccatggtttt agacctcggg cgaattgcgt ggttttaagt gactatattc cgagggtcgc 115800
ctgtaatatg gggacagtta ataaacctgt ggtgggggta ttgatggggt tcggaattat 115860
cacgggaacg ttgcgtataa cgaatccggt cagagcatcc gtcttgcgat acgatgattt 115920
tcacaccgat gaagacaaac tggatacaaa ctccgtatat gagccttact accattcaga 115980
tcatgcggag tcttcatggg taaatcgggg agagtcttcg cgaaaagcgt acgatcataa 116040
ctcaccttat atatggccac gtaatgatta tgatggattt ttagagaacg cacacgaaca 116100
ccatggggtg tataatcagg gccgtggtat cgatagcggg gaacggttaa tgcaacccac 116160
acaaatgtct gcacaggagg atcttgggga cgatacgggc atccacgtta tccctacgtt 116220
aaacggcgat gacagacata aaattgtaaa tgtggaccaa cgtcaatacg gtgacgtgtt 116280
taaaggagat cttaatccaa aaccccaagg ccaaagactc attgaggtgt cagtggaaga 116340
aaatcacccg tttactttac gcgcaccgat tcagcggatt tatggagtcc ggtacaccga 116400
gacttggagc ttttttgccgt cattaacctg tacgggagac gcagcgcccg ccatccagca 116460
tatatgtttta aaacatacaa catgctttca agacgtggtg gtggatgtgg attgcgcgga 116520
aaatactaaa gaggatcagt tggccgaaat cagttaccgt tttcaaggta agaaggaagc 116580
ggaccaaccg tggattgttg taaacacgag cacactgttt gatgaactcg aattagaccc 116640
ccccgagatt gaaccgggtg tcttgaaagt acttcggaca gaaaaacaat acttgggtgt 116700
gtacatttgg aacatgcgcg gctccgatgg tacgtctacc tacgccacgt ttttggtcac 116760
ctggaaaggg gatgaaaaaa caagaaaccc tacgcccgca gtaactcctc aaccaagagg 116820
ggctgagttt catatgtgga attaccactc gcatgtattt tcagttggtg atacgtttag 116880
cttggcaatg catcttcagt ataagataca tgaagcgcca tttgatttgc tgttagagtg 116940
```

```
gttgtatgtc cccatcgatc ctacatgtca accaatgcgg ttatattcta cgtgtttgta    117000
tcatcccaac gcaccccaat gcctctctca tatgaattcc ggttgtacat ttacctcgcc    117060
acatttagcc cagcgtgttg caagcacagt gtatcaaaat tgtgaacatg cagataacta    117120
caccgcatat tgtctgggaa tatctcatat ggagcctagc tttggtctaa tcttacacga    117180
cgggggcacc acgttaaagt ttgtagatac acccgagagt ttgtcgggat tatacgtttt    117240
tgtggtgtat tttaacgggc atgttgaagc cgtagcatac actgttgtat ccacagtaga    117300
tcattttgta aacgcaattg aagagcgtgg atttccgcca acggccggtc agccaccggc    117360
gactactaaa cccaaggaaa ttaccccgt aaacccgga acgtcaccac ttctacgata      117420
tgccgcatgg accggagggc ttgcagcagt agtactttta tgtctcgtaa tatttttaat    117480
ctgtacggct aaacgaatga gggttaaagc ctataggta gacaagtccc cgtataacca     117540
aagcatgtat tacgctggcc ttccagtgga cgatttcgag gactcggaat ctacggatac    117600
ggaagaagag tttggtaacg cgattggagg gagtcacggg ggttcgagtt acacggtgta    117660
tatagataag acccggtgat caccgaaccg gggcaacgcc gagcgtgtaa atttaaataa    117720
aaaacagtac gcttttatcc ggtgtatgtt ttaaatttat ttttttttc tatataaagg     117780 gatggggtgt caggatctct cgtaggttct tgggactcca agggacccgc agcccaggta    117840
cgcgtcaaaa agcctgtgac aaattccccc ggggcggtca tataattcgg cgcggatgca    117900
tttattatcg ggcgacaatc caatagtcgg aagtccggcg tgtcccaaac agcaccaata    117960
tgccatcaat atcagccgct cgctgagctc cagatgcgat tgtggatccg gcatgcattg    118020
ctcgcgtaat aacgataaca ccgctctgcg gatcggcgga accgagggtg gacgttgtct    118080
atccgctgcg agctccccgc acatccgtcc gaaggcgtcc tttgccctcc cccacaaact    118140
cgcgcacggt ctctcggagg ggctgtgtat aaaagcctcg taggcctcgg tagatatggc    118200
gcatagcgcg gcggcgaagt accgttcggc gtcgttcatg agagcctggt gcgcgggggt    118260
atcgtgtcgt gtgcagtaaa gtccggcata ttcaccgccc gggtgctcac cgcgggatcc    118320
gcagagattc ataccacacg gcccgtgtgg ggaccccgtg ggttaatgga gacgttcaaa    118380
ccagcaccct ctaccctcta atatccacaa caccccactc cccacagac agacatcaaa     118440 aaaagacacg agccaaacca ttgtatttat ttataaagac tacacgccat ggggggggcgg   118500 tatatcatgc cggcgcgggg cttcgtgtcg acgtcgcttc caatctacac cccctcgcc    118560 caacgcggtg agcgctttcg cggctgtata ttccgcggtt tctgcacccg cgtatcgctc    118620
gatggcacgc tgggtctct ttggggacgg ggtgttgcac ccatcccgt ctcgataaca      118680 atcgccgggt accccgtctg gttcacaaga atcggtgctc tcctctgatt cttcttccac    118740
tataaagtct tccccgtccg atgattccgc gtcggaatcc cgaaattcaa ttacatccga    118800
tggcgtagac ccatcatcgt cgctatcgtc ttcaccacca tcatcagata cgtcacattc    118860
cagtgcgctc ctatgcaaag gaacattcgg cgcctcaatg aacccgtctt ccccccgagg    118920
gggtcgatgg gacacttcca ttaaagtagc gcgtaagcac tgcgtctggg tgggttgaag    118980
ctgtaacaat tcctcccagc acgctaacgt gggacgctgt ctggtgcgac ccattagata    119040
aaagtcgagg catatgcgcc gcaatcttcg tgaatctcgc gtgacgcgtc ccgacgactg    119100
tgcaatacat aaaaaaacac ggttgatgtc ctcaacgagc ctggccgggt ggatctccca    119160
acccggagta caaaacgcgc cggggcctcg cgacgtatcc cggccgttca gggtcctgg    119220 tgcagatcca tattccatct ttccgttaac atcaaccgat gccccgggtt ttgactcgga    119280
cgagtcgccc cgcgtagccg gtgaggtgca aaacatgtcc ttggggccgt agtaaccttt    119340
```

-continued

```
tcccttaaaa ccgactcgac gctgtcgcgt tatgaatcgg acgaaccctg cacaacaaaa 119400
cacacaccca aacgtttaca tctatgaata aggctacttg ggtaaaatgg caatgggggga 119460 ttccggggcg ggagaccttc gattgggttg cctttataac accaaaaaaa ggggggggcc 119520
ccgtgtgttt tttttttatca cgtcaaatcg attttaaaaa gcctgccgct ccatttggaa 119580
tatatatatt ctgtgaaaag cccgcccaca ccccataaaa ccgcgacatc gcgggaacac 119640
gcgcgaacaa gaaactctct ctctttctct atatatatat atatatatat atatatatat 119700
agaaagaaag tgcgaacggt ggttggacac atgccaaaac atgaaaaccc atacagtgaa 119760
aaaacgggaa gtgcgaatgc agatcaaaag agtgtatccg attggcgtac accacagaca 119820
tgcggacgcc caatttaacc ccccccttt ttcaccccc caccccaccc cattccaccc 119880
caggaagtgc gaacgggttt acatgcctca gatatgaagt tcttcgactt gttttgaat 119940 aaattttttt gtgattttct acaacggttt agagaattat ggttataaac atcggcgggg 120000
taccgcgccc cctccccatc ggcggggtac cgcgcccct ccccatcggc ggggtaccgc 120060
gccccctccc catcggcggg gtaccgcgcc ccctccccat cggcgggta ccgcgccccc 120120 tccccatcgg cgggggggtta cgtgaacacc acaaccccgt gtgtatttta tgggttatcg 120180
cgggcttcgt gccgcctgac ataatcgttg ggaggggtgg tggtgtatac gcttgttgat 120240
tgcgcgaacg taatgacgac ggagagggac ccaaacacac cgtcgacgtg catttgatta 120300
actagatgcc ggatgggtgg aaacaacccg tgttatataa gatgttttgc atgtgagaca 120360
accccaattg tgtttatgta tattatatat cgtctgtaga cacacgatga ttggttgtta 120420
tttaaacata tgtaaatgaa attcacatgt ctggtatccc ttgttatgat gttgtaaggt 120480
atgcggaaat agacaccggg cgtacatcgc caaccagcgg tctctcctta aacgcatact 120540
atggtccatg aacttcccgc ctcgagtctc gtccaatcac tacatcgtct tatcattaag 120600
aatatttaca cggtgacgac acggggagga aatatgcggt cgagggggg gcacaacacg 120660 ttttaagtac tgttggaact ccctcaccaa ccgcaatcgc aatcctttga aggctgcgag 120720
agcgtttgga aaactcgggt acgtctaaat tcaccccagt gcgatggata cgccgccgat 120780
gcagcgctct acaccccaac gcgcggggtc gcctgatact ttggagttaa tggacctgtt 120840
ggacgcggcc gcggcggccg ccgaacacag ggcccgggtg gtcacctcga gtcagcctga 120900
cgatctacta tttggagaga acgggtcat ggtgggacgg gaacacgaga tcgtttcaat 120960
tccctccgta tcgggacttc aaccagaacc cagaacggaa gatgttggcg aagagctaac 121020
acaagacgac tacgtatgcg aggacggtca ggatctaatg ggctcgcctg taatcccgct 121080
ggccgaggtc ttccacaccc gattctcgga ggccggcgcg cgagaaccaa caggagccga 121140 tcgctcccctt gagacagtct ctctcggaac gaagcttgct aggtctccaa aaccaccgat 121200
gaacgatggg gaaacgggca gaggtacgac ccctccgttc ccgcaggcct tctcccctgt 121260 atccccgcg tctcctgttg gagacgccgc cgggaacgat caacgggaag accagcggtc 121320
tataccccga caaacgacga gaggaaattc accaggtttg ccgtcggtgg tccatcgaga 121380
cagacaaact cagtccatct cgggtaaaaa gccgggcgat gagcaagcgg gtcatgcgca 121440
tgcatcgggg gacggagtag ttctccagaa aactcaacgg cccgctcagg gaaagagccc 121500
gaagaaaaag actttgaagg ttaaggtccc actcccggcg cggaaacccg gtggacctgt 121560
acccggcccg gttgagcaat tgtaccacgt cctttcggac agcgttcccg ctaagggggc 121620
aaaggcggac ctgccgtttg agaccgatga taccgcccca aggaaacatg atgcccgggg 121680
tataacacct cgcgtccctg gacgttcgtc gggggggcaaa cctagagcgt ttttggcccct 121740
```

-continued

```
gccgggaaga tcccacgcac cagacccgat tgaggatgac agcccagtgg agaaaaagcc   121800
aaagagtcgt gagtttgttt cgtcttcatc ctcttcctcg tcgtggggat cgtcatcgga   121860
ggatgaagac gatgaacccc ggcgcgtttc ggtgggaagt gaaactacag gcagcaggtc   121920
cggacgcgaa cacgcccctt ccccgtcaaa ttcggatgat tcggactcaa atgatggtgg   121980
gtcgacgaaa caaatatcc aaccgggata tcgatccatc agcggtcccg atccgaggat   122040
tcgtaagacc aaacgtcttg cgggggaacc ggggcgccag agacagaaat catttcccct   122100
gccgcgatcc agaaccccga taattccccc ggtgtcgggg ccgctcatga tgcccgacgg   122160
aagcccttgg cccggatcgg caccctccc atccaacagg gtgcggtttg gaccgtccgg   122220
ggagaccaga gagggtcact gggaggatga ggctgtgaga gcggcgcggg ctcgttacga   122280
ggcctcaacg gaaccgtgc cgctttacgt gccggagttg ggagatccgg ctagacagta   122340
ccgcgcgctg attaacctga tctactgtcc agacagagac cctatagcat ggctccagaa   122400
ccccaagctg accggtgtca actcggccct gaaccagttc taccaaaagc tgttgccacc   122460
gggacgggcg ggtaccgccg ttacgggag cgtagcgtct cccgttccgc atgtaggcga   122520
agccatggcc acgggggagg ccctctgggc tctccccac gcggccgcgg ccgtggctat   122580
gagccgtcga tacgaccggg cccaaaaaca ctttatccta cagagtctcc gcagagcctt   122640
tgccagcatg gcatacccg aggcaacggg ctccagtccg gcggcgcgga tctcccgcgg   122700
tcacccttct ccaacaaccc cggccacaca ggctcccgac cctcagccgt cggccgccgc   122760
acgctctctt tctgtgtgtc caccggatga tcgtttacga actccgcgca agcgcaagtc   122820
ccagccagtc gagagcagaa gcctcctcga caagattagg gagacacccg tcgcggacgc   122880
ccgggttgca gacgatcatg tggtttccaa ggccaagagg cgggtatccg agcccgtgac   122940
catcacctcg ggccctgtgg tggatccccc cgccgtaata acgatgccac ttgacggacc   123000
ggccccaaac gggggattc ggcgtattcc ccgggggggcc ctgcataccc cggtcccgtc   123060
ggaccaggct cgcaaggcgt actgtacccc cgaaaccatc gcccgtctgg tcgacgaccc   123120
attgtttccc acggcctggc gccctgcgct aagctttgat cccggcgcct tggcggaaat   123180
cgccgctcgg cgtccgggcg gaggagaccg acggtttggt ccaccagcg gagtggaggc   123240 gctgcgacgg aggtgcgcct ggatgcggca gatcccagac ccggaggatg tgaggcttct   123300
gatcatctac gatccgttgc ccggagagga catcaacggc cccctcgaga gcaccctcgc   123360
gacagatccg ggaccgtcat ggagtccatc ccgaggggga ctgtctgtgg tcctggcagc   123420
cctgagtaac cggttgtgcc tgccgagcac tcatgcctgg gccgggaact ggaccggccc   123480 gccgacgtg tccgctttga acgcccgggg cgttttatta ctgtcgaccc gagacctggc   123540
ctttgccggg gccgtcgagt atctaggctc gcggttggcc tctgcccggc gccggttgct   123600
ggtgttggac gcggtggccc tcgagaggtg gcccagggat ggaccccgctt tgtctcagta   123660 tcacgtgtac gtccgggccc cggcgcgacc ggacgcccag gccgtcgtcc gatggccaga   123720
ctcggcggtc acagaaggac tcgcccgggc cgtgtttgca tcgtcgcgca cctttgggcc   123780
agcgagtttt gctcgtatcg agactgcgtt tgccaacctg tacccgggcg aacaacccct   123840
gtgtttgtgc cgcggtggga acgtcgcata caccgtgtgt acccgcgcgg gccccaagac   123900
ccgcgtcccc ctgtcgcccc gtgaataccg gcagtacgtg ctgccgggtt ttgacggttg   123960
caaggacctc gcgcgacagt ctcggggtct ggggctcggg gcagccgact ttgtggacga   124020
ggcggcacat agccaccgcg cagcaaaccg atggggcctg ggtgccgcgc ttcgacccgt   124080
cttccttccc gagggacgga gaccgggggc cgccgggccg gaggccggcg acgtacccac   124140
```

-continued

```
ctgggcgagg gtgttttgcc gccacgccct gctggaaccc gaccctgccg cagaaccact    124200
cgtgcttcca cccgtggccg gtcggtcggt ggcgctgtat gcgtcggcgg acgaggctcg    124260
gaatgccctc cccccgattc ccagagtaat gtggccgccc ggttttgggg ccgcggagac    124320
ggtgttggag gggagcgacg gaacacggtt cgtgttcgga caccacgggg gctcggaacg    124380
gccgtcagaa acccaggcgg ggcgacagcg gcgcaccgca gacgacagag aacacgcttt    124440
ggagctggac gattgggagg tggggtgtga agacgcgtgg gacagcgagg aggggggcgg    124500
ggacgacggg gacgcaccgg ggtcatcctt tggggtgagc atcgtgtcgg tggccccggg    124560
tgtgctgcga gaccgccggg tgggtttgcg cccggcggtc aaggtggagc tgttgtcctc    124620
gtcctcgtcc tccgaggacg aggacgatgt gtggggaggg cgcgggggga ggagcccccc    124680
gcagagtcgg gggtgacgga gtcccctcct tttctcgtga gcgccactgg cgcgcggact    124740
gtttgttgtt aataaaagcg gaacggtttt tatgaaaaaa gtgtctgtct gtctgtgcgg    124800
gcgggcgacg ggcgggctgg tcggacccccc ccccgaaaat aacccccccc cggtttctgg    124860
gcgcccggcg gaccccggga gagg                                           124884
```

```
<210> SEQ ID NO 77
<211> LENGTH: 12
<212> TYPE: DNA
<213> ORGANISM: Varicella zoster

<400> SEQUENCE: 77
ctgcagatag tt                                                              12

<210> SEQ ID NO 78
<211> LENGTH: 4
<212> TYPE: PRT
<213> ORGANISM: Varicella zoster

<400> SEQUENCE: 78

Leu Gln Ile Val
1

<210> SEQ ID NO 79
<211> LENGTH: 12
<212> TYPE: DNA
<213> ORGANISM: Varicella zoster

<400> SEQUENCE: 79
ctgcagatga ta                                                              12

<210> SEQ ID NO 80
<211> LENGTH: 4
<212> TYPE: PRT
<213> ORGANISM: Varicella zoster

<400> SEQUENCE: 80

Leu Gln Met Ile
1
```